(12) United States Patent
Kakinuma et al.

(10) Patent No.: US 8,017,792 B2
(45) Date of Patent: Sep. 13, 2011

(54) 1-THIO-D-GLUCITOL DERIVATIVES

(75) Inventors: Hiroyuki Kakinuma, Tokyo (JP); Yuko Hashimoto, Tokyo (JP); Takahiro Oi, Tokyo (JP); Hitomi Takahashi, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/982,343

(22) Filed: Dec. 30, 2010

(65) Prior Publication Data

US 2011/0098469 A1    Apr. 28, 2011

Related U.S. Application Data

(62) Division of application No. 11/794,498, filed as application No. PCT/JP2006/300135 on Jan. 10, 2006, now Pat. No. 7,910,619.

(30) Foreign Application Priority Data

Jan. 7, 2005   (JP) ................................. 2005-002913
Aug. 12, 2005  (JP) ................................. 2005-233912

(51) Int. Cl.
    *C07D 335/02*    (2006.01)
(52) U.S. Cl. ....................................................... 549/28
(58) Field of Classification Search ....................... 549/28
    See application file for complete search history.

(56) References Cited

U.S. PATENT DOCUMENTS

| | | | |
|---|---|---|---|
| 5,773,663 A | 6/1998 | Curtze et al. |
| 7,250,522 B2 | 7/2007 | Sato et al. |
| 2005/0209309 A1 | 9/2005 | Sato et al. |
| 2005/0256317 A1 | 11/2005 | Sato et al. |
| 2010/0004465 A1 | 1/2010 | Kakinuma et al. |
| 2010/0069460 A1 | 3/2010 | Kakinuma et al. |

FOREIGN PATENT DOCUMENTS

| | | |
|---|---|---|
| EP | 1 553 094 A1 | 8/2003 |
| EP | 1 609 799 A1 | 2/2004 |
| EP | 1 609 785 A1 | 3/2004 |
| JP | 5495563 A | 7/1979 |
| JP | 8277243 A | 10/1996 |
| JP | 9221458 A | 8/1997 |
| WO | 01/27128 A1 | 4/2001 |
| WO | 2004/013118 A1 | 2/2004 |
| WO | 2004/014930 A1 | 2/2004 |
| WO | 2004/014931 A1 | 2/2004 |
| WO | 2004/080990 A1 | 9/2004 |
| WO | 2004/089967 A1 | 10/2004 |

OTHER PUBLICATIONS

Al-Masoudi, Najim A. et al: "Synthesis of some novel 1-(5-thio-.beta.-D-glucopyranosyl)-6-azaur acil derivatives. Thio sugar nucleosides" NUCLEOSIDES & NUCLEOTIDES, 12(7), 687-99 CODEN: NUNUD5; ISSN: 0732-8311, 1993, XP008091463.

Bozo, Eva et al., "Synthesis of 4-cyanophenyl 1,5-dithio-beta-D-glucopyranoside and its 6-deoxy, as well as 6-deoxy-5-ene-derivatives as oral antithombotic agents", Carbohydrate Research, vol. 304, pp. 271-280, 1997.

*Primary Examiner* — Taofiq A Solola
(74) *Attorney, Agent, or Firm* — Sughrue Mion, PLLC

(57) ABSTRACT

The present invention provides a 1-thio-D-glucitol compound of the following formula, which shows the action of inhibiting the activity of SGLT2, a pharmaceutically acceptable salt of the compound, or a hydrate of the compound or the salt; and a pharmaceutical comprising such a compound as an active ingredient, especially, a pharmaceutical for preventing or treating diabetes, diabetes-related disease, or diabetic complication. The invention also provides a method for producing the 1-thio-D-glucitol compound and its intermediate.

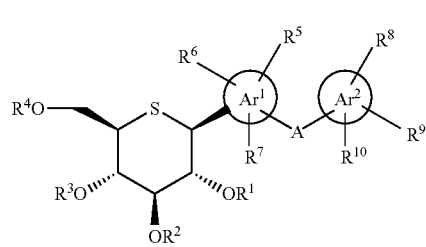

2 Claims, No Drawings

1-THIO-D-GLUCITOL DERIVATIVES

This application is a divisional of U.S. application Ser. No. 11/794,498 (Confirmation No. 2323) filed Jun. 29, 2007 (allowed), which is a U.S. National Stage Application of PCT/JP06/300135 filed Jan. 10, 2006, which claims benefit of Japanese Application Nos. 2005-002913, filed Jan. 7, 2005, and 2005-233912, filed Aug. 12, 2005, the disclosure of each of which is incorporated herein by reference in its entirety.

TECHNICAL FIELD

This invention relates to 1-thio-D-glucitol derivatives which inhibit the activity of sodium-dependent glucose cotransporter 2 (SGLT2) concerned with glucose reabsorption in the kidney.

BACKGROUND ART

It is believed that chronic hyperglycemia decreases insulin secretion and lowers insulin sensitivity, further causing increases in blood glucose levels and aggravating diabetes. Hyperglycemia is considered to be a major risk factor for complications of diabetes. Thus, maintaining blood sugar at a normal level seems to improve insulin sensitivity and suppress the onset of complications of diabetes. Biguanides, sulfonylureas, glycosidase inhibitors, and insulin sensitizing agents have so far been used as therapies of diabetes. However, adverse reactions or side effects have been reported, such as lactic acidosis for the biguanides, hypoglycemia for the sulfonylureas, and diarrhea and serious hepatic function disorder for the glycosidase inhibitors. Hence, drugs for treatment of diabetes, which have new mechanisms of action different from those of the conventional drugs, are desired to be developed.

Phlorizin, which is a glucose derivative isolated from natural products, was shown to inhibit the reabsorption of excess glucose in the kidney and promote the excretion of glucose, exhibiting an antihyperglycemic action (non-patent documents 1 and 2). Then, this reabsorption of glucose was shown to be ascribed to sodium-dependent glucose cotransporter 2 (SGLT2) present at the S1 site of the renal proximal tubule (non-patent document 3). Since the administration of phlorizin, a specific SGLT inhibitor, to rats with diabetes was demonstrated to promote glucose excretion to urine and produce an antihyperglycemic action, SGLT2-specific inhibitors have been regarded as new target molecules for therapies of diabetes.

Against such a background, numerous phlorizin-related compounds have been studied, and O-aryl glucosides have been disclosed (patent documents 1 to 11). However, when orally administered, O-aryl glucosides have their glycoside linkage hydrolyzed with β-glycosidase present in the small intestine, and in the unchanged form, are poor in absorption efficiency. Thus, their prodrugs are under development.

A report has been issued of compounds which are O-aryl glucosides converted into chemically stable C-aryl glycosides (patent document 12). Compounds having the glucose portion directly bound to aryl or heteroaryl, as described above, have also been reported (patent documents 13 to 15). However, C-aryl glycosides, which are the compounds disclosed in these documents (patent documents 12 to 15), are amorphous substances in many cases, and thus their pharmaceutical manufacturing is problematical (patent document 12). For this reason, these compounds needed to be crystallized together with suitable amino acids such as phenylalanine and proline (U.S. Pat. No. 6,774,112). Accordingly, compounds, which have excellent crystallinity, whose purification, storage and pharmaceutical manufacturing are easy, and which are easy to handle as drugs, were required.

There have been reports of methods for producing aryl 5-thio-β-D-glucopyranoside (O-aryl 5-thio-β-D-glucoside) or heteroaryl 5-thio-β-D-glucopyranoside (O-heteroaryl 5-thio-β-D-glucoside) derivatives having 5-thioglucose and aryl or heteroaryl bound via β-glucoside (patent documents 16 to 17). The SGLT-inhibiting action of these compounds is also reported (patent documents 18 to 19). As seen in the report (patent document 16), however, glycosylation completely differs in the behavior of the reaction according to the type of sugar, and the reaction conditions permitting glycosylation from glucose cannot be applied to thioglucose.

Thus, there have been no methods for producing 1-thio-D-glucitol derivatives having 5-thioglucose and an aryl or hetero ring directly bound, and there have been no reports of 1-thio-D-glucitol derivatives. Some of the compounds shown in patent documents 1 to 15 have already been subjected to clinical trials, and there is a possibility that new drugs for treatment of diabetes will be commercially available in the future. However, during clinical trials in humans, their development may become difficult for some reason, and thus a group of compounds having the same mechanism of action, but having a hitherto inexistent new skeleton are needed.

Non-patent document 1: Rossetti, L., et al. J. Clin. Invest., Vol. 80, 1037, 1987

Non-patent document 2: Rossetti, L., et al. J. Clin. Invest., Vol. 79, 1510, 1987

Non-patent document 3: Kanai, Y., et al. J. Clin. Invest., Vol. 93, 397, 1994

Patent document 1: European Patent Application Publication No. 0850948

Patent document 2: European Patent Application Publication No. 0598359

Patent document 3: International Publication No. WO01/068660 pamphlet

Patent document 4: International Publication No. WO01/016147 pamphlet

Patent document 5: International Publication No. WO01/074834 pamphlet

Patent document 6: International Publication No. WO01/074835 pamphlet

Patent document 7: International Publication No. WO02/053573 pamphlet

Patent document 8: International Publication No. WO02/068439 pamphlet

Patent document 9: International Publication No. WO02/068440 pamphlet

Patent document 10: International Publication No. WO02/036602 pamphlet

Patent document 11: International Publication No. WO02/088157 pamphlet

Patent document 12: International Publication No. WO01/027128 pamphlet

Patent document 13: US Patent Application Publication No. 2001/0041674

Patent document 14: International Publication No. WO04/013118 pamphlet

Patent document 15: International Publication No. WO04/080990 pamphlet

Patent document 16: International Publication No. WO04/014930 pamphlet

Patent document 17: International Publication No. WO04/089966 pamphlet

Patent document 18: International Publication No. WO04/014931 pamphlet

Patent document 19: International Publication No. WO04/089967 pamphlet

DISCLOSURE OF THE INVENTION

Problems to be Solved by the Invention

It is an object of the present invention to provide a hitherto inexistent new 1-thio-D-glucitol compound which inhibits the activity of sodium-dependent glucose cotransporter 2 (SGLT2) related to glucose reabsorption in the kidney, promotes the excretion of urine sugar, and exhibits an antihyperglycemic action. It is another object of the present invention to provide an excellent inhibitor selective for SGLT2 activity. It is still another object of the present invention to provide a compound which has excellent crystallinity, whose purification, storage and pharmaceutical manufacturing are easy, and which is easy to handle as a drug. It is a further object of the present invention to provide a method for producing the 1-thio-D-glucitol compound and provide its intermediate.

Means for Solving the Problems

The inventors of the present invention diligently conducted searches and studies in an attempt to solve the above problems. As a result, they discovered a method for preparation of directly binding an aryl or hetero ring to a 5-thio-glucose, and have found that a 1-thio-D-glucitol derivative obtained by this method has an excellent action of inhibiting SGLT2. This finding has led to accomplishment of the present invention. It has also been found that the 1-thio-D-glucitol derivative of the present invention is also satisfactory in crystallinity. Thus, this derivative need not be co-crystallized with an amino acid or the like, its purification, storage and pharmaceutical manufacturing are easy, and is suitable for handling as a drug.

Embodiments of the 1-thio-D-glucitol derivative of the present invention (hereinafter referred to as "the compound of the present invention") will be described below.

An embodiment of the present invention relates to a 1-thio-D-glucitol compound of the following formula I, or a pharmaceutically acceptable salt thereof, or a hydrate of the compound or the salt:

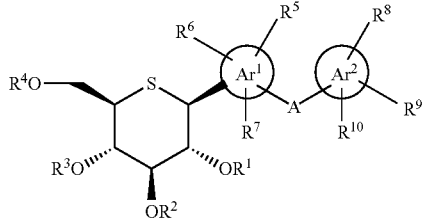

I

[where $R^1$, $R^2$, $R^3$ and $R^4$ are the same or different, and each represent a hydrogen atom, a $C_{1-6}$ alkyl group, $-CO_2R^{a2}$, $-COR^{b1}$, or a $C_{7-12}$ aralkyl group optionally substituted by one or more substituents selected from the group consisting of a halogen atom, $-NO_2$ and $-OMe$ (where $R^{a2}$ represents a $C_{1-6}$ alkyl group, and $R^{b1}$ represents a $C_{1-6}$ alkyl group, a $C_{7-10}$ aralkyl group, or a phenyl group), A represents $-(CH_2)n-$, $-CONH(CH_2)n-$, $-NHCO(CH_2)n-$, $-O-$, $-S-$, $-NH-$, or $-(CH_2)nCH=CH-$ (where n denotes an integer of 0 to 3), $Ar^1$ represents an arylene group, a heteroarylene group, or a heterocycloalkylene group, $Ar^2$ represents an aryl group, a heteroaryl group, or a heterocycloalkyl group, and $R^5$, $R^6$, $R^7$, $R^8$, $R^9$ and $R^{10}$ are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) $-(CH_2)m-Q$ (where m denotes an integer of 0 to 4, and Q represents $-CHO$, $-NH_2$, $-NO_2$, $-CN$, $-CO_2H$, $-SO_3H$, $-OR^{c1}$, $-CO_2R^{a3}$, $-CONH_2$, $-CONHR^{a4}$, $CONR^{a5}R^{a5}$, $-COR^{d1}$, $-OCOR^{d2}$, $SR^{e1}$, $-SOR^{e2}$, $-SO_2R^{e3}$, $-NHC(=O)H$, $-NHCOR^{d3}$, $-NHCO_2R^{d4}$, $-NHCONH_2$, $-NHSO_2R^{e4}$, $-NHR^{a6}$, or $-NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)}, (vi) $-O-(CH_2)m'-Q'$ {where m' denotes an integer of 1 to 4, and Q' represents a hydroxyl group, $-CO_2H$, $-OR^{c2}$, $-CO_2R^{a8}$, $-CONH_2$, $-CONHR^{a9}$, $-CONR^{a10}R^{a10}$, $-NH_2$, $-NHR^{a11}$, $-NR^{a12}R^{a12}$ or $NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represent a $C_{1-6}$ alkyl group, a $C_{7-10}$ aralkyl group, a phenyl group, or a $C_{3-7}$ cycloalkyl group)}, (vii) $-OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and $-OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and $-OR^{a14}$ (where $R^{a14}$ represents a $C_{1-6}$ alkyl group); a $C_{7-10}$ aralkyl group optionally substituted by one or more substituents selected from the group consisting of a halogen atom, a hydroxyl group, a $C_{1-6}$ alkyl group, and $-OR^{a15}$ (where $R^{a15}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and $-OR^{a16}$ (where $R^{a16}$ represents a $C_{1-6}$ alkyl group)}, (viii) $-NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and $-OR^{a17}$ (where $R^{a17}$ represents a $C_{1-6}$ alkyl group)}, (ix) a $C_{3-7}$ cycloalkyl group optionally substituted by one or more substituents selected from the group consisting of a halogen atom, a hydroxyl group, a $C_{1-6}$ alkyl group, and $-OR^{a18}$ (where $R^{a18}$ represents a $C_{1-6}$ alkyl group), (x) an aryl group optionally substituted by one or more substituents selected from the group consisting of a halogen atom, a hydroxyl group, a $C_{1-6}$ alkyl group, and $-OR^{a19}$ (where $R^{a19}$ represents a $C_{1-6}$ alkyl group), (xi) a $C_{7-10}$ aralkyl group optionally substituted by one or more substituents selected from the group consisting of a halogen atom, a hydroxyl group, a $C_{1-6}$ alkyl group, and $-OR^{a20}$ (where $R^{a20}$ represents a $C_{1-6}$ alkyl group), (xii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group),
(xiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group),
(xiv) a $C_{2-6}$ alkenyl group, or
(xv) a $C_{2-6}$ alkynyl group].

Another embodiment of the present invention relates to a 1-thio-D-glucitol compound of the following formula IA, or a pharmaceutically acceptable salt thereof, or a hydrate of the compound or the salt:

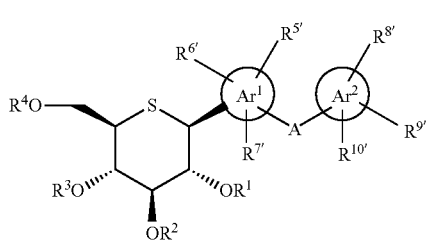

IA

[where $R^1$, $R^2$, $R^3$ and $R^4$ are the same or different, and each represent a hydrogen atom, a $C_{1-6}$ alkyl group, —$CO_2R^{a2}$, —$COR^{b1}$, or a $C_{7-12}$ aralkyl group optionally substituted by one or more substituents selected from the group consisting of a halogen atom, —$NO_2$ and —OMe (where $R^{a2}$ represents a $C_{1-6}$ alkyl group, and $R^{b1}$ represents a $C_{1-6}$ alkyl group, a $C_{7-10}$ aralkyl group, or a phenyl group),
A represents —$(CH_2)n$-, —$CONH(CH_2)n$-, —NHCO$(CH_2)n$-, —O—, —S—, —NH—, or —$(CH_2)nCH=CH$— (where n denotes an integer of 0 to 3),
$Ar^1$ represents an arylene group, a heteroarylene group, or a heterocycloalkylene group,
$Ar^2$ represents an aryl group, a heteroaryl group, or a heterocycloalkyl group, and
$R^{5'}$, $R^{6'}$, $R^{7'}$, $R^{8'}$, $R^{9'}$ and $R^{10'}$ are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group,
(v) —$(CH_2)m$-Q {where m denotes an integer of 0 to 4, and Q represents —CHO, —$NH_2$, —$NO_2$, —CN, —$CO_2H$, —$SO_3H$, —$OR^{c1}$, —$CO_2R^{a3}$, —$CONH_2$, —$CONHR^{a4}$, $CONR^{a5}R^{a5}$, $COR^{d1}$, $OCOR^{d2}$, —$SR^{e1}$, —$SOR^{e2}$, —$SO_2R^{e3}$, —NHC(=O)H, —$NHCOR^{d3}$, —$NHCO_2R^{d4}$, —$NHCONH_2$, —$NHSO_2R^{e4}$, —$NHR^{a6}$, or —$NR^{a7}R^{a7}$ (where $R^{a3}$, $R^{a4}$, $R^{a5}$, $R^{a6}$ and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)},
(vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{12}$, or $NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represent a $C_{1-6}$ alkyl group, a $C_{7-10}$ aralkyl group, a phenyl group, or a $C_{3-7}$ cycloalkyl group)}, (vii) —$OR^f$ (where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group),
(viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)},
(ix) a $C_{3-7}$ cycloalkyl group optionally substituted by one or more substituents selected from the group consisting of a halogen atom, a hydroxyl group, a $C_{1-6}$ alkyl group, and —$OR^{a18}$ (where $R^{a18}$ represents a $C_{1-6}$ alkyl group),
(x) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group),
(xi) a $C_{7-10}$ aralkyl group optionally substituted by one or more substituents selected from the group consisting of a halogen atom, a hydroxyl group, a $C_{1-6}$ alkyl group, and —$OR^{a20}$ (where $R^{a20}$ represents a $C_{1-6}$ alkyl group),
(xii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), or
(xiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group)].

The first concrete embodiments of the present invention relate to the 1-thio-D-glucitol compounds of the formula I or IA where $Ar^1$ is an arylene group, or the pharmaceutically acceptable salts thereof, or the hydrates of them.

One of the above embodiments of the present invention relates to the 1-thio-D-glucitol compound of the formula I or IA where $Ar^1$ is a phenylene group or a naphthylene group, or the pharmaceutically acceptable salt thereof, or the hydrate of the compound or the salt.

Another embodiment of the present invention relates to the 1-thio-D-glucitol compound, or the pharmaceutically acceptable salt thereof, or the hydrate of the compound or the salt, in which A is —$(CH_2)n$-, —$CONH(CH_2)n$-, —O—, or —$(CH_2)nCH=CH$— (where n denotes an integer of 0 to 3).

Another embodiment of the present invention relates to the 1-thio-D-glucitol compound, or the pharmaceutically acceptable salt thereof, or the hydrate of the compound or the salt, in which A is —$CH_2$—.

Another embodiment of the present invention relates to the 1-thio-D-glucitol compound, or the pharmaceutically acceptable salt thereof, or the hydrate of the compound or the salt, in which $Ar^2$ is a phenyl group, a thienyl group, a benzo[b]thiophenyl group, a thieno[2,3-b]thiophenyl group, a benzofuranyl group, a benzothiazolyl group, an indolyl group, a pyrrolyl group, an imidazolyl group, a pyrazolyl group, a pyridyl group, a pyrimidinyl group, a pyrazinyl group, or an isoxazolyl group.

The first concrete embodiment of the present invention relates, in particular, to a 1-thio-D-glucitol compound of the following formula II, or a pharmaceutically acceptable salt thereof, or a hydrate of the compound or the salt (hereinafter referred to as "the first concrete embodiment (1)"):

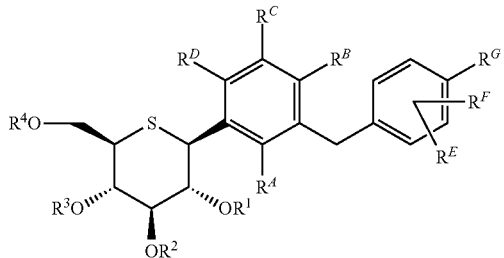

[where $R^1$, $R^2$, $R^3$ and $R^4$ are the same or different, and each represent a hydrogen atom, a $C_{1-6}$ alkyl group, —$CO_2R^{a2}$, —$COR^{b1}$, or a $C_{7-12}$ aralkyl group optionally substituted by one or more substituents selected from the group consisting of a halogen atom, —$NO_2$ and —OMe (where $R^{a2}$ represents a $C_{1-6}$ alkyl group, and $R^{b1}$ represents a $C_{1-6}$ alkyl group, a $C_{7-10}$ aralkyl group, or a phenyl group), at least one of $R^A$, $R^B$, $R^C$ and $R^D$ represents a hydrogen atom, and the other of them are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$(CH_2)m$-$Q^A$ {where m denotes an integer of 0 to 4, and $Q^A$ represents —$NH_2$, —$CO_2H$, —$OR^{c1}$, —$CO_2R^{a3}$, —$CONH_2$, —$CONHR^{a4}$ $CONR^{a5}R^{a5}$, —$COR^{d1}$, —$OCOR^{d2}$, —$SR^{e1}$, —$SOR^{e2}$, —$SO_2R^{e3}$— $NHC(=O)H$, —$NHCOR^{d3}$, —$NHCO_2R^{d4}$, —$NHCONH_2$, —$NHSO_2R^{e4}$, —$NHR^{a6}$, or —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)}, (vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or $NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represent a $C_{1-6}$ alkyl group, a $C_{7-10}$ aralkyl group, a phenyl group, or a $C_{3-7}$ cycloalkyl group)}, (vii) —$OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a1}$ represents a $C_{1-6}$ alkyl group)}, (viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)}, (ix) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), or (x) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group), and $R^E$, $R^F$ and $R^G$ are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$(CH_2)m$-Q {where m denotes an integer of 0 to 4, and Q represents —CHO, —$NH_2$, —$NO_2$, —CN, —$CO_2H$, —$SO_3H$, —$OR^{c1}$, —$CO_2R^{a3}$, —$CONH_2$, $CONHR^{a4}$— $CONR^{a5}R^{a5}$, —$COR^{d1}$, $OCOR^{d2}$, —$SR^{e1}$, —$SOR^{e2}$, —$SO_2R^{e3}$, —$NHC(=O)H$, —$NHCOR^{d3}$, —$NHCO_2R^{d4}$, —$NHCONH_2$, —$NHSO_2R^{e4}$, —$NHR^{a6}$, or —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)}, (vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or $NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represents a $C_{1-6}$ alkyl group, a $C_{7-10}$ aralkyl group, a phenyl group, or a $C_{3-7}$ cycloalkyl group)}, (vii) —$OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}, (viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)}, (ix) a $C_{3-7}$ cycloalkyl group optionally substituted by one or more substituents selected from the group consisting of a halogen atom, a hydroxyl group, a $C_{1-6}$ alkyl group, and —$OR^{a18}$ (where $R^{a18}$ represents a $C_{1-6}$ alkyl group),
(x) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group),
(xi) a $C_{7-10}$ aralkyl group optionally substituted by one or more substituents selected from the group consisting of a halogen atom, a hydroxyl group, a $C_{1-6}$ alkyl group, and —$OR^{a20}$ (where $R^{a20}$ represents a $C_{1-6}$ alkyl group),
(xii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group),
(xiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group),
(xiv) a $C_{2-6}$ alkenyl group, or
(xv) a $C_{2-6}$ alkynyl group].

Another embodiment of the present invention relates to a 1-thio-D-glucitol compound of the formula II, or a pharmaceutically acceptable salt thereof, or a hydrate of the compound or the salt (hereinafter referred to as "the first concrete embodiment (1)-1"), in which $R^A$ and $R^C$ are each a hydrogen atom, $R^B$ represents a hydrogen atom, a halogen atom, a hydroxyl group, a $C_{1-8}$ alkyl group, —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or —$NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represents a $C_{1-6}$ alkyl group, a $C_{7-10}$ aralkyl group, a phenyl group, or a $C_{3-7}$ cycloalkyl group)}, or —$OR^{f1}$ (where $R^{f1}$ represents a $C_{1-6}$ alkyl group optionally substituted by a halogen atom(s), or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group), $R^D$ represents a hydrogen atom, a halogen atom, a hydroxyl group, a $C_{1-8}$ alkyl group, or —$OR^{f2}$ {where $R^{f2}$ represents a $C_{1-6}$ alkyl group optionally substituted by a halogen atom(s), or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group), $R^E$ and $R^F$ are the same or different, and each represent a hydrogen atom, a halogen atom, a $C_{1-8}$ alkyl group, or —$OR^{c3}$ (where $R^{c3}$ represents a $C_{1-6}$ alkyl group optionally substituted by a halogen atom(s)), and $R^G$ represents (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group,
(v) —$(CH_2)m$-Q {where m denotes an integer of 0 to 4, and Q represents —CHO, —$NH_2$, —$NO_2$, —CN, —$CO_2H$, —$SO_3H$, —$OR^{c1}$, —$CO_2R^{a3}$, —$CONH_2$, —$CONHR^{a4}$, —$CONR^{a5}R^{a5}$, —$COR^{d1}$, —$OCOR^{d2}$, —$SR^{e1}$, $SOR^{e2}$, —$SO_2R^{e3}$, —NHC(=O)H, —$NHCOR^{d3}$, —$NHCO_2R^{d4}$, —$NHCONH_2$, $NHSO_2R^{a4}$, —$NHR^{a6}$, or —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)},
(vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or —$NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represents a $C_{1-6}$ alkyl group, a $C_{7-10}$ aralkyl group, a phenyl group, or a $C_{3-7}$ cycloalkyl group)},
(vii) —$OR^f$ (where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)},
(viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)},
(ix) a $C_{3-7}$ cycloalkyl group optionally substituted by one or more substituents selected from the group consisting of a halogen atom, a hydroxyl group, a $C_{1-6}$ alkyl group, and —$OR^{a18}$ (where $R^{a18}$ represents a $C_{1-6}$ alkyl group),
(x) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group),
(xi) a $C_{7-10}$ aralkyl group optionally substituted by one or more substituents selected from the group consisting of a halogen atom, a hydroxyl group, a $C_{1-6}$ alkyl group, and —$OR^{a20}$ (where $R^{a20}$ represents a $C_{1-6}$ alkyl group),
(xii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), or
(xiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group).

Another embodiment of the present invention relates to the 1-thio-D-glucitol compound, or the pharmaceutically acceptable salt thereof, or the hydrate of the compound or the salt, according to the first concrete embodiment (1)-1 (hereinafter referred to as "the first concrete embodiment (1)-2"), in which $R^B$ represents a hydrogen atom, a $C_{1-6}$ alkyl group, —$OR^{f1}$ (where $R^{f1}$ represents a $C_{1-6}$ alkyl group optionally substituted by a halogen atom(s)), or a halogen atom, and $R^D$ represents a hydrogen atom, a hydroxyl group, or —$OR^{f1}$ (where $R^{f1}$ represents a $C_{1-6}$ alkyl group optionally substituted by a halogen atom(s), or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group)}.

Another embodiment of the present invention relates to the 1-thio-D-glucitol compound, or the pharmaceutically acceptable salt thereof, or the hydrate of the compound or the salt, according to the first concrete embodiment (1)-1 or the first concrete embodiment (1)-2, in which $R^G$ represents (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$CO_2H$, (vi) —$OR^{c1}$, (vii) —$CO_2R^{a3}$, (viii) —$CONH_2$, (ix) —$CONHR^{a4}$, (x) —$CONR^{a5}R^{a5}$, (xi) —$COR^{d1}$, (xii) —$OCOR^{d2}$, (xiii) —$SR^{e1}$, (xiv) —$SOR^{e2}$, (XV) —$SO_2R^{e3}$, (xvi) —$NHR^{a6}$, (xvii) —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$ and $R^{d2}$ each represent a $C_{1-6}$ alkyl group, a $C_{7-10}$ aralkyl group, a phenyl group, or a $C_{3-7}$ cycloalkyl group, and $R^{e1}$, $R^{e2}$ and $R^{e3}$ each represent a $C_{1-6}$ alkyl group, a phenyl group, or a tolyl group), (xviii) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, or —$NR^{a12}R^{a12}$ (where $R^{a8}$, $R^{a9}$, $R^{a10}$, $R^{a11}$, and $R^{a12}$ each represent a $C_{1-6}$ alkyl group, and $R^{c2}$ represents a $C_{1-6}$ alkyl group optionally substituted by a halogen atom(s))}, (xix) —$OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}, (xx) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), (xxi) a $C_{7-10}$ aralkyl group optionally substituted by one or more substituents selected from the group consisting of a halogen atom, a hydroxyl group, a $C_{1-6}$ alkyl group, and —$OR^{a20}$ (where $R^{a20}$ represents a $C_{1-6}$ alkyl group), (xxii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), or (xxiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group).

Another embodiment of the present invention relates to the 1-thio-D-glucitol compound, or the pharmaceutically acceptable salt thereof, or the hydrate of the compound or the salt, according to the first concrete embodiment (1)-1 or the first concrete embodiment (1)-2, in which $R^G$ represents (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$CO_2H$, (vi) —$OR^{c1}$, (vii) —$CO_2R^{a3}$, (viii) —$CONH_2$, (ix) —$CONHR^{a4}$, (x) —$CONR^{a5}R^{a5}$, (xi) —$COR^{d1}$, (xii) OCOR^{d2}, (xiii) —$SR^{e1}$, (xiv) —$SOR^2$, (XV) —$SO_2R^{e3}$, (xvi) —$NHR^{a6}$, (xvii) —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$ and $R^{d2}$ each represent a $C_{1-6}$ alkyl group, a $C_{7-10}$ aralkyl group, a phenyl group, or a $C_{3-7}$ cycloalkyl group, and $R^{e1}$, $R^{e2}$ and $R^{e3}$ each represent a $C_{1-6}$ alkyl group, a phenyl group, or a tolyl group), (xviii) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, or —$NR^{a12}R^{a12}$ (where $R^{a8}$, $R^{a9}$, $R^{a10}$, $R^{a11}$, and $R^{a12}$ each represent a $C_{1-6}$ alkyl group, and $R^{c2}$ represents a $C_{1-6}$ alkyl group optionally substituted by a halogen atom(s))}, (xix) —$OR^{f2}$ {where $R^{f2}$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}, or (xx) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group).

The first concrete embodiment of the present invention also relates, in particular, to a 1-thio-D-glucitol compound of the following formula III, or a pharmaceutically acceptable salt thereof, or a hydrate of the compound or the salt (hereinafter referred to as "the first concrete embodiment (2)"):

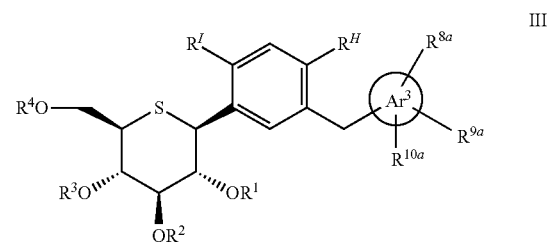

[where $R^1$, $R^2$, $R^3$ and $R^4$ are the same or different, and each represent a hydrogen atom, a $C_{1-6}$ alkyl group, —$CO_2R^{a2}$, —$COR^{b1}$, or a $C_{7-12}$ aralkyl group optionally substituted by one or more substituents selected from the group consisting of a halogen atom, —$NO_2$ and —OMe (where $R^{a2}$ represents a $C_{1-6}$ alkyl group, and $R^{b1}$ represents a $C_{1-6}$ alkyl group, a $C_{7-10}$ aralkyl group, or a phenyl group), $R^H$ and $R^I$ are the same or different, and each represent a hydrogen atom, a halogen atom, a hydroxyl group, a $C_{1-8}$ alkyl group, or —$OR^{f1}$ {where $R^{f1}$ represents a $C_{1-6}$ alkyl group optionally substituted by a halogen atom(s), or a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group)}, $Ar^3$ represents a thienyl group, a benzo[b]thiophenyl group, a thieno[2,3-b]thiophenyl group, a benzofuranyl group, a benzothiazolyl group, an indolyl group, a pyrrolyl group, an imidazolyl group, a pyrazolyl group, a pyridyl group, a pyrimidinyl group, a pyrazinyl group, or an isoxazolyl group, $R^{8a}$ and $R^{9a}$ are the same or different, and each represent a hydrogen atom, a halogen atom, a hydroxyl group, a $C_{1-8}$ alkyl group, or —$OR^{c3}$ (where $R^{c3}$ represents a $C_{1-6}$ alkyl group optionally substituted by a halogen atom(s)), and $R^{10a}$ represents a hydrogen atom, or an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), or a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group)].

The second concrete embodiment of the present invention relates to the 1-thio-D-glucitol compound of the formula I or IA where $Ar^1$ is a heteroarylene group, or the pharmaceutically acceptable salt thereof, or the hydrate of the compound or the salt.

The second concrete embodiment of the present invention further relates to the 1-thio-D-glucitol compound, or the pharmaceutically acceptable salt thereof, or the hydrate of the compound or the salt, in which A is —$(CH_2)n$- (where n denotes an integer of 0 to 3).

The second concrete embodiment of the present invention relates, in particular, to a 1-thio-D-glucitol compound of the following formula IV, or a pharmaceutically acceptable salt thereof, or a hydrate of the compound or the salt:

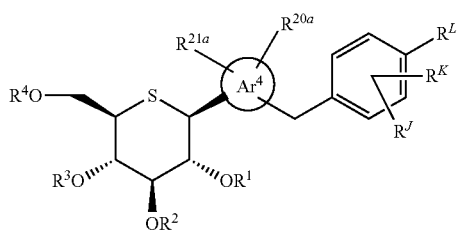

IV

[where $R^1$, $R^2$, $R^3$ and $R^4$ are the same or different, and each represent a hydrogen atom, a $C_{1-6}$ alkyl group, —$CO_2R^{a2}$, —$COR^{b1}$, or a $C_{7-12}$ aralkyl group optionally substituted by one or more substituents selected from the group consisting of a halogen atom, —$NO_2$ and —OMe (where $R^{a2}$ represents a $C_{1-6}$ alkyl group, and $R^{b1}$ represents a $C_{1-6}$ alkyl group, a $C_{7-10}$ aralkyl group, or a phenyl group), $Ar^4$ represents a thienylene group, a benzo[b]thiophenylene group, or a pyridylene group, $R^{20a}$ and $R^{21a}$ are the same or different, and each represent a hydrogen atom, a halogen atom, a hydroxyl group, a $C_{1-8}$ alkyl group, or —$OR^{c3}$ (where $R^{c3}$ represents a $C_{1-6}$ alkyl group optionally substituted by a halogen atom(s)), $R^J$ and $R^K$ are the same or different, and each represent a hydrogen atom, a halogen atom, a $C_{1-8}$ alkyl group, or —$OR^{c3}$ (where $R^{c3}$ represents a $C_{1-6}$ alkyl group optionally substituted by a halogen atom(s)), and $R^L$ represents (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$CO_2H$, (vi) —$OR^{c1}$, (vii) —$CO_2R^{a3}$, (viii) —$CONH_2$, (ix) —$CONHR^{a4}$, (x) —$CONR^{a5}R^{a5}$, (xi) —$COR^{d1}$, (xii) —$OCOR^{d2}$, (xiii) —$SR^{e1}$, (xiv) —$SOR^{e2}$, (xv) —$SO_2R^{e3}$, (xvi) —$NHR^{a6}$, (xvii) —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$ and $R^{d2}$ each represent a $C_{1-6}$ alkyl group, a $C_{7-10}$ aralkyl group, a phenyl group, or a $C_{3-7}$ cycloalkyl group, and $R^{e1}$, $R^{e2}$ and $R^{e3}$ each represent a $C_{1-6}$ alkyl group, a phenyl group, or a tolyl group), (xviii) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, or $NR^{a12}R^{a12}$ (where $R^{a8}$, $R^{a9}$, $R^{a10}$, $R^{a11}$, and $R^{a12}$ each represent a $C_{1-6}$ alkyl group, and $R^{c2}$ represents a $C_{1-6}$ alkyl group optionally substituted by a halogen atom(s))}, (xix) —$OR^{f2}$ {where $R^{f2}$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}; or (xx) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group].

Another embodiment of the present invention relates to the 1-thio-D-glucitol compound of the formula IV, or the pharmaceutically acceptable salt thereof, or the hydrate of the compound or the salt, in which $R^L$ represents a hydrogen atom, a halogen atom, a $C_{1-8}$ alkyl group, or —$OR^{c3}$ (where $R^{c3}$ represents a $C_{1-6}$ alkyl group optionally substituted by a halogen atom(s)).

The following are embodiments of the pharmaceutical comprising the compound of the present invention:

One embodiment of the present invention comprises any of the 1-thio-D-glucitol compounds, the pharmaceutically acceptable salts thereof, or the hydrates of the compounds or the salts described above.

Another embodiment of the present invention is an inhibitor of the activity of sodium-dependent glucose cotransporter 2, the inhibitor containing any such 1-thio-D-glucitol compound, pharmaceutically acceptable salt thereof, or hydrate of the compound or the salt.

Another embodiment of the present invention is the inhibitor containing any of the above 1-thio-D-glucitol compounds, pharmaceutically acceptable salts thereof, or hydrates of the compounds or the salts, and serving as a drug for prophylaxis or treatment of diabetes, diabetes-related disease, or diabetic complication.

Another embodiment of the present invention is a pharmaceutical comprising any of the above 1-thio-D-glucitol compounds, pharmaceutically acceptable salts thereof, or hydrates of them, in combination with at least one pharmaceutical selected from the group consisting of insulin sensitizing agents, which are selected from the group consisting of PPAR-γ agonists, PPAR-α/γ agonists, PPAR-δ agonists and PPAR-α/γ/δ agonists; glycosidase inhibitors; biguanides; insulin secretion accelerators; insulin preparations; and dipeptidyl peptidase IV inhibitors.

Another embodiment of the present invention is a pharmaceutical comprising any of the above 1-thio-D-glucitol compounds, pharmaceutically acceptable salts thereof, or hydrates of them, in combination with at least one pharmaceutical selected from the group consisting of hydroxymethylglutaryl-CoA reductase inhibitors, fibrate compounds, squalene synthase inhibitors, acyl-CoA:cholesterol acyltransferase inhibitors, low density lipoprotein receptor accelerators, microsome triglyceride transfer protein inhibitors, and anorectics.

The following are embodiments of the method for producing the compound of the present invention:

An embodiment of the present invention relates to a method for producing a 1-thio-D-glucitol compound of the following formula I, or a pharmaceutically acceptable salt thereof, or a hydrate of the compound or the salt:

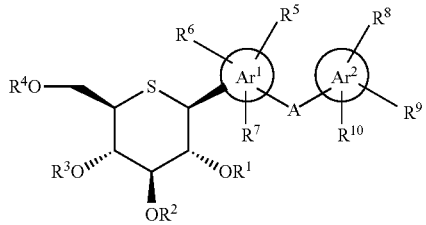

I the method comprising the steps of adding to a thiolactone of the following formula VIII more than 1 equivalent of a Grignard reagent of the following formula IX to obtain a compound V, reducing the compound V, and if desired, deprotecting the resulting compound, in accordance with the following scheme:

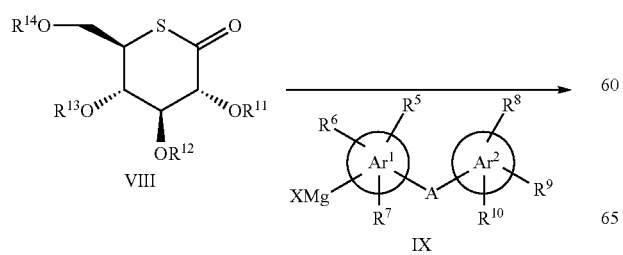

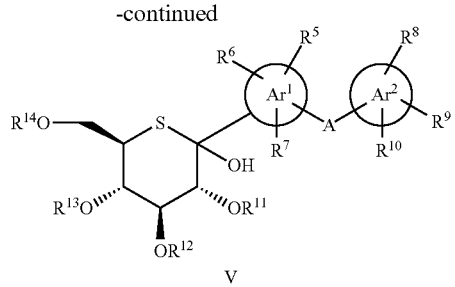

V

[where $R^{11}$, $R^{12}$, $R^{13}$ and $R^{14}$ are the same or different, and each represent a $C_{1-6}$ alkyl group, $—SiR^{a1}_3$, $—CH_2CH=CH_2$, or a $C_{7-12}$ aralkyl group optionally substituted by one or more substituents selected from the group consisting of a halogen atom, $—NO_2$ and $—OMe$ (where $R^{a1}$ represents a $C_{1-6}$ alkyl group), X represents a halogen atom, and $Ar^1$, $Ar^2$, $R^5$, $R^6$, $R^7$, $R^8$, $R^9$ and $R^{10}$ are as defined in the formula I.

Another embodiment of the present invention relates to the above-mentioned method, wherein before the step of adding the Grignard reagent of the formula IX to the thiolactone of the formula VIII to obtain a compound V, about 0.8 to 1.2 equivalents of $R^{30}MgX$ ($R^{30}$ represents a $C_{1-8}$ alkyl group or a $C_{3-7}$ cycloalkyl group, and X represents a halogen atom) is added to the thiolactone of the formula VIII.

Another embodiment of the present invention relates to a method for producing a 1-thio-D-glucitol compound of the following formula I, or a pharmaceutically acceptable salt thereof, or a hydrate of the compound or the salt:

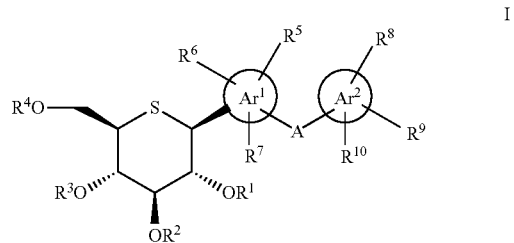

I the method comprising the step (1) of adding to a compound of the formula X a reagent of the formula XI to obtain a compound XII, and the step (2) of further reducing the compound XII, if Y is a hydroxyl group, to obtain a compound, in which Y is hydrogen, in a β type-stereoselective manner, and the step of deprotecting the compound obtained in (1) or (2), if desired, in accordance with the following scheme:

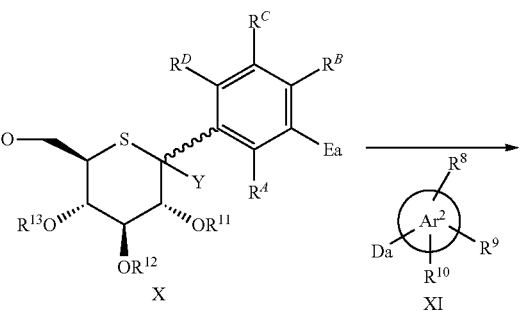

-continued

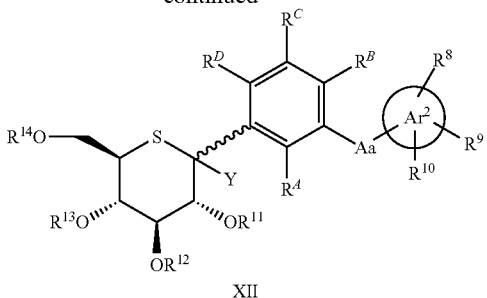

XII where Y represents a hydrogen atom or a hydroxyl group (provided that if Y is a hydrogen atom, the 1-position is of S-configuration), $R^{11}$, $R^{12}$, $R^{13}$ and $R^{14}$ are the same or different, and each represent a $C_{1-6}$ alkyl group, —SiR$^{a1}_3$, —CH$_2$CH═CH$_2$, or a $C_{7-12}$ aralkyl group optionally substituted by one or more substituents selected from the group consisting of a halogen atom, —NO$_2$ and —OMe (where $R^{a1}$ represents a $C_{1-6}$ alkyl group), $Ar^2$, $R^8$, $R^9$ and $R^{10}$ have the same meanings as in the formula I, and $R^A$, $R^B$, $R^C$ and $R^D$ have the same meanings as in the formula II, Aa represents —CH(W)(CH$_2$)n'-, —CONH(CH$_2$)n-, or —CH═CH— (where W represents a hydrogen atom or a hydroxyl group, n denotes an integer of 0 to 3, and n' denotes an integer of 0 to 2), Ea represents —CHO, —CO$_2$H, or —CH$_2$X, and Da represents —(CH$_2$)n'Li, —(CH$_2$)n'MgX, —CH$_2$PPh$_3^+$X$^-$, —CH$_2$PO(OR$^{a23}$), —(CH$_2$)nNH$_2$, or —SnBu$_4$ (where X represents a halogen atom, R$^{a23}$ represents a $C_{1-6}$ alkyl group, n denotes an integer of 0 to 3, and n' denotes an integer of 0 to 2), provided that if Ea is —CHO, the compound X reacts with the reagent XI in which Da is —(CH$_2$)n'Li, —(CH$_2$)n'MgX, —CH$_2$PPh$_3^+$X$^-$, or —CH$_2$PO(OR$^{a23}$) to obtain the compound XII in which Aa is —CH(W)(CH$_2$)n'-, or —CH═CH—, if Ea is —CO$_2$H, the compound X is condensed with the reagent XI in which Da is —(CH$_2$)nNH$_2$ to obtain the compound XII in which Aa is —CONH(CH$_2$)n-, or if Ea is —CH$_2$X, the compound X is condensed with the reagent XI in which Da is —SnBu$_4$ to obtain the compound XII in which Aa is —CH$_2$.

The following are embodiments of an intermediate in the method for producing the compound of the present invention:

An embodiment of the present invention relates to a compound of the following formula XIII, or a salt thereof, or a hydrate of the compound or the salt:

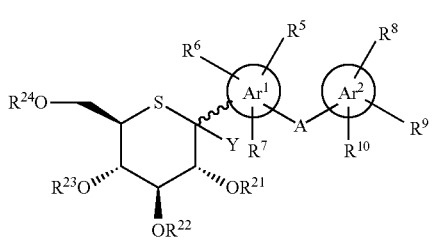

XIII

[where Y represents a hydrogen atom or a hydroxyl group (provided that if Y is a hydrogen atom, the 1-position is of S-configuration), and $R^{21}$, $R^{22}$, $R^{23}$ and $R^{24}$ are the same or different, and each represent a hydrogen atom, a $C_{1-6}$ alkyl group, —SiR$^{a1}_3$, —CH$_2$CH═CH$_2$, —CO$_2$R$^{a2}$, —COR$^{b1}$, or a $C_{7-12}$ aralkyl group optionally substituted by one or more substituents selected from the group consisting of a halogen atom, —NO$_2$ and —OMe (where $R^{a1}$ and $R^{a2}$ each represent a $C_{1-6}$ alkyl group, and $R^{b1}$ represents a $C_{1-6}$ alkyl group, a $C_{7-10}$ aralkyl group, or a phenyl group), provided that if Y is a hydrogen atom, $R^{21}$, $R^{22}$, $R^{23}$ and $R^{24}$ are not hydrogen atoms at the same time; and the other symbols are as defined in the aforementioned formula I].

The compound of the formula XIII, where Y is a hydrogen atom, and $R^{21}$ to $R^{24}$ are the substituents other than —SiR$^{a1}_3$ or —CH$_2$CH═CH$_2$, overlaps the aforementioned compound of the present invention. This is because the former compound not only functions as the intermediate, but also functions as the final product which is an active compound or its prodrug.

Another embodiment of the present invention relates to a compound of the following formula XIV, or a salt thereof, or a hydrate of the compound or the salt:

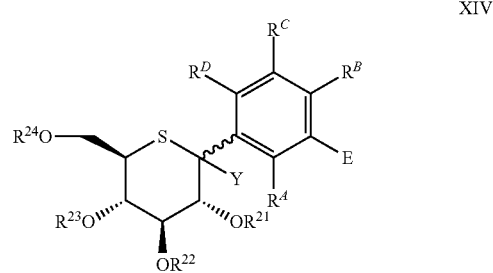

XIV

[where Y represents a hydrogen atom or a hydroxyl group (provided that if Y is a hydrogen atom, the 1-position is of S-configuration), E represents —CHO, —CO$_2$H, —CO$_2$R$^{a24}$ (where R$^{a24}$ represents a $C_{1-6}$ alkyl group), —CH$_2$M$^a$ (where M$^a$ represents a hydroxyl group or a halogen atom), a 1,3-dioxolan-2-yl group, or a 1,3-dioxan-2-yl group, $R^{21}$, $R^{22}$, $R^{23}$ and $R^{24}$ have the same meanings as in the formula XIII, and $R^A$, $R^B$, $R^C$ and $R^D$ have the same meanings as in the formula II].

Another embodiment of the present invention relates to a compound of the following formula XV, or a salt thereof:

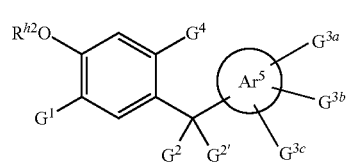

XV

[where Ar$^5$ represents a thienyl group, a benzo[b]thiophenyl group, a benzofuranyl group, a benzothiazolyl group, a pyridyl group, or a phenyl group, $G^1$ represents a halogen atom, $G^2$ represents a hydrogen atom or a hydroxyl group, and $G^{2'}$ represents a hydrogen atom or represents an oxo group together with $G^2$, $G^{3a}$ represents a hydrogen atom; a halogen atom; a hydroxyl group; a $C_{1-8}$ alkyl group optionally substituted by one or more substituents selected from the group consisting of a halogen atom and a hydroxyl group; —SR$^{a25}$; —SOR$^{a25}$; —SO$_2$R$^{a25}$; —OR$^{b1}$ (where R$^{a25}$ represents a C$_{1-6}$ alkyl group, and R$^{h1}$ represents a C$_{1-6}$ alkyl group or a C$_{7-10}$ aralkyl group optionally substituted by a halogen atom(s)); an aryl group optionally substituted by one or more substituents selected from the group consisting of a halogen atom, a hydroxyl group, a C$_{1-6}$ alkyl group, and —OR$^{a19}$ (where R$^{a19}$ represents a C$_{1-6}$ alkyl group); or a heteroaryl group optionally substituted by one or more substituents selected from the group consisting of a halogen atom, a hydroxyl group, a C$_{1-6}$ alkyl group, and —OR$^{a21}$ (where R$^{a21}$ represents a C$_{1-6}$ alkyl group), G$^{3b}$ and G$^{3c}$ are the same or different, and each represent a hydrogen atom, a halogen atom, a hydroxyl group, a C$_{1-8}$ alkyl group, or —OR$^{c3}$ (where R$^{c3}$ represents a C$_{1-6}$ alkyl group optionally substituted by a halogen atom(s)), G$^4$ represents a C$_{1-6}$ alkyl group optionally substituted by a halogen atom(s), or a halogen atom, and R$^{h2}$ represents a C$_{1-6}$ alkyl group or a C$_{7-10}$ aralkyl group wherein each substituents are optionally substituted by a halogen atom(s).

EMBODIMENTS OF THE INVENTION

The present invention will now be described in detail, but is not limited to what has been exemplified.

The definitions and exemplifications of the terms used in the present invention are intended to illustrate the specification and the scope of the claims, and they are offered without limitation.

The term "aryl group" refers to a monocyclic or condensed polycyclic aromatic hydrocarbon group having 6 to 15 carbon atoms, and may be exemplified by a phenyl group, a naphthyl group (including a 1-naphthyl group and a 2-naphthyl group), a pentalenyl group, an indenyl group, an indanyl group, an azulenyl group, a heptalenyl group, and a fluorenyl group. A phenyl group, a naphthyl group, an indenyl group, an indanyl group, and an azulenyl group are preferred, and a naphthyl group and a phenyl group are more preferred.

The term "heteroaryl group" refers to a monocyclic or condensed-ring aromatic heterocyclic group containing one or more hetero-atoms selected from O, S and N. If the aromatic heterocyclic group has a condensed ring, it includes a partially hydrogenated monocyclic group. Examples of such a heteroaryl group include a pyrazolyl group, a thiazolyl group, an isothiazolyl group, a thiadiazolyl group, an imidazolyl group, a furyl group, a thienyl group, an oxazolyl group, an isoxazolyl group, a pyrrolyl group, an imidazolyl group, a (1,2,3)- and (1,2,4)-triazolyl group, a tetrazolyl group, a pyranyl group, a pyridyl group, a pyrimidinyl group, a pyrazinyl group, a pyridazinyl group, a quinolyl group, an isoquinolyl group, a benzofuranyl group, an isobenzofuranyl group, an indolyl group, an isoindolyl group, an indazolyl group, a benzoimidazolyl group, a benzotriazolyl group, a benzoxazolyl group, a benzothiazolyl group, a benzo[b]thiophenyl group, a thieno[2,3-b]thiophenyl group, a (1,2)- and (1,3)-benzoxathiol group, a chromenyl group, a 2-oxochromenyl group, a benzothiadiazolyl group, a quinolizinyl group, a phthalazinyl group, a naphthyridinyl group, a quinoxalinyl group, a quinazolinyl group, a cinnolinyl group, and a carbazolyl group.

The term "heterocycloalkyl group" refers to a heterocycloalkyl group having 3 to 12 atoms and containing one or more hetero-atoms selected from O, S and N. This group also refers, for example, to a cyclic amino group having one or more nitrogen atoms in the ring, and optionally containing one or more oxygen atoms and sulfur atoms. Examples of the heterocycloalkyl group include a morpholino group, a piperidinyl group, a piperazinyl group, a 1-pyrrolidinyl group, an azepinyl group, a thiomorpholino group, an oxolanyl group, an oxanyl group, a dioxolanyl group, and a dioxanyl group.

The term "arylene group" refers to a divalent aromatic cyclic group bonded to a 5-thiosugar residue on one hand, and bonded to -A- on the other hand. Examples of the arylene group include a phenylene group, a naphthylene group (including a 1-naphthylene group and a 2-naphthylene group), a pentalenylene group, an indenylene group, an indanylene group, an azulenylene group, a heptalenylene group, and a fluorenylene group. A phenylene group, a naphthylene group, an indenylene group, an indanylene group, and an azulenylene group are preferred, and a naphthylene group and a phenylene group are more preferred.

The term "heteroarylene group" refers to a divalent aromatic heterocyclic group bonded to a 5-thiosugar residue on one hand, and bonded to -A- on the other hand. Examples of such a heteroarylene group include a pyrazolylene group, a thiazolylene group, an isothiazolylene group, a thiadiazolylene group, an imidazolylene group, a furylene group, a thienylene group, an oxazolylene group, an isoxazolylene group, a pyrrolylene group, an imidazolylene group, a (1,2,3)- and (1,2,4)-triazolylene group, a tetrazolylene group, a pyranylene group, a pyridylene group, a pyrimidinylene group, a pyrazinylene group, a pyridazinylene group, a quinolylene group, an isoquinolylene group, a benzofuranylene group, an isobenzofuranylene group, an indolylene group, an isoindolylene group, an indazolylene group, a benzoimidazolylene group, a benzotriazolylene group, a benzoxazolylene group, a benzothiazolylene group, a benzo[b]thiophenylene group, a chromenylene group, a 2-oxochromenylene group, a benzothiadiazolylene group, a quinolizinylene group, a phthalazinylene group, a naphthyridinylene group, a quinoxalinylene group, a quinazolinylene group, a cinnolinylene group, and a carbazolylene group.

The term "heterocycloalkylene group" refers to a divalent heterocycloalkyl ring group bonded to a 5-thiosugar residue on one hand, and bonded to -A- on the other hand. Examples of such a heterocycloalkylene group include a morpholinylene group, a piperidinylene group, a piperazinylene group, a pyrrolidinylene group, an azepinylene group, a thiomorpholinylene group, an oxolanylene group, an oxanilene group, a dioxolanylene group, and a dioxanilene group.

In the compound of the present invention, depending on the type of Ar$^1$, not all of the three substituents R$^5$, R$^6$ and R$^7$ can be bound onto this group.

The term "C$_{1-6}$ alkyl group" refers to a straight chain or branched chain alkyl group having 1 to 6 carbon atoms, and may be exemplified by a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, and an n-hexyl group.

The term "C$_{2-6}$ alkenyl group" refers to a straight chain or branched chain aliphatic hydrocarbon group having a double bond and having 2 to 6 carbon atoms, and may be exemplified by an ethenyl group, a propenyl group, and a butenyl group.

The term "C$_{2-6}$ alkynyl group" refers to a straight chain or branched chain aliphatic hydrocarbon group having a triple bond and having 2 to 6 carbon atoms and may be exemplified by an ethynyl group, a propynyl group, and a butynyl group.

As the "halogen atom", a fluorine atom, a chlorine atom, a bromine atom, or an iodine atom is named.

The term "$C_{7-10}$ aralkyl group" refers to an arylalkyl group having 7 to 10 carbon atoms, and may be exemplified by a benzyl group, and a phenylethyl group.

The term "$C_{7-12}$ aralkyl group optionally substituted" in the definitions of $R^1$ to $R^4$, $R^{11}$ to $R^{14}$ and $R^{21}$ to $R^{24}$ refers to a substituted or unsubstituted aralkyl group having 7 to 12 carbon atoms. The substituents for the $C_{7-12}$ aralkyl group are one or more substituents selected from the group consisting of a halogen atom, —$NO_2$, and —OMe. The preferred substituent is a chlorine atom, —$NO_2$, and —OMe. Examples of the substituted $C_{7-12}$ aralkyl group include a 4-methoxybenzyl group, a 3,4-dimethoxybenzyl group, a 4-chlorobenzyl group, and a 4-nitrobenzyl group.

The term "$C_{1-8}$ alkyl group optionally substituted" refers to a substituted or unsubstituted alkyl group having 1 to 8 carbon atoms. The substituents for the $C_{1-8}$ alkyl group are one or more substituents selected from the group consisting of a halogen atom and a hydroxyl group. The preferred number of the substituting halogen atoms is 1 to 6, more preferably 1 to 4. The preferred halogen atoms are a chlorine atom and a fluorine atom, and more preferably a fluorine atom. The preferred number of the substituting hydroxyl groups is 1 to 6, more preferably 1 to 3. Examples of the substituted $C_{1-8}$ alkyl group include a trifluoromethyl group, a difluoromethyl group, a 1,1,1-trifluoroethyl group, a 1,1,1-trifluoropropyl group, a 1,1,1-trifluorobutyl group, a 1,3-difluoroprop-2-yl group, a hydroxymethyl group, a hydroxyethyl group (such as a 1-hydroxyethyl group), a hydroxypropyl group, and a hydroxybutyl group. Preferred are a trifluoromethyl group, a difluoromethyl group, a 1,1,1-trifluoroethyl group, a 1,3-difluoroprop-2-yl group, a hydroxymethyl group, and a hydroxyethyl group. More preferred are a trifluoromethyl group, a difluoromethyl group, a 1,1,1-trifluoroethyl group, a hydroxymethyl group, and a hydroxyethyl group.

The term "$C_{3-7}$ cycloalkyl group" refers to a cyclic alkyl group having 3 to 7 carbon atoms, and may be exemplified by a cyclopropyl group, a cyclobutyl group, a cyclopentyl group, a cyclohexyl group, and a cycloheptyl group. A cyclopropyl group, a cyclobutyl group, a cyclopentyl group, and a cyclohexyl group are preferred, and a cyclopropyl group, and a cyclobutyl group are more preferred.

The term "$C_{1-6}$ alkyl group optionally substituted by a halogen atom(s)" refers to a substituted or unsubstituted alkyl group having 1 to 6 carbon atoms. The number of the substituting halogen atoms is 1 or more. The preferred number of the substituting halogen atoms is 1 to 6, more preferably 1 to 4. The preferred halogen atoms are a chlorine atom and a fluorine atom, and more preferably a fluorine atom. Examples of the substituted $C_{1-6}$ alkyl group include a trifluoromethyl group, a difluoromethyl group, and a 1,1,1-trifluoroethyl group.

The term "$C_{3-7}$ cycloalkyl group optionally substituted" refers to a substituted or unsubstituted cycloalkyl group having 3 to 7 carbon atoms. The substituents for the cycloalkyl group refer to one or more substituents selected from the group consisting of a halogen atom, a hydroxyl group, a $C_{1-6}$ alkyl group, and —$OR^{a13}$ (or —$OR^{a18}$) ($R^{a13}$ and $R^{a18}$ each represent a $C_{1-6}$ alkyl group).

The term "aryl group optionally substituted" refers to a substituted or unsubstituted aryl group. The substituents for the aryl group refer to one or more substituents selected from the group consisting of a halogen atom, a hydroxyl group, a $C_{1-6}$ alkyl group, and —$OR^{a14}$ (or —$OR^{a19}$) ($R^{a14}$ and $R^{a19}$ each represent a $C_{1-6}$ alkyl group). The preferred substituents are a halogen atom, a hydroxyl group, a $C_{1-4}$ alkyl group, a methoxy group, and an ethoxy group. Examples of the substituted aryl group include a 4-chlorophenyl group, a 4-fluorophenyl group, a 4-hydroxyphenyl group, and a 4-methoxyphenyl group.

The term "$C_{7-10}$ aralkyl group optionally substituted" refers to a substituted or unsubstituted aralkyl group having 7 to 10 carbon atoms. The substituents for the aralkyl group refer to one or more substituents selected from the group consisting of a halogen atom, a hydroxyl group, a $C_{1-6}$ alkyl group, and —$OR^{a15}$ (or —$OR^{a17}$ or —$OR^{a20}$) ($R^{a15}$, $R^{a17}$ and $R^{a20}$ each represent a $C_{1-6}$ alkyl group). The preferred substituents are a halogen atom, a hydroxyl group, a $C_{1-4}$ alkyl group, a methoxy group, and an ethoxy group. Examples of the substituted $C_{7-10}$ aralkyl group include a 4-methoxybenzyl group, a 3,4-dimethoxybenzyl group, a 4-chlorobenzyl group, and a 4-chlorophenylethyl group.

The term "heteroaryl group optionally substituted" refers to a substituted or unsubstituted heteroaryl group. The substituents for the heteroaryl group refer to one or more substituents selected from the group consisting of a halogen atom, a hydroxyl group, a $C_{1-6}$ alkyl group, and —$OR^{a21}$ ($R^{a21}$ represents a $C_{1-6}$ alkyl group). The preferred substituents are a halogen atom, a $C_{1-4}$ alkyl group, a methoxy group, and an ethoxy group. A methyl group and an ethyl group are more preferred. Examples of the substituted heteroaryl group include a 4-methylthiazol-2-yl group, a 2-methylpyridin-5-yl group, a 1-methylpyrazol-4-yl group, a 1-ethylpyrazol-4-yl group, a 1-methylpyrrolyl group, a 2-methylimidazolyl group, and a 4-methoxyindolyl group.

The term "heterocycloalkyl group optionally substituted" refers to a substituted or unsubstituted heterocycloalkyl group. The substituents for the heterocycloalkyl group refer to one or more substituents selected from the group consisting of a halogen atom, a hydroxyl group, a $C_{1-6}$ alkyl group, and —$OR^{a16}$ (or —$OR^{a22}$) ($R^{a16}$ and $R^{a22}$ each represent a $C_{1-6}$ alkyl group). The preferred substituents are a halogen atom and a $C_{1-4}$ alkyl group, of which a methyl group and an ethyl group are more preferred. Examples of the substituted heterocycloalkyl group include a 4-methylpiperazin-1-yl group, and a 4-ethylpiperazin-1-yl group.

The term "pharmaceutically acceptable salt" refers to a salt with an alkali metal, an alkaline earth metal, ammonium, or alkylammonium, a salt with a mineral acid, or a salt with an organic acid. Examples include a sodium salt, a potassium salt, a calcium salt, an ammonium salt, an aluminum salt, a triethylammonium salt, an acetate, a propionate, a butyrate, a formate, a trifluoroacetate, a maleate, a tartrate, a citrate, a stearate, a succinate, an ethylsuccinate, a lactobionate, a gluconate, a glucoheptonate, a benzoate, a methanesulfonate, an ethanesulfonate, a 2-hydroxyethanesulfonate, a benzenesulfonate, a paratoluenesulfonate, a lauryl sulfate, a malate, an aspartate, a glutamate, an adipate, a salt with cysteine, a salt with N-acetylcysteine, a hydrochloride, a hydrobromide, a phosphate, a sulfate, a hydriodide, a nicotinate, an oxalate, a picrate, a thiocyanate, an undecanoate, a salt with an acrylic polymer, and a salt with carboxyvinylpolymer.

The term "salt" refers to a salt with an alkali metal, an alkaline earth metal, ammonium, or alkylammonium, a salt with a mineral acid, or a salt with an organic acid, but includes a salt other than the pharmaceutically acceptable salt.

Since some of the compounds and intermediates of the present invention may have a chiral center, they are present as various diastereomers or enantiomers. Some of the compounds and intermediates of the present invention are also present, for example, as keto-enol tautomers. Moreover, some of the compounds and intermediates of the present invention are present as geometric isomers (E-form, Z-form). Thus, the compounds and intermediates of the present invention include all of the above-mentioned individual isomers and mixtures of them.

As will be shown in the Test Examples offered below, the compounds of the present invention show the activity of inhibiting the activity of sodium-dependent glucose cotransporter (SGLT2) related to glucose reabsorption in the kidney, and can provide pharmaceuticals excellent in the effect of preventing or treating diabetes, diabetes-related diseases or diabetic complications.

Furthermore, the compounds of the present invention, as will be described concretely below, are excellent in that they have high crystallinity, their purification, storage and pharmaceutical manufacturing are easy, and they are easy to handle as drugs. Of the compounds of the present invention, the compounds of the formulas I, IA, II, III and IV, in which $R^1$ to $R^4$ are hydrogen, exhibit very high crystallinity.

Among conventional glucitol compounds were many amorphous substances, which needed to be crystallized together with suitable amino acids, such as phenylalanine and proline, during pharmaceutical manufacturing (U.S. Pat. No. 6,774,112). However, the compounds of the present invention having glucitol converted into 1-thio-glucitol are highly crystalline, and thus need not be co-crystallized with amino acids.

For example, glucitol compounds Xa described in U.S. Pat. No. 6,515,117 are described as glassy, and they have low crystallinity. On the other hand, the compounds Xb of the present invention being 1-thio-glucitol are colorless powdery crystals having a melting point of 79.0 to 83.0° C.

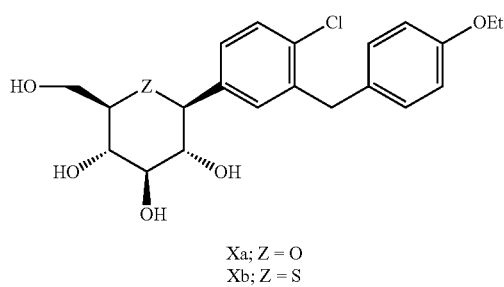

Xa; Z = O
Xb; Z = S

The preferred embodiments of the compounds of the present invention will be enumerated below.

In the formulas I and IA, preferred examples of A are —(CH$_2$)n- (where n denotes an integer of 0 to 3, preferably n=1 or 2), —CONH(CH$_2$)n- (where n denotes an integer of 0 to 3, preferably n=0) or —(CH$_2$)nCH=CH— (where n denotes an integer of 0 to 3, preferably n=0 or 1), and —O—.

The more preferred example of A is —CH$_2$—.

In the formulas I and IA, the preferred binding position of A-Ar$^2$ is at the meta-position with respect to the thiosugar.

The preferred embodiments of the compounds of the formula II according to the present invention will be mentioned below.

In the formula (II), $R^A$ and $R^C$ are preferably hydrogen atoms.

The preferred substituent as $R^B$ is a hydrogen atom, a halogen atom, a hydroxyl group, a C$_{1-8}$ alkyl group, or —O—(CH$_2$)m'-Q' (where m' denotes an integer of 1 to 4, preferably m'=1, and Q' represents a hydroxyl group, —CO$_2$H, —OR$^{c2}$, —CO$_2$R$^{a8}$, —CONH$_2$, —CONHR$^{a9}$, —CONR$^{a10}$R$^{a10}$, —NH$_2$, —NHR$^{a11}$, —NR$^{a12}$R$^{a12}$, or —NHCO$_2$R$^{a5}$ (where R$^{a8}$, R$^{a9}$, R$^{a10}$, R$^{a11}$, and R$^{a12}$ each represent a C$_{1-6}$ alkyl group, R$^{c2}$ represents a C$_{1-6}$ alkyl group optionally substituted by a halogen atom(s), and R$^{a5}$ represents a C$_{1-6}$ alkyl group, a C$_{7-10}$ aralkyl group, a phenyl group, or a C$_{3-7}$ cycloalkyl group)}, or —OR$^{f1}$ {where R$^{f1}$ represents a C$_{1-6}$ alkyl group optionally substituted by a halogen atom(s); or a C$_{7-10}$ aralkyl group optionally substituted by one or more substituents selected from the group consisting of a halogen atom, a hydroxyl group, a C$_{1-6}$ alkyl group, and —OR$^{a15}$ (where R$^{a15}$ represents a C$_{1-6}$ alkyl group)}.

Preferably, $R^B$ is a hydrogen atom, a C$_{1-6}$ alkyl group, a halogen atom, a C$_{1-6}$ alkoxy group, or —O—CH$_2$-Q' [where Q' represents —CO$_2$H or —CO$_2$R$^{a8}$ (R$^{a8}$ is as defined above)], and particularly preferably, a methyl group, a chlorine atom, or a methoxy group.

The preferred substituent as $R^D$ is a hydrogen atom, a halogen atom, a hydroxyl group, a C$_{1-8}$ alkyl group, or —OR$^{f2}$ {where R$^{f2}$ represents a C$_{1-6}$ alkyl group optionally substituted by a halogen atom(s); or a C$_{7-10}$ aralkyl group optionally substituted by one or more substituents selected from the group consisting of a halogen atom, a hydroxyl group, a C$_{1-6}$ alkyl group, and —OR$^{a15}$ (where R$^{a15}$ represents a C$_{1-6}$ alkyl group)}.

Preferably, $R^D$ is a hydrogen atom, a hydroxyl group, or a C$_{1-6}$ alkoxy group, and particularly preferably, a hydroxyl group or a methoxy group.

The preferred substituent as $R^E$ and $R^F$ are the same or different, and each represent a hydrogen atom, a halogen atom, a C$_{1-8}$ alkyl group, or —OR$^{c3}$ (where R$^{c3}$ represents a C$_{1-6}$ alkyl group optionally substituted by a halogen atom(s)).

Preferably, $R^E$ and $R^F$ are hydrogen atoms or fluorine atoms.

The preferred substituent as $R^G$ is a hydrogen atom, a halogen atom, a hydroxyl group, or a C$_{1-8}$ alkyl group optionally substituted by one or more substituents selected from the group consisting of a halogen atom and a hydroxyl group.

Preferred of them is a halogen atom, a hydroxyl group, or a C$_{1-8}$ alkyl group optionally substituted by one or more substituents selected from the group consisting of a halogen atom and a hydroxyl group. Particularly preferred is a methyl group, an ethyl group, an isopropyl group, or a hydroxymethyl group.

Other preferred substituents as $R^G$ are —CO$_2$H, —OR$^{c1}$, —CO$_2$R$^{a3}$, —CONH$_2$, —CONHR$^{a4}$, —CONR$^{a5}$R$^{a5}$, —COR$^{d1}$, —OCOR$^{d2}$, —SR$^{e1}$, —SOR$^{e2}$, —SO$_2$R$^{e3}$, —NHR$^{a6}$, or —NR$^{a7}$R$^{a7}$ (where R$^{a3}$, R$^{a4}$, R$^{a5}$, R$^{a6}$, and R$^{a7}$ each represent a C$_{1-6}$ alkyl group, R$^{c1}$ represents a C$_{1-6}$ alkyl group optionally substituted by a halogen atom(s), R$^{d1}$ and R$^{d2}$ each represent a C$_{1-6}$ alkyl group, a C$_{7-10}$ aralkyl group, a phenyl group, or a C$_{3-7}$ cycloalkyl group, and R$^{e1}$, R$^{e2}$ and R$^{e3}$ each represent a C$_{1-6}$ alkyl group, a phenyl group, or a tolyl group).

Preferred of them are —CO$_2$H, —OR$^{c1}$, —CO$_2$R$^{a3}$, —SR$^{e1}$ and —NR$^{a7}$R$^{a7}$ (where R$^{c1}$, R$^{a3}$, R$^{e1}$ and R$^{a7}$ are as defined above). Particularly preferred are a methoxy group, an ethoxy group, an isopropyloxy group, a methylthio group, and —CO$_2$Me.

Other preferred substituent as $R^G$ is —O—(CH$_2$)m'-Q' {where m' denotes an integer of 1 to 4, preferably m'=1 or 2, and Q' represents a hydroxyl group, —CO$_2$H, —OR$^{c2}$, —CO$_2$R$^{a8}$, —CONH$_2$, —CONHR$^{a9}$, —CONR$^{a10}$R$^{a10}$, —NH$_2$, —NHR$^{a11}$ or —NR$^{a12}$R$^{a12}$ (where R$^{a8}$, R$^{a9}$, R$^{a10}$, R$^{a11}$, and R$^{a12}$ each represent a C$_{1-6}$ alkyl group, and R$^{c2}$ represents a C$_{1-6}$ alkyl group optionally substituted by a halogen atom(s))}.

Preferred of them are —O—CH$_2$CO$_2$Me, —O—CH$_2$CO$_2$H, —O—CH$_2$CONMe$_2$, —O—CH$_2$CH$_2$OH—, and —O—CH$_2$CH$_2$NMe$_2$.

Other preferred substituent as $R^G$ is —$OR^{f2}$ {where $R^{f2}$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); or
a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}, or
a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group).

Preferred of them are a —O—$C_{3-7}$ cycloalkyl group, a —O-heterocycloalkyl group, and a heterocycloalkyl group. Particularly preferred are a tetrahydropyranyloxy group, a cyclopentyloxy group, and a morpholino group.

Preferred embodiments of the compound of the formula III according to the present invention will be mentioned below.

In the formula (III), $Ar^3$ preferably represents a thienyl group, a benzo[b]thiophenyl group, a thieno[2,3-b]thiophenyl group, a benzofuranyl group, a benzothiazolyl group, an indolyl group, a pyrrolyl group, an imidazolyl group, a pyrazolyl group, a pyridyl group, a pyrimidinyl group, a pyrazinyl group, or an isoxazolyl group.

$R^{8a}$, $R^{9a}$ and $R^{10a}$, which are the substituents on the $Ar^3$ group, are the same or different, and each preferably represent a hydrogen atom, a halogen atom, a hydroxyl group, a $C_{1-8}$ alkyl group, or a $C_{1-6}$ alkoxy group.

If $Ar^3$ is a thienyl group, it is preferred that at least one of $R^{8a}$, $R^{9a}$ and $R^{10a}$ be an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), or a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), and the other be each a hydrogen atom, a halogen atom, a $C_{1-8}$ alkyl group, or a $C_{1-6}$ alkoxy group.

Preferred embodiments of the compound of the formula IV according to the present invention will be mentioned below.

In the formula (IV), $Ar^4$ preferably represents a thienylene group, a benzo[b]thiophenylene group, or a pyridylene group. It is preferred that $R^{20a}$, $R^{21a}$, $R^J$ and $R^K$, which are the substituents on the $Ar^4$ group, be each a hydrogen atom, a halogen atom, a hydroxyl group, a $C_{1-8}$ alkyl group, or a $C_{1-6}$ alkoxy group. $R^L$ is preferably the same as any of those named as the preferred substituents as $R^G$.

The preferred concrete compounds of the present invention are listed below.
(1S)-1,5-Anhydro-1-[3-(4-ethylbenzyl)phenyl]-1-thio-D-glucitol
(1S)-1,5-Anhydro-1-[3-(4-ethoxybenzyl)phenyl]-1-thio-D-glucitol
(1S)-1,5-Anhydro-1-[3-[(1-benzothien-2-yl)methyl]-4-methoxyphenyl]-1-thio-D-glucitol
(1S)-1,5-Anhydro-1-[4-chloro-3-(4-ethoxybenzyl)phenyl]-1-thio-D-glucitol
(1S)-1,5-Anhydro-1-[3-(4-ethoxybenzyl)-4-methoxyphenyl]-1-thio-D-glucitol
(1S)-1,5-Anhydro-1-[3-[(1-benzothien-2-yl)methyl]-4-chlorophenyl]-1-thio-D-glucitol
(1S)-1,5-Anhydro-1-[3-[(1-benzothien-2-yl)methyl]-phenyl]-1-thio-D-glucitol
(1S)-1,5-Anhydro-1-[3-(4-ethoxybenzyl)-6-methoxy-phenyl]-1-thio-D-glucitol
(1S)-1,5-Anhydro-1-[3-[(1-benzothien-2-yl)methyl]-6-methoxyphenyl]-1-thio-D-glucitol
(1S)-1,5-Anhydro-1-[3-(4-ethoxybenzyl)-6-hydroxyphenyl]-1-thio-D-glucitol
(1S)-1,5-Anhydro-1-[4,6-dimethoxy-3-(4-ethoxybenzyl)phenyl]-1-thio-D-glucitol
(1S)-1,5-Anhydro-1-[3-(4-ethoxybenzyl)-4-fluorophenyl]-1-thio-D-glucitol
(1S)-1,5-Anhydro-1-[3-(4-ethoxybenzyl)-4-hydroxyphenyl]-1-thio-D-glucitol
(1S)-1,5-Anhydro-1-[4-chloro-3-(2,5-difluoro-4-ethoxybenzyl)phenyl]-1-thio-D-glucitol
(1S)-1,5-Anhydro-1-[4-chloro-3-(3-fluoro-4-ethoxybenzyl)phenyl]-1-thio-D-glucitol
(1S)-1,5-Anhydro-1-[4-chloro-3-(3-chloro-4-ethoxybenzyl)phenyl]-1-thio-D-glucitol
(1S)-1,5-Anhydro-1-[3-(4-ethoxybenzyl)-4-methylphenyl]-1-thio-D-glucitol
(1S)-1,5-Anhydro-1-[4-chloro-3-(3,4-dimethoxybenzyl)phenyl]-1-thio-D-glucitol
(1S)-1,5-Anhydro-1-[4-chloro-3-(4-methoxybenzyl)phenyl]-1-thio-D-glucitol
(1S)-1,5-Anhydro-1-[3-(4-ethoxybenzyl)-6-methoy-4-methylphenyl]-1-thio-D-glucitol
(1S)-1,5-Anhydro-1-[3-(4-t-butylbenzyl)-4-chlorophenyl]-1-thio-D-glucitol
(1S)-1,5-Anhydro-1-[4-chloro-3-(2-fluoro-4-ethoxybenzyl)phenyl]-1-thio-D-glucitol
(1S)-1,5-Anhydro-1-[3-[(1-benzothien-2-yl)methyl]-4,6-dimethoxyphenyl]-1-thio-D-glucitol
(1S)-1,5-Anhydro-1-[4-chloro-3-(4-methylbenzyl)phenyl]-1-thio-D-glucitol
(1S)-1,5-Anhydro-1-[4-chloro-3-(4-methylthiobenzyl)phenyl]-1-thio-D-glucitol
(1S)-1,5-Anhydro-1-[4-chloro-3-(4-hydroxybenzyl)phenyl]-1-thio-D-glucitol
(1S)-1,5-Anhydro-1-[4-chloro-3-(4-ethylbenzyl)phenyl]-1-thio-D-glucitol
(1S)-1,5-Anhydro-1-[4-chloro-3-(4-isopropylbenzyl)phenyl]-1-thio-D-glucitol
(1S)-1,5-Anhydro-1-[4-chloro-3-(4-ethoxy-methylbenzyl)phenyl]-1-thio-D-glucitol
(1S)-1,5-Anhydro-1-[3-(4-ethoxybenzyl)-6-hydroxy-4-methylphenyl]-1-thio-D-glucitol
(1S)-1,5-Anhydro-1-[3-[(1-benzofuran-2-yl)methyl]-4-chlorophenyl]-1-thio-D-glucitol
(1S)-1,5-Anhydro-1-[4-chloro-3-(4-ethoxybenzyl)-6-methoxyphenyl]-1-thio-D-glucitol
(1S)-1,5-Anhydro-1-[3-(4-ethoxybenzyl)-4,6-dihydroxyphenyl]-1-thio-D-glucitol
(1S)-1,5-Anhydro-1-[3-(4-ethylbenzyl)-6-methoxy-4-methylphenyl]-1-thio-D-glucitol
(1S)-1,5-Anhydro-1-[4-chloro-3-(4-ethylbenzyl)-6-methoxyphenyl]-1-thio-D-glucitol
(1S)-1,5-Anhydro-1-[4-chloro-3-(4-isopropylbenzyl)-6-methoxyphenyl]-1-thio-D-glucitol
(1S)-1,5-Anhydro-1-[3-(4-methylbenzyl)-6-methoxy-4-methylphenyl]-1-thio-D-glucitol (1S)-1,5-Anhydro-1-[3-(4-isopropylbenzyl)-6-methoxy-4-methylphenyl]-1-thio-D-glucitol The intermediates of the formula XV according to the present invention is characterized by having the substituent —$OR^{h2}$. Possession of this substituent produces the advantage that the yield and selectivity for synthesis of this intermediate are better than the compound lacking this substituent.

Concretely, in the method for producing the intermediate of the formula XV (for example, Scheme 8 indicated below), the yield in Friedel-Crafts reaction is high. If the desired product is the compound of the formula XV where $Ar^5$ is a phenyl group at the para-position with respect to the linker, only the para-substituted products are formed and few position isomers (ortho-substituted products) are formed by using this method.

Furthermore, of the intermediates of the formula XV according to the present invention, the compound in which $G^{2'}$ represents an oxo group together with $G^2$ (corresponding to the compound IIo of Scheme 8) and the compound in which $G^{2'}$ and $G^2$ are hydrogen atoms (corresponding to the compound IIA of Scheme 8) have good crystallinity in many cases, and can be easily recrystallized as colorless powders.

The preferred embodiments of the intermediate of the formula XV according to the present invention will be mentioned below.

If $Ar^5$ is a phenyl group, $G^{3a}$ preferably represents a hydroxyl group; a $C_{1-8}$ alkyl group optionally substituted by one or more substituents selected from the group consisting of a halogen atom and a hydroxyl group; —$SR^{a25}$; —$SOR^{a25}$; —$SO_2R^{a25}$; or —$OR^{h1}$ (where $R^{a25}$ represents a $C_{1-6}$ alkyl group, and $R^{h1}$ represents a $C_{1-6}$ alkyl group or a $C_{7-10}$ aralkyl group optionally substituted by a halogen atom(s)), and more preferably represents a $C_{1-8}$ alkyl group optionally substituted by a halogen atom(s), —SMe, —SOMe, —$SO_2$Me, or a $C_{1-6}$ alkoxy group optionally substituted by a halogen atom or a benzyloxy group optionally substituted by a halogen atom. The position of substitution by $G^{3a}$ is preferably the para-position with respect to the linker. The other symbols are as defined in the formula XV, but more preferably, $G^{3b}$ and $G^{3c}$ are the same or different, and each represent a hydrogen atom or a fluorine atom.

If $Ar^5$ is a benzo[b]thiophenyl group, a benzofuranyl group, a benzothiazolyl group, or a pyridyl group, $G^{3a}$, $G^{3b}$ and $G^{3c}$ preferably each represent a hydrogen atom, a halogen atom, a hydroxyl group, a $C_{1-8}$ alkyl group, or a $C_{1-6}$ alkoxy group.

If $Ar^5$ is a thienyl group, it is preferred that $G^{3a}$ be an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group); or a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), and $G^{3b}$ and $G^{3c}$ are the same or different, and each represent a hydrogen atom, a halogen atom, a $C_{1-8}$ alkyl group, or a $C_{1-6}$ alkoxy group.

$Ar^5$ is preferably a phenyl group.

Various methods for producing the compounds of the present invention will be described in detail below, but are not limited to those illustrated. So far, there has been a report that D-glucitol derivatives can be synthesized via C-aryl glucopyranoside which can be formed by adding one equivalent of aryl lithium or an aryl Grignard reagent to gluconolactone derivatives (patent document 12). However, 1-thio-glucitol of the present invention was not successfully produced by methods performed under the same conditions as mentioned above. The inventors have found, as a result of eager studies, that 1-thio-glucitol is produced by methods employing the conditions described below.

(Method 1 for Producing the Compound of the Present Invention)

The compound of the formula V is obtained from the compound of the formula IIA (aglycon) and the compound of the formula VIII (thiolactone) by the methods shown in Schemes 1 to 3. Then, the compound of the formula V is reduced and, if necessary, further deprotected, as shown in Scheme 4, whereby the compound of the formula I can be produced. The method of synthesizing the compound of the formula IIA (aglycon) is shown in Schemes 5 to 8, and the method of synthesizing the compound of the formula VIII (thiolactone) is shown in Scheme 9.

Scheme 1: Carbon-Carbon Linkage Forming Reaction 1 Between Aglycon and 5-thiosugar

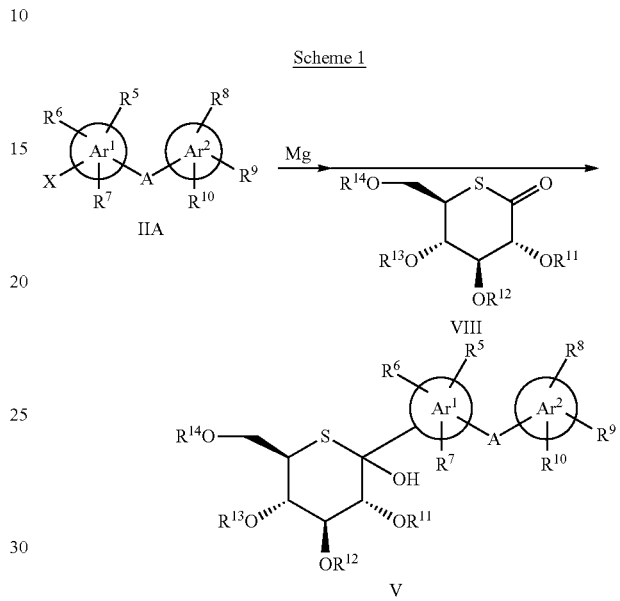

where X represents a halogen atom, especially bromine, iodine or chlorine, $Ar^1$ represents an aryl, heteroaryl or heterocycloalkyl group, and the other symbols have the same meanings as given above.

As shown in Scheme 1, the compound V can be obtained by adding a thiolactone (compound VIII) to a Grignard reagent prepared from an aryl halide, a heteroaryl halide, or a heterocycloalkyl halide (compound IIA) and magnesium. The amount of the Grignard reagent added to the thiolactone is about 2 or more equivalents, more preferably about 2 equivalents to about 2.2 equivalents in order to obtain about 1 equivalent of the desired compound V. The reaction temperature on this occasion is preferably −20° C. to 25° C. As a solvent for preparing the Grignard reagent, diethyl ether, tetrahydrofuran or diglyme is named. As an additive, a catalytic amount of iodine or 1,2-dibromoethane may be used. The reaction temperature on this occasion is 25° C. to 150° C., preferably 40° C. to 100° C.

An aryl lithium, a heteroaryl lithium or a heterocycloalkyl lithium, which has been synthesized by reacting the compound IIA and a lithium reagent selected from n-butyl lithium, tert-butyl lithium, and mesityl lithium (2,4,6-trimethylphenyl lithium) at −78° C. to −20° C., does not react with the compound VIII. However, magnesium bromide ($MgBr_2$) is added to the aryl lithium, the heteroaryl lithium or the heterocycloalkyl lithium to prepare a Grignard reagent, which can be reacted with the compound VIII. As a solvent used in this reaction, diethyl ether, tetrahydrofuran or the like is named, and the reaction temperature is preferably −20° C. to 25° C.

Scheme 2: Carbon-Carbon Linkage Forming Reaction 2 Between Aglycon and 5-thiosugar Scheme 2

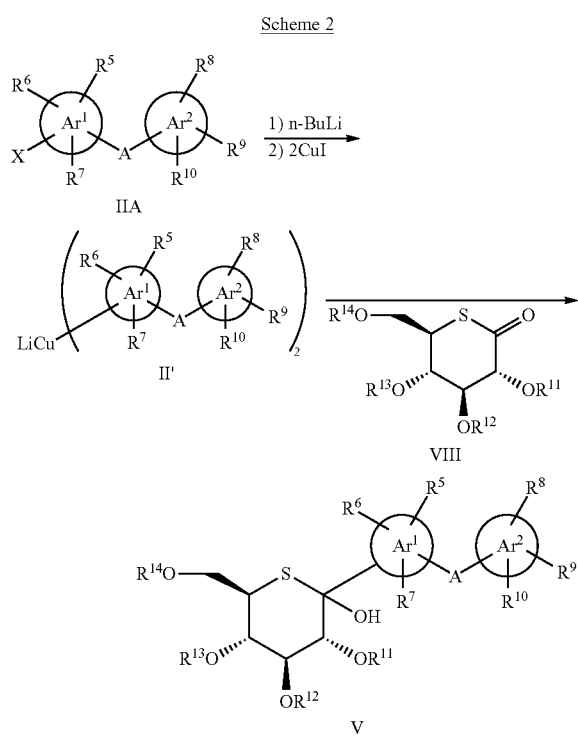

where $Ar^1$ represents an aryl, heteroaryl or heterocycloalkyl group, and the other symbols have the same meanings as given above.

As shown in Scheme 2, compound V can also be synthesized by adding a metal halide, for example, copper (I) iodide or cesium chloride, to an aryl lithium, a heteroaryl lithium or a heterocycloalkyl lithium, which can be prepared in the same manner as mentioned above, to form a complex (compound II') by transmetalation, and reacting this complex with the compound VIII. The reaction temperature during the preparation of such a lithium reagent is preferably −78° C. to −20° C. As a solvent used in this reaction, diethyl ether, tetrahydrofuran or the like is named. Then, the resulting lithium reagent is added dropwise to a suspension of copper iodide or cesium chloride and diethyl ether, whereby the complex II' can be prepared. The reaction temperature is −78° C. to 0° C., preferably −25° C. to 0° C. Then, the thiolactone VIII is added under the same conditions as in Scheme 1, or the complex II' is added to the thiolactone VIII, whereby the compound V can be obtained.

Scheme 3 Carbon-Carbon Linkage Forming Reaction 3 Between Aglycon and 5-thiosugar Scheme 3

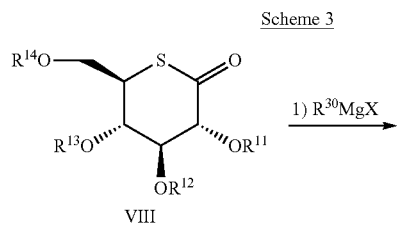

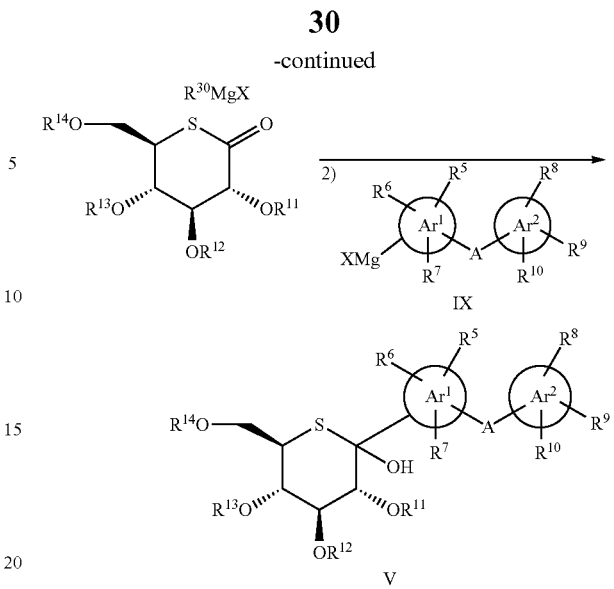

where $Ar^1$ represents an aryl, heteroaryl or heterocycloalkyl group, $R^{30}$ represents a $C_{1-8}$ alkyl group or a $C_{3-7}$ cycloalkyl group, and the other symbols have the same meanings as given above.

The method shown in Scheme 3 can decrease the number of the equivalents of the compound IIA, which is necessary for the reaction, with respect to the thiolactone VIII. Taking advantage of the fact that the thiolactone VIII does not react with 1 equivalent of a Grignard reagent, about 0.8 to about 1.2 equivalents, preferably about 0.9 to about 1.0 equivalent, of $R^{30}MgX$ is added to the thiolactone VIII. As the $C_{1-8}$ alkylmagnesium halide on this occasion, isopropylmagnesium chloride, isopropylmagnesium bromide, or t-butylmagnesium chloride is suitable. As the $C_{3-7}$ cycloalkylmagnesium halide, cyclohexylmagnesium chloride, for example, is named. As a solvent used, diethyl ether, tetrahydrofuran or the like is suitable. The reaction temperature is preferably −20° C. to 25° C. Then, a Grignard reaction IX prepared from the compound IIA is added, whereupon the thiolactone selectively reacts with IX without reacting with the $R^{30}MgX$ initially added, with the result that the desired compound V can be obtained. The amount of the Grignard reagent IX can be adjusted depending on the required amount of the desired compound V. About 1 equivalent of the Grignard reagent IX is sufficient to obtain about 1 equivalent of the desired compound. The preferred solvent on this occasion is diethyl ether or tetrahydrofuran, and the reaction temperature is preferably −20° C. to 25° C.

In accordance with the above-described method, the number of the equivalents of the expensive compound IIA can be reduced, and it has become possible to synthesize 1-thioglucitol efficiently.

Scheme 4 Reduction Reaction and Deprotection Reaction

Scheme 4

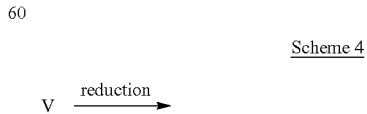

-continued

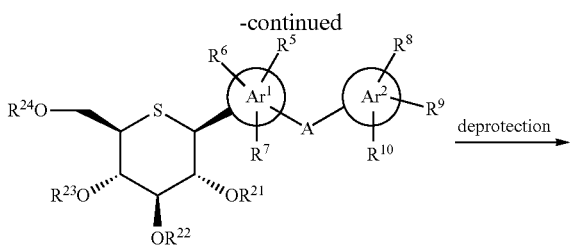

XIII

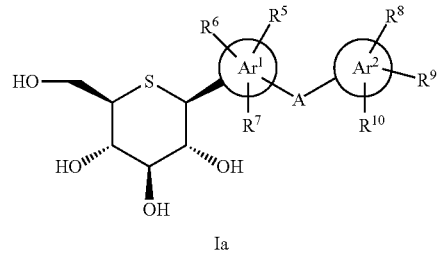

Ia where the symbols have the same meanings as given above.

Then, as shown in Scheme 4, the compound V is reduced to be capable of synthesizing the compound XIII of the present invention in a β type-stereoselective manner. As a reducing agent suitable for this reaction, $Et_3SiH$, $i-Pr_3SiH$ or $Ph_2SiHCl$ is used, and $BF_3.Et_2O$, $CF_3COOH$, or $InCl_3$ is named as a Lewis acid. As a solvent, there is named chloroform, dichloromethane, acetonitrile, ethyl acetate, diethyl ether, 1,4-dioxane, tetrahydrofuran, or a solvent mixture of these solvents. In this reduction reaction, a compounds are formed as by-products at a rate of several percent to 15%. By combining reagents or reaction solvents, however, the proportion of the by-products can be decreased. A preferred reagent as the reducing agent is $Et_3SiH$ or $i-Pr_3SiH$, more preferably $Et_3SiH$. A reagent preferred as the Lewis acid is $BF_3.Et_2O$ or $CF_3COOH$, more preferably $BF_3.Et_2O$. The reaction temperature is $-60°$ C. to $25°$ C., preferably $-40°$ C. to $0°$ C. Among others, the selection of the solvent is important, and the suitable solvent is preferably acetonitrile, or a mixture with acetonitrile, such as acetonitrile-chloroform or acetonitrile-dichloromethane.

$R^{21}$ to $R^{24}$ are removed from $—OR^{21}$ to $—OR^{24}$ of the compound XIII of the present invention by appropriate methods, whereby the substituents are converted into hydroxyl groups to be able to obtain the compound Ia of the present invention.

If $R^{21}$, $R^{22}$, $R^{23}$ and $R^{24}$ are benzyl groups or 4-methoxybenzyl groups, for example, $R^{21}$ to $R^{24}$ can be removed by catalytic hydrogenation in a hydrogen atmosphere with the use of a catalyst such as palladium activated carbon, palladium hydroxide, or platinum-palladium activated carbon. As a solvent used in this reaction, there can be named methanol, ethanol, isopropanol, ethyl acetate, and acetic acid. Alternatively, $R^{21}$ to $R^{24}$ can be removed by using a Lewis acid such as $BCl_3$, $BCl_3.Me_2S$, $BBr_3$, $AlCl_3$, $CF_3COOH$, or TfOH. Examples of a solvent used in this reaction are chloroform, dichloromethane, acetonitrile, diethyl ether, tetrahydrofuran, and anisole. Advisably, the reaction temperature is $-78°$ C. to $40°$ C.

If $R^{21}$, $R^{22}$, $R^{23}$ and $R^{24}$ are allyl groups ($—CH_2CH=CH_2$), t-BuOK is caused to act on them in dimethyl sulfoxide to isomerize them ($—CH=CHCH_3$), whereafter the isomerized groups can be removed with the use of hydrochloric acid or $HgCl_2/HgO$. Alternatively, $R^{21}$ to $R^{24}$ can be removed by using, for example, $Pd(PPh_3)_4$, $PdCl_2$, or palladium activated carbon in the presence of an organic acid such as acetic acid, p-toluenesulfonic acid hydrate, or N,N'-dimethylbarbituric acid. As a solvent used in this reaction, acetonitrile, diethyl ether, or tetrahydrofuran is named. Advisably, the reaction temperature is $25°$ C. to $100°$ C.

Scheme 5: Method 1 of Synthesizing the Aglycon Portion

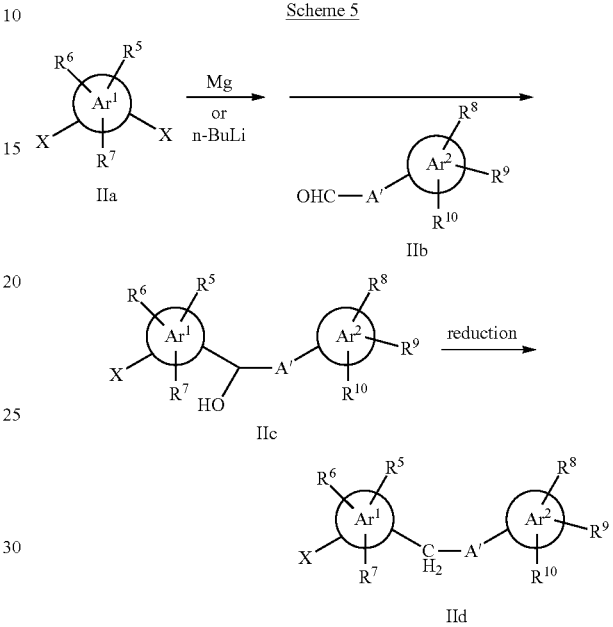

where A' represents $—(CH_2)n'-$ (n' denotes an integer of 0 to 2), $—CH=CH—$, or $—C≡C—$, $Ar^1$ represents an aryl, heteroaryl or heterocycloalkyl group, and the other symbols have the same meanings as given above.

If A is $—(CH_2)n-$ (n denotes an integer of 1 to 3) in the compound IIA as the intermediate, this compound can be synthesized with reference to International Patent Publication WO0127128. Alternatively, the intermediate IId can be produced in accordance with Scheme 5.

A compound IIa is formed into a Grignard reagent with the use of 1 equivalent of magnesium by the method described above. Alternatively, the compound IIa is formed into a monoaryl lithium with the use of 1 equivalent of n-butyl lithium or tert-butyl lithium. Then, a commercially available compound IIb is added to the Grignard reagent or the monoaryl lithium, whereby a compound IIc can be synthesized. As a solvent used in this reaction, diethyl ether or tetrahydrofuran is named. Preferably, the reaction temperature is $-78°$ C. to $25°$ C.

Then, the compound IIc is reduced, namely, reacted with $Et_3SiH$, $i-Pr_3SiH$ or $Ph_2SiHCl$, for example, in the presence of a Lewis acid, whereby a compound IId can be synthesized. As the Lewis acid used in this reaction, $BF_3.Et_2O$, $CF_3COOH$, or $InCl_3$ is named. As a solvent, there is named chloroform, dichloromethane, acetonitrile, or a solvent mixture of these solvents. Preferably, the solvent mixture with acetonitrile, such as acetonitrile-chloroform or acetonitrile-dichloromethane, is named. The reaction temperature here is $-60°$ C. to $25°$ C., preferably $-30°$ C. to $25°$ C.

Scheme 6: Method of Synthesizing the Aglycon Portion

Scheme 6

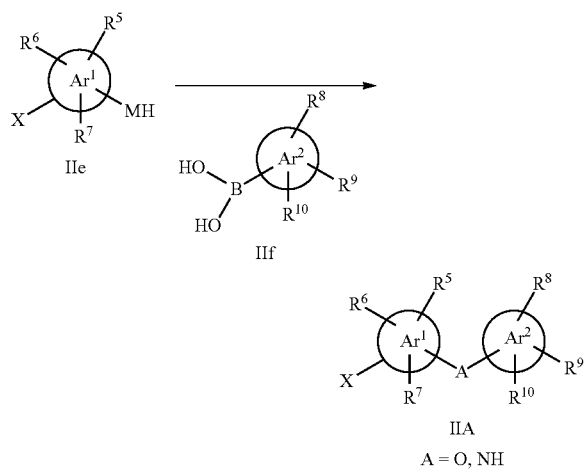

A = O, NH where M represents —O— or —NH—, Ar¹ represents an aryl, heteroaryl or heterocycloalkyl group, and the other symbols have the same meanings as given above.

A compound IIe is coupled to an arylboric acid, heteroarylboric acid or heterocycloalkylboric acid derivative IIf with the use of a palladium catalyst or a copper catalyst in the presence of a base, whereby a compound IIA where A is —O— or —NH— can be obtained. As the palladium catalyst, $Pd_2(OAc)_2$, $Pd(dba)_2$, palladium activated carbon, dba:dibenzylidene acetone, or $Pd(PPh_3)_4$, for example, is named. As the copper catalyst, $Cu(OAc)_2$ is preferred. Examples of the base used are t-BuOK, $Na_2CO_3$, $K_2CO_3$, KOH, pyridine, or triethylamine. As a solvent used in this reaction, there is named chloroform, dichloromethane, N,N-dimethylformamide, tetrahydrofuran, dioxane, or dimethoxyethane.

Scheme 7: Method 3 of Synthesizing the aglycon Portion

Scheme 7

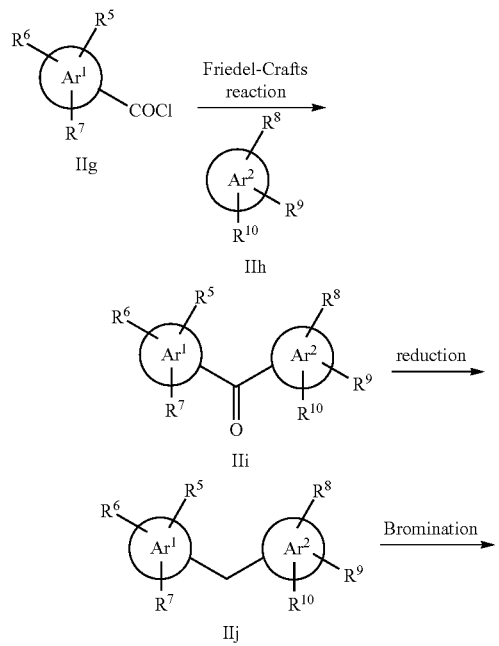

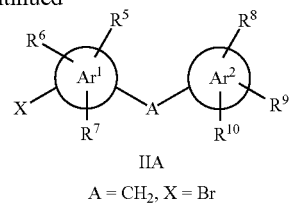

IIA

A = CH₂, X = Br where Ar¹ represents an aryl, heteroaryl or heterocycloalkyl group, and the other symbols have the same meanings as given above.

Friedel-Crafts reaction is carried out using compounds IIg and IIh, whereby a compound IIi can be obtained. As a Lewis acid used in this reaction, $AlCl_3$, $CF_3COOH$, or $EtAlCl_2$ is named. As a solvent, there is named chloroform, dichloromethane, or toluene. The reaction temperature used here is −30° C. to 60° C., preferably −15° C. to 25° C. Then, a compound IIj can be obtained by the same method as the reduction shown in Scheme 5. Further, the compound IIj is brominated position-selectively using bromine, sodium bromide, potassium bromide, hydrogen bromide, or N-bromosuccinimide (NBS), whereby a compound IIA can be produced. As a solvent used here, chloroform, dichloromethane, $CF_3COOH$, or acetic acid is preferred. Further, the mixture NBS—$CF_3COOH$—$H_2SO_4$ is more preferred.

Scheme 8: Method 4 of Synthesizing the Aglycon Portion

Scheme 8

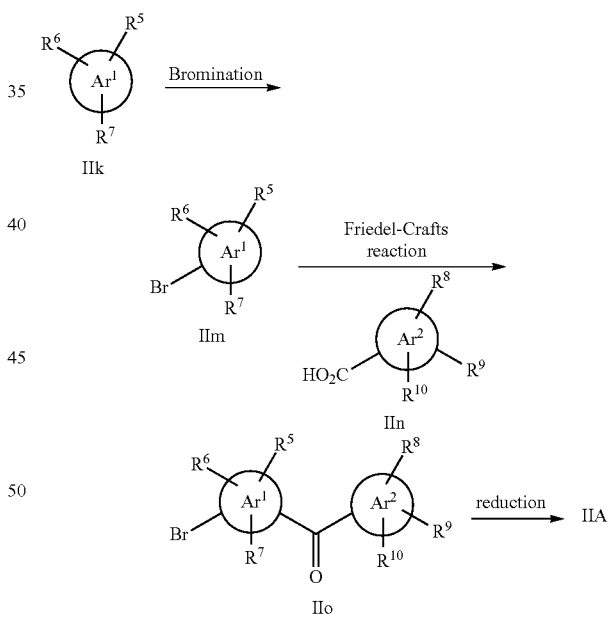

where Ar¹ represents an aryl or heteroaryl group, and the other symbols have the same meanings as given above.

If the substituents $R^5$ and $R^9$ of the raw material IIk or IIn are both alkoxy groups, for example, the reaction proceeding according to Scheme 7 may result in a decline in position selectivity for bromination, failing to obtain the desired product efficiently. In this case, as shown in Scheme 8, halogenation is performed in the first step, followed by Friedel-Crafts reaction and reduction. This manner is preferred, because the compound IIA can be produced in a higher yield. The reaction conditions for each reaction comply with Scheme 7.

Scheme 9: Synthesis of Thiolactone

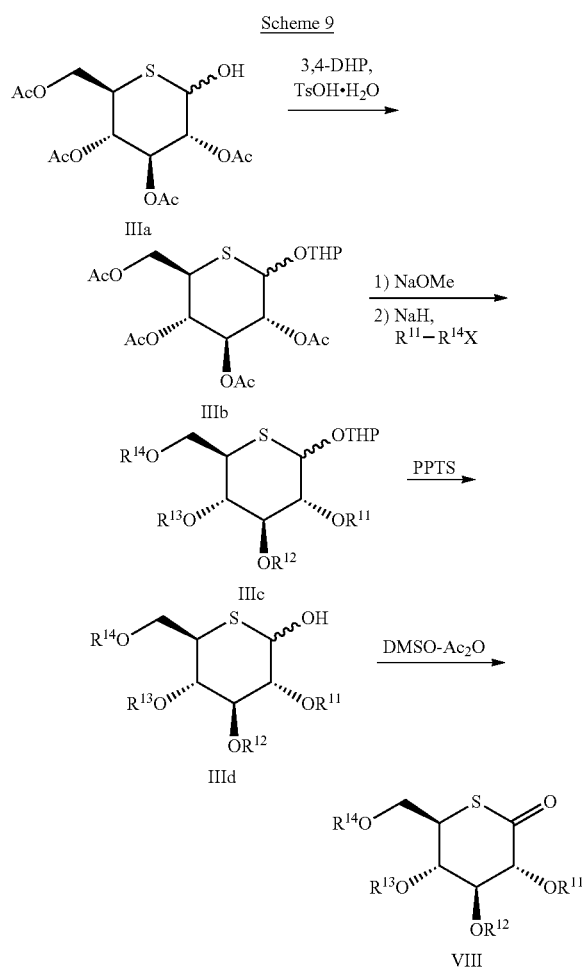

where the symbols have the same meanings as given above.

The compound VIII can be synthesized by reference to Yuasa, H., et al., J. Chem. Soc. Perkin Trans. 1, 2763, 1990. Alternatively, the compound VIII can be synthesized in accordance with Scheme 9 to be described below.

The hydroxyl group at the 1-position of a compound IIIa (can be produced with reference to International Publication WO04/106352 pamphlet) is protected with a protective group which is resistant to basic conditions and is capable of deprotection under neutral or acidic conditions. For example, this hydroxyl group is protected with a tetrahydropyranyl group with the use of 3,4-dihydro-2H-pyran (3,4-DHP), and p-toluenesulfonic acid monohydrate, or pyridinium-paratoluenesulfonate (PPTS), to synthesize a compound IIIb. As a solvent used in this reaction, N,N-dimethylformamide, tetrahydrofuran, dioxane, dimethoxyethane, chloroform, dichloromethane, or toluene is named.

Then, the acetyl groups of the compound IIIb are removed. Removal of the acetyl groups can be performed using a base such as sodium methoxide, sodium hydroxide, lithium hydroxide, potassium carbonate, cesium carbonate, or triethylamine. Methanol, ethanol, or hydrous methanol can be used as a solvent. Then, $R^{11}$—$R^{14}X$, for example, benzyl bromide, benzyl chloride, allyl bromide, or methyl iodide, is caused to act with the use of a suitable base, whereby a compound IIIc can be obtained. Examples of the base are triethylamine, N-ethyl-N,N-diisopropylamine, pyridine, potassium carbonate, calcium carbonate, cesium carbonate, sodium hydride, potassium hydride, sodium methoxide, and t-BuOK. The preferred bases are potassium carbonate, calcium carbonate, cesium carbonate, and sodium hydride. As a solvent used in this reaction, N,N-dimethylformamide, tetrahydrofuran, dioxane, or dimethoxyethane is named. The reaction temperature is −20° C. to 25° C.

Then, the protective group at the 1-position of the compound IIIc is removed to obtain a compound IIId. For example, the THP group can be removed by treating the compound IIIc with PPTS in methanol or ethanol. Finally, the compound IIId is treated with a suitable oxidizing agent, whereby a thiolactone VIII can be produced. The preferred oxidizing agent used in this reaction is dimethyl sulfoxide-acetic anhydride, Dess-Martin periodinane, or IBX, and the reaction temperature is 0° C. to 40° C.

(Method 2 for Producing the Compound of the Present Invention)

The compound I of the present invention, where A is —(CH$_2$)n- (n denotes an integer of 1 to 3), can also be synthesized by the method shown in Scheme 10. A different method for producing a synthetic intermediate VA of Scheme 10 is shown in Scheme 11.

Scheme 10: Method 2 for Producing the Compound of the Formula I

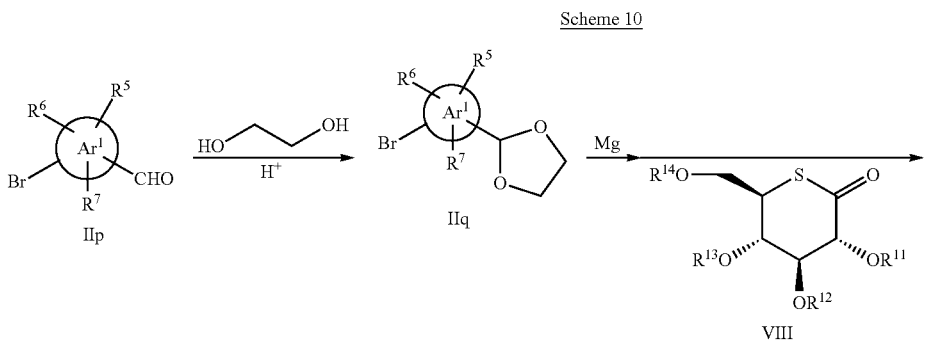

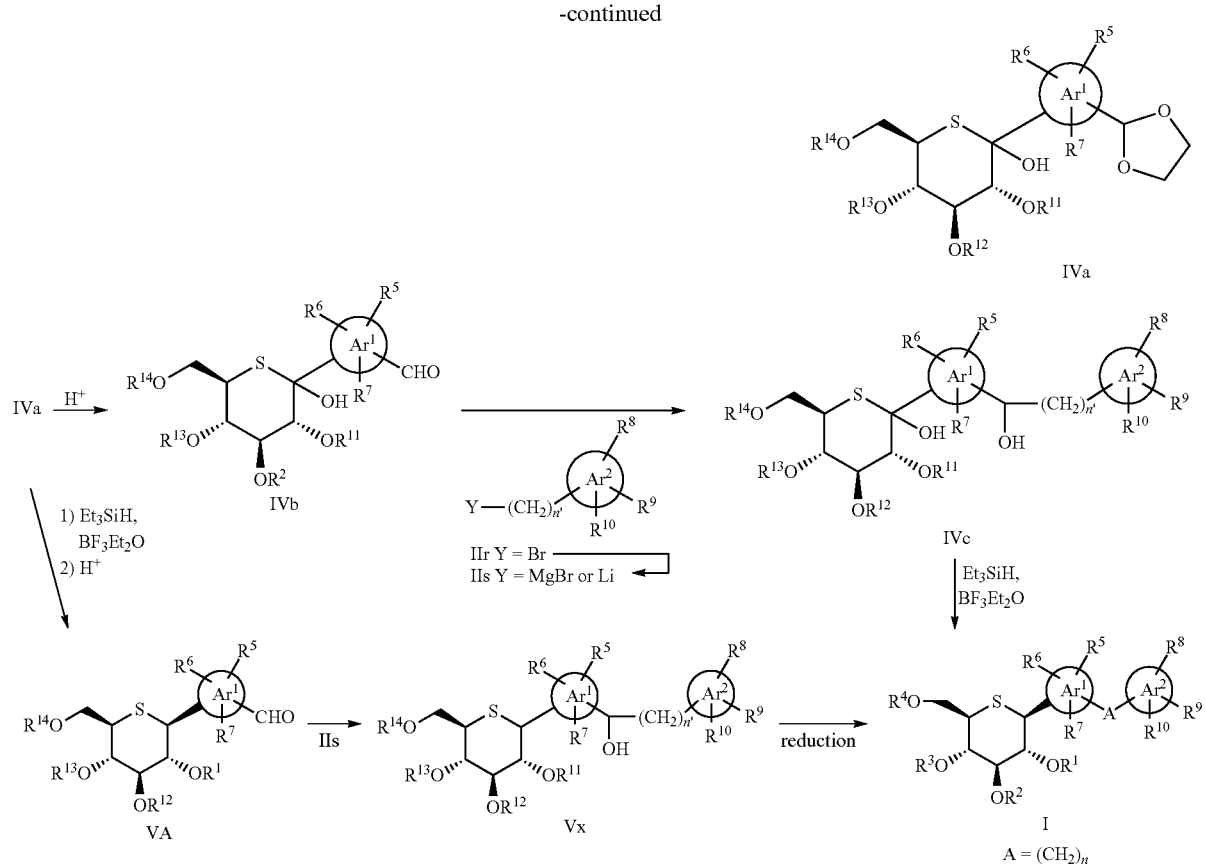

where Ar[1] represents an aryl or heteroaryl group, Y represents a bromine atom in a compound IIr, or MgBr or Li in a compound IIs, and the other symbols have the same meanings as given above.

A commercially available compound IIp is heated under reflux, together with ethylene glycol and p-toluenesulfonic acid monohydrate, in toluene or benzene to form a compound IIq. The reaction time at this time is 1 to 24 hours, and it is advisable to perform a dehydration operation using a Dean-Stark apparatus or the like during the heating. Then, in the same manner as described in the aforementioned Production Example 1, a Grignard reagent of the compound IIq is prepared, and then the thiolactone VIII is added, whereby a compound IVa can be obtained.

Next, an explanation will be offered for one route for producing the compound I of the present invention from the compound IVa. First, the ethyleneacetal group of the compound IVa is removed with an acid to be able to obtain a compound IVb. Hydrochloric acid, p-toluenesulfonic acid monohydrate, acetic acid, perchloric acid, or $Ph_3CBF_4$ is named as the acid used in this reaction. Methanol, ethanol, acetone, dichloromethane, water, or a mixture of them is named as a solvent. The reaction temperature is preferably 25° C. to 100° C.

Then, the compound IVb is added to a Grignard reagent or organolithium IIs, which can be prepared from a commercially available bromine derivative IIr by the same method as described in the aforementioned Production Example 1, Scheme 4, whereby a compound IVc can be synthesized. Diethyl ether, tetrahydrofuran, or dimethoxyethane is named as a solvent used in this reaction. The reaction temperature is −78° C. to 25° C.

Further, the hydroxyl groups in the compound IVc are reduced in the same manner as described in the aforementioned Production Example 1, Scheme 4, whereby the compound I of the present invention can be produced.

It is also possible to synthesize the compound I of the present invention from the compound IVa by a different route. First, the thiosugar hydroxyl group of the compound IVa is reduced, and then the ethyleneacetal group is removed, whereby the compound VA can be obtained. The reaction conditions for these reactions comply with the above-described methods. Then, the compound VA is added to the IIs compound, which is a Grignard reagent or organolithium, so that a compound Vx can be obtained. Further, the compound Vx is reacted with $Et_3SiH$, $i-Pr_3SiH$, or $Ph_2SiHCl$ in the presence of a Lewis acid to reduce the hydroxyl group, whereby the compound I can be synthesized. As the Lewis acid used in this reaction, $BF_3.Et_2O$, $CF_3COOH$, or $InCl_3$ is named. As a solvent, there is named chloroform, dichloromethane, acetonitrile, or a solvent mixture of these solvents. Preferably, a solvent mixture with acetonitrile, such as acetonitrile-chloroform or acetonitrile-dichloromethane, is named. The reaction temperature used here is −60° C. to 100° C., preferably −10° C. to 60° C.

Scheme 11: Method for Synthesizing Intermediate VA

Scheme 11

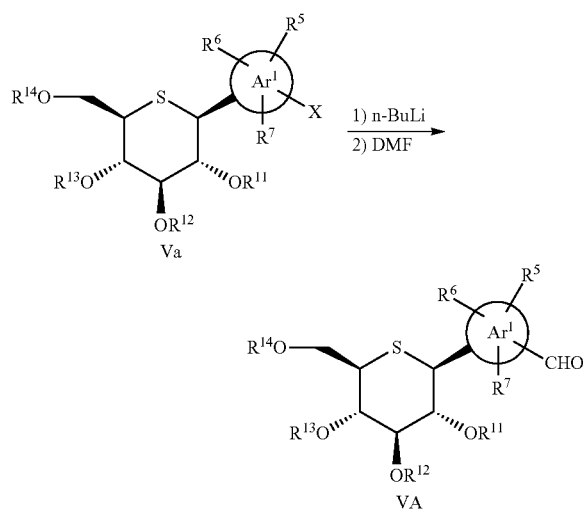

where Ar¹ represents an aryl or heteroaryl group, and the other symbols have the same meanings as given above.

Moreover, the intermediate VA can be synthesized by treating a compound Va with n-BuLi, and then adding N,N-dimethylformamide, as in Scheme 11. As a solvent used in this reaction, tetrahydrofuran or ether is named. The reaction temperature is preferably −78° C. to 25° C.

(Method 3 for Producing the Compound of the Present Invention)

The compound I of the present invention, where A is —$CH_2$—, and $R^8$ is a functional group such as —$COR^d$ or —$CO_2R^a$, in particular, can be synthesized by utilization of Stille coupling (Espinet, P., et al. Angew. Chem. Int. Ed. Engl. vol. 43, 4704, 2004; Stille, J. K., Angew. Chem. Int. Ed. Engl. vol. 25, 508, 1986) by way of a compound Vb shown in Scheme 12, or by way of an intermediate IVf shown in Scheme 13.

Scheme 12: Method 3 for Producing the Compound of the Formula I

Scheme 12

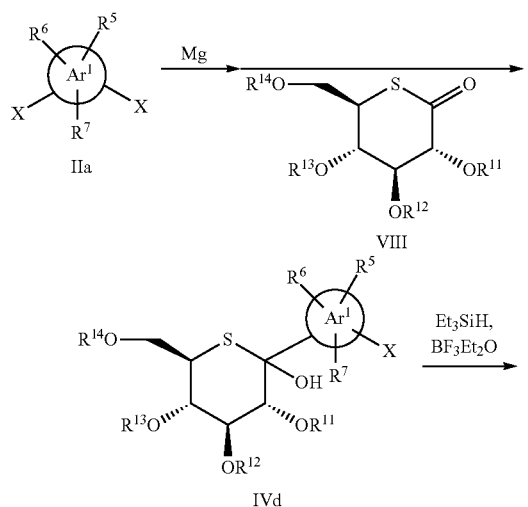

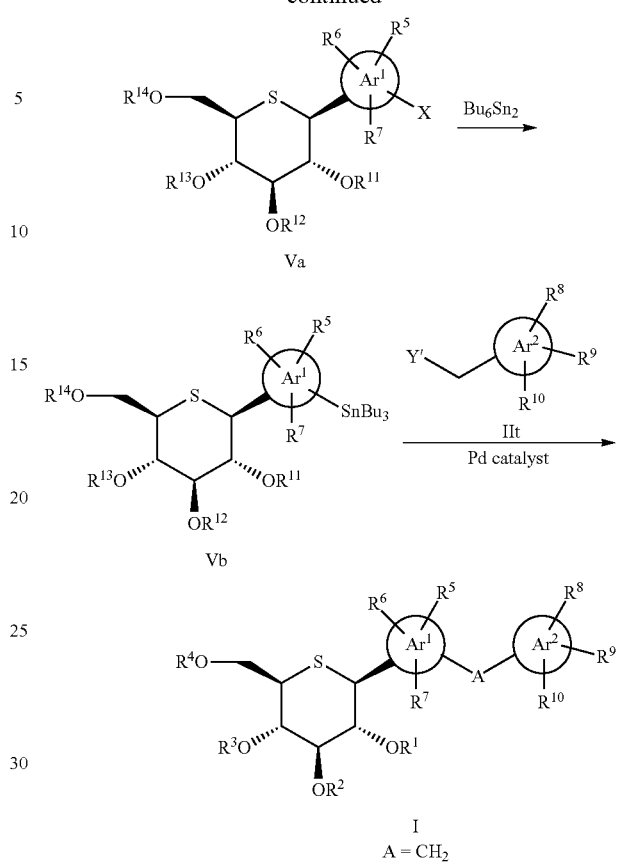

where Ar¹ represents an aryl or heteroaryl group, Y' represents a chlorine atom or a bromine atom, and the other symbols have the same meanings as given above.

A commercially available compound IIa is formed into a Grignard reagent by the method described in the aforementioned Production Method 1, Scheme 5, with the use of 1 equivalent of magnesium. Alternatively, the compound IIa is formed into an ate complex with the use of i-PrMgCl—LiCl (Kitagawa, K., et al. Angew. Chem. Int. Ed. Engl. vol. 39, 2481, 2000; Knochel, P., et al. Angew. Chem. Int. Ed. Engl. vol. 43, 3333, 2004). A compound VIII is added to the resulting reagent, whereby a compound IVd can be obtained. Then, the hydroxyl group of the compound IVd is reduced in the same manner as described in the Production Method 1, Scheme 4, whereby a compound Va can be produced. Then, the compound Va is treated with $Bu_6Sn_2$ and a palladium catalyst, so that a compound Vb can be synthesized. As the palladium catalyst used in this reaction, $Pd_2(OAc)_2$, $Pd(dba)_2$, or $Pd(PPh_3)_4$ is named. Toluene is preferred as a solvent, and the reaction temperature is 60° C. to 120° C.

Then, the compound Vb and a compound IIt are treated with a palladium catalyst, whereby the compound I of the present invention can be synthesized. As the palladium catalyst used in this reaction, $Pd_2(OAc)_2$, $Pd(dba)_2$, $Pd(PPh_3)_4$, or $PdCl_2(PPh_3)_2$ is named. As a solvent, toluene, tetrahydrofuran, or N,N-dimethylformamide is named, and the reaction temperature is 40° C. to 120° C.

Scheme 13

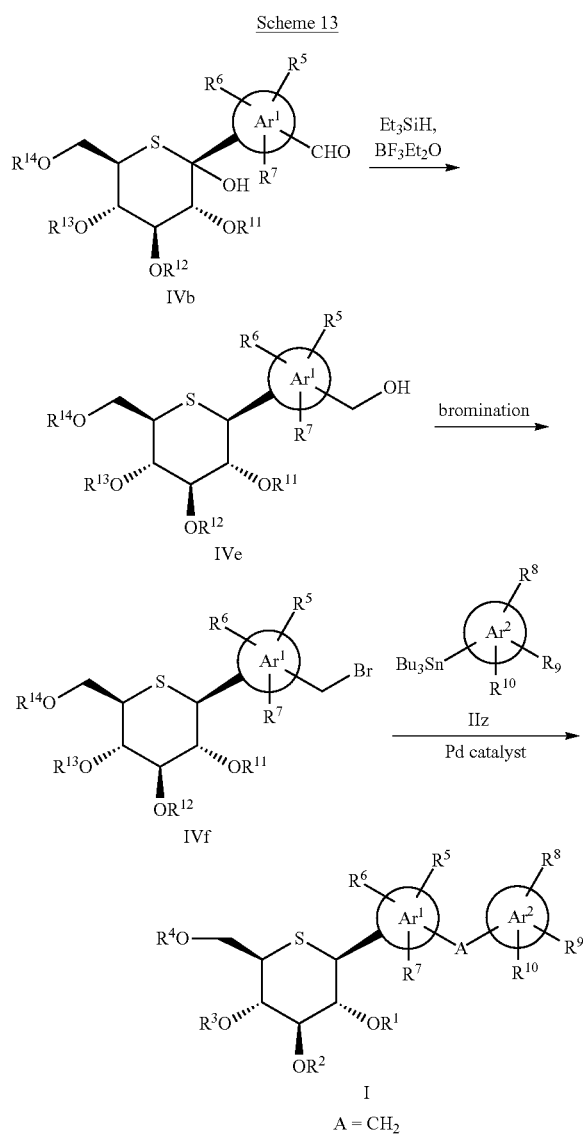

where $Ar^1$ represents an aryl or heteroaryl group, and the other symbols have the same meanings as given above.

The compound I of the present invention can also be produced by Stille coupling of an intermediate IVf and an organotin compound IIz shown in Scheme 13.

The intermediate IVf can be produced in the following manner:

First, the hydroxyl group of a compound IVb is reduced under the same conditions as in Scheme 4, whereby a compound IVe can be obtained. Then, the hydroxymethyl group of the compound IVe is brominated, whereby the intermediate IVf can be synthesized. As a method used in this bromination, a combination such as $PPh_3$-$CBr_4$ or $PPh_3$-N-bromosuccinimide can be used. Alternatively, the hydroxymethyl group of the compound IVe is sulfonated with methanesulfonyl chloride, p-toluenesulfonyl chloride, or trifluoromethanesulfonyl chloride in the presence of a base, and then brominated with the use of NaBr or LiBr. As a solvent used here, chloroform, dichloromethane, acetonitrile, diethyl ether, tetrahydrofuran, or dioxane is named. As the base, $Na_2CO_3$, $K_2CO_3$, KOH, pyridine, or triethylamine is preferred.

(Method 4 for Producing the Compound of the Present Invention)

The compound I of the present invention, where A is —$(CH_2)n''$- (n'' denotes an integer of 0 to 2), —O—, or —NH—, can be synthesized by utilization of Suzuki coupling (Bellina, F., et al. Synthesis, vol. 15, 2419, 2004, Miyaura, N., et al. Chem. Rev., vol. 95, 2457, 1995) by way of a compound Vc shown in Scheme 14.

Scheme 14: Method 4 for Producing the Compound of the Formula I

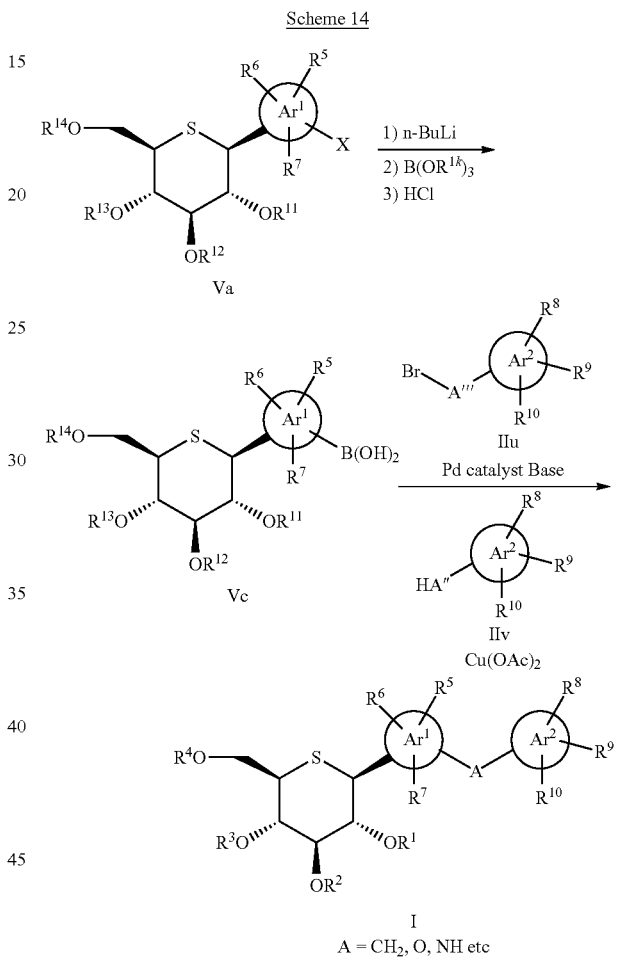

where $Ar^1$ represents an aryl or heteroaryl group, A'' represents —O— or —NH—, A''' represents a bond, —$CH_2$— or —CH=CH—, $R^{1k}$ represents a $C_{1-6}$ alkyl group, and the other symbols have the same meanings as given above.

To a compound Va in tetrahydrofuran, n-butyl lithium is added, and a tri($C_{1-6}$ alkoxy)borane ($B(OR^{1k})$) is caused to act. The reaction temperature on this occasion is −78° C. to 25° C. Then, by treatment with hydrochloric acid or the like, a boric acid derivative Vc can be synthesized.

Then, the compound Vc and a compound IIu are treated with a palladium catalyst in the presence of a suitable base, whereby the compound I of the present invention can be obtained. Examples of a solvent used in this reaction are dioxane, acetonitrile, toluene, dimethoxyethane, tetrahydrofuran, N,N-dimethylformamide, dimethoxyethane/water, ethanol/water, and toluene/ethanol. As the base, t-BuOK, Na$_2$CO$_3$, K$_2$CO$_3$, KOH, pyridine, or triethylamine is preferred. Examples of the palladium catalyst are palladium activated carbon, Pd$_2$(OAc)$_2$, Pd(dba)$_2$, Pd(PPh$_3$)$_4$, and PdCl$_2$(PPh$_3$)$_2$. In the case of the reaction involving the compound IIu in which A''' is —CH=CH—, the reaction product can be converted into the compound of the formula I, where A is —C$_2$H$_4$—, by the method relying on catalytic hydrogenation shown in the Production Method 1, Scheme 4.

By employing the method shown in the Production Method 1, Scheme 6, the compound I of the present invention (A=—O— or —NH—) can be obtained from the compound Vc and a compound IIv.

(Method 5 for Producing the Compound of the Present Invention)

The compound I of the present invention, where A is —CONH(CH$_2$)n- or —NHCO(CH$_2$)n- (n denotes an integer of 0 to 3), can be produced by a method performed via an intermediate Vd shown in Scheme 15, or a method performed via an intermediate Vf shown in Scheme 16.

Scheme 15: Method 5 for Producing the Compound of the Formula I

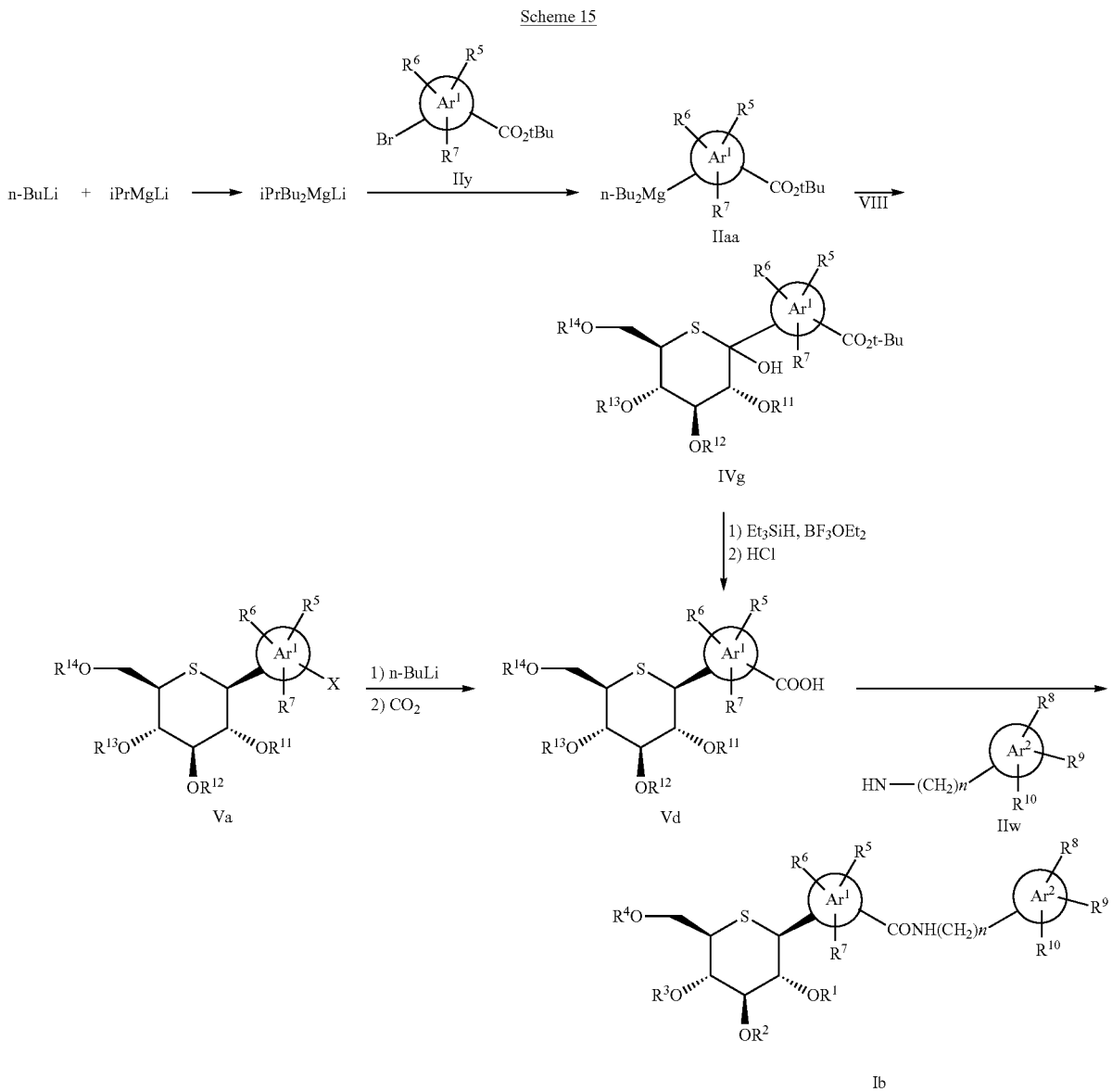

where Ar$^1$ represents an aryl or heteroaryl group, and the other symbols have the same meanings as given above.

A compound IIy is treated using an ate complex i-PrBu$_2$MgLi, which can be prepared from n-BuLi and i-PrMgCl or i-PrMgBr, whereby an organometallic reagent IIaa can be prepared. This reagent IIaa is added to the thiolactone VIII, whereby a compound IVg can be obtained. Then, the hydroxyl group is reduced under the same conditions as in Scheme 4, and then the t-butyl ester is subjected to acid hydrolysis, whereby a carboxylic acid derivative Vd can be synthesized. As a solvent used in this reaction, there is named dioxane, acetonitrile, toluene, dimethoxyethane, tetrahydrofuran, N,N-dimethylformamide, dimethoxyethane/water, ethanol/water, or toluene/ethanol. As the acid, formic acid, hydrochloric acid, or CF$_3$COOH is named. Alternatively, the carboxylic acid derivative Vd can be synthesized by treating a compound Va with n-BuLi, and then bubbling a carbon dioxide gas. Tetrahydrofuran or diethyl ether is named as a solvent used in this reaction, and the reaction temperature is −78° C. to 25° C.

Then, the compound Vd and an amine IIw are subjected to dehydration condensation, whereby the compound Ib of the present invention can be obtained. As a solvent used in this reaction, chloroform, dichloromethane, or N,N-dimethylformamide is preferred. Preferred as a dehydration condensation agent is N,N-dicyclocarbodiimide (DCC), N-ethyl-N'-3-dimethylaminopropylcarbodiimide hydrochloride (WSC), N,N-carbonyldiimidazole (CDI), or WSC/1-hydroxybenzotriazole monohydrate. The reaction temperature used here is 0° C. to 60° C.

Scheme 16: Method 5' for Producing the Compound of the Formula I

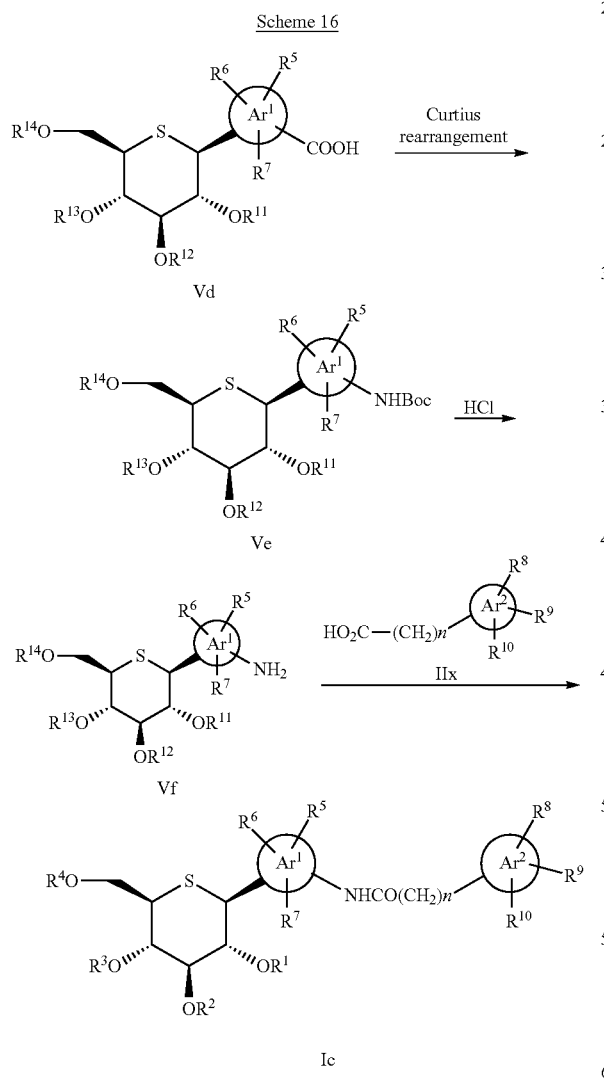

where $Ar^1$ represents an aryl or heteroaryl group, and the other symbols have the same meanings as given above.

In Scheme 16, $SOCl_2$ or $(COCl)_2$ is caused to act on a compound Vd in a solvent to form an acid chloride of the compound Vd. Chloroform or dichloromethane is named as the solvent used in this reaction. In the presence of n-$Bu_4$NBr, sodium azide is caused to act on the acid chloride to form an acid azide derivative of the compound Vd. This derivative is heated under reflux, together with t-butanol, whereby a compound Ve can be obtained. Chloroform or toluene is preferred as a solvent used in this reaction. The t-butoxycarbonyl group (Boc) of the compound Ve is removed by treatment with a suitable acid, whereby a compound VI can be obtained. The preferred acid for use in this reaction is hydrochloric acid or $CF_3COOH$.

Then, the compound Vf and a carboxylic acid IIx are subjected to dehydration condensation, whereby the compound Ic of the present invention can be obtained. As a solvent used in this reaction, chloroform, dichloromethane, or N,N-dimethylformamide is preferred. Preferred as a dehydration condensation agent is N,N-dicyclocarbodiimide (DCC), N-ethyl-N'-3-dimethylaminopropylcarbodiimide hydrochloride (WSC), N,N-carbonyldiimidazole (CDI), or WSC/1-hydroxybenzotriazole monohydrate. The reaction temperature used here is 0° C. to 60° C.

If the substituent $R^5$, $R^6$, $R^7$, $R^8$, $R^9$ or $R^{10}$ on the aryl, heteroaryl, or heterocycloalkyl ring of the compound of the present invention is a hydroxyl group or an amino group, its substituent conversion can be performed by its alkylation or acylation. An example in which the substituent is a hydroxyl group is shown in Scheme 17. The hydroxyl group is reacted with methyl bromoacetate in the presence of a base, whereby a compound Id can be obtained. As a solvent for use in this reaction, dioxane, acetonitrile, toluene, dimethoxyethane, tetrahydrofuran, or N,N-dimethylformamide is named. As the base, $Na_2CO_3$, $K_2CO_3$, KOH, pyridine, or triethylamine is preferred.

Then, the methoxycarbonyl group is hydrolyzed by a method well known to people skilled in the art, whereby the compound Id can be converted into a carboxylic acid. Alternatively, the compound Id is subjected to dehydration condensation using a primary amine or a secondary amine, whereby the compound Id can be converted into an amide derivative. Further alternatively, the carbonyl group of the compound Id is reduced, whereby the compound Id can be converted into an alcohol.

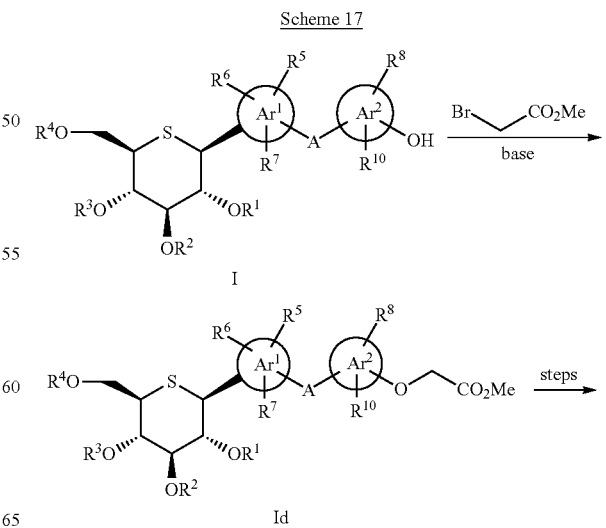

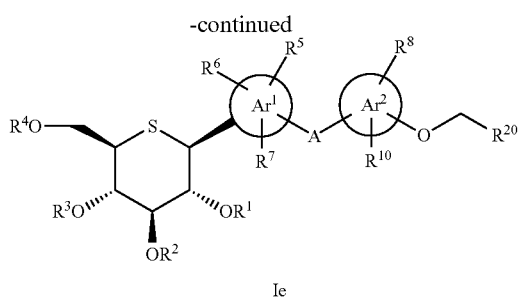

Ie $R^{20}$ = COOH (hydrolysis)
   $CONR^{a10}R^{a10}$ (hydrolysis and amination)
   $CH_2OH$ (reduction)

The compound of the present invention can inhibit sodium-dependent glucose cotransporter 2 (SGLT2) (J. Clin. Invest., vol. 93, 397, 1994) related to glucose reabsorption in the kidney.

By inhibiting SGLT2, the compound of the present invention can suppress reabsorption of sugar and excrete surplus sugar out of the body, thereby treating diabetes. Thus, this compound can correct hyperglycemia without exhaustion of the pancreatic β-cells due to glucose toxicity, and improve insulin resistance.

Hence, the present invention provides a drug for preventing or treating diseases or states, which can be ameliorated by inhibiting the activity of SGLT2, for example, diabetes, diabetes-related diseases and diabetic complications.

Here, the term "diabetes" includes type 1 diabetes mellitus, type 2 diabetes mellitus, and other types of diabetes due to other causes.

The "diabetes-related diseases" are exemplified by obesity, hyperinsulinemia, abnormal saccharometabolism, hyperlipidemia, hypercholesterolemia, hypertriglyceridemia, abnormal lipid metabolism, hypertension, congestive heart failure, edema, hyperuricemia, and gout.

Here, the "diabetic complications" are classified into acute complications and chronic complications.

The "acute complications" include, for example, hyperglycemia (ketoacidosis, etc.), and infections (dermal, soft tissue, biliary tract, respiratory, and urinary tract infections).

The "chronic complications" include, for example, microangiopathy (nephropathy, retinopathy), arteriosclerosis (atherosclerosis, myocardial infarction, cerebral infarction, obstructive arteriosclerosis of lower extremities, etc.), nerve damage (sensory nerve, motor nerve, autonomic nerve, etc.), and foot gangrene.

Main complications are diabetic retinopathy, diabetic nephropathy, and diabetic neuropathy.

Also, the compound of the present invention can be used in combination with drugs other than SGLT2 activity inhibitors and having different actions of mechanism, such as a drug for treatment of diabetes, a drug for treatment of diabetic complication, a drug for treatment of hyperlipidemia, and a drug for treatment of hypertension. By combining the compound of the present invention with the other drugs, an additive effect due to combined use can be expected as compared with the effects obtained by their individual uses in the above diseases.

Examples of "the drug for treatment of diabetes and the drug for treatment of diabetic complication" which can be used jointly are insulin sensitizing agents (PPARγ agonists, PPARα/γ agonists, PPARδ agonists, PPARα/γ/δ agonists, etc.), glycosidase inhibitors, biguanides, insulin secretion accelerators, insulin preparations, glucagon receptor antagonists, insulin receptor kinase accelerators, tripeptidyl peptidase II inhibitors, dipeptidyl peptidase IV inhibitors, protein tyrosine phosphatase 1B inhibitors, glycogen phosphorylase inhibitors, glucose-6-phosphatase inhibitors, gluconeogenesis inhibitors, fructose bisphosphatase inhibitors, pyruvate dehydrogenase inhibitors, glucokinase activators, D-kairoinositol, glycogen synthase kinase 3 inhibitors, glucagon-like peptide-1, glucagon-like peptide-1 analogues, glucagon-like peptide-1 agonists, amyrin, amyrin analogues, amyrin agonists, glucocorticoid receptor antagonists, 11β-hydroxysteroid dehydrogenase inhibitors, aldose reductase inhibitors, protein kinase C inhibitors, γ-aminobutyric acid receptor antagonists, sodium channel antagonists, transcription factor NF-κB inhibitors, IKKβ inhibitors, liquid peroxidase inhibitors, N-acetylated-α-linked-acid-dipeptidase inhibitors, insulin-like growth factor-I, platelet-derived growth factor (PDGF), platelet-derived growth factor (PDGF) analogues, epidermal growth factor (EGF), nerve growth factor, carnitine derivatives, uridine, 5-hydroxy-1-methylhydantoin, EGB-761, vimochromor, sulodexide, Y-128, and TAK-428.

The following pharmaceuticals are shown by example as the drug for treatment of diabetes and the drug for treatment of diabetic complication:

As the "biguanides", metformin hydrochloride and phenformin are named.

Of the "insulin secretion accelerators", sulfonylureas named are glyburide (glibenclamide), glipizide, gliclazide, and chlorpropamide, and non-sulfonylureas named are nateglinide, repaglinide, and mitiglinide.

The "insulin preparations" include genetically engineered human insulin and animal-derived insulin. These preparations are classified into 3 types according to the duration of action, namely, an immediate-action type (human insulin, human neutral insulin), an intermediate-action type (insulin-human isophane insulin suspension, human neutral insulin-human isophane insulin suspension, human insulin zinc suspension, insulin zinc suspension), and a prolonged-action type (human crystalline insulin zinc suspension).

As the "glycosidase inhibitors", acarbose, voglibose, and miglitol are named.

Of the "insulin sensitizing agents", the PPARγ agonists named are troglitazone, pioglitazone, and rosiglitazone, the PPARα/γ dual agonists named are MK-767 (KRP-297), Tesaglitazar, LM4156, LY510929, DRF-4823, and TY-51501, and the PPARδ agonists named are GW-501516, etc.

As the "tripeptidyl peptidase II inhibitors", UCL-139, etc. are named.

As the "dipeptidyl peptidase IV inhibitors", NVP-DPP728A, LAF-237, P32/98, and TSL-225 are named.

As the "aldose reductase inhibitors", ascorbyl gamolenate, tolrestat, epalrestat, fidarestat, sorbinil, ponalrestat, risarestat, and zenarestat.

As the "γ-aminobutyric acid receptor antagonists", topiramate, etc. are named.

As the "sodium channel antagonists", mexiletine hydrochloride, etc. are named.

As the "transcription factor NF-κB inhibitors", dexlipotam, etc. are named.

As the "lipid peroxidase inhibitors," tirilazad mesilate, etc. are named.

As the "N-acetylated-α-linked-acid-dipeptidase inhibitors," GPI-5693, etc. are named.

As the "carnitine derivatives", carnitine, levacecamine hydrochloride, etc. are named.

Examples of "the drug for treatment of hyperlipidemia and the drug for treatment of hypertension" which can be used concomitantly are hydroxymethylglutaryl-CoA reductase inhibitors, fibrate compounds, $\beta_3$-adrenergic receptor agonists, AMPK activators, acyl-CoA:cholesterol acyltransferase inhibitors, probucol, thyroid hormone receptor agonists, cholesterol absorption inhibitors, lipase inhibitors, microsome triglyceride transfer protein inhibitors, lipoxygenase inhibitors, carnitine palmitoyl transferase inhibitors, squalene synthase inhibitors, low density lipoprotein receptor accelerators, nicotinic acid derivatives, bile acid adsorbents, sodium coupled bile acid transporter inhibitors, cholesteryl ester transfer protein inhibitors, angiotensin converting enzyme inhibitors, angiotensin II receptor antagonists, endothelin converting enzyme inhibitors, endothelin receptor antagonists, diuretics, calcium antagonists, vasodilative antihypertensive agents, sympathetic blocking agents, centrally acting antihypertensive agents, $\alpha_2$-adrenergic receptor agonists, antiplatelet agents, uricogenesis inhibitors, uric acid excretion stimulators, urine alkalizing agents, anorectics, AGE inhibitors, adiponectin receptor agonists, GPR40 agonists, and GPR40 antagonists.

As the drug for treatment of hyperlipidemia and the drug for treatment of hypertension, the following pharmaceuticals are illustrated by example:

As the "hydroxymethylglutaryl-CoA reductase inhibitors," fluvastatin, lovastatin, pravastatin, cerivastatin, and pitavastatin are named.

As the "fibrate compounds", bezafibrate, beclobrate, and binifibrate are named.

As the "squalene synthase inhibitors", TAK-475, and $\alpha$-phosphonosulfonate derivatives (U.S. Pat. No. 5,712,396) are named.

As the "acyl-CoA:cholesterol acyltransferase inhibitors", CI-1011, NTE-122, FCE-27677, RP-73163, MCC-147, and DPU-129 are named.

As the "low density lipoprotein receptor accelerators", MD-700 and LY-295427 are named.

As the "microsome triglyceride transfer protein inhibitors (MTP inhibitors)", the compounds described in U.S. Pat. No. 5,739,135, U.S. Pat. No. 5,712,279 and U.S. Pat. No. 5,760,246 are named.

Examples of the "anorectics" are adrenergic-noradrenergic agents (e.g., Mazindol and ephedrine), serotonergic agents (selective serotonin reuptake inhibitors, e.g., Fluvoxamine), adrenergic-serotonergic agents (Sibutramine, etc.), melanocortin 4 receptor (MC4R) agonists, $\alpha$-melanocyte-stimulating hormone ($\alpha$-MCH), leptin, and cocaine- and amphetamine-regulated transcript (CART).

Examples of the "thyroid hormone receptor agonists" are liothyronine sodium and levothyroxine sodium.

An example of the "cholesterol absorption inhibitor" is ezetimibe.

An example of the "lipase inhibitor" is orlistat.

Among the "carnitine palmitoyl transferase inhibitors" is etomoxir.

Examples of the "nicotinic acid derivatives" are nicotinic acid, nicotinamide, nicomol, and nicorandil.

Examples of the "bile acid adsorbents" are colestyramine, colestilan, and colesevelam hydrochloride.

Examples of the "angiotensin converting enzyme inhibitors" are Captoril, enalapril maleate, alacepril, and cilazapril.

Examples of the "angiotensin II receptor antagonists" are candesartan cilexetil, losartan potassium, eprosartan mesilate, and olmesartan medoxomil.

Examples of the "endothelin converting enzyme inhibitors" are CGS-31447 and CGS-35066.

Examples of the "endothelin receptor antagonists" are L-749805, TBC-3214, and BMS-182874.

In the treatment of diabetes, etc., for example, the compound of the present invention is considered to be preferably used in combination with at least one drug selected from the group consisting of insulin sensitizing agents (PPAR$\gamma$ agonists, PPAR$\alpha/\gamma$ agonists, PPAR$\delta$ agonists, PPAR$\alpha/\gamma/\delta$ agonists, etc.), glycosidase inhibitors, biguanides, insulin secretion accelerators, insulin preparations, and dipeptidyl peptidase IV inhibitors.

Alternatively, it is considered preferable to use the compound of the present invention in combination with at least one drug selected from the group consisting of hydroxymethylglutaryl-CoA reductase inhibitors, fibrate compounds, squalene synthase inhibitors, acyl-CoA:cholesterol acyltransferase inhibitors, low density lipoprotein receptor accelerators, microsome triglyceride transfer protein inhibitors, and anorectics.

The pharmaceutical of the present invention can be administered systemically or locally by an oral route or a parenteral route such as intrarectal, subcutaneous, intramuscular, intravenous or percutaneous route.

In order to use the compound of the present invention as a pharmaceutical, any form, such as a solid composition, a liquid composition, or any other composition, may be employed, and an optimum form is selected as required. The pharmaceutical of the present invention can be produced by blending a pharmaceutically acceptable carrier with the compound of the present invention. Concretely, an excipient, a bulking agent, a binder, a disintegrant, a coating agent, a sugar coating agent, a pH regulator, a solubilizing agent, or an aqueous or nonaqueous solvent, any of which is in common use, is added to the compound of the present invention. The resulting mixture can be formed, by a common pharmaceutical manufacturing technique, into a dosage form such as tablets, pills, capsules, granules, a powder, a solution or liquid, an emulsion, a suspension, or an injection. Examples of the excipient and the bulking agent are lactose, magnesium stearate, starch, talc, gelatin, agar, pectin, acacia, olive oil, sesame oil, cacao butter, ethylene glycol, or any other material in common use.

Alternatively, the compound of the present invention can be pharmaceutically manufactured by forming an inclusion compound with $\alpha$-, $\beta$- or $\gamma$-cyclodextrin or methylated cyclodextrin.

The dose of the compound of the present invention differs according to the disease, symptoms, body weight, age, or sex of a patient, or the route of administration to the patient. For adults, the dose is preferably 0.1 to 1,000 mg/kg body weight/day, more preferably 0.1 to 200 mg/kg body weight/day, which can be administered once daily or in several divided portions daily.

EXAMPLES

Preparation Examples

Hereinbelow, preparation examples for aglycon moieties of the compounds of the present invention are described.

Preparation Example 1

Synthesis of 2,3,4,6-tetra-O-benzyl-5-thio-D-glucono-1,5-lactone 3,4-Dihydro-2H-pyran (1.5 mL, 16.5 mmol) and p-toluenesulfonic acid monohydrate (104 mg, 0.549 mmol) were added to a chloroform (40 mL) solution of 2,3,4,6-tetra-O-acetyl-5-thio-D-glucopyranose (2.0 g, 5.49 mmol) and stirred at room temperature for one hour. The reaction mixture was added with a saturated sodium bicarbonate aqueous solution and extracted with chloroform, and after the organic layer was washed with brine, it was dried with anhydrous magnesium sulfate. After the desiccant was filtered off, the residue obtained by evaporating the solvent under reduced pressure was purified by silica gel column chromatography (hexane: ethyl acetate=1:1) to obtain pale yellow amorphous tetrahydro-2H-pyran-2-yl 2,3,4,6-tetra-O-acetyl-5-thio-D-glucopyranose (2.56 g).

Then, a 25 wt % sodium methoxide solution (0.11 mL, 0.55 mmol) in methanol was added to a methanol (40 mL) solution of tetrahydro-2H-pyran-2-yl 2,3,4,6-tetra-O-acetyl-5-thio-D-glucopyranose (2.5 g), and stirred for three hours. After a little amount of dry ice was added to neutralize the reaction mixture, the reaction mixture was concentrated. The obtained residue was dissolved in N,N-dimethylformamide (20 mL). This solution was added dropwise to a suspension of sodium hydride (1.3 g, 32.9 mmol; 60% oil) and N,N-dimethylformamide (4 mL) while ice-cooled. After the reaction mixture was stirred at room temperature for 20 minutes, it was cooled to 4° C. and added with benzyl bromide (5.6 g, 32.9 mmol). The reaction mixture was stirred at room temperature for 12 hours, added with methanol (5 mL) and stirred for 30 minutes. After the reaction mixture was added with an iced water and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=6:1) to obtain tetrahydro-2H-pyran-2-yl 2,3,4,6-tetra-O-benzyl-5-thio-D-glucopyranose (3.36 g, 96% for three steps).

A mixture of tetrahydro-2H-pyran-2-yl 2,3,4,6-tetra-O-benzyl-5-thio-D-glucopyranose (3.30 g, 5.15 mmol), pyridinium p-toluenesulfonate (518 mg, 2.06 mmol) and ethanol (58 mL) was stirred at 80° C. for two hours. The reaction mixture was cooled to room temperature and the solvent was concentrated. The obtained residue was dissolved in ethyl acetate. After this solution was washed with a saturated sodium bicarbonate aqueous solution and brine, it was dried with anhydrous magnesium sulfate. After the desiccant was filtered off, the residue was purified by silica gel column chromatography (hexane:ethyl acetate=3:1) to obtain 2,3,4,6-tetra-O-benzyl-5-thio-D-glucopyranose (2.89 g, quant) as a colorless crystal. $^{13}$C NMR (125 MHz, CHLOROFORM-d) δ 41.3, 67.8, 71.6, 73.0, 73.2, 75.6, 76.2, 81.9, 82.9, 84.4, 127.5, 127.7, 127.8, 127.9, 128.0, 128.3, 128.4, 128.5, 137.8, 138.3, 138.8.

A mixture of 2,3,4,6-tetra-O-benzyl-5-thio-D-glucopyranose (2.82 g, 5.07 mmol), dimethylsulfoxide (47 mL) and acetic anhydride (39 mL) was stirred at room temperature for 12 hours. The reaction mixture was added with an iced water and extracted with ethyl acetate, and the organic phase was washed with water, a saturated sodium bicarbonate aqueous solution, brine and dried with anhydrous magnesium sulfate. After the desiccant was filtered off, the residue obtained by evaporating the solvent under reduced pressure was purified by silica gel column chromatography (hexane:ethyl acetate=6:1) to obtain a colorless oily title compound (2.3 g, 82%).
$^1$H NMR (200 MHz, CHLOROFORM-d) δ ppm 3.70 (d, J=4.8 Hz, 2H) 3.86-4.02 (m, 2H) 4.09-4.22 (m, 2H) 4.40-4.68 (m, 7H) 4.83 (d, J=11.4 Hz, 1H) 7.12-7.41 (m, 20H).

Preparation Example 2

Synthesis of 2,3,4,6-tetra-O-(4-methoxybenzyl)-5-thio-D-glucono-1,5-lactone

Synthesis was performed in a similar manner as in Preparation Example 1 using 4-methoxybenzyl chloride in place of benzyl bromide.
$^1$H NMR (300 MHz, CHLOROFORM-d) δ ppm 3.60-3.66 (m, 2H) 3.77-3.81 (m, 12H) 3.81-3.91 (m, 2H) 4.01-4.15 (m, 2H) 4.29-4.58 (m, 7H) 4.74 (d, J=11.2 Hz, 1H) 6.78-6.90 (m, 8H) 7.03-7.10 (m, 2H) 7.11-7.30 (m, 6H).

Preparation Example 3

Synthesis of 1-bromo-3-(4-ethoxybenzyl)benzene

A 2.6 M n-butyllithium hexane solution (5.8 mL) was added to a mixture of 4-bromophenetole (2.87 g, 0.0143 mol) and tetrahydrofuran (30 mL) at −78° C. After the mixture was stirred for 0.5 hours, a tetrahydrofuran (15 mL) solution of 3-bromobenzaldehyde (2.65 g, 0.0143 mol) was added, and further stirred for 15 minutes to warm the reaction mixture to room temperature. After the reaction mixture was added with a saturated ammonium chloride aqueous solution and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=7:1 to 5:1) to obtain colorless oily (3-bromophenyl)(4-ethoxyphenyl)methanol (3.94 g, 90%).

Then, Et$_3$SiH (4.09 mL, 0.0256 mol) and BF$_3$.Et$_2$O (1.47 mL, 0.0116 mol) were added sequentially to a chloroform (22 mL) solution of (3-bromophenyl)(4-ethoxyphenyl)methanol (3.92 g, 0.0128 mol) at −60° C. After stirred for one hour, the reaction solution was warmed to room temperature. After the reaction mixture was added with a saturated sodium carbonate aqueous solution and extracted with chloroform, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=50:1) to obtain a colorless oily title compound (2.84 g, 76%).
$^1$H NMR (300 MHz, CHLOROFORM-d) δ ppm 1.40 (t, J=7.0 Hz, 3H) 3.88 (s, 2H) 4.01 (q, J=7.0 Hz, 2H) 6.83 (d, J=8.9 Hz, 2H) 7.07 (d, J=8.9 Hz, 2H) 7.09-7.18 (m, 2H) 7.29-7.34 (m, 2H).

Preparation Example 4

Synthesis of 2-(5-bromo-2-methoxybenzyl)-1-benzothiophene 1.6 M n-butyllithium hexane solution (30.5 mL) was added to a mixture of benzo[b]thiophene (6.6 g, 0.049 mol) and tetrahydrofuran (66 mL) at −78° C. After stirred for 0.5 hours, the reaction mixture was added with a tetrahydrofuran (50 mL) solution of 5-bromo-2-methoxybenzaldehyde (10.0 g, 0.047 mol), further stirred for five minutes and warmed to room temperature. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=6:1) to obtain pale yellow crystal (1-benzothien-2-yl)(5-bromo-2-methoxyphenyl)methanol (11.3 g, 69%).

Then, Et$_3$SiH (10.3 mL, 0.0642 mol) and BF$_3$.Et$_2$O (4.10 mL, 0.0321 mol) were added sequentially to a chloroform (110 mL) solution of (1-benzothien-2-yl)(5-bromo-2-methoxyphenyl)methanol (1.2 g, 0.0321 mol) at −15° C. After the mixture was stirred for 0.5 hours, a saturated sodium bicarbonate aqueous solution was added. The mixture was extracted with chloroform, and the organic phase was washed with brine and then dried with anhydrous magnesium sulfate. The residue obtained by evaporating the solvent under reduced pressure was purified by silica gel column chromatography (hexane:ethyl acetate=30:1) to obtain a title compound (9.84 g, 92%) as a yellow crystal.

$^1$H NMR (300 MHz, CHLOROFORM-d) δ ppm 3.84 (s, 3H) 4.17 (s, 2H) 6.76 (d, J=8.7 Hz, 1H) 7.01 (s, 1H) 7.19-7.37 (m, 4H) 7.65 (d, J=7.8 Hz, 1H) 7.73 (d, J=7.8 Hz, 1H)

EI 332, 334 (M$^+$, M+2)

Preparation Example 5

Synthesis of
2-(5-bromo-2-chlorobenzyl)-1-benzothiophene

Oxalyl chloride (3.78 mL, 0.0441 mmol) and N,N-dimethylformamide (0.06 mL) were added to a chloroform (20 mL) solution of 5-bromo-2-chlorobenzoic acid (10.0 g, 0.0425 mol). After the reaction mixture was stirred at room temperature for one day, the reaction mixture was evaporated under reduced pressure. The obtained yellow oily substance was dissolved in chloroform (20 mL). This solution was added dropwise to a mixture of N,O-dimethoxyhydroxylamine hydrochloride (4.56 g, 0.0468 mol), triethylamine (12.3 mL, 0.0882 mol) and chloroform (50 mL) for 15 minutes, while maintaining the reaction temperature at 5° C. to 10° C. After stirred for 15 minutes, the reaction mixture was warmed to room temperature. After water (20 mL) was added to the reaction mixture, the organic layer was separated and the organic layer was washed with a saturated sodium bicarbonate aqueous solution and brine, and then dried with anhydrous magnesium sulfate. After the desiccant was filtered off, the solvent was evaporated under reduced pressure to obtain 5-bromo-2-chloro-N-methoxy-N-methylbenzamide (11.8 g, 99.7%) as a colorless crystal. This was used in the next reaction without purification.

LiAlH$_4$ (1.47 g, 0.0388 mol) was added little by little to a tetrahydrofuran (108 mL) solution of 5-bromo-2-chloro-N-methoxy-N-methylbenzamide (10.8 g, 0.0388 mol) so that the internal temperature did not exceed −10° C. The reaction mixture was stirred at −15° C. for one hour and carefully added with a saturated ammonium chloride aqueous solution and deposited insolubles were filtered off with celite. After the filtrate was extracted with ethyl acetate, the organic layer was washed with 1M hydrochloric acid, a saturated sodium bicarbonate aqueous solution, brine, and then dried with anhydrous magnesium sulfate. After the desiccant was filtered off, the solvent was evaporated under reduced pressure to obtain 5-bromo-2-chlorobenzaldehyde (8.1 g, 95%) as a pale yellow crystal. This was used in the next reaction without purification.

1.6 M n-butyllithium hexane solution (26.9 mL) was added to a mixture of benzo[b]thiophene (5.8 g, 0.043 mol) and tetrahydrofuran (58 mL) at −78° C. over 20 minutes. After stirred for 0.5 hours, the mixture was added with a tetrahydrofuran (50 mL) solution of 5-bromo-2-chlorobenzaldehyde (9.0 g, 0.041 mol) and stirred for further five minutes. The reaction mixture was warmed to room temperature. After the reaction mixture was added with a saturated ammonium chloride aqueous solution and extracted with ethyl acetate, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=10:1) to obtain pale yellow oily (1-benzothien-2-yl)(5-bromo-2-chlorophenyl)methanol (10.3 g, 71%).

Then, Et$_3$SiH (9.2 mL, 0.058 mol) and BF$_3$.Et$_2$O (3.6 mL, 0.029 mol) were added sequentially to a chloroform (110 mL) solution of (1-benzothien-2-yl)(5-bromo-2-chlorophenyl)methanol (10.2 g, 0.0288 mol) at −15° C. The reaction mixture was warmed to room temperature and stirred at the temperature for ten hours. After the reaction mixture was added with a saturated sodium bicarbonate aqueous solution, the organic phase was separated, washed with brine and then dried with anhydrous magnesium sulfate. After the desiccant was filtered off, the residue obtained by evaporating the solvent under reduced pressure was purified by silica gel column chromatography (hexane:ethyl acetate=60:1) to obtain a colorless oily title compound (5.5 g, 56%).

$^1$H NMR (300 MHz, CHLOROFORM-d) δ ppm 4.30 (s, 2H) 6.98-7.06 (m, 1H) 7.22-7.37 (m, 4H) 7.43 (d, J=2.3 Hz, 1H) 7.64-7.71 (m, 1H) 7.72-7.80 (m, 1H).

EI 336 (M$^+$), 338 (M+2), 340 (M+4).

Preparation Example 6

Synthesis of
1-(benzyloxy)-2-bromo-4-(4-ethoxybenzyl)benzene

Benzyl bromide (3.1 mL, 0.026 mol) was added to a mixture of 3-bromo-4-hydroxybenzaldehyde (5.0 g, 0.025 mol), tetrabutylammonium iodide (0.92 g, 2.5 mmol), potassium carbonate (6.9 g, 0.050 mol) and N,N-dimethylformamide (70 mL) at room temperature and stirred for 2.5 hours. An ice-water mixture (100 mL) was poured to the reaction mixture and the resultant solution was stirred for one hour. A resulting precipitate was filtered and dried to obtain 4-benzyloxy-3-bromobenzaldehyde (7.1 g, 98%) as a pale yellow powder.

Then, 1.6 M n-butyllithium hexane solution (22.9 mL) was added to a mixture of 4-bromophenetole (7.3 g, 0.037 mol) and tetrahydrofuran (70 mL) at −78° C. After stirred for 0.5 hours, 4-benzyloxy-3-bromobenzaldehyde (7.0 g, 0.024 mol) in a tetrahydrofuran (70 mL) solution was added and further stirred for 15 minutes, and the reaction mixture was warmed to room temperature. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain colorless oily [4-(benzyloxy)-3-bromophenyl](4-ethoxyphenyl)methanol (8.7 g, 86%).

Then, Et$_3$SiH (6.7 mL, 0.042 mol) and BF$_3$.Et$_2$O (2.7 mL, 0.021 mol) were added sequentially to a chloroform (90 mL) solution of [4-(benzyloxy)-3-bromophenyl](4-ethoxyphenyl)methanol (8.7 g, 0.021 mol) at −15° C. After stirred for one hour, the reaction mixture was warmed to room temperature. After the reaction mixture was added with a saturated sodium carbonate aqueous solution and extracted with chloroform, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=10:1) to obtain a colorless oily title compound (8.8 g, quant).

$^1$H NMR (300 MHz, CHLOROFORM-d) δ ppm 1.40 (t, J=7.0 Hz, 3H) 3.82 (s, 2H) 4.00 (q, J=7.0 Hz, 2H) 5.12 (s, 2H) 6.78-6.87 (m, 3H) 6.98-7.10 (m, 3H) 7.27-7.50 (m, 6H).

Preparation Example 7

Synthesis of 1-bromo-3-(4-ethoxybenzyl)-4-methoxybenzene

Preparation was performed in a similar manner as in Preparation Example 3 using 5-bromo-2-methoxybenzaldehyde and 4-bromophenetole.

$^1$H NMR (300 MHz, CHLOROFORM-d) δ ppm 1.40 (t, J=7.0 Hz, 3H) 3.79 (s, 3H) 3.85 (s, 2H) 4.01 (q, J=7.0 Hz, 2H) 6.72 (d, J=8.6 Hz, 1H) 6.81 (d, J=8.7 Hz, 2H) 7.09 (d, J=8.7 Hz, 1H) 7.13 (d, J=2.5 Hz, 1H) 7.27 (dd, J=8.6, 2.5 Hz, 1H).

Preparation Example 8

Synthesis of 1-bromo-3-(4-ethoxybenzyl)-6-methoxybenzene

Preparation was performed in a similar manner as in Preparation Example 3 using 3-bromo-4-methoxybenzaldehyde and 4-bromophenetole.

$^1$H NMR (300 MHz, CHLOROFORM-d) δ ppm 1.40 (t, J=7.0 Hz, 3H) 3.83 (s, 2H) 3.86 (s, 3H) 4.01 (q, J=7.0 Hz, 2H) 6.78-6.85 (m, 3H) 7.03-7.10 (m, 3H) 7.35 (d, J=2.2 Hz, 1H).
EI 320, 322 (M$^+$, M+2).

Preparation Example 9

Synthesis of 2-(3-bromobenzyl)-1-benzothiophene

Preparation was performed in a similar manner as in Preparation Example 4 using 3-bromobenzaldehyde and benzo[b]thiophene.

$^1$H NMR (300 MHz, CHLOROFORM-d) δ ppm 4.19 (s, 2H) 7.02 (s, 1H) 7.15-7.47 (m, 6H) 7.65-7.70 (m, 1H) 7.71-7.77 (m, 1H).
EI 302, 304 (M$^+$, M+2).

Preparation Example 10

Synthesis of 2-(3-bromo-4-methoxybenzyl)-1-benzothiophene

Preparation was performed in a similar manner as in Preparation Example 4 using 3-bromo-4-methoxybenzaldehyde and benzo[b]thiophene.

$^1$H NMR (300 MHz, CHLOROFORM-d) δ ppm 3.89 (s, 3H) 4.15 (s, 2H) 6.86 (d, J=8.4 Hz, 1H) 7.01 (s, 1H) 7.16-7.35 (m, 3H) 7.48 (d, J=1.9 Hz, 1H) 7.64-7.70 (m, 1H) 7.71-7.77 (m, 1H).
EI 332, 334 (M$^+$, M+2).

Preparation Example 11

Synthesis of 1-bromo-3-(4-ethoxybenzyl)-4,6-dimethoxybenzene

Preparation was performed in a similar manner as in Preparation Example 3 using 5-bromo-2,4-dimethoxybenzaldehyde and 4-bromophenetole.

$^1$H NMR (200 MHz, CHLOROFORM-d) δ ppm 1.39 (t, J=7.0 Hz, 3H) 3.80 (s, 2H) 3.82 (s, 3H) 3.88 (s, 3H) 4.00 (q, J=7.0 Hz, 2H) 6.47 (s, 1H) 6.75-6.85 (m, 2H) 7.02-7.12 (m, 2H) 7.17 (s, 1H)
EI 350, 352 (M$^+$, M+2).

Preparation Example 12

Synthesis of 1-bromo-3-(4-ethoxybenzyl)-4-fluorobenzene

Preparation was performed in a similar manner as in Preparation Example 3 using 5-bromo-2-fluorobenzaldehyde and 4-bromophenetole.

$^1$H NMR (200 MHz, CHLOROFORM-d) δ ppm 1.40 (t, J=7.0 Hz, 3H) 3.88 (s, 2H) 4.01 (q, J=7.0 Hz, 2H) 6.79-6.96 (m, 3H) 7.05-7.16 (m, 2H) 7.19-7.32 (m, 2H).
EI 309, 311 (M$^+$, M+2).

Preparation Example 13

Synthesis of 1-(benzyloxy)-4-bromo-2-(4-ethoxybenzyl)benzene

Synthesis was performed in a similar manner as in Preparation Example 6 from 3-bromo-2-hydroxybenzaldehyde.

$^1$H NMR (200 MHz, CHLOROFORM-d) δ ppm 1.40 (t, J=6.8 Hz, 3H) 3.90 (s, 2H) 4.01 (q, J=6.8 Hz, 2H) 5.03 (s, 2H) 6.72-6.85 (m, 3H) 7.02-7.13 (m, 2H) 7.15-7.43 (m, 7H).

Preparation Example 14

Synthesis of 1-bromo-4-chloro-3-(4-ethoxy-2,5-difluorobenzyl)benzene

Oxalyl chloride (1.89 mL, 0.0220 mol) and N,N-dimethylformamide (0.03 mL) were added to 5-bromo-2-chlorobenzoic acid (5.0 g, 0.0212 mol) in chloroform (10 mL) and stirred for three hours. The yellow oil obtained by evaporating the solvent under reduced pressure was dissolved in chloroform (10 mL). To this solution, 2,5-difluorophenetole (3.4 g, 0.0214 mol) was added and then aluminum chloride (2.9 g, 0.0214 mol) was added portion wise at −10° C. over five minutes. After the reaction mixture was stirred at 5° C. for two hours, an iced water was added. This was extracted with chloroform three times. After the combined organic layer was washed with 1M hydrochloric acid, water, brine, it was dried with anhydrous magnesium sulfate. After the desiccant was filtered off, the residue obtained by evaporating the solvent under reduced pressure was purified by silica gel column chromatography (hexane:ethyl acetate=10:1) to obtain (5-bromo-2-chlorophenyl)(4-ethoxy-2,5-difluorophenyl)methanone (5.59 g, 70%) as a colorless crystal.

Then, Et$_3$SiH (5.93 mL, 0.0371 mol) and BF$_3$.Et$_2$O (2.83 mL, 0.0224 mol) were added sequentially to a chloroform-acetonitrile (1:1; 60 mL) solution of (5-bromo-2-chlorophenyl)(4-ethoxy-2,5-difluorophenyl)methanone (5.58 g, 0.0149 mol) at 4° C. The reaction mixture was warmed to room temperature, stirred for 12 hours and stirred at 45° C. for further three hours. After the reaction mixture was added with a saturated sodium carbonate aqueous solution and extracted with chloroform, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=10:1) to obtain a colorless oily title compound (3.8 g, 71%).

¹H NMR (300 MHz, CHLOROFORM-d) δ ppm 1.46 (t, J=7.0 Hz, 3H) 3.98 (s, 2H) 4.08 (q, J=7.0 Hz, 2H) 6.71 (dd, J=11.3, 7.1 Hz, 1H) 6.82 (dd, J=11.3, 7.1 Hz, 1H) 7.18-7.38 (m, 3H).
EI 360 (M⁺), 362 (M+2), 364 (M+4).

Preparation Example 15

Synthesis of 1-bromo-4-chloro-3-(4-ethoxy-3-fluorobenzyl)benzene

Synthesis was performed by a similar method as in Preparation Example 14 using 5-bromo-2-chlorobenzoic acid and 2-fluorophenetole.
¹H NMR (300 MHz, CHLOROFORM-d) δ ppm 1.44 (t, J=7.0 Hz, 3H) 3.97 (s, 2H) 4.09 (q, J=7.0 Hz, 2H) 6.79-6.95 (m, 3H) 7.18-7.35 (m, 3H)
EI 342 (M⁺), 344 (M+2), 346 (M+4).

Preparation Example 16

Synthesis of 1-bromo-4-chloro-3-(3-chloro-4-ethoxybenzyl)benzene

Synthesis was performed by a similar method as in Preparation Example 14 using 5-bromo-2-chlorobenzoic acid and 2-chlorophenetole.
¹H NMR (300 MHz, CHLOROFORM-d) δ ppm 1.46 (t, J=7.0 Hz, 3H) 3.96 (s, 2H) 4.08 (q, J=7.0 Hz, 2H) 6.85 (d, J=8.4 Hz, 1H) 6.95-7.03 (m, 1H) 7.18 (d, J=2.2 Hz, 1H) 7.23-7.33 (m, 3H).

Preparation Example 17

Synthesis of 1-bromo-3-(4-ethoxybenzyl)-4-methylbenzene

Synthesis was performed by a similar method as in Preparation Example 14 using 5-bromo-2-methylbenzoic acid (synthesized in reference to International Patent Publication WO0127128) and phenetole.
¹H NMR (200 MHz, CHLOROFORM-d) δ ppm 1.40 (t, J=7.0 Hz, 3H) 2.18 (s, 3H) 3.86 (s, 2H) 4.00 (g, J=7.0 Hz, 2H) 6.76-6.87 (m, 2H) 6.94-7.07 (m, 3H) 7.17-7.30 (m, 2H).
EI 304 (M⁺), 306 (M+2).

Preparation Example 18

Synthesis of 1-bromo-4-chloro-3-(2,4-dimethoxybenzyl)benzene

Synthesis was performed by a similar method as in Preparation Example 14 using 5-bromo-2-chlorobenzoic acid and 1,3-dimethoxybenzene.
¹H NMR (200 MHz, CHLOROFORM-d) δ ppm 3.79 (s, 3H) 3.80 (s, 3H) 3.95 (s, 2H) 6.36-6.53 (m, 2H) 6.94 (d, J=8.4 Hz, 1H) 7.13-7.28 (m, 3H).

Preparation Example 19

Synthesis of 1-bromo-4-chloro-3-(4-methoxybenzyl)benzene

Synthesis was performed by a similar method as in Preparation Example 14 using 5-bromo-2-chlorobenzoic acid and anisole.
¹H NMR (300 MHz, CHLOROFORM-d) δ ppm 3.80 (s, 3H) 3.99 (s, 2H) 6.82-6.89 (m, 2H) 7.06-7.13 (m, 2H) 7.19-7.30 (m, 3H).

Preparation Example 20

Synthesis of 1-bromo-4-chloro-3-(4-tert-butylbenzyl)benzene

Synthesis was performed by a similar method as in Preparation Example 14 using 5-bromo-2-chlorobenzoic acid and tert-butylbenzene.
¹H NMR (200 MHz, CHLOROFORM-d) δ ppm 1.31 (s, 9H) 4.03 (s, 2H) 7.11 (d, J=7.9 Hz, 2H) 7.22-7.37 (m, 5H).

Preparation Example 21

Synthesis of 1-bromo-4-chloro-3-(4-methylbenzyl)benzene

Synthesis was performed by a similar method as in Preparation Example 14 using 5-bromo-2-chlorobenzoic acid and toluene.
¹H NMR (200 MHz, CHLOROFORM-d) δ ppm 2.33 (s, 3H) 4.02 (s, 2H) 7.03-7.16 (m, 4H) 7.18-7.32 (m, 3H).
EI 294 (M⁺), 296 (M+2).

Preparation Example 22

Synthesis of 1-bromo-4-chloro-3-(4-methylthiobenzyl)benzene

Synthesis was performed by a similar method as in Preparation Example 14 using 5-bromo-2-chlorobenzoic acid and thioanisole.
¹H NMR (300 MHz, CHLOROFORM-d) δ ppm 2.47 (s, 3H) 4.01 (s, 2H) 7.06-7.14 (m, 2H) 7.17-7.32 (m, 5H).

Preparation Example 23

Synthesis of 1-bromo-4-chloro-3-(4-ethylbenzyl)benzene

Synthesis was performed by a similar method as in Preparation Example 14 using 5-bromo-2-chlorobenzoic acid and ethylbenzene.
¹H NMR (200 MHz, CHLOROFORM-d) δ ppm 1.23 (t, J=7.7 Hz, 3H) 2.63 (q, J=7.7 Hz, 2H) 4.02 (s, 2H) 7.04-7.18 (m, 4H) 7.18-7.32 (m, 3H)
EI 308 (M⁺), 310 (M+2).

Preparation Example 24

Synthesis of 1-bromo-4-chloro-3-(4-isopropylbenzyl)benzene

Synthesis was performed by a similar method as in Preparation Example 14 using 5-bromo-2-chlorobenzoic acid and cumene.
¹H NMR (200 MHz, CHLOROFORM-d) δ ppm 1.22 (s, 3H) 1.26 (s, 3H) 2.79-2.97 (m, 1H) 4.02 (s, 2H) 7.05-7.32 (m, 7H).

EI 322 (M+), 324 (M+2).

Preparation Example 25

Synthesis of 2-(5-bromo-2-chlorobenzyl)benzofuran

Synthesis was performed in a similar manner as in Preparation Example 5 using benzofuran in place of benzothiophene.

$^1$H NMR (200 MHz, CHLOROFORM-d) δ ppm 4.20 (s, 2H) 6.40-6.46 (m, 1H) 7.13-7.54 (m, 7H).
EI 319 (M+), 321 (M+2).

Preparation Example 26

Synthesis of 1-bromo-3-(4-ethoxybenzyl)-6-methoxy-4-methylbenzene

Bromine (3.87 mL, 0.076 mol) was added dropwise at 5° C. to a mixture of 4-methoxy-2-methylbenzoic acid (10 g, 0.060 mol), Fe (0.20 g, 3.61 mmol) and chloroform (10 mL). After the reaction mixture was warmed to room temperature, it was stirred overnight. After chloroform (600 mL) was added, this suspension was washed with 10% sodium hydrogensulfate (200 mL×2) and brine, and dried with anhydrous magnesium sulfate. After the desiccant was filtered off, the pale yellow powder obtained by evaporating the solvent under reduced pressure was recrystallized from methanol twice to obtain 5-bromo-4-methoxy-2-methylbenzoic acid (4.96 g, 34%).

Alternatively, 5-bromo-4-methoxy-2-methylbenzoic acid can be synthesized from 4'-hydroxy-2'-methylacetophenone as a starting material. Potassium carbonate (0.720 mg, 5.21 mmol) and methyl iodide (0.542 g, 3.82 mmol) were added to an acetone (10 mL) solution of 4'-hydroxy-2'-methylacetophenone (0.552 g, 3.47 mmol) and stirred at room temperature for 12 hours. Methyl iodide (0.24 g, 1.73 mmol) was further added, and the mixture was heated to reflux for two hours. After cooled to room temperature, the solvent was evaporated under reduced pressure. After chloroform was added to the residue, insolubles were filtered off and the filtrate was concentrated to obtain 4'-methoxy-2'-methylacetophenone (0.57 g). Then, oxone (0.79 g, 1.27 mmol) and NaBr (0.13 g, 1.27 mmol) were added to an acetone (4 mL) water (4 mL) solution of 4'-methoxy-2'-methylacetophenone (0.21 g, 1.27 mmol), and stirred at room temperature for one hour. After water and ethyl acetate were added to the reaction mixture, the organic layer was separated and washed with water, a saturated sodium carbonate aqueous solution and brine and dried with anhydrous magnesium sulfate. After the desiccant was filtered off, the solvent was evaporated under reduced pressure to obtain 4:1 mixture (0.28 g) of 5'-bromo-4'-methoxy-2'-methylacetophenone and 3'-bromo-4'-methoxy-2'-methylacetophenone. Then, 4:1 mixture (0.26 g) of 5'-bromo-4'-methoxy-2'-methylacetophenone and 3'-bromo-4'-methoxy-2'-methylacetophenone was added with 5% NaOCl solution (3 mL) and potassium hydroxide (0.92 g) and heated to reflux for 2.5 hours. After cooled to room temperature, the reaction mixture was made acidic with 2M HCl. After the mixture was extracted with ethyl acetate, the organic phase was washed with 1M HCl, brine and then dried with anhydrous magnesium sulfate. After the desiccant was filtered off, the residue obtained by evaporating the solvent under reduced pressure was washed with methanol to obtain 5-bromo-4-methoxy-2-methylbenzoic acid (112 mg) as a colorless powder.

Then, the title compound (5.80 g) was synthesized from 5-bromo-4-methoxy-2-methylbenzoic acid (4.93 g, 0.0201 mol) and phenetole by a similar method as in Preparation Example 14.

$^1$H NMR (300 MHz, CHLOROFORM-d) δ ppm 1.40 (t, J=7.0 Hz, 3H) 2.19 (s, 3H) 3.82 (s, 2H) 3.87 (s, 3H) 4.00 (q, J=7.0 Hz, 2H) 6.71 (s, 1H) 6.77-6.83 (m, 2H) 6.95-7.04 (m, 2H) 7.24 (s, 1H).
EI 335 (M+), 337 (M+2).

Preparation Example 27

Synthesis of 1-bromo-4-chloro-3-(4-ethoxybenzyl)-6-methoxybenzene

A suspension of 2-bromo-5-chlorophenol (2.85 g, 13.7 mmol; synthesized in reference to International Patent Publication WO0109122), potassium carbonate (1.89 g, 13.7 mmol), n-Bu$_4$NI (50 mg, 0.137 mmol), methyl iodide (1.28 mL, 20.6 mmol) and N,N-dimethylformamide (8.0 mL) was stirred for two hours. An iced water was added and the obtained mixture was extracted with ethyl acetate twice. The combined organic phase was washed with brine and dried with anhydrous magnesium sulfate. After the desiccant was filtered off, the residue obtained by evaporating the solvent under reduced pressure was purified by silica gel column chromatography (hexane:ethyl acetate=95:5) to obtain colorless oily 2-bromo-5-chloroanisole (2.94 g, 97%). Then, oxalyl chloride (1.23 mL, 15.1 mmol) and N,N-dimethylformamide (2 drops) were added to 4-ethoxybenzoic acid (2.28 g, 13.7 mmol) in chloroform (8 mL) and stirred for five hours. The yellow oil obtained by evaporating the solvent under reduced pressure was dissolved in chloroform (5 mL). To this solution, a chloroform solution (10 mL) of 2-bromo-5-chloroanisole (2.94 g, 13.3 mmol) was added and then aluminum chloride (2.07 g, 15.5 mmol) was added portion wise at −10° C. over five minutes. After stirred at 5° C. for one hour, the reaction mixture was to room temperature and stirred for 13 hours. The reaction mixture was poured into an iced water and extracted with chloroform three times. After washed with 1 M hydrochloric acid, water, brine, the combined organic layer was dried with anhydrous magnesium sulfate. After the desiccant was filtered off, the residue obtained by evaporating the solvent under reduced pressure was purified by NH type silica gel column chromatography (hexane:ethyl acetate=9:1) to obtain (5-bromo-2-chloro-6-methoxyphenyl)(4-ethoxyphenyl)methanone (1.53 g, 31%) as a colorless crystal.

Then, Et$_3$SiH (1.62 mL, 10.1 mmol) and BF$_3$.Et$_2$O (0.772 mL, 6.09 mmol) were added sequentially to a chloroform-acetonitrile (1:1; 16 mL) solution of (5-bromo-2-chloro-6-methoxyphenyl)(4-ethoxyphenyl)methanone (1.50 g, 4.06 mmol) at −5° C. The reaction mixture was warmed to room temperature and stirred for 16 hours. After the reaction mixture was added with a saturated sodium carbonate aqueous solution and extracted with chloroform, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=20:1) to obtain a colorless oily title compound (1.48 g, 99%).

$^1$H NMR (200 MHz, CHLOROFORM-d) δ ppm 1.40 (t, J=7.0 Hz, 3H) 3.87 (s, 3H) 3.93 (s, 2H) 4.01 (q, J=7.0 Hz, 2H) 6.77-6.87 (m, 2H) 6.90 (s, 1H) 7.03-7.12 (m, 2H) 7.29 (s, 1H).

EI 354 (M⁺), 356 (M+2), 358 (M+4).

Preparation Example 28

Synthesis of 1-bromo-4-chloro-3-(4-ethylbenzyl)-6-methoxybenzene

Synthesis was performed in a similar manner as in Preparation Example 27 using 4-ethylbenzoic acid in place of 4-ethoxybenzoic acid.

$^1$H NMR (300 MHz, CHLOROFORM-d) δ ppm 1.22 (t, J=7.6 Hz, 3H) 2.62 (q, J=7.6 Hz, 2H) 3.87 (s, 3H) 3.97 (s, 2H) 6.91 (s, 1H) 7.04-7.18 (m, 4H) 7.32 (s, 1H).

EI 338, 340, 342 (M⁺, M+2, M+4).

Preparation Example 29

Synthesis of 1-bromo-4-chloro-3-(4-isopropylbenzyl)-6-methoxybenzene

Synthesis was performed in a similar manner as in Preparation Example 27 using 4-isopropylbenzoic acid in place of 4-ethoxybenzoic acid.

$^1$H NMR (300 MHz, CHLOROFORM-d) δ ppm 1.24 (d, J=7.0 Hz, 6H) 2.82-2.94 (m, 1H) 3.87 (s, 3H) 3.97 (s, 2H) 6.91 (s, 1H) 7.05-7.20 (m, 4H) 7.33 (s, 1H).

EI 352, 354, 356 (M⁺, M+2, M+4).

Preparation Example 30

Synthesis of 1-benzyloxy-2-bromo-4-(4-ethoxybenzyl)-5-methylbenzene

Synthesis was performed in a similar manner as in Preparation Example 3 using 4-benzyloxy-3-bromo-6-methylbenzaldehyde in place of 3-bromobenzaldehyde.

$^1$H NMR (300 MHz, CHLOROFORM-d) δ ppm 1.40 (t, J=7.0 Hz, 3H) 2.17 (s, 3H) 3.82 (s, 2H) 4.00 (q, J=7.0 Hz, 2H) 5.12 (s, 2H) 6.76 (s, 1H) 6.77-6.85 (m, 2H) 6.96-7.05 (m, 2H) 7.27 (s, 1H) 7.30-7.44 (m, 3H) 7.45-7.53 (m, 2H). EI 410 (M⁺), 412 (M+2).

Preparation Example 31

Synthesis of 1-bromo-2,4-(dibenzyloxy)-5-(4-ethoxybenzyl)benzene

A suspension of 5-bromo-2,4-dihydroxybenzoic acid (5.0 g, 0.0215 mol), potassium carbonate (9.8 g, 0.0710 mol), n-Bu₄NI (79 mg, 0.215 mmol), benzyl bromide (8.4 mL, 0.0710 mol) and N,N-dimethylformamide (40.0 mL) was stirred for 60 hours. An iced water was added and the obtained mixture was extracted with ethyl acetate twice. The combined organic phase was washed with brine and dried with anhydrous magnesium sulfate. After the desiccant was filtered off, the residue obtained by evaporating the solvent under reduced pressure was dissolved in tetrahydrofuran (150 mL). This solution was cooled to −15° C. and LiAlH₄ (1.22 g, 0.0323 mol) was added little by little. After the mixture was stirred at −5° C. for 1.5 hours, LiAlH₄ (0.41 g, 0.011 mol) was further added. The reaction mixture was stirred at 5° C. for one hour and carefully added with a saturated ammonium chloride aqueous solution, and resulting insolubles were filtered off with celite. After the filtrate was extracted with ethyl acetate, the organic layer was washed with 1M hydrochloric acid, a saturated sodium bicarbonate aqueous solution and brine and then dried with anhydrous magnesium sulfate. The solvent was evaporated under reduced pressure after the desiccant was filtered off to obtain 5-bromo-2,4-(dibenzyloxy)benzyl alcohol (12.1 g). This was used in the next reaction without purification.

Manganese dioxide (IV) (13.1 g, 0.150 mol) was added to a toluene (150 mL) solution of 5-bromo-2,4-(dibenzyloxy) benzyl alcohol (12.1 g). This mixture was stirred at room temperature for 15 hours and further stirred at 80° C. for four hours and at 100° C. for two hours. Manganese dioxide (IV) (4.0 g) was further added and the mixture was stirred at 100° C. for four hours. The mixture was cooled to room temperature and insolubles were filtered off with celite. The solids obtained by concentrating the filtrate were recrystallized from a mixed solvent of hexane-ethyl acetate to obtain 5-bromo-2,4-(dibenzyloxy)benzaldehyde (3.6 g, 43%) as a colorless powder.

Then, the title compound was synthesized by a similar method as in Preparation Example 3 using 5-bromo-2,4-(dibenzyloxy)benzaldehyde in place of 3-bromobenzaldehyde.

$^1$H NMR (300 MHz, CHLOROFORM-d) δ ppm 1.40 (t, J=7.0 Hz, 3H) 3.84 (s, 2H) 4.01 (q, J=7.0 Hz, 2H) 4.96 (s, 2H) 5.07 (s, 2H) 6.53 (s, 1H) 6.75-6.82 (m, 2H) 7.02-7.10 (m, 2H) 7.20-7.48 (m, 11H).

EI 525 (M⁺), 527 (M+2).

Preparation Example 32

Synthesis of 1-bromo-2-methoxy-4-methyl-5-(4-methylbenzyl)benzene

Oxalyl chloride (3.43 mL, 0.0400 mmol) and N,N-dimethylformamide (2 drops) were added to chloroform (60 mL) solution of 4-methoxy-2-methylbenzoic acid (5.0 g, 0.0300 mol). After the reaction mixture was stirred at room temperature for one hour, the reaction solvent was evaporated under reduced pressure. The obtained yellow oily substance was dissolved in chloroform (60 mL). Toluene (3.52 mL, 0.0330 mol) and aluminum chloride (8.02 g, 0.0601 mol) were added to this solution while cooled on ice, and the reaction mixture was stirred for three and a half hours while keeping the reaction mixture cooled ice. After 5% hydrochloric acid was added to the reaction mixture and extracted with chloroform, the organic phase was washed with 10% hydrochloric acid, water, a saturated sodium bicarbonate aqueous solution and brine, and dried with anhydrous magnesium sulfate. After the desiccant was filtered off, the residue obtained by evaporating the solvent under reduced pressure was purified by silica gel column chromatography (hexane:ethyl acetate=15:1) to obtain yellow oily (4-methoxy-2-methylphenyl) (4-methylphenyl)methanone (4.26 g, 58.9%).

$^1$H NMR (300 MHz, CHLOROFORM-d) δ ppm 2.39 (s, 3H) 2.42 (s, 3H) 3.86 (s, 3H) 6.74 (dd, J=8.5, 2.56 Hz, 1H) 6.81 (d, J=2.6 Hz, 1H) 7.21-7.27 (m, 2H) 7.31 (d, J=8.4 Hz, 1H) 7.64-7.71 (m, 2H)

ESI m/z=263 (M+Na)

Et₃SiH (8.5 mL, 0.0531 mol) was added to a mixed solution of chloroform (8 mL) and acetonitrile (32 mL) of (4-methoxy-2-methyl phenyl)(4-methylphenyl)methanone and BF₃.Et₂O (4.5 mL, 0.0354 mol) was added dropwise while cooled on ice. The reaction mixture was warmed to room temperature and stirred at 50° C. for one hour. After the reaction mixture was added with a saturated sodium bicarbonate aqueous solution and extracted with ethyl acetate while cooled on ice, the organic phase was washed with brine and dried with anhydrous magnesium sulfate. After the desiccant was filtered off, the residue obtained by evaporating the solvent under reduced pressure was purified by silica gel column chromatography-(hexane:ethyl acetate=15:1) to obtain colorless oily 4-methoxy-2-methyl-1-(4-methylbenzyl)benzene (3.89 g, 97%).

$^1$H NMR (300 MHz, CHLOROFORM-d) δ ppm 2.21 (s, 3H) 2.31 (s, 3H) 3.78 (s, 3H) 3.88 (s, 2H) 6.65-6.74 (m, 2H) 6.97-7.03 (m, 3H) 7.03-7.11 (m, 2H)

EI 226 (M$^+$)

Br$_2$ was added dropwise to an acetic acid (35 mL) solution of 4-methoxy-2-methyl-1-(4-methylbenzyl)benzene while cooled on ice. The reaction mixture was stirred at 110° C. for two hours. After the reaction mixture was added with water while cooled on ice and extracted with ethyl acetate, the organic phase was washed with a saturated sodium bicarbonate aqueous solution and brine and dried with anhydrous magnesium sulfate. After the desiccant was filtered off, the residue obtained by evaporating the solvent under reduced pressure was purified by silica gel column chromatography (hexane:ethyl acetate=15:1) to obtain a yellow oily title compound (4.21 g, 80%).

$^1$H NMR (300 MHz, CHLOROFORM-d) δ ppm 2.20 (s, 3H) 2.31 (s, 3H) 3.85 (s, 2H) 3.87 (s, 3H) 6.71 (s, 1H) 6.94-7.11 (m, 4H) 7.26 (s, 1H).

EI 304 (M$^+$), 306 (M+2).

Preparation Example 33

Synthesis of 1-bromo-2-methoxy-4-methyl-5-(4-ethylbenzyl)benzene

The title compound was synthesized by a similar method as in Preparation Example 32 using ethylbenzene in place of toluene.

$^1$H NMR (300 MHz, CHLOROFORM-d) δ ppm 1.22 (t, J=7.6 Hz, 3H) 2.20 (s, 3H) 2.61 (q, J=7.6 Hz, 2H) 3.85 (s, 2H) 3.87 (s, 3H) 6.71 (s, 1H) 6.97-7.14 (m, 4H) 7.27 (s, 1H).

EI 318 (M$^+$).

Preparation Example 34

Synthesis of 1-bromo-2-methoxy-4-methyl-5-(4-isopropylbenzyl)benzene

The title compound was synthesized by a similar method as in Preparation Example 32 using cumene in place of toluene.

$^1$H NMR (300 MHz, CHLOROFORM-d) δ ppm 1.22 (s, 3H) 1.24 (s, 3H) 2.21 (s, 3H) 2.81-2.92 (m, 1H) 3.85 (bs, 2H) 3.87 (s, 3H) 6.71 (s, 1H) 6.98-7.06 (m, 2H) 7.10-7.16 (m, 2H) 7.28 (s, 1H).

EI 322 (M$^+$), 334 (M+2).

Preparation Example 35

Synthesis of 2-(4-ethylbenzyl)phenol

1-Bromo-4-ethylbenzene (6.69 g, 0.036 mol) was added to a suspension of magnesium (17.2 g) and tetrahydrofuran (50 mL) and heated to reflux. Subsequently, a tetrahydrofuran (300 mL) solution of 1-bromo-4-ethylbenzene (97.9 g, 0.529 mol) was added for two hours at room temperature. After stirred at room temperature for 1.5 hours, the reaction mixture was cooled to 4° C. and a tetrahydrofuran (100 mL) solution of 2-benzyloxybenzaldehyde (100 g, 0.471 mol) was added for one hour. After stirred for two hours, the reaction mixture was poured into a saturated ammonium chloride aqueous solution. After the mixture was extracted with ethyl acetate, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=95:5) to obtain (2-benzyloxyphenyl)(4-ethylphenyl)methanol (152 g) as a colorless solid.

$^1$H-NMR (CDCl$_3$) δ 1.23 (t, J=7.6 Hz, 3H), 2.64 (q, J=7.6 Hz, 2H), 2.90 (d, J=5.6 Hz, 1H), 5.03 (s, 2H), 6.03 (d, 1H, J=5.6 Hz), 6.90-7.37 (m, 12H).

Then a mixture of (2-benzyloxyphenyl)(4-ethylphenyl)methanol (78.5 g), 10% palladium activated carbon (5.2 g), concentrated hydrochloric acid (10.4 mL) and methanol (850 mL) was stirred under hydrogen atmosphere at room temperature for 24 hours. After filtering off the insolubles, the filtrate was evaporated under reduced pressure and then, the residue was distilled under reduced pressure to obtain the title compound (56.8 g) as a colorless oil.

$^1$H-NMR (CDCl$_3$) δ ppm 1.21 (t, J=7.7 Hz, 3H), 2.62 (q, J=7.7 Hz, 2H), 4.00 (s, 2H), 4.64 (s, 1H), 6.77-7.18 (m, 8H).

EI 213 (M+H).

Preparation Example 36

Synthesis of 3-(4-ethylphenyloxy)-bromobenzene

A suspension of 3-bromophenol (2.3 g, 13.3 mmol), 4-ethylphenyl boronic acid (1.0 g, 6.67 mmol), molecular sieve 4 A (14.7 g), Cu(OAc)$_2$ (1.21 g, 6.67 mmol) and chloroform (25 mL) was stirred at room temperature for three minutes and added with triethylamine (3.6 mL) and pyridine (2.7 mL). The insolubles were filtered off with celite after the mixture was stirred for 15 hours. After the filtrate was concentrated, the residue was purified by silica gel column chromatography (hexane:ethyl acetate=95:5) to obtain 1.89 g of a colorless oily title compound.

EI 276 (M$^+$), 278 (M+2).

Preparation Example 37

Synthesis of 3-bromo-5-(4-ethoxybenzyl)pyridine

A tetrahydrofuran solution (25 mL) of 3,5-dibromo pyridine (5 g, 0.0211 mol) was added dropwise to a mixture of a tetrahydrofuran solution (21.1 mL) of 1M isopropyl magnesium chloride and tetrahydrofuran (10 mL) at 4° C. for 15 minutes. After stirred at room temperature for 2.5 hours, the reaction mixture was added with 4-ethoxybenzaldehyde (2.93 mL, 0.0211 mol) and stirred for further 1.5 hours. After the reaction mixture was added with water while cooled on ice and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=1:1) to obtain (5-bromopyridine-3-yl)(4-ethoxyphenyl)methanol (5.0 g, 77%) as a yellow oily substance.

Then, trifluoroacetic acid (12.5 mL, 0.162 mol) was added dropwise to a chloroform solution of (5-bromopyridine-3-yl)(4-ethoxyphenyl)methanol (2.5 g, 8.11 mmol) and Et$_3$SiH (5.1 mL, 40.6 mmol) at 4° C. and stirred at room temperature for 2.5 hours. The reaction mixture was added with water and extracted with chloroform. After washed with brine, the organic phase was dried with anhydrous magnesium sulfate. After the desiccant was filtered off, the residue obtained by evaporating the solvent under reduced pressure was purified by silica gel column chromatography (hexane:ethyl acetate=5:1) to obtain the title compound in a colorless needle form (1.83 g, 77%).

1H NMR (300 MHz, CHLOROFORM-D) δ ppm 1.41 (t, J=6.99 Hz, 3H) 3.90 (s, 2H) 4.02 (q, J=6.99 Hz, 2H) 6.85 (d, J=8.70 Hz, 2H) 7.07 (d, J=8.70 Hz, 2H) 7.59 (t, J=2.02 Hz, 1H) 8.40 (s, 1H) 8.52 (s, 1H)

ESI m/z=292 (M+H), 294 (M+2+H).

Preparation Example 38

Synthesis of 1-bromo-3-[(2E or Z)-3-(4-ethylphenyl) prop-2-en-1-yl]benzene

A mixture of (4-ethylbenzyl)triphenylphosphonium chloride (3.52 g, 8.44 mmol) and tetrahydrofuran (20 mL) was added with 2M lithium diisopropylamine (heptane/tetrahydrofuran/ethylbenzene solution, 4.2 mL, 8.4 mmol) while cooled on ice and stirred at room temperature for one hour. This solution was added dropwise to a tetrahydrofuran solution (10 mL) of (3-bromophenyl)acetaldehyde (0.56 g, 2.81 mmol), and stirred at room temperature for one hour. After the reaction mixture was added with a saturated ammonium chloride aqueous solution while cooled on ice and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:chloroform=20:1) to obtain a colorless oily title compound (0.41 g, 50%, E/Z mixture).

1H NMR (300 MHz, CHLOROFORM-d) δ ppm 1.17-1.30 (m, J=7.41, 7.41, 7.41 Hz, 3H) 2.56-2.72 (m, 2H) 3.47-3.68 (m, 2H) 5.70-6.63 (m, 2H) 7.04-7.46 (m, 8H).

EI 300, 302 (M+, M+2).

Preparation Example 39

Synthesis of 3-bromo-7-(4-methylbenzyl)-1-benzothiophene

An acetonitrile (30 mL) solution of 7-(4-methylbenzyl)-1-benzothiophene (1.24 g, 5.20 mmol) was added with N-bromosuccinimide (1.01 g, 5.72 mmol) and stirred at room temperature for two hours. The solvent was evaporated under reduced pressure and diluted with ethyl acetate. After washed with 20 wt % sodium thiosulfate aqueous solution and brine, the organic phase was dried with anhydrous magnesium sulfate. After the desiccant was filtered off, the residue obtained by evaporating the solvent under reduced pressure was purified by silica gel column chromatography (hexane:ethyl acetate=100:1-50:1) to obtain a colorless powdered title compound (0.92 g, 56%).

1H NMR (300 MHz, CHLOROFORM-d) δ ppm 2.31 (s, 3H) 4.12-4.26 (m, 2H) 7.07-7.23 (m, 5H) 7.37-7.50 (m, 2H) 7.72 (d, J=7.46 Hz, 1H).

EI 316, 318 (M+, M+2).

Example 1

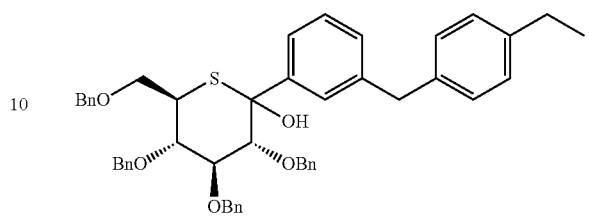

Synthesis of 2,3,4,6-tetra-O-benzyl-1-C-[3-(4-ethylbenzyl)]phenyl]-5-thio-D-glucopyranose A mixture of magnesium (55 mg, 2.25 mmol), 1-bromo-3-(4-ethylbenzyl)benzene (496 mg, 1.80 mmol; synthesized in reference to International Patent Publication WO0127128) and tetrahydrofuran (2.0 mL) was heated to reflux for one hour. The reaction mixture was further stirred at room temperature for one hour and then cooled to 0° C. To this solution, a tetrahydrofuran (5.0 mL) solution of 2,3,4,6-tetra-O-benzyl-5-thio-D-glucono-1,5-lactone (500 mg, 0.901 mmol) was added dropwise and stirred at room temperature for one hour. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=5:1) to obtain the title compound (440 mg, 65%) as a colorless oily substance.

1H NMR (300 MHz, CHLOROFORM-D) δ ppm 1.19 (t, J=7.6 Hz, 3H) 2.59 (q, J=7.6 Hz, 2H) 3.04 (s, 1H) 3.48-3.57 (m, 1H) 3.64 (dd, J=10.1, 2.7 Hz, 1H) 3.74 (d, J=10.1 Hz, 1H) 3.88-4.17 (m, 6H) 4.41 (d, J=10.1 Hz, 1H) 4.52 (s, 2H) 4.65 (d, J=10.7 Hz, 1H) 4.81-4.95 (m, 3H) 6.67-6.74 (m, 2H) 7.03-7.21 (m, 10H) 7.22-7.36 (m, 14H) 7.47-7.57 (m, 2H).

ESI m/z=773 (M+Na).

Example 2

Synthesis of 2,3,4,6-tetra-O-benzyl-1-C-[3-(4-ethylbenzyl)phenyl]-5-thio-D-glucopyranose via ate complex A mixture of 1-bromo-3-(4-ethylbenzyl)benzene (1.0 g, 3.63 mmol) and diethyl ether (10 mL) was cooled to −78° C. and added with 2.6 M n-butyllithium hexane solution (1.4 mL) in an Ar atmosphere. After stirred for 20 minutes, the reaction mixture was warmed to −20° C. and stirred for 45 minutes. This solution was added dropwise to a suspension of CuI (347 mg, 1.82 mmol) in diethyl ether (10 mL) using a canule. The suspension turned black during the dropwise addition and it was heated up to −9° C. After the dropwise addition, the suspension was stirred at −15° C. for 15 minutes, a diethyl ether (4.0 mL) solution of 2,3,4,6-tetra-O-benzyl-5-thio-D-glucono-1,5-lactone (671 mg, 1.21 mmol) was added dropwise, and the mixture was stirred for 20 minutes. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain the title compound (1.0 g) as a colorless oily substance. The NMR spectrum accorded with that of Example 1.

Example 3

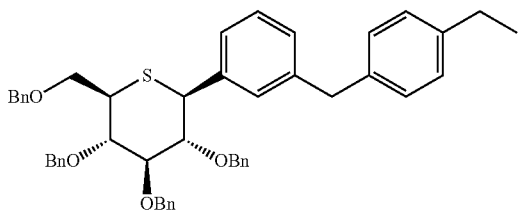

Synthesis of (1S)-1,5-anhydro-2,3,4,6-tetra-O-benzyl-1-[3-(4-ethylbenzyl)phenyl]-1-thio-D-glucitol A dichloromethane (20 mL) solution of 2,3,4,6-tetra-O-benzyl-1-C-[3-(4-ethylbenzyl)phenyl]-5-thio-D-glucopyranose (410 mg, 0.546 mmol) was added sequentially with Et$_3$SiH (0.523 mL, 3.28 mmol) and BF$_3$.Et$_2$O (0.276 mL, 2.18 mmol) at −18° C. and stirred for 0.5 hours. After the reaction mixture was added with a saturated sodium bicarbonate aqueous solution and extracted with chloroform, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=10:1) to obtain the title compound (250 mg, 62%) as a colorless powder substance.

$^1$H NMR (300 MHz, CHLOROFORM-d) δ ppm 1.19 (t, J=7.6 Hz, 3H) 2.59 (q, J=7.6 Hz, 2H) 3.05-3.16 (m, 1H) 3.53 (t, J=8.9 Hz, 1H) 3.67-3.99 (m, 8H) 4.47 (d, J=10.0 Hz, 1H) 4.53 (s, 2H) 4.60 (d, J=10.7 Hz, 1H) 4.85-4.94 (m, 3H) 6.62-6.69 (m, 2H) 7.00-7.20 (m, 10H) 7.22-7.36 (m, 16H).
ESI m/Z=757 (M+Na).
mp 100.0-102.5° C.

Example 4

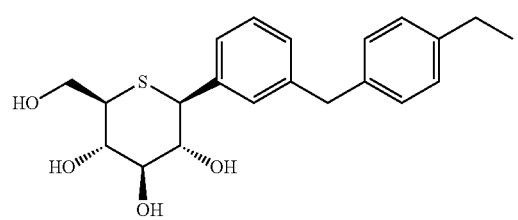

Synthesis of (1S)-1,5-anhydro-1-[3-(4-ethylbenzyl) phenyl]-1-thio-D-glucitol

1 M dichloromethane (4.08 mL) solution of BBr$_3$ was added dropwise to a dichloromethane (20 mL) solution of (1S)-1,5-anhydro-2,3,4,6-tetra-O-benzyl-1-[3-(4-ethylbenzyl)phenyl]-1-thio-D-glucitol (200 mg, 0.272 mmol) at −78° C. After stirred at this temperature for 2.5 hours, the mixture was added with methanol (5.0 mL) and pyridine (3.0 mL) sequentially. This mixture was warmed to room temperature and concentrated. The obtained residue was purified by silica gel column chromatography (chloroform:methanol=10:1) to obtain a colorless amorphous title compound (23 mg, 23%).

$^1$H NMR (300 MHz, METHANOL-d$_4$) δ ppm 1.19 (t, J=7.6 Hz, 3H) 2.58 (q, J=7.6 Hz, 2H) 2.95-3.03 (m, 1H) 3.20-3.28 (m, 1H) 3.60 (dd, J=10.3, 9.0 Hz, 1H) 3.70-3.78 (m, 3H) 3.88-3.98 (m, 3H) 7.09 (brs, 5H) 7.17-7.23 (m, 3H).
ESI m/z=397 (M+Na), 373 (M−H).

Example 5

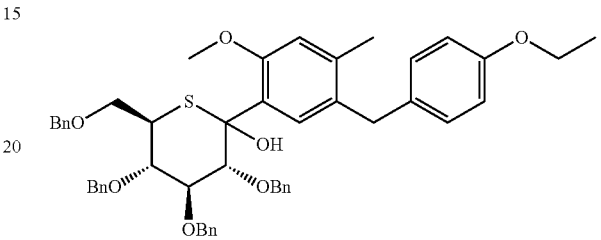

Synthesis of 2,3,4,6-tetra-O-benzyl-1-C-[2-methoxy-4-methyl-(4-ethoxybenzyl)phenyl]-5-thio-D-glucopyranose Five drops of 1,2-dibromoethane were added to a mixture of magnesium (41 mg, 1.67 mmol), 1-bromo-3-(4-ethoxybenzyl)-6-methoxy-4-methylbenzene (0.51 g, 1.51 mmol) and tetrahydrofuran (2 mL). After heated to reflux for one hour, this mixture was allowed to stand still to room temperature to prepare a Grignard reagent. A tetrahydrofuran solution (1.40 mL) of 1.0 M i-propyl magnesium chloride and the prepared Grignard reagent were added dropwise sequentially to a tetrahydrofuran (5 mL) solution of 2,3,4,6-tetra-O-benzyl-5-thio-D-glucono-1,5-lactone (0.76 g, 1.38 mmol) while cooled on ice and the mixture was stirred for 30 minutes. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain (0.76 g, 68%) a yellow oily title compound.

$^1$H NMR (300 MHz, CHLOROFORM-d) δ ppm 1.37 (t, J=6.92 Hz, 3H) 2.21 (s, 3H) 3.51-4.20 (m, 12H) 3.85-3.89 (m, 3H) 4.51 (s, 2H) 4.65 (d, J=10.72 Hz, 1H) 4.71 (d, J=5.75 Hz, 1H) 4.78-4.99 (m, 3H) 6.59-7.43 (m, 26H)

Example 6

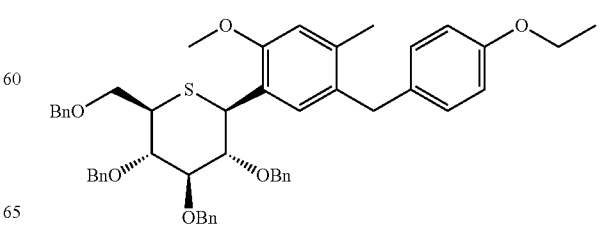

Synthesis of (1S)-1,5-anhydro-2,3,4,6-tetra-O-benzyl-1-[2-methoxy-4-methyl-5-(4-ethoxybenzyl)phenyl]-1-thio-D-glucitol An acetonitrile (18 mL) solution of 2,3,4,6-tetra-O-benzyl-1-C-[2-methoxy-4-methyl-5-(4-ethoxybenzyl)phenyl]-5-thio-D-glucopyranose (840 mg, 1.04 mmol) was added sequentially with Et$_3$SiH (0.415 mL, 2.60 mmol) and BF$_3$.Et$_2$O (0.198 mL, 1.56 mmol) at −18° C. and stirred for an hour. After the reaction mixture was added with a saturated sodium bicarbonate aqueous solution and extracted with ethyl acetate, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=4:1) to obtain the title compound (640 mg, 77%).

$^1$H NMR (600 MHz, CHLOROFORM-d) δ ppm 1.35 (t, J=6.88 Hz, 3H) 2.21 (s, 3H) 3.02-3.21 (m, 1H) 3.55 (t, J=9.40 Hz, 1H) 3.71 (s, 1H) 3.74-3.97 (m, 10H) 4.01 (s, 1H) 4.45-4.56 (m, 3H) 4.60 (d, J=10.55 Hz, 2H) 4.86 (s, 2H) 4.90 (d, J=10.55 Hz, 1H) 6.58-6.76 (m, 5H) 6.90 (d, J=7.34 Hz, 1H) 7.09-7.19 (m, 5H) 7.23-7.35 (m, 15H).

ESI m/z=812 (M+NH$_4$).

Example 7

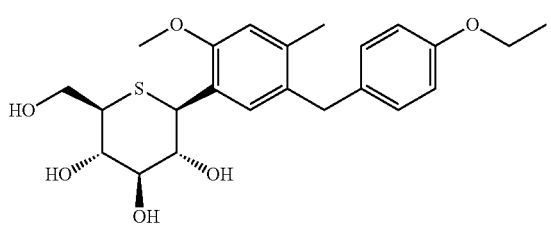

Synthesis of (1S)-1,5-anhydro-1-[3-(4-ethoxybenzyl)-6-methoxy-4-methylphenyl]-1-thio-D-glucitol A mixture of (1S)-1,5-anhydro-2,3,4,6-tetra-O-benzyl-1-[2-methoxy-4-methyl-5-(4-ethoxybenzyl)phenyl]-1-thio-D-glucitol (630 mg, 0.792 mmol), 20% palladium hydroxide on activated carbon (650 mg) and ethyl acetate (10 mL)-ethanol (10 mL) was stirred under hydrogen atmosphere at room temperature for 66 hours. The insolubles in the reaction mixture were filtered off with celite and the filtrate was concentrated. The obtained residue was purified by silica gel column chromatography (chloroform:methanol=10:1) to obtain a colorless powdery title compound (280 mg, 81%) as 0.5 hydrate.

1H NMR (600 MHz, METHANOL-d$_4$) δ ppm 1.35 (t, J=6.9 Hz, 3H) 2.17 (s, 3H) 2.92-3.01 (m, 1H) 3.24 (t, J=8.71 Hz, 1H) 3.54-3.60 (m, 1H) 3.72 (dd, J=11.5, 6.4 Hz, 1H) 3.81 (s, 3H) 3.83 (s, 2H) 3.94 (dd, J=11.5, 3.7 Hz, 1H) 3.97 (q, J=6.9 Hz, 2H) 4.33 (s, 1H) 6.77 (d, J=8.3 Hz, 2H) 6.76 (s, 1H) 6.99 (d, J=8.3 Hz, 2H) 7.10 (s, 1H). ESI m/z=452 (M+NH4+), 493 (M+CH3CO2-). mp 155.0-157.0° C. Anal. Calcd for C$_{23}$H$_{30}$O$_6$S.0.5H$_2$O: C, 62.28; H, 7.06. Found: C, 62.39; H, 7.10.

Example 8

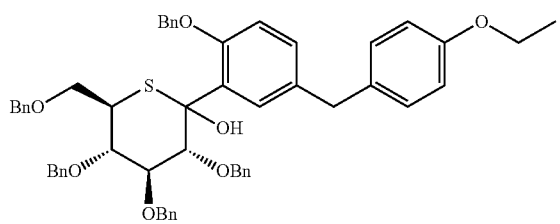

Synthesis of 2,3,4,6-tetra-O-benzyl-1-C-[2-(benzyloxy)-5-(4-ethoxybenzyl)phenyl]-5-thio-D-glucopyranose Three drops of 1,2-dibromoethane were added to a mixture of magnesium (175 mg, 7.20 mmol), 1-(benzyloxy)-2-bromo-4-(4-ethoxybenzyl)benzene (2.29 g, 5.76 mmol) and tetrahydrofuran (6.0 mL) and this mixture was heated to reflux for one hour. The reaction mixture was cooled to room temperature, and tetrahydrofuran (5.0 mL) of 2,3,4,6-tetra-O-benzyl-5-thio-D-glucono-1,5-lactone (1.6 g, 2.9 mmol) was added dropwise to this solution and stirred at room temperature for one hour. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=6:1) to obtain the title compound (1.48 g, 59%) as a pale yellow powder.

$^1$H NMR (300 MHz, CHLOROFORM-d) δ ppm 1.38 (t, J=7.0 Hz, 3H) 3.48-3.71 (m, 2H) 3.77-4.10 (m, 9H) 4.51 (brs, 2H) 4.59-4.74 (m, 2H) 4.77-4.94 (m, 3H) 5.09 (s, 2H) 6.64-7.40 (m, 32H).

ESI m/z=895 (M+Na).

Example 9

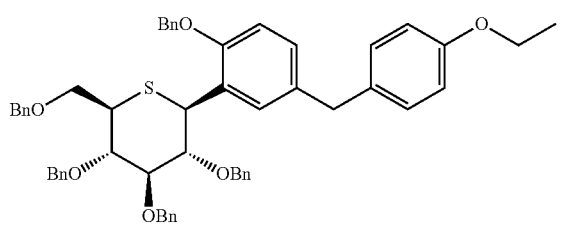

Synthesis of (1S)-1,5-anhydro-2,3,4,6-tetra-O-benzyl-1-[2-(benzyloxy)-5-(4-ethoxybenzyl)phenyl]-1-thio-D-glucitol A chloroform (8.0 mL) and acetonitrile (8.0 mL) solution of 2,3,4,6-tetra-O-benzyl-1-C-[2-(benzyloxy)-5-(4-ethoxybenzyl)phenyl]-5-thio-D-glucopyranose (850 mg, 0.974 mmol) was added sequentially with Et₃SiH (0.933 mL, 5.84 mmol) and BF₃·Et₂O (0.494 mL, 3.90 mmol) at −20° C. and stirred for one hour. After the reaction mixture was added with a saturated sodium bicarbonate aqueous solution and extracted with chloroform, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=8:1) to obtain the title compound (810 mg, 97%) as a colorless powder substance.

¹H NMR (300 MHz, CHLOROFORM-d) δ ppm 1.36 (t, J=7.0 Hz, 3H) 3.04-3.18 (m, 1H) 3.54 (t, J=8.4 Hz, 1H) 3.65-3.76 (m, 1H) 3.77-4.06 (m, 8H) 4.40-4.73 (m, 5H) 4.83-5.12 (m, 5H) 6.62-6.87 (m, 5H) 6.92-7.46 (m, 27H).

ESI m/z=879 (M+Na)

Example 10

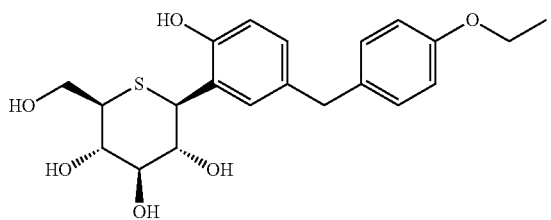

Synthesis of (1S)-1,5-anhydro-1-[5-(4-ethylbenzyl)-2-hydroxy phenyl]-1-thio-D-glucitol A mixture of (1S)-1,5-anhydro-2,3,4,6-tetra-O-benzyl-1-[2-(benzyloxy)-5-(4-ethoxybenzyl)phenyl]-1-thio-D-glucitol (810 mg, 0.954 mmol), 20% palladium hydroxide on activated carbon (800 mg) and ethyl acetate (5.0 mL)-ethanol (5.0 mL) was stirred under hydrogen atmosphere at room temperature for 46 hours. The insolubles of reaction mixture were filtered off with celite and the filtrate was concentrated. The obtained residue was purified by silica gel column chromatography (chloroform:methanol=10:1 to 5:1) to obtain a colorless powdery title compound (202 mg, 53%) as 0.7 hydrate.

¹H NMR (300 MHz, METHANOL-d₄) δ ppm 1.37 (t, J=7.0 Hz, 3H) 2.94-3.05 (m, 1H) 3.22-3.29 (m, 1H) 3.60 (m, 1H) 3.69-3.88 (m, 4H) 3.90-4.04 (m, 3H) 4.33 (d, J=10.6 Hz, 1H) 6.71 (d, J=8.2 Hz, 1H) 6.76-6.90 (m, 3H) 7.03-7.15 (m, 3H). ESI m/z=429 (M+Na), 405 (M−H). mp 145.0-150.0° C. Anal. Calcd for C₂₂H₂₈O₆S0.7H₂O: C, 61.00; H, 6.86. Found: C, 60.81; H, 6.89.

Example 11

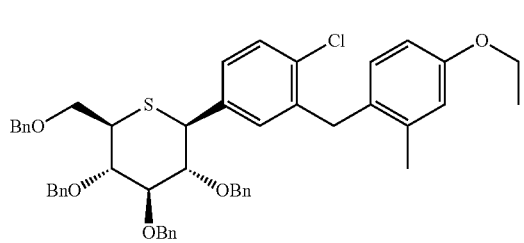

Synthesis of (1S)-1,5-anhydro-2,3,4,6-tetra-O-benzyl-1-[4-chloro-3-(4-ethoxy-2-methylbenzyl)phenyl]-1-thio-D-glucitol Five drops of 1,2-dibromoethane were added to a mixture of magnesium (1.11 g, 45.7 mmol), 2-(5-bromo-2-chlorophenyl)-1,3-dioxolane (9.64 g, 36.5 mmol) and tetrahydrofuran (20 mL) and this mixture was heated to reflux for two hours. The reaction mixture was cooled to room temperature, and tetrahydrofuran (15 mL) of 2,3,4,6-tetra-O-benzyl-5-thio-D-glucono-1,5-lactone (10.14 g, 36.5 mmol) was added dropwise to this solution and stirred at room temperature for 30 minutes. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=4:1 to 3:1) to obtain a colorless amorphous 2,3,4,6-tetra-O-benzyl-1-C-[4-chloro-3-(1,3-dioxolan-2-yl)phenyl]-5-thio-D-glucopyranose (11.81 g, 87%).

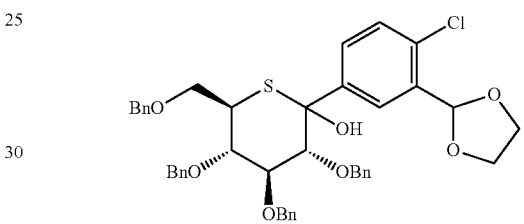

¹H NMR (300 MHz, CHLOROFORM-d) δ ppm 3.06 (s, 1H) 3.47-3.58 (m, 1H) 3.64 (dd, J=10.0, 2.9 Hz, 1H) 3.83-4.21 (m, 9H) 4.48-4.56 (m, 3H) 4.66 (d, J=10.6 Hz, 1H) 4.82-4.97 (m, 3H) 6.15 (s, 1H) 6.77 (dd, J=7.9, 1.5 Hz, 2H) 7.08-7.21 (m, 5H) 7.23-7.37 (m, 14H) 7.55 (dd, J=8.4, 2.5 Hz, 1H) 7.92 (d, J=2.5 Hz, 1H).

Then, 6M hydrochloric acid (120 mL) was added to a tetrahydrofuran (50 mL) solution of 2,3,4,6-tetra-O-benzyl-1-C-[4-chloro-3-(1,3-dioxolane-2-yl)phenyl]-5-thio-D-glucopyranose (6.01 g, 8.12 mmol) while ice-cooled, and stirred at room temperature for two days. The reaction mixture was added with an iced water and extracted with ethyl acetate and the organic phase was washed with a saturated sodium bicarbonate aqueous solution, brine and dried with anhydrous magnesium sulfate. After the desiccant was filtered off, the residue obtained by evaporating the solvent under reduced pressure was purified by silica gel column chromatography (hexane:ethyl acetate=3:1) to obtain colorless amorphous 2,3,4,6-tetra-O-benzyl-1-C-(4-chloro-3-formylphenyl)-5-thio-D-glucopyranose (4.53 g, 80%).

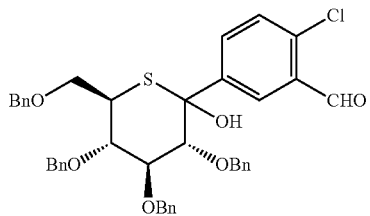

¹H NMR (300 MHz, CHLOROFORM-d) δ ppm 3.14 (s, 1H) 3.43-3.58 (m, 1H) 3.63 (dd, J=10.0, 2.6 Hz, 1H) 3.87-

4.16 (m, 5H) 4.45-4.72 (m, 4H) 4.80-5.05 (m, 3H) 6.73 (d, J=7.8 Hz, 2H) 7.02-7.43 (m, 19H) 7.74 (dd, J=8.4, 2.5 Hz, 1H) 8.06 (d, J=2.5 Hz, 1H) 10.39 (s, 1H).

Then, 2.6 M n-butyllithium hexane solution (1.6 mL) was added to a mixture of 1-bromo-4-ethoxy-2-methylbenzene (0.94 g, 4.37 mmol) and tetrahydrofuran (12 mL) at −78° C. After stirred for one hour, the mixture was added with a tetrahydrofuran (10 mL) solution of 2,3,4,6-tetra-O-benzyl-1-C-(4-chloro-3-formylphenyl)-5-thio-D-glucopyranose (1.52 g, 2.18 mmol), and, further stirred for 20 minutes, and the reaction mixture was warmed to room temperature. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=2:1) to obtain 2,3,4,6-tetra-O-benzyl-1-C-{4-chloro-3-[(4-ethoxy-2-methylphenyl)(hydroxy)methyl]phenyl}-5-thio-D-glucopyranose (1.72 g, 95%) as a yellow amorphous diastereomer mixture.

Then, an acetonitrile (20 mL) solution of 2,3,4,6-tetra-O-benzyl-1-C-(4-chloro-3-[(4-ethoxy-2-methylphenyl)(hydroxy)methyl]phenyl)-5-thio-D-glucopyranose (1.72 g, 2.06 mmol) was added sequentially with $Et_3SiH$ (1.98 mL, 12.4 mmol) and $BF_3.Et_2O$ (1.04 mL, 8.27 mmol) while cooled on ice. After stirred for one hour, the reaction mixture was warmed up to room temperature and stirred for three hours. After the reaction mixture was added with a saturated sodium carbonate aqueous solution and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=5:1) to obtain (1S)-1,5-anhydro-2,3,4,6-tetra-O-benzyl-1-[4-chloro-3-(4-ethoxy-2-methylbenzyl)phenyl]-1-thio-D-glucitol (1.01 g, 61%) as a colorless powder.

1H NMR (300 MHz, CHLOROFORM-d) δ ppm 1.40 (t, J=7.0 Hz, 3H) 2.14 (s, 3H) 3.01-3.12 (m, 1H) 3.48 (t, J=8.9 Hz, 1H) 3.65-4.06 (m, 10H) 4.46-4.61 (m, 4H) 4.80-4.91 (m, 3H) 6.58 (dd, J=8.2, 2.5 Hz, 1H) 6.68-6.76 (m, 2H) 6.81 (d, J=8.4 Hz, 1H) 6.98 (d, J=2.2 Hz, 1H) 7.10-7.39 (m, 21H).

Example 12

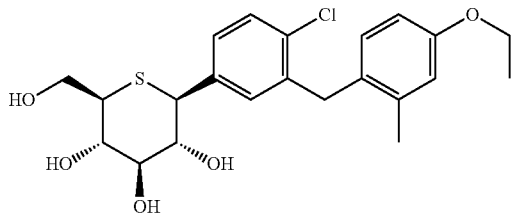

Synthesis of (1S)-1,5-anhydro-1-[4-chloro-3-(4-ethoxy-2-methylbenzyl)phenyl]-1-thio-D-glucitol An anisole (10 mL) solution of (1S)-1,5-anhydro-2,3,4,6-tetra-O-benzyl-1-[4-chloro-3-(4-ethoxy-2-methylbenzyl)phenyl]-1-thio-D-glucitol (0.99 g, 1.23 mmol) was added with $AlCl_3$ (0.83 g, 6.19 mmol) at room temperature and stirred for 30 minutes. The reaction mixture was added with an iced water and extracted with ethyl acetate and the organic phase was washed with 1M hydrochloric acid, a saturated sodium bicarbonate aqueous solution, brine and dried with anhydrous magnesium sulfate. After the desiccant was filtered off, the residue obtained by evaporating the solvent under reduced pressure was purified by silica gel column chromatography (chloroform:methanol=10:1) to obtain a colorless amorphous title compound (55 mg, 10%).

$^1$H NMR (300 MHz, METHANOL-$d_4$) δ ppm 1.37 (t, J=6.9 Hz, 3H) 2.17 (s, 3H) 2.90-3.01 (m, 1H) 3.14-3.24 (m, 1H) 3.54 (dd, J=10.3, 9.2 Hz, 1H) 3.60-3.76 (m, 3H) 3.86-4.06 (m, 5H) 6.66 (dd, J=8.6, 2.7 Hz, 1H) 6.75 (d, J=3.0 Hz, 1H) 6.85-6.95 (m, 2H) 7.19 (dd, J=8.2, 2.2 Hz, 1H) 7.35 (d, J=8.2 Hz, 1H).

ESI m/z=461 (M+Na), 437 (M−H).

Example 13

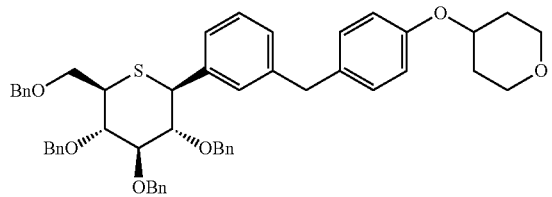

Synthesis of (1S)-1,5-anhydro-2,3,4,6-tetra-O-benzyl-1-[3-[4-(4-tetrahydropyranyloxy)benzyl]phenyl]-1-thio-D-glucitol 2.6 M n-butyllithium hexane solution (0.8 mL) was added to a mixture of 1-bromo-4-(4-tetrahydropyranyloxy)benzene (0.545 g, 2.12 mmol) and tetrahydrofuran (6 mL) at −78° C. After stirred for 1.5 hours, a tetrahydrofuran (8 mL) solution of 2,3,4,6-tetra-O-benzyl-1-C-(3-formylphenyl)-5-thio-D-glucopyranose (0.70 g, 1.06 mmol) was added and further stirred for three hours, and the reaction mixture was warmed to room temperature. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=2:1) to obtain 2,3,4,6-tetra-O-benzyl-1-C-[3-[(4-(4-tetrahydropyranyloxy)phenyl)(hydroxy)methyl]phenyl]-5-thio-D-glucopyranose (0.67 g, 76%).

Then, an acetonitrile (8 mL) solution of 2,3,4,6-tetra-O-benzyl-1-C-[3-[(4-(4-tetrahydropyranyloxy)phenyl)(hydroxy)methyl]phenyl]-5-thio-D-glucopyranose (0.67 g, 0.802 mmol) was added sequentially with $Et_3SiH$ (0.78 mL, 4.90 mmol) and $BF_3.Et_2O$ (0.41 mL, 3.27 mmol) at −15° C. After stirred for one hour, the reaction mixture was warmed up to room temperature and stirred for three hours. After the reaction mixture was added with a saturated sodium carbonate aqueous solution and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain a colorless powdered title compound (0.37 g, 57%).

1H NMR (300 MHz, CHLOROFORM-d) δ ppm 1.66-1.81 (m, 2H) 1.88-2.02 (m, 2H) 3.05-3.15 (m, 1H) 3.47-3.59 (m, 3H) 3.64-4.00 (m, 10H) 4.33-4.42 (m, 1H) 4.46 (d, J=9.95 Hz, 1H) 4.52 (s, 2H) 4.60 (d, J=10.41 Hz, 1H) 4.84-4.93 (m, 3H) 6.60-6.67 (m, 2H) 6.72-6.79 (m, 2H) 6.99-7.19 (m, 8H) 7.20-7.35 (m, 16H). ESI m/Z=824 (M+NH4).

Example 14

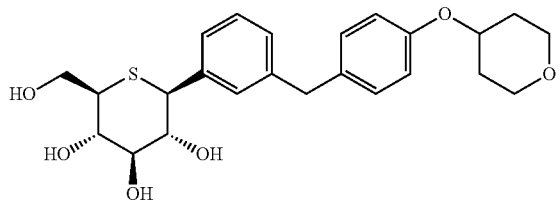

Synthesis of (1S)-1,5-anhydro-1-[3-[4-(4-tetrahydropyranyloxy)benzyl]phenyl]-1-thio-D-glucitol An amorphous title compound (18 mg) was obtained by a similar method as in Example 7 from (1S)-1,5-anhydro-2,3,4,6-tetra-O-benzyl-1-[3-[4-(4-tetrahydropyranyloxy)benzyl]phenyl]-1-thio-D-glucitol.

Example 15

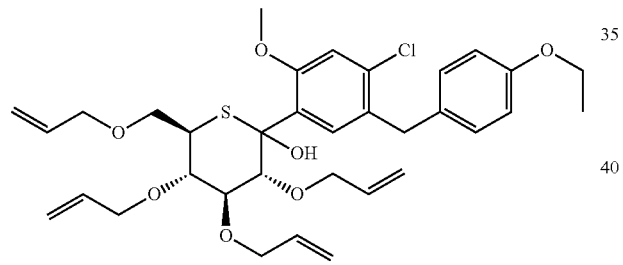

Synthesis of 2,3,4,6-tetra-O-allyl-1-C-[4-chloro-5-(4-ethoxybenzyl)-2-methoxyphenyl]-5-thio-D-glucopyranose Three drops of 1,2-dibromoethane were added to a mixture of magnesium (171 mg, 7.03 mmol), 1-bromo-4-chloro-3-(4-ethoxybenzyl)-6-methoxybenzene (2.0 g, 5.62 mmol) and tetrahydrofuran (5 mL) and this mixture was heated to reflux for 30 minutes. The reaction mixture was cooled to room temperature, and tetrahydrofuran (20 mL) of 2,3,4,6-tetra-O-allyl-5-thio-D-glucono-1,5-lactone (1.5 g, 4.22 mmol) was added dropwise to this solution and stirred at room temperature for two hours. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=6:1→5:1) to obtain the title compound (1.41 g, 53%) as a pale yellow oil.

$^1$H NMR (300 MHz, CHLOROFORM-d) δ ppm 1.39 (t, J=7.0 Hz, 3H) 3.36-3.47 (m, 1H) 3.49-4.10 (m, 17H) 4.10-4.44 (m, 4H) 4.84-4.97 (m, 2H) 5.08-5.35 (m, 5H) 5.42-5.60 (m, 1H) 5.75-6.07 (m, 3H) 6.78 (d, J=8.6 Hz, 2H) 6.92 (s, 1H) 7.03 (d, J=8.6 Hz, 2H) 7.32 (brs, 1H)
ESI m/z=653 (M+Na), 655 (M+2+Na).

Example 16

Synthesis of (1S)-1,5-anhydro-2,3,4,6-tetra-O-allyl-1-[4-chloro-5-(4-ethoxybenzyl)-2-methoxyphenyl]-1-thio-D-glucitol A chloroform (20 mL)-acetonitrile (20 mL) solution of 2,3,4,6-tetra-O-allyl-1-C-[4-chloro-5-(4-ethoxybenzyl)-2-methoxyphenyl]-5-thio-D-glucopyranose (1.41 g, 2.23 mmol) was added sequentially with Et$_3$SiH (2.16 mL, 13.4 mmol) and BF$_3$.Et$_2$O (1.13 mL, 8.92 mmol) at −15° C. and stirred for one hour. After the reaction mixture was added with a saturated sodium bicarbonate aqueous solution and extracted with chloroform, the organic phase was washed with brine and then dried with anhydrous magnesium sulfate. After the desiccant was filtered off, the residue obtained by evaporating the solvent under reduced pressure was purified by silica gel column chromatography (hexane:ethyl acetate=10:1) to obtain the title compound (895 mg, 65%) as a colorless powder substance.

$^1$H NMR (300 MHz, CHLOROFORM-d) δ ppm 1.39 (t, J=7.0 Hz, 3H) 2.95-3.04 (m, 1H) 3.21-3.30 (m, 1H) 3.41-3.79 (m, 5H) 3.81 (s, 3H) 3.84-4.20 (m, 8H) 4.25-4.42 (m, 4H) 4.81-4.91 (m, 2H) 5.09-5.33 (m, 6H) 5.34-5.52 (m, 1H) 5.79-6.04 (m, 3H) 6.78 (d, J=8.9 Hz, 2H) 6.87 (s, 1H) 7.03 (d, J=8.9 Hz, 2H) 7.21 (brs, 1H)
ESI m/z=637 (M+Na), 639 (M+2+Na).

Example 17

Synthesis of (1S)-1,5-anhydro-1-[4-chloro-5-(4-ethoxybenzyl)-2-methoxyphenyl]-1-thio-D-glucitol

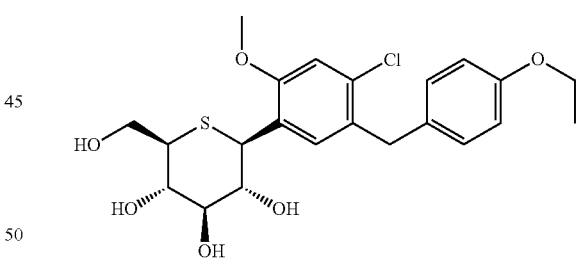

A mixture of (1S)-1,5-anhydro-2,3,4,6-tetra-O-allyl-1-[4-chloro-5-(4-ethoxybenzyl)-2-methoxyphenyl]-1-thio-D-glucitol (100 mg, 0.163 mmol), tetrakis(triphenylphosphine)palladium (38 mg, 0.0325 mmol), N,N'-dimethyl barbituric acid (203 mg, 1.3 mmol) and tetrahydrofuran (1.0 mL) was stirred under Ar atmosphere at 90° C. for 1.5 hours. After the reaction mixture was cooled to room temperature, added with a saturated sodium carbonate aqueous solution and extracted with ethyl acetate, the organic phase was washed with brine and then dried with anhydrous magnesium sulfate. After the desiccant was filtered off, the residue obtained by evaporating the solvent under reduced pressure was purified by silica gel column chromatography (chloroform:methanol=10:1→5:1) to obtain the title compound (63 mg, 85%) as a colorless powder substance.

1H NMR (600 MHz, METHANOL-d$_4$) δ ppm 1.35 (t, J=6.9 Hz, 3H) 2.92-3.00 (m, 1H) 3.22 (t, J=8.9 Hz, 1H) 3.53-3.59 (m, 1H) 3.72 (dd, J=11.7, 6.7 Hz, 1H) 3.82 (s, 3H) 3.88-3.95 (m, 3H) 3.99 (q, J=6.9 Hz, 2H) 6.79 (d, J=8.7 Hz, 2H) 6.98 (s, 1H) 7.06 (d, J=8.71 Hz, 2H) 7.20 (s, 1H). ESI m/z=477 (M+Na), 479 (M+2+Na), 453 (M–H), 455 (M+2–H). mp 177.0-179.0° C.

Example 18

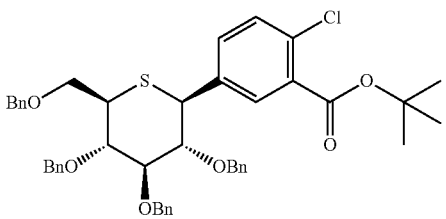

Synthesis of (1S)-1,5-anhydro-2,3,4,6-tetra-O-benzyl-1-[4-chloro-3-(t-butoxycarbonyl)phenyl]-1-thio-D-glucitol 2.6 M n-butyllithium hexane solution (1.72 mL) was added to a mixture of 1.0 M i-propyl magnesium bromide tetrahydrofuran solution (2.23 mL) and tetrahydrofuran (9 mL) at –5° C. After stirred for 0.5 hours, the reaction mixture was cooled to –78° C. and added with a tetrahydrofuran (4.0 mL) solution of t-butyl 5-bromo-2-chlorobenzoate (542 mg, 1.86 mmol). After stirred for one hour, a tetrahydrofuran (3.0 mL) solution of 2,3,4,6-tetra-O-benzyl-5-thio-D-glucono-1,5-lactone (430 mg, 0.798 mmol) was added and further stirred for 15 minutes. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=5:1) to obtain 2,3,4,6-tetra-O-benzyl-1-C-[4-chloro-3-(t-butoxycarbonyl)phenyl]-5-thio-D-glucopyranose (60 mg, 10%).

ESI m/z=789 (M+Na), 791 (M+2+Na)

Then, a chloroform (1.0 mL)-acetonitrile (1.0 mL) solution of 2,3,4,6-tetra-O-benzyl-1-C-[4-chloro-3-(t-butoxycarbonyl)phenyl]-5-thio-D-glucopyranose (60 mg, 0.0782 mmol) was added sequentially with Et$_3$SiH (0.031 mL, 0.195 mmol) and BF$_3$.Et$_2$O (0.015 mL, 0.117 mmol) at –40° C. After stirred for 1.5 hours, the reaction mixture was added with a saturated sodium carbonate aqueous solution and an organic solvent was concentrated under reduced pressure. After the residue was extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane: ethyl acetate=5:1) to obtain the title compound (26 mg, 44%).

1H NMR (300 MHz, CHLOROFORM-d) δ ppm 1.61 (s, 9H) 3.06-3.21 (m, 1H) 3.51-3.64 (m, 1H) 3.66-3.77 (m, 1H) 3.78-4.06 (m, 5H) 4.48-4.67 (m, 4H) 4.84-4.95 (m, 3H) 6.75 (dd, J=7.54, 1.79 Hz, 2H) 7.08-7.20 (m, 5H) 7.24-7.46 (m, 15H) 7.77 (d, J=2.02 Hz, 1H). ESI m/z=768 (M+Na), 770 (M+2+Na).

Example 19

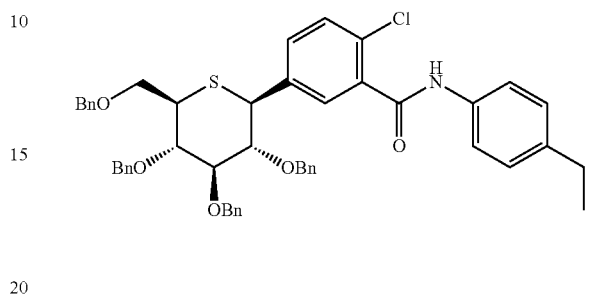

Synthesis of (1S)-1,5-anhydro-2,3,4,6-tetra-O-benzyl-1-[4-chloro-3-[[(4-ethylphenyl)amino]carbonyl]phenyl]-1-thio-D-glucitol After a tetrahydrofuran (2.0 mL) solution of (1S)-1,5-anhydro-1-[4-chloro-5-(4-ethoxybenzyl)-2-methoxyphenyl]-1-thio-D-glucitol (30 mg, 0.040 mmol) was added with concentrated hydrochloric acid (1.0 mL), the reaction mixture was stirred at room temperature for 24 hours and at 40° C. for two hours and then added with ethyl acetate. This was washed with water, brine and dried with anhydrous magnesium sulfate. After the desiccant was filtered off, the solvent was evaporated the under reduced pressure to obtain (1S)-1,5-anhydro-2,3,4,6-tetra-O-benzyl-1-[4-chloro-3-carboxyphenyl]-1-thio-D-glucitol.

Then, 1-ethyl-3-(3-dimethylaminopropyl)carbodiimide hydrochloride (13 mg, 0.069 mmol) and 1-hydroxybenzotriazole (9 mg, 0.069 mmol) were added to a chloroform solution of (1S)-1,5-anhydro-2,3,4,6-tetra-O-benzyl-1-[4-chloro-3-carboxyphenyl]-1-thio-D-glucitol and 4-ethylaniline (13 mg, 0.104 mmol). After stirred at room temperature for 21 hours, the reaction mixture was diluted with chloroform and the organic phase was washed with a saturated sodium bicarbonate aqueous solution, brine and dried with anhydrous magnesium sulfate. After the desiccant was filtered off, the residue obtained by evaporating the solvent under reduced pressure was purified by silica gel column chromatography (hexane:ethyl acetate=4:1) to obtain the above anilide compound (22 mg).

1H NMR (300 MHz, CHLOROFORM-d) δ ppm 1.26 (t, J=7.15 Hz, 3H) 2.65 (q, J=7.67 Hz, 1H) 3.06-3.24 (m, 1H) 3.50-3.61 (m, 1H) 3.71 (dd, J=9.87, 3.03 Hz, 1H) 3.78-4.09 (m, 6H) 4.52 (s, 2H) 4.62 (t, J=10.34 Hz, 2H) 4.84-4.98 (m, 3H) 6.75-6.85 (m, 2H) 7.08-7.56 (m, 25H) 7.72 (d, J=2.02 Hz, 1H).

ESI m/Z=769 (M−H). pale yellow powder.

Example 20

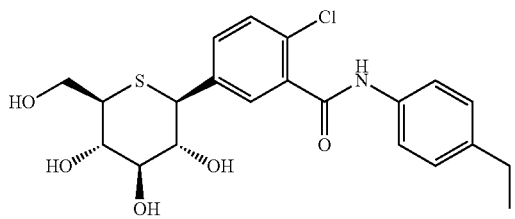

Synthesis of (1S)-1,5-anhydro-1-[4-chloro-3-[[(4-ethylphenyl)amino]carbonyl]phenyl]-1-thio-D-glucitol Trifluoromethane sulfonic acid (0.1 mL) was added to a mixture of (1S)-1,5-anhydro-2,3,4,6-tetra-O-benzyl-1-[4-chloro-3-[[(4-ethylphenyl)amino]carbonyl]phenyl]-1-thio-D-glucitol (20 mg, 0.025 mmol), trifluoroacetic acid (0.5 mL), dimethylsulfide (0.3 mL), m-cresol (0.08 mL) and ethanedithiol (0.02 mL) at −15° C. After stirred for 15 minutes, the mixture was added with a saturated sodium bicarbonate aqueous solution and extracted with ethyl acetate. The organic layer was washed with a saturated sodium bicarbonate aqueous solution, brine and dried with anhydrous magnesium sulfate. After the desiccant was filtered off, the residue obtained by evaporating the solvent under reduced pressure was purified by silica gel column chromatography (chloroform:methanol=10:1) to obtain a colorless powdered title compound (6 mg, 54%).

1H NMR (600 MHz, METHANOL-d$_4$) δ ppm 1.23 (t, J=7.57 Hz, 3H) 2.64 (q, J=7.79 Hz, 2H) 3.00-3.07 (m, 1H) 3.27 (t, J=8.71 Hz, 1H) 3.59-3.64 (m, 1H) 3.73-3.82 (m, 2H) 3.89 (d, J=10.09 Hz, 1H) 3.95 (dd, J=11.69, 3.44 Hz, 1H) 7.20 (d, J=8.25 Hz, 2H) 7.47 (s, 2H) 7.53 (s, 1H) 7.56 (d, J=8.71 Hz, 2H). ESI m/Z=438 (M+Na), 440 (M+2+Na). colorless powder.

Example 21

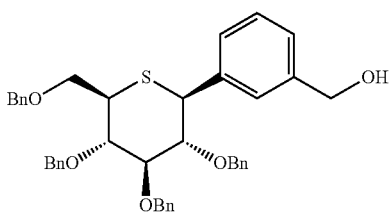

Synthesis of (1S)-1,5-anhydro-2,3,4,6-tetra-O-benzyl-1-[3-(hydroxymethyl)phenyl]-1-thio-D-glucitol A chloroform (35 mL)-acetonitrile (35 mL) solution of 2,3,4,6-tetra-O-benzyl-1-C-(3-formylphenyl)-5-thio-D-glucopyranose (4.0 g, 6.05 mmol) was added sequentially with Et$_3$SiH (5.8 mL, 36.3 mmol) and BF$_3$.Et$_2$O (3.1 mL, 24.2 mmol) at −15° C. After stirred for 1.5 hours, the reaction mixture was added with a saturated sodium bicarbonate aqueous solution and extracted with chloroform, the organic phase was washed with brine and dried with anhydrous magnesium sulfate. After the desiccant was filtered off, the solids obtained by evaporating the solvent under reduced pressure were washed with hexane:ethyl acetate=10:1 to obtain the title compound (3.2 g, 77%) as a colorless powder substance.

1H NMR (300 MHz, CHLOROFORM-d) δ ppm 3.07-3.18 (m, 1H) 3.55 (t, 1H) 3.72 (dd, 1H) 3.78-4.01 (m, 5H) 4.46-4.69 (m, 6H) 4.87-4.96 (m, 3H) 6.69 (dd, J=7.69, 1.48 Hz, 2H) 7.07-7.45 (m, 22H).

Example 22

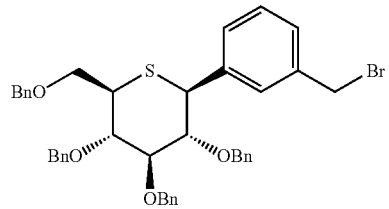

Synthesis of (1S)-1,5-anhydro-2,3,4,6-tetra-O-benzyl-1-[3-(bromomethyl)phenyl]-1-thio-D-glucitol Methanesulfonyl chloride (0.018 mL) and triethylamine (0.021 mL) were added to a tetrahydrofuran (1.5 mL) solution of (1S)-1,5-anhydro-2,3,4,6-tetra-O-benzyl-1-[3-(hydroxymethyl)phenyl]-1-thio-D-glucitol (100 mg, 0.155 mmol) at 4° C. The reaction mixture was stirred at room temperature for three hours and diluted with ethyl acetate. After washed this with a saturated sodium bicarbonate aqueous solution and brine, this mixture was dried with anhydrous magnesium sulfate. After the desiccant was filtered off and the solvent was evaporated under reduced pressure to obtain (1S)-1,5-anhydro-2,3,4,6-tetra-O-benzyl-1-[3-(methanesulfonyloxymethyl)phenyl]-1-thio-D-glucitol (150 mg). Then, a mixture of (1S)-1,5-anhydro-2,3,4,6-tetra-O-benzyl-1-[3-(methanesulfonyloxymethyl)phenyl]-1-thio-D-glucitol (150 mg), LiBr (40 mg, 0.466 mmol) and acetone (3 mL) was stirred at room temperature for two hours. After the reaction mixture was concentrated, ethyl acetate and water were added. After organic layer was separated, it was washed with brine and dried with anhydrous magnesium sulfate. After the desiccant was filtered off, the residue obtained by evaporating the solvent under reduced pressure was purified by silica gel column chromatography (hexane:ethyl acetate=5:1) to obtain the title compound (70 mg; 64%).

1H NMR (300 MHz, CHLOROFORM-d) δ ppm 3.06-3.17 (m, 1H) 3.55 (t, J=8.94 Hz, 1H) 3.72 (dd, 1H) 3.78-4.02 (m, 5H) 4.41-4.65 (m, 6H) 4.85-4.96 (m, 3H) 6.66-6.72 (m, J=7.46, 2.02 Hz, 2H) 7.10-7.51 (m, 22H).

ESI m/z=726 (M+NH$_4^+$), 728 (M+2+NH$_4^+$)

Example 23

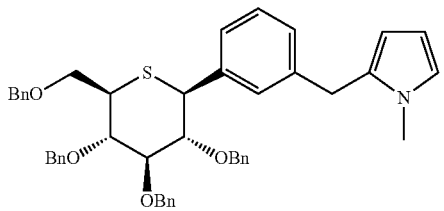

Synthesis of (1S)-1,5-anhydro-2,3,4,6-tetra-O-benzyl-1-[3-[(1-methyl-1H-pyrrol-2-yl)methyl]phenyl]-1-thio-D-glucitol A mixture of (1S)-1,5-anhydro-2,3,4,6-tetra-O-benzyl-1-[3-(bromomethyl)phenyl]-1-thio-D-glucitol (200 mg, 0.282 mmol), 1-methyl-2-(tributylstannyl)-1H-pyrrole (208 mg, 0.564 mmol), tris(dibenzylideneacetone)dipalladium (38 mg, 0.0423 mmol), 2(dicyclohexylphosphino)biphenyl (36 mg, 0.0987 mmol), KF (67 mg, 1.16 mmol), CsCO$_3$ (257 mg, 0.792 mmol) and 1,4-dioxan (5 mL) was stirred at 60° C. for eight hours. After insolubles are filtered off, the residue obtained by concentrating the filtrate was purified by silica gel column chromatography (hexane:ethyl acetate=5:1) to obtain the title compound (190 mg, 95%).

1H NMR (300 MHz, CHLOROFORM-d) δ ppm 3.04-3.16 (m, 1H) 3.32 (s, 3H) 3.53 (t, J=8.70 Hz, 1H) 3.67-3.75 (m, 1H) 3.75-4.00 (m, 7H) 4.46-4.56 (m, 3H) 4.60 (d, J=10.57 Hz, 1H) 4.84-4.96 (m, 3H) 5.89 (dd, J=3.73, 1.55 Hz, 1H) 6.04 (t, J=3.03 Hz, 1H) 6.49-6.54 (m, 1H) 6.70 (dd, J=7.62, 1.71 Hz, 2H) 7.05-7.18 (m, 7H) 7.22-7.36 (m, 14H) 7.39-7.46 (m, 1H). ESI m/Z=710 (M+H), 732 (M+Na).

Example 24

Synthesis of (1S)-1,5-anhydro-1-[3-[(1-methyl-1H-pyrrol-2-yl)methyl]phenyl]-1-thio-D-glucitol

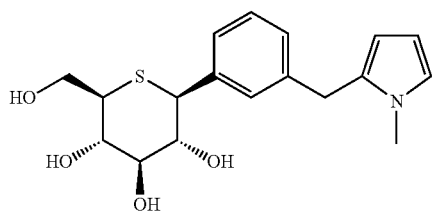

Trifluoromethane sulfonic acid (0.2 mL) was added to a mixture of (1S)-1,5-anhydro-2,3,4,6-tetra-O-benzyl-1-[3-[(1-methyl-1H-pyrrol-2-yl)methyl]phenyl]-1-thio-D-glucitol (190 mg), trifluoroacetic acid (1.0 mL), dimethylsulfide (0.6 mL), m-cresol (0.16 mL) and ethanedithiol (0.04 mL) at −15° C. After stirred for 15 minutes, the mixture was added with a saturated sodium bicarbonate aqueous solution and extracted with ethyl acetate. The organic layer was washed with a saturated sodium bicarbonate aqueous solution, brine and dried with anhydrous magnesium sulfate. After the desiccant was filtered off, the residue obtained by evaporating the solvent under reduced pressure was purified by silica gel column chromatography (chloroform:methanol=10:1) to obtain a colorless powdered title compound (16 mg, 17%).

1H NMR (300 MHz, METHANOL-d$_4$) δ ppm 2.92-3.05 (m, 1H) 3.19-3.29 (m, 1H) 3.39 (s, 3H) 3.59 (t, J=9.64 Hz, 1H) 3.68-3.83 (m, 3H) 3.86-4.02 (m, 3H) 5.80-5.87 (m, 1H) 5.94 (t, J=3.11 Hz, 1H) 6.55 (d, J=1.87 Hz, 1H) 7.03 (dd, J=6.99, 1.71 Hz, 1H) 7.12-7.28 (m, 3H). ESI m/Z=372 (M+Na).

Example 25

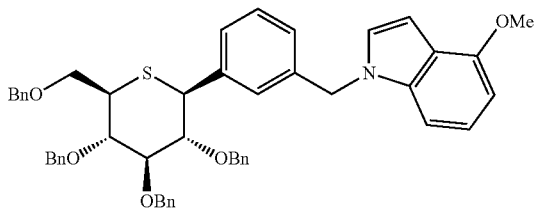

Synthesis of (1S)-1,5-anhydro-2,3,4,6-tetra-O-benzyl-1-[3-[(4-methoxy-1H-indol-1-yl)methyl]phenyl]-1-thio-D-glucitol An N,N-dimethylformamide (1.0 mL) solution of 4-methoxy indole (83 mg, 0.564 mmol) was added with sodium hydride (22 mg, 0.564 mmol; 60% oil) and stirred at room temperature for 20 minutes. This solution was added with an N,N-dimethylformamide (2.0 mL) solution of (1S)-1,5-anhydro-2,3,4,6-tetra-O-benzyl-1-[3-(bromomethyl)phenyl]-1-thio-D-glucitol (200 mg, 0.282 mmol), stirred at room temperature for three hours, and added with water. This was extracted with ethyl acetate and the organic layer was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain the title compound (290 mg).

1H NMR (300 MHz, CHLOROFORM-d) δ ppm 3.05-3.14 (m, 1H) 3.46-3.56 (m, 1H) 3.66-3.74 (m, 1H) 3.76-3.92 (m, 5H) 3.95 (s, 3H) 4.46 (d, J=10.10 Hz, 1H) 4.52 (s, 2H) 4.59 (d, J=10.57 Hz, 1H) 4.84-4.93 (m, 3H) 5.25 (d, J=2.49 Hz, 2H) 6.46-7.39 (m, 29H). ESI m/z=793 (M+NH$_4$)

Example 26

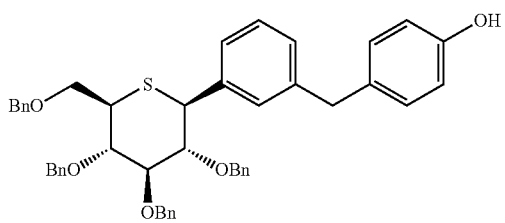

Synthesis of (1S)-1,5-anhydro-2,3,4,6-tetra-O-benzyl-1-[3-[(4-hydroxyphenyl)methyl]phenyl]-1-thio-D-glucitol The title compound (253 mg) in the form of colorless oil was obtained from (4-bromophenoxy)t-butyl-dimethylsilane (2.17 g) and 2,3,4,6-tetra-O-benzyl-1-C-(3-formylphenyl)-5-thio-D-glucopyranose (2.50 g) by a similar method as in Example 11.

1H NMR (300 MHz, CHLOROFORM-d) δ ppm 3.03-3.15 (m, 1H) 3.52 (t, J=8.78 Hz, 1H) 3.66-3.74 (m, 1H) 3.75-3.97 (m, 6H) 4.43-4.55 (m, 3H) 4.56-4.74 (m, 3H) 4.84-4.94 (m, 3H) 6.62-6.70 (m, 4H) 7.00 (d, J=8.70 Hz, 2H) 7.06-7.20 (m, 6H) 7.21-7.41 (m, 16H)

ESI m/z=740 (M+NH$_4$).

Example 27

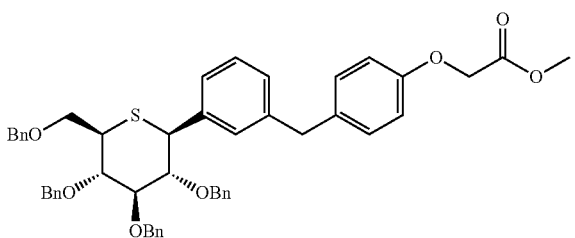

Synthesis of (1S)-1,5-anhydro-2,3,4,6-tetra-O-benzyl-1-[3-[4-(2-methoxy-2-oxyethoxy)benzyl]phenyl]-1-thio-D-glucitol An N,N-dimethylformamide (5 mL) solution of (1S)-1,5-anhydro-2,3,4,6-tetra-O-benzyl-1-[3-[(4-hydroxyphenyl)methyl]phenyl]-1-thio-D-glucitol (364 mg, 0.504 mmol) was added with potassium carbonate (91 mg, 0.660 mmol) and methyl bromoacetate (0.058 mL, 0.610 mmol) at 4° C. and stirred at room temperature for five hours. After the mixture was added with water and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain a colorless oily title compound (334 mg, 83%).

1H NMR (300 MHz, CHLOROFORM-d) δ ppm 3.05-3.15 (m, 1H) 3.52 (t, J=8.94 Hz, 1H) 3.66-3.75 (m, 1H) 3.75-3.98 (m, 10H) 4.41-4.64 (m, 6H) 4.83-4.95 (m, 3H) 6.60-6.79 (m, 4H) 6.98-7.19 (m, 8H) 7.22-7.36 (m, 16H). ESI m/Z=817 (M+Na).

Example 28

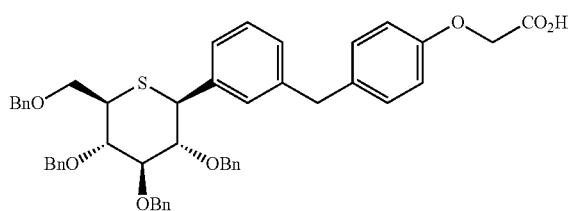

Synthesis of (1S)-1,5-anhydro-2,3,4,6-tetra-O-benzyl-1-[3-[4-(carboxymethoxy)benzyl]phenyl]-1-thio-D-glucitol A water-methanol-tetrahydrofuran (1:3:3, 1.4 mL) solution of (1S)-1,5-anhydro-2,3,4,6-tetra-O-benzyl-1-[3-[[4-(methoxycarbonylmethyloxy)phenyl]methyl]phenyl]-1-thio-D-glucitol (180 mg, 0.226 mmol) was added with lithium hydroxide monohydrate (11 mg, 0.27 mmol) and stirred at room temperature for 30 minutes. The reaction mixture was made acidic by adding 10% HCl and the deposited residue was extracted with ethyl acetate. After the organic layer was washed with brine and dried with anhydrous magnesium sulfate, the desiccant was filtered off and the solvent was evaporated under reduced pressure to obtain the title compound (149 mg, 84%) as a colorless powder.

1H NMR (300 MHz, CHLOROFORM-d) δ ppm 3.04-3.15 (m, 1H) 3.46-3.58 (m, 1H) 3.66-3.96 (m, 7H) 4.41-4.54 (m, 3H) 4.55-4.63 (m, 3H) 4.82-4.95 (m, 3H) 6.65 (dd, J=8.00, 1.48 Hz, 2H) 6.76 (d, J=8.86 Hz, 2H) 7.00-7.36 (m, 24H). ESI m/z=798 (M+NH$_4$), 779 (M−H).

Example 29

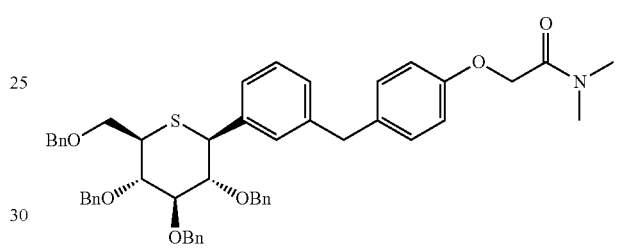

Synthesis of (1S)-1,5-anhydro-2,3,4,6-tetra-O-benzyl-1-[3-[4-[2-(dimethylamino)-2-oxoethoxy)benzyl]phenyl]-1-thio-D-glucitol A chloroform solution (2 mL) of (1S)-1,5-anhydro-2,3,4,6-tetra-O-benzyl-1-[3-[4-(carboxymethoxy)benzyl]phenyl]-1-thio-D-glucitol (149 mg, 0.191 mmol) was added with a tetrahydrofuran solution (0.19 mL, 0.382 mmol) of 2M dimethylamine, 1-ethyl-3-(3-dimethylaminopropyl)carbodiimide hydrochloride (44 mg, 0.229 mmol) and 1-hydroxybenzotriazole (31 mg, 0.229 mmol). After stirred at room temperature for 1.5 hours, the reaction mixture was diluted with chloroform and the organic phase was washed with water, brine and dried with anhydrous magnesium sulfate. After the desiccant was filtered off, the residue obtained by evaporating the solvent under reduced pressure was purified by silica gel column chromatography (hexane:ethyl acetate=1:2) to obtain the title compound (128 mg, 83%).

1H NMR (300 MHz, CHLOROFORM-d) δ ppm 2.96 (s, 3H) 3.05 (s, 3H) 3.06-3.14 (m, 1H) 3.52 (t, J=8.86 Hz, 1H) 3.68-3.74 (m, 1H) 3.76-3.96 (m, 7H) 4.44-4.54 (m, 3H) 4.56-

4.63 (m, 3H) 4.85-4.93 (m, 3H) 6.65 (dd, J=7.93, 1.55 Hz, 2H) 6.76-6.83 (m, 2H) 7.01-7.18 (m, 8H) 7.22-7.35 (m, 16H). ESI m/Z=825 (M+NH4).

Example 30

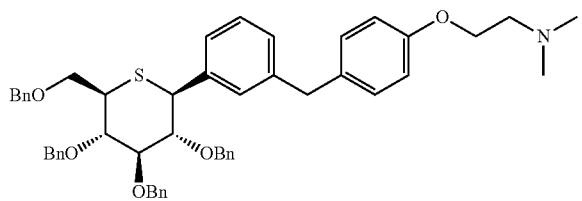

Synthesis of (1S)-1,5-anhydro-2,3,4,6-tetra-O-benzyl-1-[3-[[[4-(2-N,N-dimethylaminoethyl)oxy]phenyl]methyl]phenyl]-1-thio-D-glucitol A tetrahydrofuran solution (2 mL) of (1S)-1,5-anhydro-2,3,4,6-tetra-O-benzyl-1-[3-[4-[2-(dimethylamino)-2-oxoethoxy]benzyl]phenyl]-1-thio-D-glucitol (88 mg, 0.109 mmol) was added with 1.2M borane tetrahydrofuran complex (0.54 mL) at 4° C. and stirred at room temperature for two hours. The reaction mixture was cooled to 4° C., added with methanol and concentrated. 1,4-Dioxan (1.0 mL) and 6M HCl (0.5 mL) were added to the obtained residue and stirred at 40° C. for two minutes. This mixture was added with 2M aqueous sodium hydroxide solution so as to adjust it to be alkaline and extracted with ethyl acetate. The organic layer was washed with brine and dried with anhydrous magnesium sulfate. After the desiccant was filtered off, the residue obtained by evaporating the solvent under reduced pressure was purified by NH type silica gel column chromatography (hexane:ethyl acetate=1:1) to obtain the title compound (43 mg, 50%) as a colorless solid.

1H NMR (300 MHz, CHLOROFORM-d) δ ppm 2.35 (s, 6H) 2.68-2.81 (m, 2H) 3.04-3.16 (m, 1H) 3.52 (t, J=8.70 Hz, 1H) 3.66-3.76 (m, 1H) 3.76-4.10 (m, 9H) 4.47 (d, J=10.10 Hz, 1H) 4.52 (s, 2H) 4.60 (d, J=10.72 Hz, 1H) 4.84-4.94 (m, 3H) 6.65 (dd, J=7.85, 1.32 Hz, 2H) 6.72-6.81 (m, 2H) 7.00-7.18 (m, 8H) 7.20-7.36 (m, 16H). ESI m/Z=794 (M+H).

Example 31

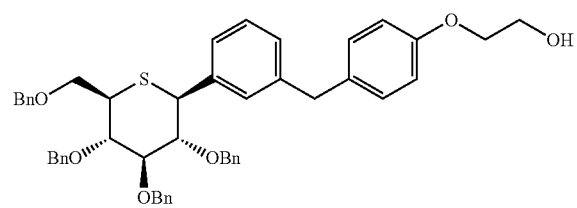

Synthesis of (1S)-1,5-anhydro-2,3,4,6-tetra-O-benzyl-1-[3-[[[4-(2-hydroxyethyl)oxy]phenyl]methyl]phenyl]-1-thio-D-glucitol A tetrahydrofuran (2.5 mL) solution of (1S)-1,5-anhydro-2,3,4,6-tetra-O-benzyl-1-[3-[4-(2-methoxy-2-oxoethoxy)benzyl]phenyl]-1-thio-D-glucitol (102 mg, 0.128 mmol) was added with LiAlH4 (12 mg, 0.321 mmol) at 4° C. and stirred for 2.5 hours. After water was added dropwise, 28% ammonium solution was added and the insolubles were filtered off. The filtrate was extracted with ethyl acetate and the organic layer washed with brine and dried with anhydrous magnesium sulfate. After the desiccant was filtered off, the solvent was evaporated under reduced pressure to obtain the title compound (100 mg) as a colorless crystal.

1H NMR (300 MHz, CHLOROFORM-d) δ ppm 3.06-3.14 (m, 1H) 3.52 (t, J=8.86 Hz, 1H) 3.67-3.74 (m, 1H) 3.77-4.04 (m, 11H) 4.47 (d, J=9.95 Hz, 1H) 4.52 (s, 2H) 4.60 (d, J=10.72 Hz, 1H) 4.86-4.93 (m, 3H) 6.62-6.68 (m, 2H) 6.73-6.79 (m, 2H) 7.02-7.18 (m, 8H) 7.21-7.35 (m, 16H). ESI m/Z=784 (M+NH4).

Example 32

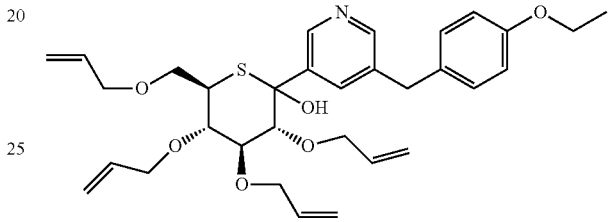

Synthesis of 2,3,4,6-tetra-O-allyl-1-C-[5-(4-ethoxybenzyl)pyridin-3-yl]-5-thio-D-glucopyranose Grignard reagent was prepared from 3-bromo-5-(4-ethoxybenzyl)pyridine (1.83 g, 6.26 mmol) by a similar method as in Example 15 and the title compound (508 mg, 29%) was obtained as a brown oily substance.

1H NMR (300 MHz, CHLOROFORM-d) δ ppm 1.40 (t, J=6.99 Hz, 3H) 2.98-3.18 (m, 1H) 3.29-3.47 (m, 2H) 3.56-4.05 (m, 12H) 4.06-4.43 (m, 4H) 4.77-4.91 (m, 2H) 5.07-5.37 (m, 7H) 5.79-6.04 (m, 3H) 6.81 (d, J=8.86 Hz, 2H) 7.04 (d, J=8.86 Hz, 2H) 7.72 (s, 1H) 8.41 (d, J=1.86 Hz, 1H) 8.70 (d, J=2.18 Hz, 1H). ESI m/z=568 (M+H), 590 (M+Na).

Example 33

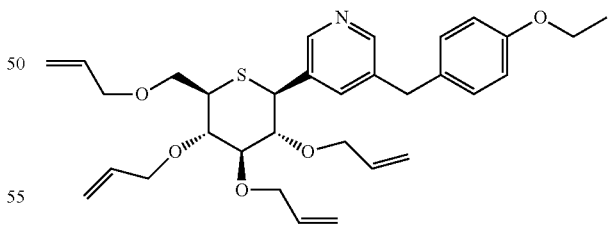

Synthesis of (1S)-1,5-anhydro-2,3,4,6-tetra-O-allyl-1-[5-(4-ethoxybenzyl)pyridin-3-yl]-1-thio-D-glucitol A colorless oily title compound (137 mg, 28%) was obtained from 2,3,4,6-tetra-O-benzyl-1-C-[5-(4-ethoxybenzyl)pyridin-3-yl]-5-thio-D-glucopyranose (508 mg, 0.894 mmol) by a similar method as in Example 16.

1H NMR (300 MHz, CHLOROFORM-d) δ ppm 1.40 (t, J=6.99 Hz, 3H) 2.93-3.06 (m, 1H) 3.25 (t, J=8.94 Hz, 1H)

3.30-3.44 (m, 1H) 3.49-4.05 (m, 12H) 4.15 (dd, J=12.05, 5.98 Hz, 1H) 4.24-4.42 (m, 3H) 4.80-4.92 (m, 2H) 5.08-5.42 (m, 7H) 5.78-6.03 (m, 3H) 6.81 (d, J=8.70 Hz, 2H) 7.03 (d, J=8.70 Hz, 2H) 7.48 (s, 1H) 8.42 (dd, J=16.16, 2.18 Hz, 2H). ESI m/Z=552 (M+H).

Example 34

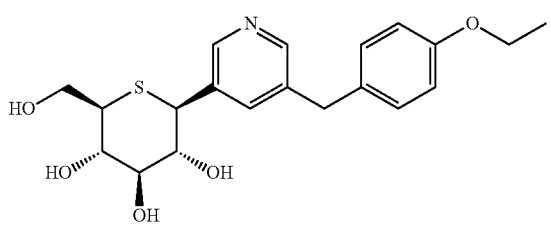

Synthesis of (1S)-1,5-anhydro-1-[5-(4-ethoxybenzyl) pyridin-3-yl]-1-thio-D-glucitol A colorless powdery title compound (71 mg, 73%) was obtained from (1S)-1,5-anhydro-2,3,4,6-tetra-O-allyl-1-[5-(4-ethoxybenzyl)pyridin-3-yl]-1-thio-D-glucitol (137 mg, 0.248 mmol) by a similar method as in Example 17.

1H NMR (600 MHz, METHANOL-$d_4$) δ ppm 1.36 (t, J=7.18 Hz, 3H) 3.01-3.05 (m, 1H) 3.23-3.27 (m, 1H) 3.60 (dd, J=10.32, 8.94 Hz, 1H) 3.71-3.78 (m, 2H) 3.84 (d, J=10.55 Hz, 1H) 3.92-3.97 (m, 3H) 3.99 (q, J=7.18 Hz, 2H) 6.82-6.85 (m, 2H) 7.10-7.13 (m, 2H) 7.64 (t, J=2.06 Hz, 1H) 8.28 (d, J=2.29 Hz, 1H) 8.34 (d, J=2.29 Hz, 1H). ESI m/Z=392 (M+Na), 390 (M−H).

Example 35

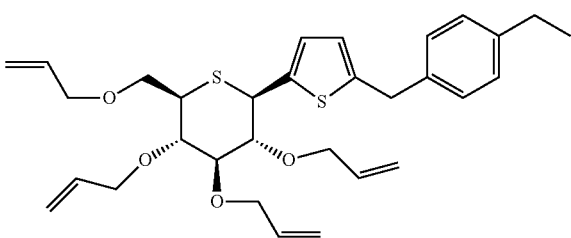

Synthesis of (1S)-1,5-anhydro-2,3,4,6-tetra-O-allyl-1-[5-(4-ethylbenzyl)-thiophen-2-yl]-1-thio-D-glucitol An yellow oily title compound (890 mg, 94%) was obtained from 2-bromo-5-(4-ethylbenzyl)thiophene (1.0 g, 3.55 mmol) by a similar method as in Examples 15 and 16.

1H NMR (300 MHz, CHLOROFORM-d) δ ppm 1.22 (t, J=7.62 Hz, 3H) 2.62 (q, J=7.62 Hz, 2H) 2.91-3.03 (m, 1H) 3.20 (t, J=9.01 Hz, 1H) 3.43-3.79 (m, 5H) 3.90-4.07 (m, 6H) 4.09-4.18 (m, 1H) 4.24-4.41 (m, 3H) 4.92-5.02 (m, 2H) 5.09-5.32 (m, 6H) 5.50-5.66 (m, 1H) 5.79-6.05 (m, 3H) 6.61 (d, J=3.57 Hz, 1H) 6.85 (d, J=3.42 Hz, 1H) 7.07-7.16 (m, 4H).

ESI m/z=563 (M+Na).

Example 36

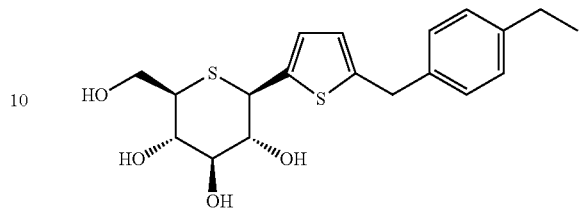

Synthesis of (1S)-1,5-anhydro-1-[5-(4-ethylbenzyl) thiophen-2-yl]-1-thio-D-glucitol A colorless powdery title compound (570 mg, 92%) was obtained from (1S)-1,5-anhydro-2,3,4,6-tetra-O-allyl-1-[5-(4-ethylbenzyl)thiophen-2-yl]-1-thio-D-glucitol (890 mg, 1.64 mmol) by a similar method as in Example 17.

1H NMR (300 MHz, METHANOL-$d_4$) δ ppm 1.20 (t, J=7.62 Hz, 3H) 2.60 (q, J=7.62 Hz, 2H) 2.92-3.03 (m, 1H) 3.19 (t, J=8.86 Hz, 1H) 3.50-3.63 (m, 2H) 3.72 (dd, J=11.58, 6.45 Hz, 1H) 3.93 (dd, J=11.50, 3.73 Hz, 1H) 4.03 (t, J=4.97 Hz, 3H) 6.58-6.67 (m, 1H) 6.83 (d, J=3.57 Hz, 1H) 7.08-7.17 (m, 4H).

ESI m/z=403 (M+Na), 379 (M−H).

Example 37

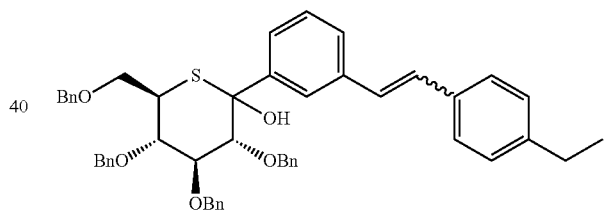

Synthesis of 2,3,4,6-tetra-O-benzyl-1-C-{3-[(E or Z)-2-(4-ethylphenyl)vinyl]phenyl}-5-thio-D-glucopyranose A mixture of (4-ethylbenzyl)triphenylphosphonium chloride (1.64 g, 3.93 mmol) and tetrahydrofuran (20 mL) was added with 2M lithium diisopropylamine (heptane/tetrahydrofuran/ethylbenzene solution, 2.0 mL, 4.0 mmol) while cooled on ice and stirred at room temperature for one hour. This solution was added dropwise to a tetrahydrofuran solution (10 mL) of 2,3,4,6-tetra-O-benzyl-1-C-(3-formylphenyl)-5-thio-D-glucopyranose (0.52 g, 786 μmol) and stirred at room temperature for one hour. After the reaction mixture was added with a saturated ammonium chloride aqueous solution while cooled on ice and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=6:1 to 3:1) to obtain a colorless oily title compound (0.49 g, 82%, E/Z mixture).

1H NMR (300 MHz, CHLOROFORM-d) δ ppm 1.10-1.32 (m, 3H) 2.48-2.74 (m, 2H) 2.90-3.10 (m, J=38.55 Hz, 1H) 3.47-3.71 (m, 2H) 3.78-4.21 (m, 5H) 4.41-4.73 (m, 4H) 4.80-4.99 (m, 3H) 6.50-6.99 (m, 3H) 7.03-7.61 (m, 27H). ESI m/z=785 (M+Na).

Example 38

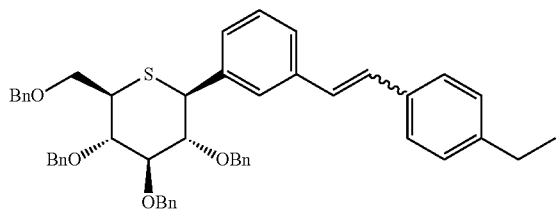

Synthesis of (1S)-1,5-anhydro-2,3,4,6-tetra-O-benzyl-1-{3-[(E or Z)-2-(4-ethylphenyl)vinyl]phenyl}-1-thio-D-glucitol An acetonitrile (20 mL) solution of 2,3,4,6-tetra-O-benzyl-1-C-{3-[(E or Z)-2-(4-ethylphenyl)vinyl]phenyl}-5-thio-D-glucopyranose (0.49 g, 642 μmol) was added sequentially with Et₃SiH (0.35 mL, 1.92 mmol) and BF₃·Et₂O (0.20 mL, 1.28 mmol) at −10° C. and stirred for 10 minutes at the same temperature. After the reaction mixture was added with a saturated sodium carbonate aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=8:1) to obtain a colorless powdery title compound (0.31 g, 66%, E/Z mixture).

1H NMR (300 MHz, CHLOROFORM-d) δ ppm 1.13-1.31 (m, 3H) 2.46-2.72 (m, 2H) 3.04-3.18 (m, 1H) 3.47-3.62 (m, 1H) 3.68-4.02 (m, 6H) 4.45-4.66 (m, 4H) 4.85-4.96 (m, 3H) 6.49-6.80 (m, 3H) 6.92-7.62 (m, 27H). ESI m/z=769 (M+Na)

Example 39

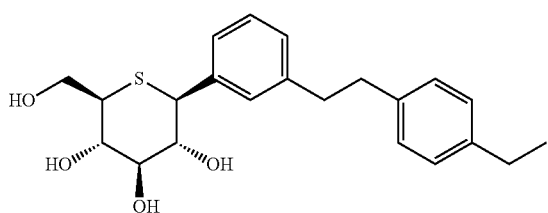

Synthesis of (1S)-1,5-anhydro-1-{3-[2-(4-ethylphenyl)ethyl]phenyl}-1-thio-D-glucitol 20 wt % palladium hydroxide on activated carbon (300 mg) was added to an ethanol (5 mL) solution of (1S)-1,5-anhydro-2,3,4,6-tetra-O-benzyl-1-{3-[(E or Z)-2-(4-ethylphenyl)vinyl]phenyl}-1-thio-D-glucitol (0.30 g, 401 μmol) and the atmosphere inside the system was substituted with hydrogen. After stirred for at room temperature for three days, insolubles in the system were removed by celite filtration. The residue obtained by evaporating the solvent under reduced pressure was purified by silica gel column chromatography (chloroform:methanol=10:1) to obtain a colorless powdery title compound (13 mg, 8%).

1H NMR (300 MHz, METHANOL-d₄) δ ppm 1.20 (t, J=7.62 Hz, 3H) 2.59 (q, J=7.62 Hz, 2H) 2.85 (s, 4H) 2.95-3.07 (m, 1H) 3.21-3.28 (m, 1H) 3.54-3.68 (m, 1H) 3.69-3.83 (m, 3H) 3.95 (dd, J=11.42, 3.65 Hz, 1H) 7.00-7.11 (m, 5H) 7.13-7.28 (m, 3H). ESI m/z=411 (M+Na), 387 (M−H).

Example 40

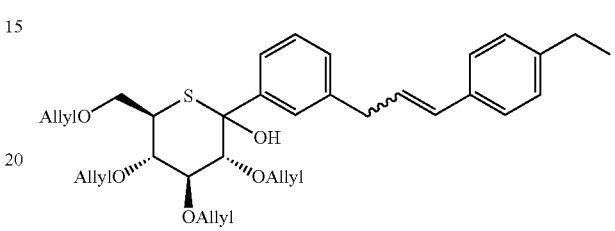

Synthesis of 2,3,4,6-tetra-O-allyl-1-C-{3-[(2E or Z)-3-(4-ethylphenyl)prop-2-en-1-yl]phenyl}-5-thio-D-glucopyranose Five drops of 1,2-dibromoethane were added to a mixture of magnesium (1.11 g, 45.7 mmol), 1-bromo-3-[(2E or Z)-3-(4-ethylphenyl)prop-2-en-1-yl)benzene (0.401 g, 1.33 mmol) and tetrahydrofuran (7 mL) and this mixture was heated to reflux for 1.5 hours. The reaction mixture was cooled to room temperature, and tetrahydrofuran (5 mL) of 2,3,4,6-tetra-O-allyl-5-thio-D-glucono-lactone (0.38 g, 1.06 mmol) was added dropwise to this solution and stirred at room temperature for 30 minutes. After the reaction mixture was added with a saturated ammonium chloride aqueous solution and extracted with ethyl acetate while cooled on ice, the organic phase was washed with brine and dried with anhydrous magnesium sulfate. After the desiccant was filtered off, the residue obtained by evaporating the solvent under reduced pressure was purified by silica gel column chromatography (hexane:ethyl acetate=4:1) to obtain a colorless oily title compound (42 mg, 7%).

1H NMR (300 MHz, CHLOROFORM-d) δ ppm 1.16-1.30 (m, 3H) 2.55-2.72 (m, 2H) 2.90-3.03 (m, 1H) 3.31-4.44 (m, 16H) 4.82-4.94 (m, 2H) 5.09-5.49 (m, 6H) 5.80-6.05 (m, 5H) 6.29-6.45 (m, 1H) 7.08-7.32 (m, 6H) 7.42-7.52 (m, 2H).

ESI m/z=599 (M+Na), 575 (M−H).

Example 41

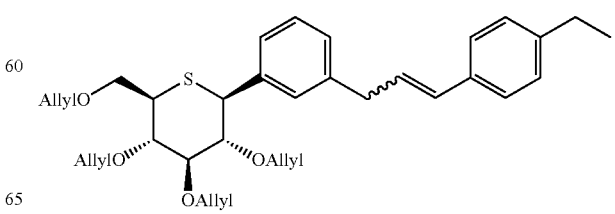

Synthesis of (1S)-2,3,4,6-tetra-O-allyl-1,5-anhydro-1-{3-[(2E or Z)-3-(4-ethylphenyl)prop-2-en-1-yl]phenyl}-1-thio-D-glucitol An acetonitrile (3 mL) solution of 2,3,4,6-tetra-O-allyl-1-C-{3-[(2E or Z)-3-(4-ethylphenyl)prop-2-en-1-yl]phenyl}-5-thio-D-glucopyranose (42 mg, 72 μmol) was added sequentially with Et₃SiH (35 μL, 218 μmol) and BF₃·Et₂O (20 μL, 145 μmol) at −10° C. and stirred for 10 minutes at the same temperature. After the reaction mixture was added with a saturated sodium carbonate aqueous solution and extracted with ethyl acetate, the organic layer was washed with brine and dried with anhydrous magnesium sulfate. After the desiccant was filtered off, the residue obtained by evaporating the solvent under reduced pressure was purified by silica gel column chromatography (hexane:ethyl acetate=10:1 to 8:1) to obtain a colorless oily title compound (28 mg, 70%).

1H NMR (300 MHz, CHLOROFORM-d) δ ppm 1.17-1.30 (m, J=7.62, 7.62, 7.62 Hz, 3H) 2.57-2.71 (m, 2H) 2.95-3.05 (m, 1H) 3.26 (t, J=8.86 Hz, 1H) 3.50 (d, J=6.68 Hz, 2H) 3.58-3.91 (m, 5H) 3.94-4.21 (m, 3H) 4.23-4.44 (m, 3H) 4.84-4.95 (m, 2H) 5.09-5.52 (m, 8H) 5.71-6.46 (m, 6H) 7.09-7.29 (m, 8H). ESI m/z=583 (M+Na).

Example 42

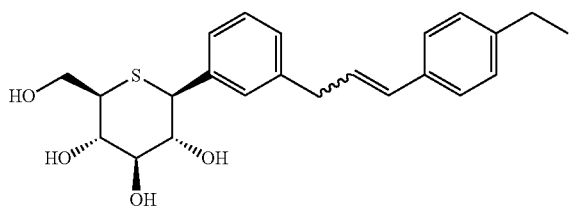

Synthesis of (1S)-1,5-anhydro-1-{3-[(2E or Z)-3-(4-ethylphenyl)prop-2-en-1-yl]phenyl}-1-thio-D-glucitol A tetrahydrofuran (3 mL) solution of (1S)-2,3,4,6-tetra-O-allyl-1,5-anhydro-1-{3-[(2E or Z)-3-(4-ethylphenyl)prop-2-en-1-yl]phenyl}-1-thio-D-glucitol (26 mg, 46 μmol) was added with tetrakis(triphenylphosphine) palladium (11 mg, 9 μmol) and 1,3-dimethyl barbituric acid (58 mg, 370 μmol) and heated to reflux for 2.5 hours. After the reaction mixture was added with a saturated sodium carbonate aqueous solution and extracted with ethyl acetate while cooled on ice, the organic phase was washed with brine and dried with anhydrous magnesium sulfate. After the desiccant was filtered off, the residue obtained by evaporating the solvent under reduced pressure was purified by silica gel column chromatography (chloroform:methanol=10:1). Further purification was performed by silica gel column chromatography (NH silica gel, chloroform:methanol=9:1) to obtain the title compound (13 mg, 72%).

1H NMR (300 MHz, METHANOL-d₄) δ ppm 1.14-1.27 (m, J=7.98, 7.98, 7.98 Hz, 3H) 2.54-2.68 (m, 2H) 2.95-3.05 (m, 1H) 3.22-3.30 (m, 1H) 3.51 (d, J=6.37 Hz, 1H) 3.56-3.68 (m, 2H) 3.70-3.83 (m, 3H) 3.95 (dd, J=11.35, 3.57 Hz, 1H) 5.72-6.59 (m, 2H) 7.07-7.30 (m, 8H). ESI m/z=423 (M+Na), 399 (M−H).

Example 43

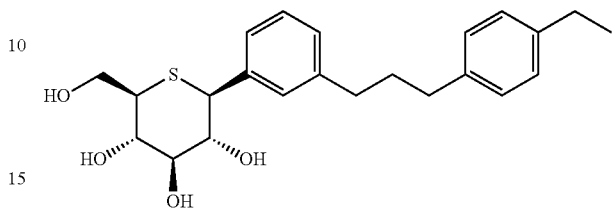

Synthesis of (1S)-1,5-anhydro-1-{3-[3-(4-ethylphenyl)propyl]phenyl}-1-thio-D-glucitol 20 wt % palladium hydroxide on activated carbon (20 mg) was added to an ethanol (2 mL) solution of (1S)-1,5-anhydro-1-{3-[(2E or Z)-3-(4-ethylphenyl)prop-2-en-1-yl]phenyl}-1-thio-D-glucitol (13 mg, 32 μmol) and the atmosphere inside the system was substituted with hydrogen. After stirred for at room temperature for two days, insolubles in the system were removed by celite filtration. The residue obtained by evaporating the solvent under reduced pressure was purified by silica gel column chromatography (chloroform:methanol=9:1) to obtain a colorless powdery title compound (8 mg, 62%).

1H NMR (600 MHz, METHANOL-d₄) δ ppm 1.20 (t, J=7.57 Hz, 3H) 1.87-1.94 (m, 2H) 2.56-2.63 (m, 6H) 2.98-3.03 (m, 1H) 3.26 (t, J=8.25 Hz, 1H) 3.59-3.64 (m, J=10.32, 8.94 Hz, 1H) 3.71-3.82 (m, 3H) 3.95 (dd, J=11.46, 3.67 Hz, 1H) 7.05-7.12 (m, 5H) 7.14-7.25 (m, 3H). ESI m/z=425 (M+Na), 401 (M−H).

Example 44

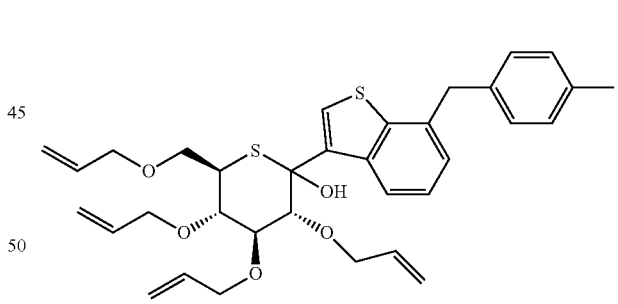

Synthesis of 2,3,4,6-tetra-O-allyl-1-C-[7-(4-methylbenzyl)-1-benzothien-3-yl]-5-thio-D-glucopyranose Five drops of 1,2-dibromoethane were added to a mixture of magnesium (77 mg, 3.19 mmol), 3-bromo-7-(4-methylbenzyl)-1-benzothiophene (0.92 g, 2.90 mmol) and tetrahydrofuran (5 mL) and this mixture was heated to reflux for 30 minutes. The reaction mixture was cooled to room temperature, and tetrahydrofuran (5 mL) of 2,3,4,6-tetra-O-allyl-5-thio-D-glucono-1,5-lactone (0.51 g, 1.45 mmol) was added dropwise to this solution while cooled on ice and stirred at room temperature for 30 minutes. After the reaction mixture was added with a saturated ammonium chloride aqueous solution and extracted with ethyl acetate, the organic phase was washed with brine and dried with anhydrous magnesium sulfate. After the desiccant was filtered off, the residue obtained by evaporating the solvent under reduced pressure was purified by silica gel column chromatography (hexane: ethyl acetate=4:1) to obtain a yellow oily title compound (0.76 g, 89%).

1H NMR (300 MHz, CHLOROFORM-d) δ ppm 2.31 (s, 3H) 3.21 (dd, J=11.81, 6.06 Hz, 1H) 3.29 (s, 1H) 3.46-3.93 (m, 6H) 3.96-4.02 (m, J=4.66 Hz, 2H) 4.15-4.26 (m, 4H) 4.30 (d, J=5.75 Hz, 2H) 4.42 (dd, J=12.12, 5.91 Hz, 1H) 4.57-4.78 (m, 2H) 5.10-5.40 (m, 7H) 5.80-6.08 (m, 3H) 7.05-7.17 (m, 5H) 7.32 (t, 1H) 7.63 (s, 1H) 8.19 (d, J=7.46 Hz, 1H).

ESI m/z=615 (M+Na), 591 (M−H).

Example 45

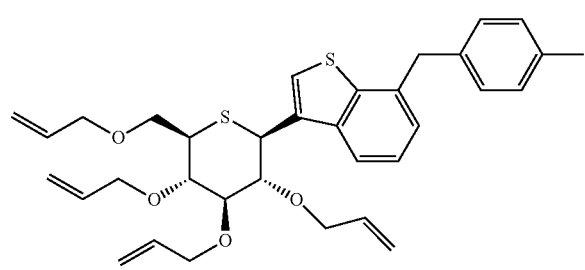

Synthesis of (1S)-2,3,4,6-tetra-O-allyl-1,5-anhydro-1-[7-(4-methylbenzyl)-1-benzothien-3-yl]-1-thio-D-glucitol The title compound (86%) was synthesized by a similar method as in Example 16 from 2,3,4,6-tetra-O-allyl-1-C-[7-(4-methylbenzyl)-1-benzothien-3-yl]-5-thio-D-glucopyranose.

1H NMR (300 MHz, CHLOROFORM-d) δ ppm 2.31 (s, 3H) 2.99-3.10 (m, 1H) 3.27-3.40 (m, 2H) 3.66-3.87 (m, 5H) 4.00 (d, J=5.75 Hz, 2H) 4.15-4.26 (m, 4H) 4.31 (d, J=6.84 Hz, 2H) 4.40 (dd, J=12.05, 5.83 Hz, 1H) 4.63-4.82 (m, 2H) 5.09-5.37 (m, 7H) 5.80-6.07 (m, 3H) 7.04-7.17 (m, 5H) 7.32 (t, 1H) 7.41 (s, 1H) 7.89 (d, J=7.93 Hz, 1H). ESI m/z=599 (M+Na).

Example 46

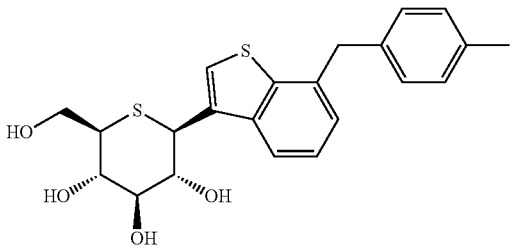

Synthesis of (1S)-1,5-anhydro-1-[7-(4-methylbenzyl)-1-benzothien-3-yl]-1-thio-D-glucitol The title compound (76%) was synthesized as a colorless powder by a similar method as in Example 17 from (1S)-2,3,4,6-tetra-O-allyl-1,5-anhydro-1-[7-(4-methylbenzyl)-1-benzothien-3-yl]-1-thio-D-glucitol.

1H NMR (300 MHz, METHANOL-$d_4$) δ ppm 2.26 (s, 2H) 3.03-3.14 (m, 1H) 3.32-3.40 (m, 1H) 3.62-3.72 (m, 1H) 3.77 (dd, J=11.50, 6.37 Hz, 1H) 3.93-4.06 (m, 2H) 4.14 (s, 2H) 4.32 (d, J=10.26 Hz, 1H) 7.01-7.17 (m, 5H) 7.33 (t, 1H) 7.48 (s, 1H) 7.90 (d, J=7.31 Hz, 1H). ESI m/z=439 (M+Na), 415 (M−H).

Compounds of the present invention shown in the following tables were obtained by performing the similar operations as in the above Examples using corresponding starting materials and reactants. Compounds of the present invention obtained by the above Examples are also shown in Table 1.

TABLE 1

| Compound No. | Structural formula | ¹NMR, MS, mp, Elemantal analysis |
|---|---|---|
| Compound 1 | | 1H NMR (300 MHz, CHLOROFORM-d) δ ppm 1.19 (t, J = 7.6 Hz, 3 H) 2.59 (q, J = 7.6 Hz, 2 H) 3.05-3.16 (m, 1 H) 3.53 (t, J = 8.9 Hz, 1 H) 3.67-3.99 (m, 8H) 4.47 (d, J = 10.0 Hz, 1 H) 4.53 (s, 2 H) 4.60 (d, J = 10.7 Hz, 1 H) 4.85-4.94 (m, 3 H) 6.62-6.69 (m, 2 H) 7.00-7.20 (m, 10 H) 7.22-7.36 (m, 16 H). ESI m/Z = 757 (M + Na). mp 100.0-102.5° C. |
| Compound 2 | | 1H NMR (300 MHz, CHLOROFORM-d) δ ppm 1.38 (t, J = 6.99 Hz, 3 H) 2.93-3.17 (m, 1 H) 3.52 (t, J = 8.86 Hz, 1 H) 3.64-3.76 (m, 1 H) 3.76-4.07 (m, 9 H) 4.46 (d, J = 9.95 Hz, 1 H) 4.52 (s, 2 H) 4.60 (d, J = 10.57 Hz, 1 H) 4.83-4.97 (m, 3 H) 6.59-6.80 (m, 4 H) 6.97-7.21 (m, 8 H) 7.22-7.39 (m, 16 H). ESI m/Z = 773 (M + Na). |

TABLE 1-continued

| Compound No. | Structural formula | ¹NMR, MS, mp, Elemental analysis |
|---|---|---|
| Compound 3 | 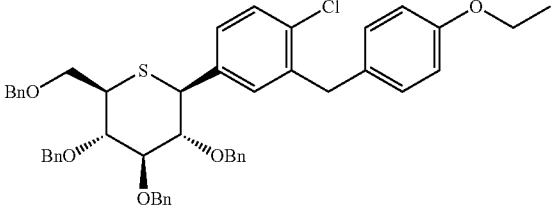 | 1H NMR (600 MHz, CHLOROFORM-d) δ ppm 1.38 (t, J = 6.88 Hz, 3 H) 3.00-3.15 (m, 1 H) 3.50 (t, J = 8.94 Hz, 1 H) 3.70 (dd, J = 9.86, 2.98 Hz, 1 H) 3.75-3.80 (m, 2 H) 3.82-3.99 (m, 6 H) 4.06 (d, J = 15.59 Hz, 1 H) 4.47-4.53 (m, 3 H) 4.59 (d, J = 10.55 Hz, 1 H) 4.82-4.88 (m, 2 H) 4.89 (d, J = 10.55 Hz, 1 H) 6.70 (d, J = 6.88 Hz, 2 H) 6.74 (d, J = 8.71 Hz, 2 H) 7.03 (d, J = 8.71 Hz, 2 H) 7.09-7.37 (m, 21 H). ESI m/Z = 807 (M + Na). mp 126.0-128.0° C. colorless powder. |
| Compound 4 | 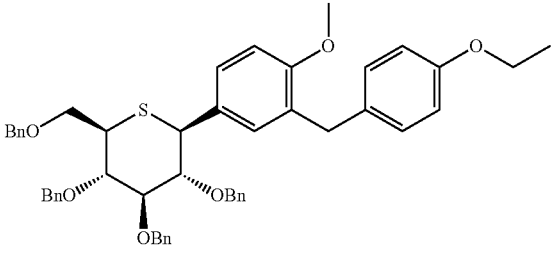 | 1H NMR (600 MHz, CHLOROFORM-d) δ ppm 1.37 (t, J = 6.88 Hz, 3 H) 3.05-3.11 (m, 1 H) 3.50 (t, J = 8.94 Hz, 1 H) 3.70 (dd, J = 9.63, 2.75 Hz, 1 H) 3.76-3.84 (m, 6 H) 3.84-3.92 (m, 3 H) 3.92-3.99 (m, 3 H) 4.45 (d, J = 10.09 Hz, 1 H) 4.52 (s, 2 H) 4.59 (d, J = 10.55 Hz, 1 H) 4.85 (s, 2 H) 4.89 (d, J = 11.00 Hz, 1 H) 6.67-6.75 (m, 4 H) 6.83 (d, J = 8.25 Hz, 1 H) 7.02-7.18 (m, 8 H) 7.22-7.35 (m, 14 H). ESI m/Z = 803 (M + Na). |
| Compound 5 | 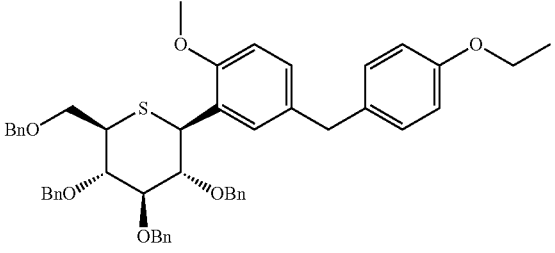 | 1H NMR (600 MHz, CHLOROFORM-d) δ ppm 1.37 (t, J = 7.11 Hz, 3 H) 3.07-3.15 (m, 1 H) 3.54 (t, J = 9.17 Hz, 1 H) 3.62-3.99 (m, 11 H) 4.47-4.62 (m, 6 H) 4.84-4.93 (m, 3 H) 6.61-7.41 (m, 27 H). ESI m/Z = 803 (M + Na). |
| Compound 6 | 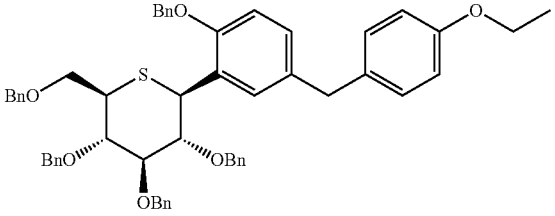 | 1H NMR (300 MHz, CHLOROFORM-d) δ ppm 1.36 (t, J = 6.92 Hz, 3 H) 2.97-3.17 (m, 1 H) 3.47-3.62 (m, 1 H) 3.62-3.75 (m, 1 H) 3.76-4.03 (m, 8 H) 4.40-4.67 (m, 5 H) 4.82-5.12 (m, 5 H) 6.62-7.42 (m, 32 H). ESI m/Z = 879 (M + Na). |
| Compound 7 | 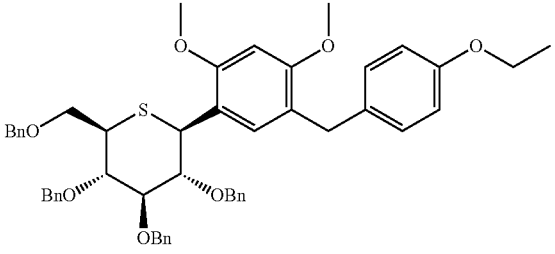 | 1H NMR (300 MHz, CHLOROFORM-d) δ ppm 1.35 (t, J = 6.92 Hz, 3 H) 3.06-3.15 (m, 1 H) 3.52 (t, J = 8.86 Hz, 1 H) 3.64-3.98 (m, 14 H) 4.45-4.62 (m, 4 H) 4.71 (s, 2 H) 4.84-4.93 (m, 3 H) 6.45 (s, 1 H) 6.63-6.72 (m, 4 H) 6.99-7.34 (m, 17 H) 7.37 (d, J = 4.35 Hz, 4 H). ESI m/Z = 828 (M + NH₄). yellow oil. |
| Compound 8 | 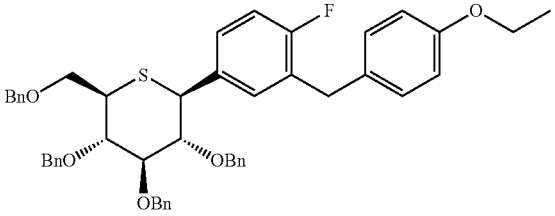 | 1H NMR (300 MHz, CHLOROFORM-d) δ ppm 1.38 (t, J = 6.99 Hz, 3 H) 3.03-3.13 (m, 1 H) 3.46-3.54 (m, 1 H) 3.66-4.00 (m, 10 H) 4.45-4.53 (m, 3 H) 4.59 (d, J = 10.72 Hz, 1 H) 4.84-4.93 (m, 3 H) 6.65-6.77 (m, 4 H) 6.96-7.34 (m, 23 H). ESI m/Z = 791 (M + Na). colorless powder. |

TABLE 1-continued

| Compound No. | Structural formula | ¹NMR, MS, mp, Elemental analysis |
|---|---|---|
| Compound 9 | | 1H NMR (300 MHz, CHLOROFORM-d) δ ppm 1.38 (t, J = 6.92 Hz, 3 H) 3.02-3.14 (m, 1 H) 3.51 (t, J = 8.70 Hz, 1 H) 3.66-4.05 (m, 10 H) 4.47 (d, J = 10.26 Hz, 1 H) 4.52 (s, 2 H) 4.59 (d, J = 10.41 Hz, 1 H) 4.83-4.94 (m, 3 H) 5.06 (s, 2 H) 6.64-6.74 (m, 4 H) 6.84-6.91 (m, 1 H) 6.96-7.38 (m, 27 H). ESI m/Z = 874 (M + NH4). colorless powder. |
| Compound 10 | | 1H NMR (600 MHz, CHLOROFORM-d) δ ppm 1.43 (t, J = 6.88 Hz, 3 H) 3.06-3.12 (m, 1 H) 3.51 (t, J = 8.94 Hz, 1 H) 3.70 (dd, J = 9.63, 2.75 Hz, 1 H) 3.75-3.81 (m, 2 H) 3.83-4.06 (m, 8 H) 4.49-4.55 (m, 3 H) 4.59 (d, J = 10.55 Hz, 1 H) 4.84-4.94 (m, 3 H) 6.63 (dd, J = 10.55, 6.88 Hz, 1 H) 6.69 (d, J = 6.88 Hz, 2 H) 6.77 (dd, J = 11.23, 7.11 Hz, 1 H) 7.08-7.38 (m, 20 H). ESI m/Z = 843 (M + Na). colorless powder. |
| Compound 11 | | 1H NMR (600 MHz, CHLOROFORM-d) δ ppm 1.40 (t, J = 7.11 Hz, 3 H) 3.01-3.11 (m, 1 H) 3.50 (t, J = 8.94 Hz, 1 H) 3.69 (dd, J = 9.63, 2.75 Hz, 1 H) 3.75-3.80 (m, 2 H) 3.81-3.95 (m, 4 H) 3.99-4.07 (m, 3 H) 4.49-4.53 (m, 3 H) 4.58 (d, J = 10.55 Hz, 1 H) 4.82-4.93 (m, 3 H) 6.65-6.90 (m, 5 H) 7.09-7.36 (m, 21 H). ESI m/Z = 825 (M + Na). colorless powder. |
| Compound 12 | | 1H NMR (600 MHz, CHLOROFORM-d) δ ppm 1.42 (t, J = 6.88 Hz, 3 H) 3.05-3.16 (m, 1 H) 3.50 (t, J = 8.94 Hz, 1 H) 3.69 (dd, J = 10.09, 2.75 Hz, 1 H) 3.73-3.81 (m, 2 H) 3.82-3.95 (m, 4 H) 4.02 (q, J = 7.03 Hz, 2 H) 4.48-4.54 (m, 3 H) 4.58 (d, J = 10.55 Hz, 1 H) 4.82-4.90 (m, 3 H) 6.63-6.75 (m, 3 H) 6.91 (dd, J = 8.25, 2.29 Hz, 1 H) 7.07-7.36 (m, 22 H). ESI m/Z = 841 (M + Na). |
| Compound 13 | | 1H NMR (300 MHz, CHLOROFORM-d) δ ppm 1.38 (t, J = 6.99 Hz, 3 H) 2.22 (s, 3 H) 3.06-3.14 (m, 1 H) 3.52 (t, J = 8.86 Hz, 1 H) 3.68-4.00 (m, 10 H) 4.46-4.54 (m, 3 H) 4.60 (d, J = 10.72 Hz, 1 H) 4.84-4.93 (m, 3 H) 6.67-6.76 (m, 4 H) 6.92-6.98 (m, 2 H) 7.08-7.35 (m, 21 H). ESI m/Z = 782 (M + Na). colorless powder. |
| Compound 14 | | 1H NMR (600 MHz, CHLOROFORM-d) δ ppm 3.01-3.13 (m, 1 H) 3.49 (t, J = 8.94 Hz, 1 H) 3.65-3.69 (m, 1 H) 3.71 (s, 3 H) 3.73-3.78 (m, 2 H) 3.76 (s, 3H) 3.80-3.96 (m, 4 H) 4.01-4.07 (m, 1 H) 4.45-4.53 (m, 3 H) 4.59 (d, J = 11.00 Hz, 1 H) 4.83-4.92 (m, 3 H) 6.30 (dd, J = 8.25, 2.29 Hz, 1 H) 6.41 (d, J = 2.29 Hz, 1 H) 6.71 (d, J = 8.25 Hz, 1 H) 6.84 (d, J = 8.25 Hz, 1 H) 7.10-7.35 (m, 21 H). ESI m/Z = 818 (M + NH₄). |

TABLE 1-continued

| Compound No. | Structural formula | ¹NMR, MS, mp, Elemantal analysis |
|---|---|---|
| Compound 15 | | 1H NMR (300 MHz, CHLOROFORM-d) δ ppm 3.01-3.16 (m, 1 H) 3.50 (t, J = 8.86 Hz, 1 H) 3.66-3.72 (m, 1 H) 3.76 (s, 3 H) 3.76-3.99 (m, 6 H) 4.02-4.14 (m, 1 H) 4.46-4.53 (m, 3 H) 4.59 (d, J = 10.72 Hz, 1 H) 4.82-4.95 (m, 3 H) 6.63-6.82 (m, 4 H) 7.01-7.36 (m, 23 H). ESI m/Z = 788 (M + NH$_4$). |
| Compound 16 | | 1H NMR (600 MHz, CHLOROFORM-d) δ ppm 1.35 (t, J = 6.88 Hz, 3 H) 2.21 (s, 3 H) 3.02-3.21 (m, 1 H) 3.55 (t, J = 9.40 Hz, 1 H) 3.71 (s, 1 H) 3.74-3.97 (m, 10 H) 4.01 (s, 1 H) 4.45-4.56 (m, 3 H) 4.60 (d, J = 10.55 Hz, 2 H) 4.86 (s, 2 H) 4.90 (d, J = 10.55 Hz, 1 H) 6.58-6.76 (m, 5 H) 6.90 (d, J = 7.34 Hz, 1 H) 7.09-7.19 (m, 5 H) 7.23-7.35 (m, 15 H). ESI m/z = 812 (M + NH$_4$). colorless powder. |
| Compound 17 | | 1H NMR (300 MHz, CHLOROFORM-d) δ ppm 1.39 (t, J = 6.99 Hz, 3 H) 2.18 (s, 3 H) 2.93-3.08 (m, 1 H) 3.27 (t, J = 9.01 Hz, 1 H) 3.50-3.77 (m, 6 H) 3.80 (s, 3 H) 3.83-4.05 (m, 6 H) 4.08-4.51 (m, 5 H) 4.82-4.95 (m, 2 H) 5.06-5.34 (m, 6 H) 5.38-5.58 (m, 1 H) 5.77-6.07 (m, 3 H) 6.66 (s, 1 H) 6.75 (d, J = 8.70 Hz, 2 H) 6.94 (d, J = 8.70 Hz, 2 H) 7.16 (s, 1 H). ESI m/Z = 617 (M + Na). |
| Compound 18 | | 1H NMR (300 MHz, CHLOROFORM-d) δ ppm 1.26 (s, 9 H) 2.93-3.20 (m, 1 H) 3.51 (t, J = 8.94 Hz, 1 H) 3.63-3.93 (m, 6 H) 3.93-4.03 (m, 1 H) 4.06-4.17 (m, 1 H) 4.45-4.54 (m, 3 H) 4.59 (d, J = 10.57 Hz, 1 H) 4.84-4.93 (m, 3 H) 6.69 (dd, J = 8.00, 1.48 Hz, 2 H) 7.04-7.38 (m, 25 H). ESI m/z = 819 (M + Na). colorless powder. |
| Compound 19 | | 1H NMR (300 MHz, CHLOROFORM-d) δ ppm 1.38 (t, J = 6.99 Hz, 3 H) 3.03-3.15 (m, 1 H) 3.50 (t, J = 8.86 Hz, 1 H) 3.65-4.06 (m, 10 H) 4.46-4.62 (m, 4 H) 4.82-4.93 (m, 3 H) 6.45-6.61 (m, 2 H) 6.69 (d, J = 8.08 Hz, 2 H) 6.91 (t, J = 8.63 Hz, 1 H) 7.08-7.38 (m, J = 1.00 Hz, 21 H), colorless oil |
| Compound 20 | | 1H NMR (300 MHz, CHLOROFORM-d) δ ppm 2.25-2.31 (s, 3 H) 3.04-3.13 (m, 1 H) 3.46-3.54 (m, 1 H) 3.66-4.13 (m, 8 H) 4.47-4.53 (m, 3 H) 4.59 (d, J = 11.04 Hz, 1 H) 4.84-4.92 (m, 3 H) 6.67-6.72 (m, 2 H) 7.02 (s, 4 H) 7.08-7.35 (m, 21 H). ESI m/Z = 772 (M + NH4), 774 (M + 2 + NH4). colorless powder. |

TABLE 1-continued

| Compound No. | Structural formula | ¹NMR, MS, mp, Elemantal analysis |
| --- | --- | --- |
| Compound 21 | | 1H NMR (600 MHz, CHLOROFORM-d) δ ppm 2.42 (s, 3 H) 3.05-3.12 (m, 1 H) 3.51 (t, J = 8.94 Hz, 1 H) 3.70 (dd, J = 9.86, 2.98 Hz, 1 H) 3.74-3.82 (m, 2 H) 3.82-3.92 (m, 3 H) 3.93-4.01 (m, 1 H) 4.07 (d, J = 15.13 Hz, 1 H) 4.48-4.54 (m, 3 H) 4.59 (d, J = 10.55 Hz, 1 H) 4.82-4.87 (m, 2 H) 4.89 (d, J = 10.55 Hz, 1 H) 6.70 (d, J = 7.34 Hz, 2 H) 7.00-7.38 (m, 25 H). ESI m/Z = 804 (M + NH4). colorless powder. |
| Compound 22 | | 1H NMR (300 MHz, CHLOROFORM-d) δ ppm 1.29 (d, J = 6.06 Hz, 6 H) 3.04-3.14 (m, 1 H) 3.50 (t, J = 8.70 Hz, 1 H) 3.65-4.11 (m, 6 H) 4.38-4.63 (m, 5 H) 4.83-4.92 (m, 3 H) 6.65-6.77 (m, 3 H) 6.99-7.37 (m, 24 H). ESI m/z = 821 (M + Na). yellow powder |
| Compound 23 | | 1H NMR (300 MHz, CHLOROFORM-d) δ ppm 1.19 (t, J = 7.54 Hz, 3 H) 2.58 (q, J = 7.77 Hz, 2 H) 3.04-3.13 (m, 1 H) 3.50 (t, J = 8.70 Hz, 1 H) 3.66-4.14 (m, 8 H) 4.46-4.53 (m, 3 H) 4.59 (d, J = 10.72 Hz, 1 H) 4.84-4.92 (m, 3 H) 6.66-6.72 (m, 2 H) 7.00-7.36 (m, 25 H). ESI m/Z = 791 (M + Na). pale yellow powder. |
| Compound 24 | | 1H NMR (300 MHz, CHLOROFORM-d) δ ppm 1.18 (s, 3 H) 1.21 (s, 3 H) 2.77-2.89 (m, 1 H) 3.05-3.13 (m, 1 H) 3.51 (t, J = 8.86 Hz, 1 H) 3.66-4.15 (m, 8 H) 4.46-4.54 (m, 3 H) 4.59 (d, J = 10.72 Hz, 1 H) 4.83-4.92 (m, 3 H) 6.69 (dd, J = 7.85, 1.32 Hz, 2 H) 7.06 (s, 4 H) 7.08-7.36 (m, 21 H). ESI m/Z = 805 (M + Na). colorless powder. |
| Compound 25 | | 1H NMR (300 MHz, CHLOROFORM-d) δ ppm 1.40 (t, J = 6.99 Hz, 3 H) 2.14 (s, 3 H) 3.01-3.12 (m, 1 H) 3.48 (t, J = 8.86 Hz, 1 H) 3.65-4.06 (m, 10 H) 4.46-4.61 (m, 4 H) 4.80-4.91 (m, 3 H) 6.58 (dd, J = 8.24, 2.49 Hz, 1 H) 6.68-6.76 (m, 2 H) 6.81 (d, J = 8.39 Hz, 1 H) 6.98 (d, J = 2.18 Hz, 1 H) 7.10-7.39 (m, 21 H). colorless powder. |
| Compound 26 | | 1H NMR (300 MHz, CHLOROFORM-d) δ ppm 3.14 (s, 1 H) 3.43-3.58 (m, 1 H) 3.63 (dd, J = 9.95, 2.64 Hz, 1 H) 3.87-4.16 (m, 5 H) 4.45-4.72 (m, 4 H) 4.80-5.05 (m, 3 H) 6.73 (d, J = 7.77 Hz, 2 H) 7.02-7.43 (m, 19 H) 7.74 (dd, J = 8.39, 2.49 Hz, 1 H) 8.06 (d, J = 2.49 Hz, 1 H) 10.39 (s, 1 H). colorless amorphous. |

TABLE 1-continued

| Compound No. | Structural formula | ¹NMR, MS, mp, Elemantal analysis |
|---|---|---|
| Compound 27 | | 1H NMR (300 MHz, CHLOROFORM-d) δ ppm 3.06 (s, 1 H) 3.47-3.58 (m, 1 H) 3.64 (dd, J = 10.03, 2.88 Hz, 1 H) 3.83-4.21 (m, 9 H) 4.48-4.56 (m, 3 H) 4.66 (d, J = 10.57 Hz, 1 H) 4.82-4.97 (m, 3 H) 6.15 (s, 1 H) 6.77 (dd, J = 7.85, 1.48 Hz, 2 H) 7.08-7.21 (m, 5 H) 7.23-7.37 (m, 14 H) 7.55 (dd, J = 8.39, 2.49 Hz, 1 H) 7.92 (d, J = 2.49 Hz, 1 H). ESI m/z = 761 (M + Na). colorless amorphous. |
| Compound 28 | | 1H NMR (300 MHz, CHLOROFORM-d) δ ppm 1.36 (t, J = 6.92 Hz, 3 H) 2.17 (s, 3 H) 3.04-3.19 (m, 1 H) 3.47-4.17 (m, 10 H) 4.42-4.66 (m, 5 H) 4.77-5.12 (m, 5 H) 6.55-7.51 (m, 31 H). ESI m/Z = 893 (M + Na). colorless oil. |
| Compound 29 | | 1H NMR (300 MHz, CHLOROFORM-d) δ ppm 1.35 (t, J = 6.99 Hz, 3 H) 3.01-3.16 (m, 1 H) 3.53 (t, J = 9.01 Hz, 1 H) 3.65-3.74 (m, 1 H) 3.78 (s, 3 H) 3.81-4.08 (m, 8 H) 4.43-4.56 (m, 4 H) 4.59 (d, J = 10.88 Hz, 1 H) 4.85 (s, 2 H) 4.89 (d, J = 10.72 Hz, 1 H) 6.68 (dd, J = 7.77, 1.71 Hz, 4 H) 6.89 (s, 1 H) 7.00 (d, J = 8.39 Hz, 2 H) 7.06-7.20 (m, 5 H) 7.21-7.38 (m, 14 H). ). ESI m/Z = 837 (M + Na). |
| Compound 30 | | 1H NMR (300 MHz, CHLOROFORM-d) δ ppm 1.39 (t, J = 6.99 Hz, 3 H) 2.95-3.04 (m, 1 H) 3.21-3.30 (m, 1 H) 3.41-3.79 (m, 5 H) 3.81 (s, 3 H) 3.84-4.20 (m, 8H) 4.25-4.42 (m, 4 H) 4.81-4.91 (m, 2 H) 5.09-5.33 (m, 6 H) 5.34-5.52 (m, 1 H) 5.79-6.04 (m, 3 H) 6.78 (d, J = 8.86 Hz, 2 H) 6.87 (s, 1 H) 7.03 (d, J = 8.70 Hz, 2 H) 7.21 (brs, 1 H). ESI m/z = 637 (M + Na), 639 (M + 2 + Na). |
| Compound 31 | | 1H NMR (300 MHz, CHLOROFORM-d) δ ppm 1.36 (t, J = 6.99 Hz, 3 H) 3.03-3.17 (m, 1 H) 3.46-4.03 (m, 10 H) 4.44-4.62 (m, 5 H) 4.76-5.04 (m, 7 H) 6.47 (s, 1 H) 6.61-6.78 (m, 4 H) 6.94-7.37 (m, 31 H). colorless oil. |
| Compound 32 | | 1H NMR (300 MHz, CHLOROFORM-d) δ ppm 1.15 (t, J = 7.54 Hz, 3 H) 2.22 (s, 3 H) 2.54 (q, J = 7.54 Hz, 2 H) 3.06-3.16 (m, 1 H) 3.49-4.07 (m, 11 H) 4.45-4.65 (m, 5 H) 4.84-4.94 (m, 3 H) 6.69-6.76 (m, 3 H) 6.94 (s, 4 H) 7.07-7.19 (m, 5 H) 7.22-7.35 (m, 14 H). ESI m/Z = 801 (M + Na). colorless oil. |

TABLE 1-continued

| Compound No. | Structural formula | ¹NMR, MS, mp, Elemental analysis |
|---|---|---|
| Compound 33 | | 1H NMR (300 MHz, CHLOROFORM-d) δ ppm 1.14 (t, J = 7.54 Hz, 3 H) 2.54 (q, J = 8.13 Hz, 2 H) 3.06-3.16 (m, 1 H) 3.53 (t, J = 8.78 Hz, 1 H) 3.64-4.13 (m, 10 H) 4.46-4.65 (m, 5 H) 4.83-4.95 (m, 3 H) 6.64-6.72 (m, 2 H) 6.87-7.35 (m, 24 H). ESI m/z = 821 (M + Na). colorless oil. |
| Compound 34 | | 1H NMR (300 MHz, CHLOROFORM-d) δ ppm 0.34-0.38 (m, 9 H) 0.47 (s, 9 H) 0.51 (s, 9 H) 0.53 (s, 9 H) 1.56 (t, J = 7.54 Hz, 3 H) 2.96 (q, J = 7.51 Hz, 2 H) 3.30-3.45 (m, 1 H) 3.63 (t, J = 8.16 Hz, 1 H) 3.82-4.08 (m, 3 H) 4.14 (s, 3 H) 4.29 (dd, J = 10.41, 3.73 Hz, 1 H) 4.35 (d, J = 3.57 Hz, 2 H) 4.73 (d, J = 10.96 Hz, 1 H) 7.20 (s, 1 H) 7.42-7.51 (m, 4 H) 7.62 (s, 1 H). ). ESI m/Z = 749 (M + Na). |
| Compound 35 | | 1H NMR (300 MHz, CHLOROFORM-d) δ ppm 1.15 (d, J = 6.84 Hz, 6 H) 2.72-2.85 (m, 1 H) 3.06-3.15 (m, 1 H) 3.53 (t, J = 9.17 Hz, 1 H) 3.64-4.11 (m, 10 H) 4.44-4.63 (m, 5 H) 4.83-4.93 (m, 3 H) 6.67 (d, J = 7.69, 1.48 Hz, 2 H) 6.89 (s, 1 H) 6.94-7.36 (m, 23 H). colorless oil. |
| Compound 36 | | 1H NMR (300 MHz, CHLOROFORM-d) δ ppm 2.21 (s, 3 H) 2.24 (s, 3 H) 3.07-3.18 (m, 1 H) 3.55 (t, J = 8.39 Hz, 1 H) 3.64-4.07 (m, 10 H) 4.47-4.64 (m, 5 H) 4.84-4.94 (m, 3 H) 6.69-6.77 (m, 3 H) 6.91 (s, 4 H) 7.07-7.20 (m, 5 H) 7.22-7.36 (m, 14 H). ESI m/Z = 787 (M + Na). colorless amorphous. |
| Compound 37 | | 1H NMR (300 MHz, CHLOROFORM-d) δ ppm 1.15 (s, 3 H) 1.17 (s, 3 H) 2.23 (s, 3 H) 2.70-2.86 (m, 1 H) 3.03-3.20 (m, 1 H) 3.55 (t, J = 8.94 Hz, 1 H) 3.64-4.08 (m, 10 H) 4.43-4.66 (m, 5 H) 4.80-4.95 (m, 3 H) 6.67-6.78 (m, 3 H) 6.95 (s, 4 H) 7.05-7.19 (m, 5 H) 7.21-7.37 (m, 14 H). ESI m/Z = 815 (M + Na). pale yellow amorphous. |
| Compound 38 | | 1H NMR (300 MHz, CHLOROFORM-d) δ ppm 1.26 (t, J = 7.15 Hz, 3 H) 2.65 (q, J = 7.67 Hz, 1 H) 3.06-3.24 (m, 1 H) 3.50-3.61 (m, 1 H) 3.71 (dd, J = 9.87, 3.03 Hz, 1 H) 3.78-4.09 (m, 6 H) 4.52 (s, 2 H) 4.62 (t, J = 10.34 Hz, 2 H) 4.84-4.98 (m, 3 H) 6.75-6.85 (m, 2 H) 7.08-7.56 (m, 25 H) 7.72 (d, J = 2.02 Hz, 1 H). ESI m/Z = 796 (M − H). pale yellow powder. |

TABLE 1-continued

| Compound No. | Structural formula | ¹NMR, MS, mp, Elemental analysis |
| --- | --- | --- |
| Compound 39 | | 1H NMR (300 MHz, CHLOROFORM-d) δ ppm 3.06-3.29 (m, 1 H) 3.77-4.12 (m, 8 H) 4.46-4.68 (m, 4 H) 4.84-5.00 (m, 2 H) 7.01-7.45 (m, 23 H). |
| Compound 40 | | 1H NMR (300 MHz, CHLOROFORM-d) δ ppm 1.61 (s, 9 H) 3.06-3.21 (m, 1 H) 3.51-3.64 (m, 1 H) 3.66-3.77 (m, 1 H) 3.78-4.06 (m, 5 H) 4.48-4.67 (m, 4 H) 4.84-4.95 (m, 3 H) 6.75 (dd, J = 7.54, 1.79 Hz, 2 H) 7.08-7.20 (m, 5 H) 7.24-7.46 (m, 15 H) 7.77 (d, J = 2.02 Hz, 1 H). ESI m/Z = 768 (M + NH4). |
| Compound 41 | | 1H NMR (300 MHz, CHLOROFORM-d) δ ppm 1.13-1.31 (m, 3 H) 2.46-2.72 (m, 2 H) 3.04-3.18 (m, 1 H) 3.47-3.62 (m, 1 H) 3.68-4.02 (m, 6 H) 4.45-4.66 (m, 4 H) 4.85-4.96 (m, 3 H) 6.49-6.80 (m, 3 H) 6.92-7.62 (m, 27 H). ESI m/z = 769 (M + Na). colorless powder. |
| Compound 42 | | 1H NMR (300 MHz, CHLOROFORM-d) δ ppm 1.22 (t, J = 7.62 Hz, 3 H) 2.62 (q, J = 7.62 Hz, 2 H) 2.91-3.03 (m, 1 H) 3.20 (t, J = 9.01 Hz, 1 H) 3.43-3.79 (m, 5 H) 3.90-4.07 (m, 6 H) 4.09-4.18 (m, 1 H) 4.24-4.41 (m, 3 H) 4.92-5.02 (m, 2 H) 5.09-5.32 (m, 6 H) 5.50-5.66 (m, 1 H) 5.79-6.05 (m, 3 H) 6.61 (d, J = 3.57 Hz, 1 H) 6.85 (d, J = 3.42 Hz, 1 H) 7.07-7.16 (m, 4 H). ESI m/z = 563 (M + Na). yellow oil. |
| Compound 43 | | 1H NMR (300 MHz, CHLOROFORM-d) δ ppm 1.21 (t, J = 7.62 Hz, 3 H) 2.61 (q, J = 7.56 Hz, 2 H) 3.06-3.15 (m, 1 H) 3.53 (t, J = 8.94 Hz, 1 H) 3.68-3.98 (m, 8 H) 4.47-4.54 (m, 3 H) 4.61 (d, J = 10.41 Hz, 1 H) 4.87-4.94 (m, 3 H) 6.61-6.67 (m, 2 H) 7.01-7.39 (m, 26 H). ESI m/Z = 757 (M + Na). colorless powder. |
| Compound 44 | | 1H NMR (300 MHz, CHLOROFORM-d) δ ppm 2.91-3.03 (m, 1 H) 3.19-3.40 (m, 2 H) 3.56-3.87 (m, 6 H) 3.92-4.02 (m, 4 H) 4.11-4.20 (m, 1 H) 4.25-4.43 (m, 3 H) 4.63-4.68 (m, 2 H) 4.80-4.95 (m, 2 H) 5.09-5.48 (m, 7 H) 5.81-6.04 (m, 3 H) 7.00-7.39 (m, 8 H). ESI m/Z = 554 (M + NH4). pale yellow oil. |
| Compound 45 | | 1H NMR (300 MHz, CHLOROFORM-d) δ ppm 1.61 (s, 9 H) 3.06-3.21 (m, 1 H) 3.51-3.64 (m, 1 H) 3.66-3.77 (m, 1 H) 3.78-4.06 (m, 5 H) 4.48-4.67 (m, 4 H) 4.84-4.95 (m, 3 H) 6.75 (dd, J = 7.54, 1.79 Hz, 2 H) 7.08-7.20 (m, 5 H) 7.24-7.46 (m, 15 H) 7.77 (d, J = 2.02 Hz, 1 H). ESI m/Z = 759 (M + Na). |

TABLE 1-continued

| Compound No. | Structural formula | ¹NMR, MS, mp, Elemental analysis |
| --- | --- | --- |
| Compound 46 | | 1H NMR (300 MHz, DMSO-d₆) δ ppm 1.21 (t, J = 7.54 Hz, 3 H) 2.65 (q, 2 H) 3.58 (t, J = 8.86 Hz, 1 H) 3.69-3.85 (m, 3 H) 3.89-4.16 (m, 3 H) 4.41-4.62 (m, 5 H) 4.78-4.85 (m, 3 H) 6.65 (d, J = 7.62 Hz, 2 H) 7.01-7.12 (m, 3 H) 7.16-7.22 (m, 2 H) 7.26-7.35 (m, 15 H) 7.40-7.71 (m, 6 H). ESI m/z = 743 (M + Na). colorless powder. |
| Compound 47 | | 1H NMR (300 MHz, CHLOROFORM-d) δ ppm 1.66-1.81 (m, 2 H) 1.88-2.02 (m, 2 H) 3.05-3.15 (m, 1 H) 3.47-3.59 (m, 3 H) 3.64-4.00 (m, 10 H) 4.33-4.42 (m, 1 H) 4.46 (d, J = 9.95 Hz, 1 H) 4.52 (s, 2 H) 4.60 (d, J = 10.41 Hz, 1 H) 4.84-4.93 (m, 3 H) 6.60-6.67 (m, 2 H) 6.72-6.79 (m, 2 H) 6.99-7.19 (m, 8 H) 7.20-7.35 (m, 16 H). ESI m/Z = 824 (M + NH4). colorless powder. |
| Compound 48 | | 1H NMR (300 MHz, CHLOROFORM-d) δ ppm 1.56-1.66 (m, 2 H) 1.68-1.92 (m, 6 H) 3.06-3.14 (m, 1 H) 3.52 (t, J = 8.86 Hz, 1 H) 3.67-3.74 (m, 1 H) 3.75-3.98 (m, 7 H) 4.42-4.70 (m, 5 H) 4.83-4.93 (m, 3 H) 6.61-6.75 (m, 4 H) 6.98-7.19 (m, 8 H) 7.19-7.34 (m, 16 H). ESI m/Z = 808 (M + NH4). colorless powder. |
| Compound 49 | | 1H NMR (300 MHz, CHLOROFORM-d) δ ppm 3.00-3.13 (m, 3 H) 3.30-3.44 (m, 4 H) 3.67-3.89 (m, 5 H) 3.94-4.05 (m, 3 H) 4.15-4.24 (m, 1 H) 4.33 (d, J = 5.75 Hz, 2 H) 4.37-4.46 (m, 1 H) 4.77-4.87 (m, 2 H) 5.10-5.45 (m, 7 H) 5.81-6.06 (m, 3 H) 7.19-7.39 (m, 7 H) 7.53 (dd, J = 8.63, 1.63 Hz, 1 H) 7.70 (d, J = 7.62 Hz, 1 H) 7.82 (d, J = 8.39 Hz, 1 H) 8.08 (s, 1 H). ESI m/Z = 593 (M + Na). colorless powder. |
| Compound 50 | | 1H NMR (300 MHz, CHLOROFORM-d) δ ppm 2.98-3.18 (m, 5 H) 3.40-4.02 (m, 12 H) 4.36-4.66 (m, 5 H) 4.81-4.97 (m, 3 H) 6.58-7.50 (m, 28 H). FAB m/Z = 791 (M). colorless oil. |
| Compound 51 | | 1H NMR (300 MHz, CHLOROFORM-d) δ ppm 2.88 (s, 6 H) 3.05-3.16 (m, 1 H) 3.41-4.01 (m, 8 H) 4.39-4.64 (m, 5 H) 4.84-4.90 (m, 3 H) 6.52-7.37 (m, 28 H). ESI m/Z = 772 (M + Na). colorless oil. |

TABLE 1-continued

| Compound No. | Structural formula | ¹NMR, MS, mp, Elemantal analysis |
| --- | --- | --- |
| Compound 52 | (structure) | 1H NMR (300 MHz, CHLOROFORM-d) δ ppm 3.05-3.15 (m, 1 H) 3.52 (t, J = 8.94 Hz, 1 H) 3.66-3.75 (m, 1 H) 3.75-3.98 (m, 10 H) 4.41-4.64 (m, 6 H) 4.83-4.95 (m, 3 H) 6.60-6.79 (m, 4 H) 6.98-7.19 (m, 8 H) 7.22-7.36 (m, 16 H). ESI m/Z = 817 (M + Na). colorless oil. |
| Compound 53 | (structure) | 1H NMR (300 MHz, CHLOROFORM-d) δ ppm 2.96 (s, 3 H) 3.05 (s, 3 H) 3.06-3.14 (m, 1 H) 3.52 (t, J = 8.86 Hz, 1 H) 3.68-3.74 (m, 1 H) 3.76-3.96 (m, 7 H) 4.44-4.54 (m, 3 H) 4.56-4.63 (m, 3 H) 4.85-4.93 (m, 3 H) 6.65 (dd, J = 7.93, 1.55 Hz, 2 H) 6.76-6.83 (m, 2 H) 7.01-7.18 (m, 8 H) 7.22-7.35 (m, 16 H). ESI m/Z = 825 (M + NH4). colorless solid. |
| Compound 54 | (structure) | 1H NMR (300 MHz, CHLOROFORM-d) δ ppm 2.35 (s, 6 H) 2.68-2.81 (m, 2 H) 3.04-3.16 (m, 1 H) 3.52 (t, J = 8.70 Hz, 1 H) 3.66-3.76 (m, 1 H) 3.76-4.10 (m, 9 H) 4.47 (d, J = 10.10 Hz, 1 H) 4.52 (s, 2 H) 4.60 (d, J = 10.72 Hz, 1 H) 4.84-4.94 (m, 3 H) 6.65 (dd, J = 7.85, 1.32 Hz, 2 H) 6.72-6.81 (m, 2 H) 7.00-7.18 (m, 8 H) 7.20-7.36 (m, 16 H). ESI m/Z = 794 (M + H). colorless solid. |
| Compound 55 | (structure) | 1H NMR (300 MHz, CHLOROFORM-d) δ ppm 3.06-3.14 (m, 1 H) 3.52 (t, J = 8.86 Hz, 1 H) 3.67-3.74 (m, 1 H) 3.77-4.04 (m, 11 H) 4.47 (d, J = 9.95 Hz, 1 H) 4.52 (s, 2 H) 4.60 (d, J = 10.72 Hz, 1 H) 4.86-4.93 (m, 3 H) 6.62-6.68 (m, 2 H) 6.73-6.79 (m, 2 H) 7.02-7.18 (m, 8 H) 7.21-7.35 (m, 16 H). ESI m/Z = 784 (M + NH4). colorless solid. |
| Compound 56 | (structure) | 1H NMR (600 MHz, CHLOROFORM-d) δ ppm 3.03-3.12 (m, 1 H) 3.50 (t, J = 9.17 Hz, 1 H) 3.70 (dd, J = 9.86, 2.98 Hz, 1 H) 3.76-3.84 (m, 2 H) 3.86 (s, 3 H) 3.87-3.92 (m, 2 H) 3.94 (d, J = 10.09 Hz, 1 H) 4.13-4.18 (m, 1 H) 4.22-4.27 (m, 1 H) 4.46 (d, J = 10.09 Hz, 1 H) 4.51 (s, 2 H) 4.59 (d, J = 10.55 Hz, 1 H) 4.85 (s, 2 H) 4.89 (d, J = 11.00 Hz, 1 H) 6.69 (d, J = 6.88 Hz, 2 H) 6.87 (d, J = 9.17 Hz, 1 H) 6.94 (s, 1 H) 7.01 (t, J = 7.57 Hz, 2 H) 7.09 (t, J = 7.34 Hz, 1 H) 7.12-7.16 (m, J = 9.17 Hz, 2 H) 7.20 (t, J = 7.57 Hz, 1 H) 7.23-7.35 (m, 16 H) 7.54 (d, J = 7.79 Hz, 1 H) 7.67 (d, J = 8.71 Hz, 1 H). ESI m/Z = 815 (M + Na). mp 133.0-135.0° C. colorless powder. |
| Compound 57 | (structure) | 1H NMR (600 MHz, CHLOROFORM-d) δ ppm 3.02-3.14 (m, 1 H) 3.51 (t, J = 8.94 Hz, 1 H) 3.70 (dd, J = 9.63, 2.75 Hz, 1 H) 3.76-3.92 (m, 4 H) 3.96 (d, J = 10.55 Hz, 1 H) 4.24-4.30 (m, 1 H) 4.32-4.39 (m, 1 H) 4.48-4.54 (m, 3 H) 4.58 (d, J = 10.55 Hz, 1 H) 4.81-4.91 (m, 3 H) 6.70 (d, J = 7.34 Hz, 2 H) 6.95 (s, 1 H) 7.07 (t, J = 7.57 Hz, 2 H) 7.11-7.42 (m, 21 H) 7.56 (d, J = 7.79 Hz, 1 H) 7.68 (d, J = 7.79 Hz, 1 H). ESI m/Z = 819 (M + Na). mp 140.0-143.0° C. colorless powder. |

TABLE 1-continued

| Compound No. | Structural formula | ¹NMR, MS, mp, Elemental analysis |
|---|---|---|
| Compound 58 | | 1H NMR (600 MHz, CHLOROFORM-d) δ ppm 3.08-3.14 (m, 1 H) 3.53 (t, J = 8.94 Hz, 1 H) 3.71 (dd, J = 9.63, 2.75 Hz, 1 H) 3.77-3.88 (m, 2 H) 3.88-3.97 (m, 3 H) 4.16-4.25 (m, 2 H) 4.48 (d, J = 9.63 Hz, 1 H) 4.52 (s, 2 H) 4.59 (d, J = 11.00 Hz, 1 H) 4.85-4.91 (m, 3 H) 6.67 (d, J = 6.88 Hz, 2 H) 6.97 (s, 1 H) 7.03-7.09 (m, J = 6.65, 6.65 Hz, 2 H) 7.10-7.16 (m, 3 H) 7.19-7.42 (m, 19 H) 7.57 (d, J = 7.79 Hz, 1 H) 7.68 (d, J = 8.25 Hz, 1 H). ESI m/Z = 785 (M + Na). pale yellow solid. |
| Compound 59 | | 1H NMR (600 MHz, CHLOROFORM-d) δ ppm 3.09-3.15 (m, 1 H) 3.53-3.58 (m, 1 H) 3.66-3.74 (m, 1 H) 3.81 (s, 4 H) 3.91 (t, J = 9.63 Hz, 2 H) 3.98-4.04 (m, 1 H) 4.09-4.19 (m, 2 H) 4.48-4.54 (m, 3 H) 4.58-4.67 (m, 2 H) 4.83-4.92 (m, 3 H) 6.69 (d, J = 6.88 Hz, 2 H) 6.84-6.94 (m, 2 H) 7.07-7.35 (m, 21 H) 7.45-7.66 (m, 3 H). ESI m/Z = 815 (M + Na). colorless powder. |
| Compound 60 | | 1H NMR (300 MHz, CHLOROFORM-d) δ ppm 3.06-3.18 (m, 1 H) 3.54 (t, J = 9.17 Hz, 1 H) 3.63-4.31 (m, 13 H) 4.44-4.64 (m, 5 H) 4.82-4.95 (m, 3 H) 6.47 (s, 1 H) 6.72 (d, J = 9.33 Hz, 2 H) 6.88 (s, 1 H) 7.00-7.52 (m, 22 H) 7.58-7.67 (m, 1 H). ESI m/Z = 845 (M + Na). colorless amorphous. |
| Compound 61 | | 1H NMR (300 MHz, CHLOROFORM-d) δ ppm 3.03-3.15 (m, 1 H) 3.46-3.56 (m, 1 H) 3.66-4.02 (m, 6 H) 4.11-4.29 (m, 2 H) 4.48-4.63 (m, 4 H) 4.83-4.93 (m, 3 H) 6.28 (s, 1 H) 6.71 (dd, J = 8.16, 1.32 Hz, 2 H) 7.04-7.19 (m, 6 H) 7.22-7.43 (m, 19 H). ESI m/Z = 798 (M + NH4). pink powder. |
| Compound 62 | | 1H NMR (300 MHz, CHLOROFORM-d) δ ppm 3.07-3.15 (m, 1 H) 3.53 (t, J = 8.94 Hz, 1 H) 3.68-3.75 (m, 1 H) 3.78-4.00 (m, 5 H) 4.07-4.17 (m, 2 H) 4.46-4.54 (m, 3 H) 4.60 (d, J = 10.57 Hz, 1 H) 4.86-4.93 (m, 3 H) 6.65-6.71 (m, J = 7.54, 1.94 Hz, 2 H) 6.75 (d, J = 3.89 Hz, 1 H) 7.06-7.17 (m, 7 H) 7.24-7.40 (m, 17 H) 7.47-7.53 (m, 1 H) 7.58-7.65 (m, 1 H) 8.48-8.52 (m, 1 H). ESI m/z = 790 (M + H). colorless powder. |
| Compound 63 | | 1H NMR (300 MHz, CHLOROFORM-d) δ ppm 1.22 (t, J = 7.62 Hz, 3 H) 2.62 (q, J = 7.62 Hz, 2 H) 2.91-3.03 (m, 1 H) 3.20 (t, J = 9.01 Hz, 1 H) 3.43-3.79 (m, 5 H) 3.90-4.07 (m, 6 H) 4.09-4.18 (m, 1 H) 4.24-4.41 (m, 3 H) 4.92-5.02 (m, 2 H) 5.09-5.32 (m, 6 H) 5.50-5.66 (m, 1 H) 5.79-6.05 (m, 3 H) 6.61 (d, J = 3.57 Hz, 1 H) 6.85 (d, J = 3.42 Hz, 1 H) 7.07-7.16 (m, 4 H). ESI m/z = 611 (M + Na). yellow oil. |

TABLE 1-continued

| Compound No. | Structural formula | ¹NMR, MS, mp, Elemantal analysis |
| --- | --- | --- |
| Compound 64 | | 1H NMR (300 MHz, CHLOROFORM-d) δ ppm 3.53 (t, J = 8.86 Hz, 1 H) 3.66-3.76 (m, 1 H) 3.67-3.74 (m, 1 H) 3.77-4.00 (m, 5 H) 4.18 (s, 2 H) 4.45-4.54 (m, 3 H) 4.60 (d, J = 10.57 Hz, 1 H) 4.86-4.94 (m, 3 H) 6.67 (dd, J = 8.00, 1.32 Hz, 2 H) 6.90 (s, 1 H) 7.03-7.41 (m, 24 H). ESI m/Z = 791 (M + Na). |
| Compound 65 | | 1H NMR (300 MHz, CHLOROFORM-d) δ ppm 3.04-3.16 (m, 1 H) 3.32 (s, 3 H) 3.53 (t, J = 8.70 Hz, 1 H) 3.67-3.75 (m, 1 H) 3.75-4.00 (m, 7 H) 4.46-4.56 (m, 3 H) 4.60 (d, J = 10.57 Hz, 1 H) 4.84-4.96 (m, 3 H) 5.89 (dd, J = 3.73, 1.55 Hz, 1 H) 6.04 (t, J = 3.03 Hz, 1 H) 6.49-6.54 (m, 1 H) 6.70 (dd, J = 7.62, 1.71 Hz, 2 H) 7.05-7.18 (m, 7 H) 7.22-7.36 (m, 14 H) 7.39-7.46 (m, 1 H). ESI m/Z = 710 (M + H), 732 (M + Na). |
| Compound 66 | | 1H NMR (300 MHz, CHLOROFORM-d) δ ppm 3.06-3.17 (m, 1 H) 3.54 (t, J = 8.78 Hz, 1 H) 3.68-3.75 (m, 1 H) 3.77-4.01 (m, 5 H) 4.43 (s, 2 H) 4.46-4.56 (m, 3 H) 4.60 (d, J = 10.57 Hz, 1 H) 4.85-4.94 (m, 3 H) 6.67 (dd, J = 7.93, 1.40 Hz, 2 H) 7.00-7.19 (m, 6 H) 7.21-7.51 (m, 18 H) 7.71 (d, J = 7.31 Hz, 1 H) 7.97 (d, J = 8.08 Hz, 1 H). ESI m/Z = 764 (M + H), 786 (M + Na). |
| Compound 67 | | 1H NMR (300 MHz, CHLOROFORM-d) δ ppm 1.40 (t, J = 6.99 Hz, 3 H) 2.93-3.06 (m, 1 H) 3.25 (t, J = 8.94 Hz, 1 H) 3.30-3.44 (m, 1 H) 3.49-4.05 (m, 12 H) 4.15 (dd, J = 12.05, 5.98 Hz, 1 H) 4.24-4.42 (m, 3 H) 4.80-4.92 (m, 2 H) 5.08-5.42 (m, 7 H) 5.78-6.03 (m, 3 H) 6.81 (d, J = 8.70 Hz, 2 H) 7.03 (d, J = 8.70 Hz, 2 H) 7.48 (s, 1 H) 8.42 (dd, J = 16.16, 2.18 Hz, 2 H). ESI m/Z = 552 (M + H) |
| Compound 68 | | 1H NMR (300 MHz, CHLOROFORM-d) δ ppm 2.31 (s, 3 H) 2.99-3.10 (m, 1 H) 3.27-3.40 (m, 2 H) 3.66-3.87 (m, 5 H) 4.00 (d, J = 5.75 Hz, 2 H) 4.15-4.26 (m, 4 H) 4.31 (d, J = 6.84 Hz, 2 H) 4.40 (dd, J = 12.05, 5.83 Hz, 1 H) 4.63-4.82 (m, 2 H) 5.09-5.37 (m, 7 H) 5.80-6.07 (m, 3 H) 7.04-7.17 (m, 5 H) 7.32 (t, J = 1 H) 7.41 (s, 1 H) 7.89 (d, J = 7.93 Hz, 1 H). ESI m/z = 599 (M + Na). yellow powder. |
| Compound 69 | | 1H NMR (300 MHz, CHLOROFORM-d) δ ppm 2.28 (s, 3 H) 3.07-3.16 (m, 1 H) 3.53 (t, J = 8.78 Hz, 1 H) 3.68-3.97 (m, 6 H) 4.49-4.63 (m, 5 H) 4.86-4.91 (m, 2 H) 4.99 (d, J = 3.11 Hz, 2 H) 6.68 (dd, J = 7.85, 1.63 Hz, 2 H) 6.76 (d, J = 1.24 Hz, 1 H) 6.92-7.00 (m, 2 H) 7.08-7.19 (m, 6 H) 7.23-7.44 (m, 15 H). ESI m/Z = 711 (M + H). |
| Compound 70 | | 1H NMR (300 MHz, CHLOROFORM-d) δ ppm 3.05-3.14 (m, 1 H) 3.46-3.56 (m, 1 H) 3.66-3.74 (m, 1 H) 3.76-3.92 (m, 5 H) 3.95 (s, 3 H) 4.46 (d, J = 10.10 Hz, 1 H) 4.52 (s, 2 H) 4.59 (d, J = 10.57 Hz, 1 H) 4.84-4.93 (m, 3 H) 5.25 (d, J = 2.49 Hz, 2 H) 6.46-7.39 (m, 29 H). ESI m/Z = 793 (M + NH4). |

TABLE 1-continued

| Compound No. | Structural formula | ¹NMR, MS, mp, Elemantal analysis |
|---|---|---|
| Compound 71 | | 1H NMR (300 MHz, CHLOROFORM-d) δ ppm 3.05-3.17 (m, 1 H) 3.47-3.60 (m, 1 H) 3.66-3.99 (m, 6 H) 4.15 (s, 1 H) 4.43-4.70 (m, 5 H) 4.84-4.95 (m, 3 H) 6.60-6.73 (m, 2 H) 6.97-7.20 (m, 6 H) 7.19-7.49 (m, 17 H) 7.78-7.87 (m, 1 H) 8.36-8.43 (m, 1 H) 8.65-8.73 (m, 1 H). ESI m/Z = 708 (M + H), 730 (M + Na). pale yellow powder. |
| Compound 72 | | 1H NMR (300 MHz, CHLOROFORM-d) δ ppm 3.05-3.15 (m, 1 H) 3.52 (t, J = 8.94 Hz, 1 H) 3.66-3.75 (m, 1 H) 3.75-4.01 (m, 5 H) 4.28 (s, 2 H) 4.46 (d, J = 9.79 Hz, 1 H) 4.52 (s, 2 H) 4.60 (d, J = 10.72 Hz, 1 H) 4.85-4.95 (m, 3 H) 6.55-6.62 (m, 2 H) 6.98-7.37 (m, 22 H) 7.49 (s, 1 H) 8.57 (d, J = 4.97 Hz, 2 H). ESI m/Z = 731 (M + Na), 709 (M +H). |
| Compound 73 | | 1H NMR (300 MHz, CHLOROFORM-d) δ ppm 3.05-3.16 (m, 1 H) 3.48-3.58 (m, 1 H) 3.66-3.75 (m, 1 H) 3.77-3.99 (m, 5 H) 4.15 (s, 2 H) 4.45-4.55 (m, 3 H) 4.60 (d, J = 10.57 Hz, 1 H) 4.84-4.95 (m, 3 H) 6.62 (d, J = 6.84 Hz, 2 H) 7.02-7.19 (m, 6 H) 7.20-7.42 (m, 16 H) 8.36 (d, J = 2.64 Hz, 1 H) 8.40-8.47 (m, 1 H) 8.67 (s, 1 H). ESI m/Z = 731 (M + Na). |
| Compound 74 | | 1H NMR (300 MHz, METHANOL-$d_4$) δ ppm 1.19 (t, J = 7.6 Hz, 3 H) 2.58 (q, J = 7.6 Hz, 2 H) 2.95-3.03 (m, 1 H) 3.20-3.28 (m, 1 H) 3.60 (dd, J = 10.3, 9.0 Hz, 1 H) 3.70-3.78 (m, 3 H) 3.88-3.98 (m, 3 H) 7.09 (brs, 5 H) 7.17-7.23 (m, 3 H). ESI m/z = 397 (M + Na), 373 (M − H). |
| Compound 75 | | 1H NMR (300 MHz, METHANOL-$d_4$) δ ppm 1.35 (t, J = 7.0 Hz, 3 H) 2.92-3.03 (m, 1 H) 3.19-3.28 (m, 1 H) 3.59 (dd, J = 10.2, 9.1 Hz, 1 H) 3.69-3.78 (m, 3 H) 3.88 (s, 2 H) 3.90-4.04 (m, 3 H) 6.80 (d, J = 8.7 Hz, 2 H) 7.04-7.11 (m, 3 H) 7.14-7.25 (m, 3 H). ESI m/z = 413 (M + Na), 389 (M − H). |
| Compound 76 | | 1H NMR (300 MHz, METHANOL-$d_4$) δ ppm 1.36 (t, J = 7.0 Hz, 3 H) 2.94-3.03 (m, 1 H) 3.22 (t, J = 8.2 Hz, 1 H) 3.57 (dd, J = 10.3, 9.0 Hz, 1 H) 3.65-3.78 (m, 3 H) 3.89-4.05 (m, 5 H) 6.80 (d, J = 8.7 Hz, 2 H) 7.08 (d, J = 8.7 Hz, 2 H) 7.16-7.23 (m, 2 H) 7.32 (d, 1 H). ESI m/z = 447, 449 (M + Na). mp 79.0-83.0° C. |

TABLE 1-continued

| Compound No. | Structural formula | ¹NMR, MS, mp, Elemental analysis |
|---|---|---|
| Compound 77 | | 1H NMR (300 MHz, METHANOL-d₄) δ ppm 1.35 (t, J = 7.0 Hz, 3 H) 2.91-3.01 (m, 1 H) 3.18-3.25 (m, 1 H) 3.57 (dd, J = 10.3, 9.0 Hz, 1 H) 3.68-3.76 (m, 3 H) 3.79 (s, 3 H) 3.84 (s, 2 H) 3.89-4.02 (m, 3 H) 6.76 (d, J = 8.7 Hz, 2 H) 6.88 (d, J = 8.7 Hz, 1 H) 7.03-7.11 (m, 3 H) 7.17 (dd, J = 8.6, 2.3 Hz, 1 H). ESI m/z = 443 (M + Na), 419 (M − H). mp 89.0-95.0° C. |
| Compound 78 | | 1H NMR (600 MHz, METHANOL-d₄) δ ppm 1.33 (t, J = 7.1 Hz, 3 H) 2.90-2.98 (m, 1 H) 3.22 (t, J = 8.9 Hz, 1 H) 3.51-3.61 (m, 1 H) 3.65-3.74 (dd, J = 11.5, 6.4 Hz, 1 H) 3.76-3.84 (m, 6 H) 3.91 (dd, J = 11.5, 3.7 Hz, 1 H) 3.96 (q, J = 7.1 Hz, 2 H) 4.31 (brs, 1 H) 6.77 (d, J = 8.7 Hz, 2 H) 6.85 (d, J = 8.7 Hz, 1 H) 7.00 (dd, J = 8.7, 2.3 Hz, 1 H) 7.04 (d, J = 8.7 Hz, 2 H) 7.16 (brs, 1 H). ESI m/z = 443 (M + Na). mp 130.0-130.5° C. |
| Compound 79 | | 1H NMR (300 MHz, METHANOL-d₄) δ ppm 1.37 (t, J = 7.0 Hz, 3 H) 2.94-3.05 (m, 1 H) 3.22-3.29 (m, 1 H) 3.60 (m, 1 H) 3.69-3.88 (m, 4 H) 3.90-4.04 (m, 3 H) 4.33 (d, J = 10.6 Hz, 1 H) 6.71 (d, J = 8.2 Hz, 1 H) 6.76-6.90 (m, 3 H) 7.03-7.15 (m, 3 H). ESI m/z = 429 (M + Na), 405 (M − H). mp 145.0-150.0° C. |
| Compound 80 | | 1H NMR (300 MHz, METHANOL-d₄) δ ppm 1.34 (t, J = 7.0 Hz, 3 H) 2.88-2.99 (m, 1 H) 3.22 (t, J = 8.8 Hz, 1 H) 3.51-3.59 (m, 1 H) 3.66-3.79 (m, 4H) 3.81 (s, 3 H) 3.84 (s, 3 H) 3.88-4.01 (m, 3 H) 4.21-4.32 (m, 1 H) 6.57 (s, 1 H) 6.75 (d, J = 8.7 Hz, 2 H) 7.03 (s, 1 H) 7.04 (d, J = 8.7 Hz, 2 H). ESI m/z = 449 (M + Na). mp 158.0-160.0° C. |
| Compound 81 | | 1H NMR (300 MHz, METHANOL-d₄) δ ppm 1.35 (t, J = 7.0 Hz, 3 H) 2.91-3.03 (m, 1 H) 3.19-3.25 (m, 1 H) 3.58 (dd, J = 10.3, 9.0 Hz, 1 H) 3.68-3.79 (m, 3 H) 3.86-4.04 (m, 5 H) 6.77-6.82 (m, 2 H) 6.95-7.04 (m, 1 H) 7.07-7.12 (m, 2 H) 7.15-7.24 (m, 2 H). ESI m/z = 431 (M + Na). mp 60.0-65.0° C. |
| Compound 82 | | 1H NMR (300 MHz, METHANOL-d₄) δ ppm 1.35 (t, J = 6.9 Hz, 3 H) 2.89-2.98 (m, 1 H) 3.16-3.24 (m, 1 H) 3.56 (dd, J = 10.2, 9.0 Hz, 1 H) 3.60-3.76 (m, 3 H) 3.83 (bs, 2 H) 3.88-3.95 (m, 1 H) 3.98 (q, J = 6.9 Hz, 2 H) 6.69-6.80 (m, 3 H) 6.96-7.04 (m, 2 H) 7.06-7.15 (m, 2 H). ESI m/z = 424 (M + NH4), 405 (M − H). |

TABLE 1-continued

| Compound No. | Structural formula | ¹NMR, MS, mp, Elemental analysis |
|---|---|---|
| Compound 83 | | 1H NMR (600 MHz, METHANOL-d$_4$) δ ppm 1.40 (t, J = 7.1 Hz, 3 H) 2.94-3.04 (m, 1 H) 3.23 (t, J = 8.9 Hz, 1 H) 3.58 (dd, J = 10.3, 8.9 Hz, 1 H) 3.67-3.79 (m, 3 H) 3.94 (dd, J = 11.5, 3.2 Hz, 1 H) 3.96-4.04 (m, 2 H) 4.07 (q, J = 7.1 Hz, 2 H) 6.79 (dd, J = 11.2, 7.1 Hz, 1 H) 6.87 (dd, J = 11.2, 7.1 Hz, 1 H) 7.20 (d, J = 2.3 Hz, 1 H) 7.24 (dd, J = 8.3, 2.3 Hz, 1 H) 7.35 (d, J = 8.3 Hz, 1 H). ESI m/z = 483 (M + Na), 459 (M − H). mp 72.0-76.0° C. |
| Compound 84 | | 1H NMR (600 MHz, METHANOL-d$_4$) δ ppm 1.38 (t, J = 7.1 Hz, 3 H) 2.94-3.03 (m, 1 H) 3.23 (t, J = 8.7 Hz, 1 H) 3.55-3.61 (m, 1 H) 3.67-3.79 (m, 3 H) 3.94 (dd, J = 11.7, 3.4 Hz, 1 H) 3.98-4.02 (m, 2 H) 4.06 (q, J = 7.1 Hz, 2 H) 6.85-6.92 (m, 2 H) 6.96 (t, J = 8.7 Hz, 1 H) 7.19-7.27 (m, 2 H) 7.34 (d, J = 8.3 Hz, 1 H). ESI m/z = 465 (M + Na), 467 (M + 2 + Na), 441 (M − H), 443 (M + 2 − H). mp 73.0-81.0° C. |
| Compound 85 | | 1H NMR (600 MHz, METHANOL-d$_4$) δ ppm 1.40 (t, J = 6.9 Hz, 3 H) 2.96-3.03 (m, 1 H) 3.23 (t, J = 8.9 Hz, 1 H) 3.58 (dd, J = 10.3, 8.9 Hz, 1 H) 3.68-3.80 (m, 3 H) 3.94 (dd, J = 11.7, 3.4 Hz, 1 H) 3.96-4.04 (m, 2 H) 4.06 (q, J = 6.9 Hz, 2 H) 6.93 (d, J = 8.5 Hz, 1 H) 7.05 (dd, J = 8.5, 2.3 Hz, 1 H) 7.16 (d, J = 2.3 Hz, 1 H) 7.20-7.27 (m, 2 H) 7.34 (d, J = 7.8 Hz, 1 H). ESI m/z = 481 (M + Na), 483 (M + 2 +Na), 485 (M + 4 + Na), 457 (M − H) 459 (M + 2 − H), 461 (M + 4 − H). mp 79.0-82.0° C. Anal. Calcd for C21H24ClO5S•0.5H2O: C, 53.84; H, 5.39. Found: C, 53.64; H, 5.39. |
| Compound 86 | | 1H NMR (300 MHz, METHANOL-d$_4$) δ ppm 1.35 (t, J = 6.9 Hz, 3 H) 2.17 (s, 3 H) 2.93-3.03 (m, 1 H) 3.19-3.28 (m, 1 H) 3.59 (dd, J = 10.2, 9.0 Hz, 1 H) 3.68-3.79 (m, 3 H) 3.89 (bs, 2 H) 3.93 (dd, J = 7.9, 3.7 Hz, 1 H) 3.97 (q, 2 H) 6.74-6.82 (m, 2 H) 6.96-7.04 (m, 2 H) 7.05-7.15 (m, 3 H). ESI m/z = 422 (M + NH4), 403 (M − H). |
| Compound 87 | | 1H NMR (600 MHz, METHANOL-d$_4$) δ ppm 2.94-3.00 (m, 1 H) 3.17-3.24 (m, 1 H) 3.55 (dd, J = 10.3, 8.9 Hz, 1 H) 3.61-3.75 (m, 4 H) 3.77 (s, 3 H) 3.78 (s, 3 H) 3.88-3.98 (m, 2 H) 6.42 (dd, J = 8.3, 2.3 Hz, 1 H) 6.52 (d, J = 2.3 Hz, 1 H) 6.90 (d, J = 8.3 Hz, 1 H) 7.09 (d, J = 2.3 Hz, 1 H) 7.16 (dd, J = 8.3, 2.3 Hz, 1 H) 7.30 (d, J = 8.3 Hz, 1 H). ESI m/z = 463 (M + Na), 465 (M + 2 + Na), 439 (M − H). |
| Compound 88 | | 1H NMR (600 MHz, METHANOL-d$_4$) δ ppm 2.96-3.01 (m, 1 H) 3.21-3.25 (m, 1 H) 3.57 (dd, J = 10.3, 8.9 Hz, 1 H) 3.66-3.74 (m, 3 H) 3.75 (s, 3 H) 3.93 (dd, J = 11.5, 3.7 Hz, 1 H) 3.98-4.05 (m, 2 H) 6.82 (d, J = 8.7 Hz, 2 H) 7.09 (d, J = 8.7 Hz, 2 H) 7.18-7.22 (m, 2 H) 7.32 (d, J = 8.3 Hz, 1 H). ESI m/z = 428 (M + NH4$^+$), 430 (M + 2 + NH4$^+$), 409 (M − H), 411 (M + 2 − H). mp 71.0-74.0° C. Anal. Calcd for C20H23ClO5S: C, 58.46; H, 5.46. Found: C, 58.36; H, 5.55. |

TABLE 1-continued

| Compound No. | Structural formula | ¹NMR, MS, mp, Elemental analysis |
|---|---|---|
| Compound 89 | | 1H NMR (600 MHz, METHANOL-$d_4$) δ ppm 1.35 (t, J = 6.9 Hz, 3 H) 2.17 (s, 3 H) 2.92-3.01 (m, 1 H) 3.24 (t, J = 8.71 Hz, 1 H) 3.54-3.60 (m, 1 H) 3.72 (dd, J = 11.5, 6.4 Hz, 1 H) 3.81 (s, 3 H) 3.83 (s, 2 H) 3.94 (dd, J = 11.5, 3.7 Hz, 1 H) 3.97 (q, J = 6.9 Hz, 2 H) 4.33 (s, 1 H) 6.77 (d, J = 8.3 Hz, 2 H) 6.76 (s, 1 H) 6.99 (d, J = 8.3 Hz, 2 H) 7.10 (s, 1 H). ESI m/z = 452 (M + NH$_4^+$), 493 (M + CH$_3$CO$_2^-$). mp 155.0-157.0° C. Anal. Calcd for C23H30O6S•0.5H2O: C, 62.28; H, 7.06. Found: C, 62.39; H, 7.10. |
| Compound 90 | | 1H NMR (300 MHz, METHANOL-$d_4$) δ ppm 1.29 (s, 9 H) 2.90-3.05 (m, 1 H) 3.23 (t, J = 8.7 Hz, 1 H) 3.58 (dd, J = 10.1, 8.7 Hz, 1 H) 3.64-3.80 (m, 3 H) 3.94 (dd, J = 11.4, 3.5 Hz, 1 H) 4.04 (s, 2 H) 7.10 (d, J = 8.2 Hz, 2 H) 7.16-7.37 (m, 5 H). ESI m/z = 454 (M + NH$_4^+$), 456 (M + 2 + NH$_4^+$), 435 (M − H), 437 (M + 2 − H). mp 94.0-100.0° C. Anal. Calcd for C23H29ClO4S: C, 63.22; H, 6.69. Found: C, 62.82; H, 6.64. |
| Compound 91 | | 1H NMR (300 MHz, METHANOL-$d_4$) δ ppm 1.36 (t, J = 7.0 Hz, 3 H) 2.93-3.05 (m, 1 H) 3.18-3.27 (m, 1 H) 3.58 (dd, J = 10.3, 9.0 Hz, 1 H) 3.67-3.78 (m, 3 H) 3.89-4.04 (m, 5 H) 6.58-6.69 (m, 2 H) 6.97 (t, J = 8.9 Hz, 1 H) 7.11-7.24 (m, 2 H) 7.33 (d, 1 H). ESI m/z = 465 (M + Na), 441 (M − H). |
| Compound 92 | | 1H NMR (300 MHz, METHANOL-$d_4$) δ ppm 2.28 (s, 3 H) 2.94-3.02 (m, 1 H) 3.18-3.26 (m, 1 H) 3.57 (dd, J = 10.2, 8.9 Hz, 1 H) 3.65-3.77 (m, 3 H) 3.93 (dd, J = 11.4, 3.7 Hz, 1 H) 4.02 (s, 2 H) 7.02-7.10 (m, 4 H) 7.16-7.24 (m, 2 H) 7.29-7.35 (m, 1 H). ESI m/z = 412, 414 (M + Na), 393 (M − H). |
| Compound 93 | | 1H NMR (600 MHz, METHANOL-$d_4$) δ ppm 2.43 (s, 3 H) 2.95-3.03 (m, 1 H) 3.23 (t, J = 8.7 Hz, 1 H) 3.58 (dd, J = 10.3, 8.9 Hz, 1 H) 3.68-3.77 (m, 3 H) 3.93 (dd, J = 11.5, 3.2 Hz, 1 H) 4.00-4.09 (m, 2 H) 7.09-7.13 (m, 2 H) 7.15-7.19 (m, 2 H) 7.21 (dd, J = 8.3, 2.3 Hz, 1 H) 7.23 (d, J = 2.3 Hz, 1 H) 7.33 (d, J = 8.3 Hz, 1 H). ESI m/z = 449 (M + Na), 451 (M + 2 + Na), 425 (M − H) 427 (M + 2 − H). |
| Compound 94 | | 1H NMR (300 MHz, METHANOL-$d_4$) δ ppm 2.93-3.05 (m, 1 H) 3.18-3.28 (m, 1 H) 3.54-3.64 (m, 1 H) 3.66-3.78 (m, 3 H) 3.89-3.99 (m, 3 H) 6.69 (d, J = 8.6 Hz, 2 H) 6.99 (d, J = 8.6 Hz, 2 H) 7.15-7.22 (m, 2 H) 7.31 (d, 1 H). ESI m/z = 419 (M + Na), 395 (M − H). |

TABLE 1-continued

| Compound No. | Structural formula | ¹NMR, MS, mp, Elemantal analysis |
|---|---|---|
| Compound 95 | | 1H NMR (300 MHz, METHANOL-$d_4$) δ ppm 1.20 (t, J = 7.62 Hz, 3 H) 2.59 (q, J = 7.62 Hz, 2 H) 2.94-3.03 (m, 1 H) 3.18-3.27 (m, 1 H) 3.57 (dd, J = 10.26, 9.01 Hz, 1 H) 3.66-3.78 (m, 3 H) 3.93 (dd, J = 11.50, 3.57 Hz, 1 H) 4.03 (s, 2 H) 7.06-7.11 (m, 4 H) 7.17-7.25 (m, 2 H) 7.33 (d, J = 8.08 Hz, 1 H). ESI m/z = 431,433 (M + Na), 407 (M − H). |
| Compound 96 | | 1H NMR (300 MHz, METHANOL-$d_4$) δ ppm 1.20 (s, 3 H) 1.22 (s, 3 H) 2.76-2.92 (m, 1 H) 2.94-3.03 (m, 1 H) 3.19-3.27 (m, 1 H) 3.58 (dd, J = 10.1, 9.2 Hz, 1 H) 3.66-3.79 (m, 3 H) 3.94 (dd, J = 11.4, 3.6 Hz, 1 H) 4.03 (s, 2 H) 7.06-7.15 (m, 4 H) 7.17-7.26 (m, 2 H) 7.33 (d, 1 H). ESI m/z = 445,447 (M + Na), 421 (M − H). |
| Compound 97 | | 1H NMR (300 MHz, METHANOL-$d_4$) δ ppm 1.37 (t, J = 6.9 Hz, 3 H) 2.17 (s, 3 H) 2.90-3.01 (m, 1 H) 3.14-3.24 (m, 1 H) 3.54 (dd, J = 10.3, 9.2 Hz, 1 H) 3.60-3.76 (m, 3 H) 3.86-4.06 (m, 5 H) 6.66 (dd, J = 8.6, 2.7 Hz, 1 H) 6.75 (d, J = 3.0 Hz, 1 H) 6.85-6.95 (m, 2 H) 7.19 (dd, J = 8.2, 2.2 Hz, 1 H) 7.35 (d, J = 8.2 Hz, 1 H). ESI m/z = 461 (M + Na), 437 (M − H). Anal. Calcd for C22H27O5ClS•0.6H2O: C, 58.59; H, 6.33. Found: C, 58.28; H, 6.10. |
| Compound 98 | | 1H NMR (300 MHz, METHANOL-$d_4$) δ ppm 1.35 (t, J = 7.0 Hz, 3 H) 2.08 (s, 3 H) 2.92-3.04 (m, 1 H) 3.22-3.27 (m, 1 H) 3.59 (dd, J = 10.3, 8.9 Hz, 1 H) 3.69-3.88 (m, 4 H) 3.89-4.03 (m, 3 H) 4.29 (d, J = 10.57 Hz, 1 H) 6.60 (s, 1 H) 6.73-6.80 (m, 2 H) 6.95-7.02 (m, 2 H) 7.04 (s, 1 H). ESI m/z = 443 (M + Na), 419 (M − H). mp 183.0-187.0° C. Anal. Calcd for C22H28O6S•0.5H2O: C, 61.00; H, 6.86. Found: C, 60.81; H, 6.89. |
| Compound 99 | | 1H NMR (600 MHz, METHANOL-$d_4$) δ ppm 1.35 (t, J = 6.9 Hz, 3 H) 2.92-3.00 (m, 1 H) 3.22 (t, J = 8.9 Hz, 1 H) 3.53-3.59 (m, 1 H) 3.72 (dd, J = 11.7, 6.7 Hz, 1 H) 3.82 (s, 3 H) 3.88-3.95 (m, 3 H) 3.99 (q, J = 6.9 Hz, 2 H) 6.79 (d, J = 8.7 Hz, 2 H) 6.98 (s, 1 H) 7.06 (d, J = 8.71 Hz, 2 H) 7.20 (s, 1 H). ESI m/z = 477 (M + Na), 479 (M + 2 + Na), 453 (M − H), 455 (M + 2 − H). mp 177.0-179.0° C. Anal. Calcd for C22H27ClO6S•0.7H2O: C, 56.95; H, 6.10. Found: C, 56.89; H, 5.98. |
| Compound 100 | | 1H NMR (600 MHz, METHANOL-$d_4$) δ ppm 1.35 (t, J = 7.1 Hz, 3 H) 2.89-2.98 (m, 1 H) 3.19-3.26 (m, 1 H) 3.52-3.58 (m, 1 H) 3.68-3.79 (m, 4 H) 3.92 (dd, J = 11.5, 3.7 Hz, 1 H) 3.97 (q, J = 7.1 Hz, 2 H) 4.21 (d, J = 10.1 Hz, 1 H) 6.32 (s, 1 H) 6.76 (d, J = 8.7 Hz, 2 H) 6.91 (s, 1 H) 7.08 (d, J = 8.7 Hz, 2 H). ESI m/z = 445 (M + Na), 421 (M − H). mp 186.0-190.0° C. |

TABLE 1-continued

| Compound No. | Structural formula | ¹NMR, MS, mp, Elemental analysis |
|---|---|---|
| Compound 101 | | 1H NMR (300 MHz, METHANOL-d$_4$) δ ppm 1.19 (t, J = 7.6 Hz, 3 H) 2.17 (s, 3 H) 2.58 (q, J = 7.6 Hz, 2 H) 2.91-3.02 (m, 1 H) 3.19-3.28 (m, 1 H) 3.58 (dd, J = 10.3, 9.2 Hz, 1 H) 3.67-3.89 (m, 7 H) 3.94 (dd, J = 11.5, 3.7 Hz, 1 H) 4.25-4.39 (m, 1 H) 6.76 (s, 1 H) 6.96-7.09 (m, 4 H) 7.12 (s, 1 H). ESI m/z = 441 (M + Na), 417 (M − H). |
| Compound 102 | | 1H NMR (300 MHz, METHANOL-d$_4$) δ ppm 1.23 (t, J = 7.6 Hz, 3 H) 2.62 (q, J = 7.6 Hz, 2 H) 2.93-3.07 (m, 1 H) 3.27 (t, J = 8.8 Hz, 1 H) 3.60 (t, 1 H) 3.70-4.09 (m, 8 H) 4.25-4.39 (m, 1 H) 6.99-7.18 (m, 5 H) 7.27 (s, 1 H). ESI m/z = 461 (M + Na). Anal. Calcd for C22H27ClO5S•H2O: C, 56.70; H, 6.50. Found: C, 56.40; H, 6.45. |
| Compound 103 | | 1H NMR (600 MHz, METHANOL-d$_4$) δ ppm 1.21 (d, J = 7.3 Hz, 6 H) 2.79-2.88 (m, 1 H) 2.94-3.01 (m, 1 H) 3.23 (t, J = 8.9 Hz, 1 H) 3.53-3.61 (m, 1 H) 3.69-3.76 (m, 2 H) 3.82 (s, 3 H) 3.91-4.02 (m, 3 H) 4.24-4.36 (m, 1 H) 6.99 (s, 1 H) 7.05-7.14 (m, 4 H) 7.24 (s, 1 H). ESI m/z = 475 (M + Na). |
| Compound 104 | | 1H NMR (600 MHz, METHANOL-d$_4$) δ ppm 2.16 (s, 3 H) 2.27 (s, 3 H) 2.94-2.99 (m, 1 H) 3.24 (m, 1 H) 3.55-3.60 (m, 1 H) 3.72 (dd, J = 11.5, 6.4 Hz, 1 H) 3.77-3.90 (m, 6 H) 3.94 (dd, J = 11.5, 3.7 Hz, 1 H) 6.76 (s, 1 H) 6.97 (m, 2 H) 7.00-7.04 (m, 2 H) 7.11 (s, 1 H). ESI m/z = 427 (M + Na), 403 (M − H). |
| Compound 105 | | 1H NMR (600 MHz, METHANOL-d$_4$) δ ppm 1.20 (s, 3 H) 1.21 (s, 3 H) 2.17 (s, 3 H) 2.80-2.86 (m, 1 H) 2.94-2.99 (m, 1 H) 3.25 (m, 1 H) 3.58 (dd, J = 10.1, 9.2 Hz, 1 H) 3.72 (dd, J = 11.2, 6.6 Hz, 1 H) 3.77-3.91 (m, 6 H) 3.94 (dd, J = 11.5, 3.7 Hz, 1 H) 6.76 (s, 1 H) 7.00 (d, J = 8.3 Hz, 2 H) 7.08 (d, J = 8.3 Hz, 2 H) 7.13 (s, 1 H). ESI m/z = 455 (M + Na), 431 (M − H). |
| Compound 106 | | 1H NMR (600 MHz, METHANOL-d$_4$) δ ppm 1.23 (t, J = 7.57 Hz, 3 H) 2.64 (q, J = 7.79 Hz, 2 H) 3.00-3.07 (m, 1 H) 3.27 (t, J = 8.71 Hz, 1 H) 3.59-3.64 (m, 1 H) 3.73-3.82 (m, 2 H) 3.89 (d, J = 10.09 Hz, 1 H) 3.95 (dd, J = 11.69, 3.44 Hz, 1 H) 7.20 (d, J = 8.25 Hz, 2 H) 7.47 (s, 2 H) 7.53 (s, 1 H) 7.56 (d, J = 8.71 Hz, 2 H). ESI m/Z = 438 (M + H), 440 (M + 2 + H). colorless powder. |

TABLE 1-continued

| Compound No. | Structural formula | ¹NMR, MS, mp, Elemantal analysis |
|---|---|---|
| Compound 107 | | 1H NMR (300 MHz, METHANOL-d₄) δ ppm 1.20 (t, J = 7.62 Hz, 3 H) 2.59 (q, J = 7.62 Hz, 2 H) 2.85 (s, 4 H) 2.95-3.07 (m, 1 H) 3.21-3.28 (m, 1 H) 3.54-3.68 (m, 1 H) 3.69-3.83 (m, 3 H) 3.95 (dd, J = 11.42, 3.65 Hz, 1 H) 7.00-7.11 (m, 5 H) 7.13-7.28 (m, 3 H). ESI m/z = 411 (M + Na), 387 (M − H). colorless powder. |
| Compound 108 | | 1H NMR (600 MHz, METHANOL-d₄) δ ppm 1.20 (t, J = 7.57 Hz, 3 H) 1.87-1.94 (m, 2 H) 2.56-2.63 (m, 6 H) 2.98-3.03 (m, 1 H) 3.26 (t, J = 8.25 Hz, 1 H) 3.59-3.64 (m, J = 10.32, 8.94 Hz, 1 H) 3.71-3.82 (m, 3 H) 3.95 (dd, J = 11.46, 3.67 Hz, 1 H) 7.05-7.12 (m, 5 H) 7.14-7.25 (m, 3 H). ESI m/z = 425 (M + Na), 401 (M − H). colorless powder. |
| Compound 109 | | 1H NMR (600 MHz, METHANOL-d₄) δ ppm 1.19 (t, J = 7.79 Hz, 3 H) 2.58 (q, J = 7.79 Hz, 2 H) 2.96-3.02 (m, 1 H) 3.22-3.27 (m, 1 H) 3.59 (dd, J = 10.32, 8.94 Hz, 1 H) 3.70-3.77 (m, 3 H) 3.88-3.97 (m, 3 H) 7.08 (s, 4 H) 7.14 (d, J = 7.79 Hz, 2 H) 7.25 (d, J = 7.79 Hz, 2 H). ESI m/Z = 397 (M + Na), 373 (M − H). colorless powder. |
| Compound 110 | | 1H NMR (300 MHz, METHANOL-d₄) δ ppm 2.94-3.03 (m, 1 H) 3.20-3.28 (m, 1 H) 3.54-3.65 (m, 1 H) 3.68-3.78 (m, 3 H) 3.89-3.98 (m, 3 H) 4.55 (s, 2 H) 7.05-7.11 (m, 2 H) 7.12-7.28 (m, 7 H). ESI m/Z = 377 (M + H), 375 (M − H). pale yellw powder. |
| Compound 111 | | 1H NMR (300 MHz, METHANOL-d₄) δ ppm 1.14-1.27 (m, 3 H) 2.54-2.68 (m, 2 H) 2.95-3.05 (m, 1 H) 3.22-3.30 (m, 1 H) 3.51 (d, J = 6.37 Hz, 1 H) 3.56-3.68 (m, 2 H) 3.70-3.83 (m, 3 H) 3.95 (dd, J = 11.35, 3.57 Hz, 1 H) 5.72-6.59 (m, 2 H) 7.07-7.30 (m, 8 H). ESI m/z = 423 (M + Na), 399 (M − H). yellow oil. |
| Compound 112 | | 1H NMR (600 MHz, METHANOL-d₄) δ ppm 1.23 (t, J = 7.57 Hz, 3 H) 2.63 (q, J = 7.79 Hz, 2 H) 2.95-3.04 (m, 1 H) 3.23 (t, J = 8.71 Hz, 1 H) 3.56-3.61 (m, 1 H) 3.69-3.78 (m, 3 H) 3.94 (dd, J = 11.46, 3.67 Hz, 1 H) 6.84 (dd, J = 8.02, 2.52 Hz, 1 H) 6.91 (d, J = 8.25 Hz, 2 H) 6.95-6.98 (m, 1 H) 7.08 (d, J = 7.79 Hz, 1 H) 7.18 (d, J = 8.71 Hz, 2 H) 7.27 (t, J = 7.79 Hz, 1 H). ESI m/Z = 399 (M + Na), 375 (M − H). |
| Compound 113 | | 1H NMR (300 MHz, METHANOL-d₄) δ ppm 1.29 (t, J = 7.62 Hz, 3 H) 2.71 (q, J = 7.62 Hz, 2 H) 3.01-3.15 (m, 1 H) 3.28-3.36 (m, 1 H) 3.62-4.07 (m, 5 H) 7.22-7.66 (m, 8 H). ESI m/z = 383 (M + Na), 359 (M − H). colorless amorphous. |

TABLE 1-continued

| Compound No. | Structural formula | ¹NMR, MS, mp, Elemantal analysis |
|---|---|---|
| Compound 114 | | 1H NMR (300 MHz, METHANOL-d$_4$) δ ppm 2.94-3.03 (m, 1 H) 3.20-3.28 (m, 1 H) 3.55-3.64 (m, 1 H) 3.69-3.79 (m, 3 H) 3.87 (s, 3 H) 3.90-3.98 (m, 1 H) 4.03 (s, 2 H) 7.08-7.14 (m, 1 H) 7.18-7.35 (m, 5 H) 7.89-7.95 (m, 2 H). ESI m/Z = 427 (M + Na), 403 (M − H). pale yellow powder. |
| Compound 115 | | 1H NMR (300 MHz, METHANOL-d$_4$) δ ppm 1.61-1.76 (m, 2 H) 1.93-2.05 (m, 2 H) 2.94-3.03 (m, 1 H) 3.20-3.27 (m, 1 H) 3.51-3.64 (m, 3 H) 3.68-3.79 (m, 3 H) 3.84-3.98 (m, 5 H) 4.45-4.54 (m, 1 H) 6.81-6.88 (m, 2 H) 7.04-7.13 (m, 3 H) 7.14-7.25 (m, 3 H). ESI m/Z = 469 (M + Na), 445 (M − H). pale yellow oil. |
| Compound 116 | | 1H NMR (600 MHz, METHANOL-d$_4$) δ ppm 1.57-1.67 (m, 2 H) 1.72-1.82 (m, 4 H) 1.84-1.94 (m, 2 H) 2.95-3.02 (m, 1 H) 3.21-3.28 (m, 1 H) 3.60 (dd, J = 10.32, 8.94 Hz, 1 H) 3.70-3.80 (m, 3 H) 3.87 (s, 2 H) 3.91-3.97 (m, 1 H) 4.71-4.77 (m, 1 H) 6.73-6.79 (m, 2 H) 7.03-7.10 (m, 3 H) 7.15-7.24 (m, 3 H). ESI m/Z = 453 (M + Na). colorless powder. |
| Compound 117 | | 1H NMR (600 MHz, METHANOL-d$_4$) δ ppm 2.96-3.00 (m, 1 H) 3.21-3.26 (m, 1 H) 3.59 (dd, J = 10.09, 9.17 Hz, 1 H) 3.71-3.79 (m, 3 H) 3.82-3.87 (m, 2 H) 3.88 (s, 2 H) 3.94 (dd, J = 11.46, 3.67 Hz, 1 H) 3.98-4.02 (m, 2 H) 6.82-6.88 (m, 2 H) 7.05-7.12 (m, 3 H) 7.15-7.24 (m, 3 H). ESI m/Z = 429 (M + Na), 405 (M − H). colorless powder. |
| Compound 118 | | 1H NMR (600 MHz, METHANOL-d$_4$) δ ppm 2.97 (s, 3 H) 2.99-3.04 (m, 1 H) 3.07 (s, 3 H) 3.63-3.68 (m, 1 H) 3.74-3.82 (m, 3 H) 3.88-3.94 (m, 3 H) 4.74 (s, 2 H) 6.87 (d, J = 8.71 Hz, 2 H) 7.06-7.14 (m, 3 H) 7.16-7.24 (m, 3 H). colorless powder. |
| Compound 119 | | 1H NMR (300 MHz, METHANOL-d$_4$) δ ppm 1.35 (t, J = 6.99 Hz, 3 H) 2.92-3.00 (m, 1 H) 3.17-3.25 (m, 1 H) 3.57 (dd, J = 10.18, 9.09 Hz, 1 H) 3.68-3.78 (m, 6 H) 3.88-4.02 (m, 5 H) 4.68 (s, 2 H) 6.73-6.80 (m, 3 H) 7.09-7.18 (m, 4 H). ESI m/Z = 501 (M + Na), 477 (M − H). |

TABLE 1-continued

| Compound No. | Structural formula | ¹NMR, MS, mp, Elemental analysis |
|---|---|---|
| Compound 120 | 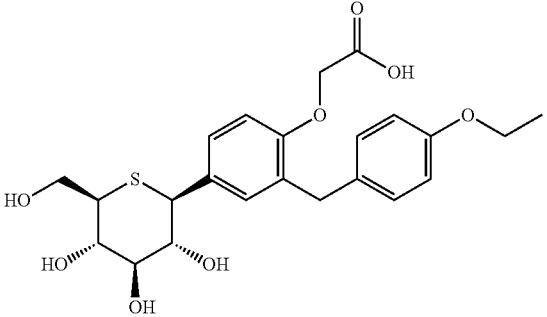 | 1H NMR (300 MHz, METHANOL-$d_4$) δ ppm 1.35 (t, J = 6.99 Hz, 3 H) 2.91-3.00 (m, 1 H) 3.17-3.25 (m, 1 H) 3.57 (dd, J = 10.26, 9.01 Hz, 1 H) 3.66-3.77 (m, 3 H) 3.88-4.03 (m, 5 H) 4.63 (s, 2 H) 6.73-6.82 (m, 3 H) 7.07-7.19 (m, 4 H). ESI m/Z = 487 (M + Na), 463 (M − H). colorless crystal. |
| Compound 121 | 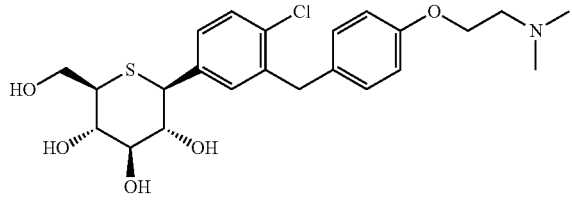 | 1H NMR (600 MHz, METHANOL-$d_4$) δ ppm 2.34 (s, 6 H) 2.76 (t, J = 5.50 Hz, 2 H) 2.96-3.01 (m, 1 H) 3.22 (t, J = 8.71 Hz, 1 H) 3.57 (dd, J = 10.32, 8.94 Hz, 1 H) 3.68-3.76 (m, 3 H) 3.93 (dd, J = 11.46, 3.67 Hz, 1 H) 4.01 (s, 2 H) 4.07 (t, J = 5.50 Hz, 2 H) 6.83-6.87 (m, 2 H) 7.08-7.12 (m, 2 H) 7.18-7.23 (m, 2 H) 7.32 (d, J = 8.25 Hz, 1 H). ESI m/Z = 468 (M + H), 470 (M + 2 + H). colorless powder. |
| Compound 122 | 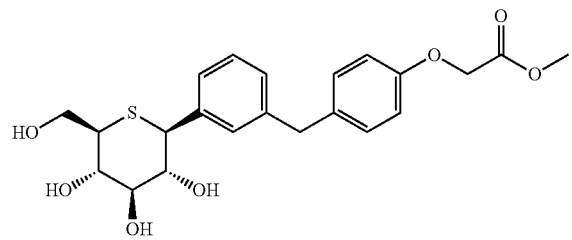 | 1H NMR (600 MHz, METHANOL-$d_4$) δ ppm 2.96-3.01 (m, 1 H) 3.22-3.26 (m, 1 H) 3.59 (dd, J = 10.09, 9.17 Hz, 1 H) 3.71-3.79 (m, 6 H) 3.89 (s, 2 H) 3.94 (dd, J = 11.46, 3.67 Hz, 1 H) 4.66 (s, 2 H) 6.81-6.85 (m, 2 H) 7.05-7.13 (m, 3 H) 7.16-7.23 (m, 3 H). ESI m/Z = 457 (M + Na). pale yellow oil. |
| Compound 123 | 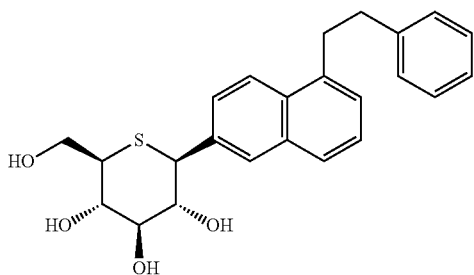 | 1H NMR (600 MHz, METHANOL-$d_4$) δ ppm 2.98-3.07 (m, 2 H) 3.07-3.13 (m, 1 H) 3.33-3.40 (m, 3 H) 3.69 (dd, J = 10.09, 9.17 Hz, 1 H) 3.80 (dd, J = 11.69, 6.65 Hz, 1 H) 3.94 (dd, J = 10.09, 8.71 Hz, 1 H) 4.00 (dd, J = 11.46, 3.67 Hz, 1 H) 4.04 (d, J = 10.55 Hz, 1 H) 7.14-7.20 (m, 1 H) 7.21-7.29 (m, 5 H) 7.30-7.35 (m, 1 H) 7.51 (dd, J = 8.48, 1.60 Hz, 1 H) 7.69 (d, J = 8.25 Hz, 1 H) 7.84 (d, J = 8.25 Hz, 1 H) 8.13 (s, 1 H). ESI m/Z = 433 (M + Na). pale yellow powder. |
| Compound 124 | 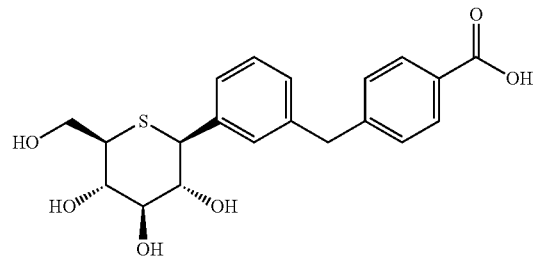 | 1H NMR (600 MHz, METHANOL-$d_4$) δ ppm 2.92-2.97 (m, 1 H) 3.17-3.22 (m, 1 H) 3.55 (dd, J = 10.09, 9.17 Hz, 1 H) 3.66-3.75 (m, 3 H) 3.90 (dd, J = 11.46, 3.67 Hz, 1 H) 3.99 (s, 2 H) 7.07 (d, J = 7.79 Hz, 1 H) 7.15-7.23 (m, 3 H) 7.27 (d, J = 8.25 Hz, 2 H) 7.88 (d, J = 8.25 Hz, 2 H). pale yellow oil. |

TABLE 1-continued

| Compound No. | Structural formula | ¹NMR, MS, mp, Elemental analysis |
|---|---|---|
| Compound 125 | 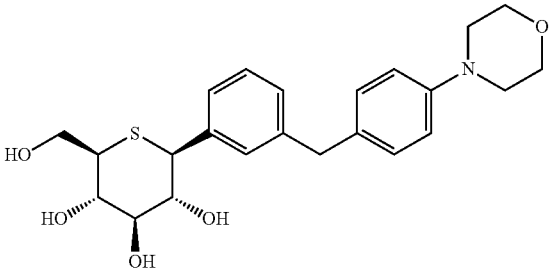 | 1H NMR (600 MHz, METHANOL-d₄) δ ppm 2.94-3.00 (m, 1 H) 3.04-3.11 (m, 4 H) 3.19-3.25 (m, 1 H) 3.54-3.61 (m, 1 H) 3.69-3.77 (m, 3 H) 3.77-3.81 (m, 4 H) 3.85 (s, 2 H) 3.90-3.95 (m, 1 H) 6.84-6.91 (m, 2 H) 7.03-7.09 (m, 2 H) 7.13-7.36 (m, 4 H). ESI m/Z = 454 (M + Na). colorless powder. |
| Compound 126 | 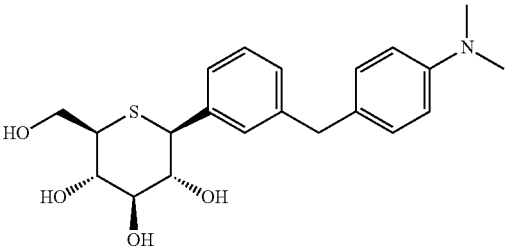 | 1H NMR (600 MHz, METHANOL-d₄) δ ppm 2.85 (s, 6 H) 2.93-3.01 (m, 1 H) 3.19-3.25 (m, 1 H) 3.57 (dd, J = 10.1, 9.2 Hz, 1 H) 3.68-3.78 (m, 3 H) 3.82 (s, 2 H) 3.89-3.95 (m, 1 H) 6.67-6.74 (m, 2 H) 6.99-7.07 (m, 2 H) 7.11-7.26 (m, 4 H). ESI m/Z = 412 (M + Na). colorless powder. |
| Compound 127 | 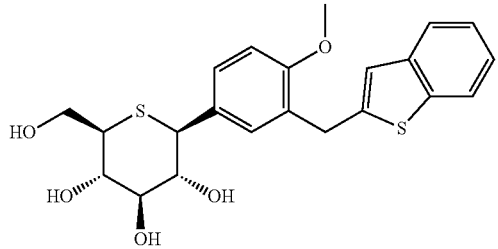 | 1H NMR (600 MHz, METHANOL-d₄) δ ppm 2.91-2.98 (m, 1 H) 3.17-3.23 (m, 1 H) 3.56 (t, J = 9.6 Hz, 1 H) 3.67-3.78 (m, 3 H) 3.82 (s, 3 H) 3.91 (dd, J = 11.5, 3.7 Hz, 1 H) 4.11-4.20 (m, 2 H) 6.92 (d, J = 7.8 Hz, 1 H) 6.98 (s, 1 H) 7.16-7.26 (m, 4 H) 7.60 (d, J = 7.8 Hz, 1 H) 7.68 (d, J = 7.8 Hz, 1 H). ESI m/z = 455 (M + Na), 431 (M − H). mp 91.0-105.0° C. |
| Compound 128 | 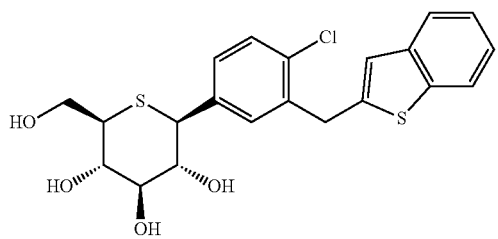 | 1H NMR (300 MHz, METHANOL-d₄) δ ppm 2.93-3.05 (m, 1 H) 3.20-3.27 (m, 1 H) 3.58 (dd, J = 10.3, 9.0 Hz, 1 H) 3.69-3.83 (m, 2 H) 3.93 (dd, J = 11.5, 3.6 Hz, 1 H) 4.35 (s, 2 H) 7.01-7.05 (m, 1 H) 7.19-7.32 (m, 3 H) 7.35-7.41 (m, 2 H) 7.63-7.77 (m, 2 H). ESI m/z = 459 (M + Na), 461 (M + 2 + Na), 435 (M − H). mp 105.0-115.0° C. |
| Compound 129 | 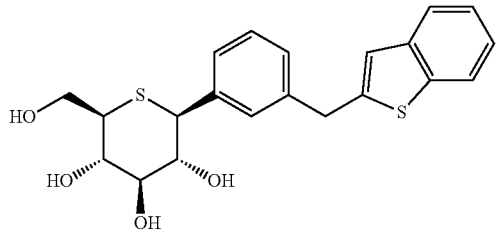 | 1H NMR (300 MHz, METHANOL-d₄) δ ppm 2.95-3.05 (m, 1 H) 3.21-3.36 (m, 1 H) 3.60 (dd, J = 10.3, 9.0 Hz, 1 H) 3.70-3.81 (m, 3 H) 3.90-3.98 (m, 1 H) 4.23 (s, 2 H) 7.06 (s, 1 H) 7.19-7.34 (m, 6 H) 7.62-7.75 (m, 2 H). ESI m/z = 425 (M + Na). mp 159.5-160.0° C. |
| Compound 130 | 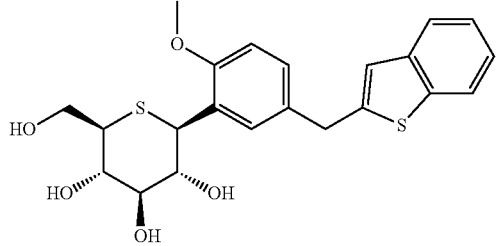 | 1H NMR (300 MHz, METHANOL-d₄) δ ppm 2.92-3.01 (m, 1 H) 3.25 (t, J = 8.9 Hz, 1 H) 3.52-3.65 (m, 1 H) 3.72 (dd, J = 11.4, 6.5 Hz, 1 H) 3.76-3.87 (m, 4 H) 3.93 (dd, J = 11.4, 3.6 Hz, 1 H) 4.16 (brs, 2 H) 4.31-4.43 (m, 1 H) 6.92 (d, J = 8.6 Hz, 1 H) 7.03 (s, 1 H) 7.12-7.35 (m, 4 H) 7.59-7.78 (m, 2 H). ESI m/z = 455 (M + Na). mp 97.5-98.0° C. |

TABLE 1-continued

| Compound No. | Structural formula | ¹NMR, MS, mp, Elemantal analysis |
|---|---|---|
| Compound 131 | | 1H NMR (300 MHz, METHANOL-d₄) δ ppm 2.89-3.00 (m, 1 H) 3.22 (m, 1 H) 3.51-3.96 (m, 10 H) 4.04-4.19 (m, 2 H) 6.62 (s, 1 H) 6.97 (s, 1 H) 7.17-7.28 (m, 3 H) 7.58-7.73 (m, 2 H). ESI m/z = 485 (M + Na), 461 (M − H). |
| Compound 132 | | 1H NMR (300 MHz, METHANOL-d₄) δ ppm 2.94-3.05 (m, 1 H) 3.18-3.28 (m, 1 H) 3.58 (dd, J = 10.2, 8.9 Hz, 1 H) 3.66-3.83 (m, 3 H) 3.94 (dd, J = 11.5, 3.6 Hz, 1 H) 4.16-4.32 (m, 2 H) 6.40 (s, 1 H) 7.10-7.51 (m, 7 H). ESI m/z = 443 (M + Na), 445 (M + 2 + Na). |
| Compound 133 | | 1H NMR (300 MHz, METHANOL-d₄) δ ppm 2.96-3.04 (m, 1 H) 3.22-3.29 (m, 1 H) 3.56-3.64 (m, 1 H) 3.70-3.81 (m, 3 H) 3.94 (dd, J = 11.42, 3.65 Hz, 1 H) 4.21 (s, 2 H) 6.94-6.97 (m, 1 H) 7.18-7.33 (m, 4 H) 7.36-7.43 (m, 1 H) 7.62 (d, J = 3.73 Hz, 1 H) 7.85-7.90 (m, 1 H) 7.96-8.03 (m, 1 H) 8.44-8.49 (m, 1 H). ESI m/z = 430 (M + H). yellow powder. |
| Compound 134 | | 1H NMR (300 MHz, METHANOL-d₄) δ ppm 2.95-3.06 (m, 1 H) 3.22-3.29 (m, 1 H) 3.57-3.66 (m, 1 H) 3.70-3.83 (m, 3 H) 3.95 (dd, J = 11.50, 3.73 Hz, 1 H) 4.12 (s, 2 H) 6.79 (d, J = 3.57 Hz, 1 H) 7.14-7.36 (m, 8 H) 7.48-7.57 (m, J = 8.32, 1.17 Hz, 2 H). ESI m/z = 451 (M + Na), 427 (M − H). colorless powder. Anal. Calcd for C23H24O4S2•0.3H2O: C, 63.57; H, 5.72. Found: C, 63.89; H, 5.63. |
| Compound 135 | | 1H NMR (300 MHz, METHANOL-d₄) δ ppm 2.95-3.04 (m, 1 H) 3.20-3.28 (m, 1 H) 3.54-3.64 (m, 1 H) 3.69-3.81 (m, 3 H) 3.94 (dd, J = 11.35, 3.57 Hz, 1 H) 4.19 (s, 2 H) 7.00 (s, 1 H) 7.14 (d, J = 5.60 Hz, 1 H) 7.16-7.33 (m, 4 H) 7.37 (dd, J = 5.13, 0.47 Hz, 1 H). ESI m/Z = 431 (M + Na), 407 (M − H). colorless powder. |
| Compound 136 | | 1H NMR (300 MHz, METHANOL-d₄) δ ppm 2.92-3.05 (m, 1 H) 3.19-3.29 (m, 1 H) 3.39 (s, 3 H) 3.59 (t, J = 9.64 Hz, 1 H) 3.68-3.83 (m, 3 H) 3.86-4.02 (m, 3 H) 5.80-5.87 (m, 1 H) 5.94 (t, J = 3.11 Hz, 1 H) 6.55 (d, J = 1.87 Hz, 1 H) 7.03 (dd, J = 6.99, 1.71 Hz, 1 H) 7.12-7.28 (m, 3 H). ESI m/Z = 372 (M + Na). |

TABLE 1-continued

| Compound No. | Structural formula | ¹NMR, MS, mp, Elemantal analysis |
|---|---|---|
| Compound 137 | | 1H NMR (300 MHz, METHANOL-$d_4$) δ ppm 2.95-3.05 (m, 1 H) 3.21-3.28 (m, 1 H) 3.55-3.66 (m, 1 H) 3.69-3.83 (m, 3 H) 3.94 (dd, J = 11.50, 3.57 Hz, 1 H) 4.44 (s, 2 H) 7.24-7.52 (m, 6 H) 7.85-7.95 (m, 2 H). |
| Compound 138 | | 1H NMR (600 MHz, METHANOL-$d_4$) δ ppm 1.36 (t, J = 7.18 Hz, 3 H) 3.01-3.05 (m, 1 H) 3.23-3.27 (m, 1 H) 3.60 (dd, J = 10.32, 8.94 Hz, 1 H) 3.71-3.78 (m, 2 H) 3.84 (d, J = 10.55 Hz, 1 H) 3.92-3.97 (m, 3 H) 3.99 (q, J = 7.18 Hz, 2 H) 6.82-6.85 (m, 2 H) 7.10-7.13 (m, 2 H) 7.64 (t, J = 2.06 Hz, 1 H) 8.28 (d, J = 2.29 Hz, 1 H) 8.34 (d, J = 2.29 Hz, 1 H). ESI m/Z = 392 (M + H), 390 (M – H). colorless powder. |
| Compound 139 | | 1H NMR (300 MHz, METHANOL-$d_4$) δ ppm 1.20 (t, J = 7.62 Hz, 3 H) 2.60 (q, J = 7.62 Hz, 2 H) 2.92-3.03 (m, 1 H) 3.19 (t, J = 8.86 Hz, 1 H) 3.50-3.63 (m, 2 H) 3.72 (dd, J = 11.58, 6.45 Hz, 1 H) 3.93 (dd, J = 11.50, 3.73 Hz, 1 H) 4.03 (t, J = 4.97 Hz, 3 H) 6.58-6.67 (m, 1 H) 6.83 (d, J = 3.57 Hz, 1 H) 7.08-7.17 (m, 4 H). ESI m/z = 403 (M + Na), 379 (M – H). colorless powder. Anal. Calcd for C19H24O4S2: C, 59.97; H, 6.36. Found: C, 59.93; H, 6.33. |
| Compound 140 | | 1H NMR (300 MHz, METHANOL-$d_4$) δ ppm 2.26 (s, 2 H) 3.03-3.14 (m, 1 H) 3.32-3.40 (m, 1 H) 3.62-3.72 (m, 1 H) 3.77 (dd, J = 11.50, 6.37 Hz, 1 H) 3.93-4.06 (m, 2 H) 4.14 (s, 2 H) 4.32 (d, J = 10.26 Hz, 1 H) 7.01-7.17 (m, 5 H) 7.33 (t, 1 H) 7.48 (s, 1 H) 7.90 (d, J = 7.31 Hz, 1 H). ESI m/z = 439 (M + Na), 415 (M – H). colorless powder. |

Test Example 1

After 50 µL of a suspension (protein concentration: 4 mg/mL) of rat kidney brush border membrane vesicles (brush border membrane vehicle: BBMV) prepared following the method described in a document (Anal. Biochem., Vol. 201, Clause 301, 1984) was preincubated at 37° C. for two minutes, 150 µL of a reaction mixture which was a mixture of a test compound dissolved in DMSO (DMSO final concentration: 1%), 100 mM mannitol, 100 mM NaSCN or KSCN, 10 mM HEPES/Tris pH 7.4, D-glucose (final concentration: 0.1 mM) and 1 µCi of D-[6-³H] glucose (Amersham) was added to this. After performing a reaction at 37° C. for five seconds, 1 mL of an ice cooled reaction terminating solution (150 mM NaCl, 10 mM HEPES/Tris pH 7.4, 0.3 mM phlorizin) was added to the reaction mixture to terminate the reaction, and BBMV was immediately separated by rapid filtration using a membrane filter (HAWP02500 having a pore size of 0.45 µm, Millipore). The membrane filter was washed three times with 4.5 mL of the ice cooled reaction terminating solution. After the membrane was dried sufficiently, radioactivity was measured with a liquid scintillation counter (Beckman) to quantify the amount of glucose taken in BBMV on the membrane filter.

The concentration of compound at which glucose uptake was inhibited by 50% ($IC_{50}$ value) was calculated assuming the glucose uptake without the addition of the compounds to be 100%.

The results are shown in Table 2.

TABLE 2

| Compound No. | $IC_{50}$ (µM) |
|---|---|
| Compound 75 | 1.600 |
| Compound 76 | 0.320 |
| Compound 79 | 0.220 |
| Compound 127 | 0.350 |
| Compound 128 | 0.790 |

Test Example 2

Cloning of Human SGLT1 and Human SGLT2 and Introduction Thereof into Expression Vector Human SGLT1 sequence (NM_000343) was reverse-transcripted from human small intestinal mRNA, then amplified, and then introduced into pCMV-tag5A from Stratagene Corporation. Human SGLT2 sequence (NM_003041) was prepared from human nephric mRNA as with the above method, and then introduced into pcDNA3.1+hygro from Invitrogen Corporation. Each cloned sequence was confirmed to be identical with the reported sequence.

Preparation of CHO-k1 Cell Stably Expressing Human SGLT1 and Human SGLT2

CHO-K1 cells were transfected with the human SGLT1 and human SGLT2 expression vectors using Lipofectamine 2000 (Invitrogen Corporation). SGLT expression cells were cultured in the presence of geneticin (SGLT1) or hygromycin B (SGLT2) of the concentration of 500 µg/mL to select resistant strains. Cells were obtained using sugar uptake specific activity as an index in the following system.

Sodium-Dependent Sugar Uptake Inhibition Test in the Cells

Cells stably expressing human SGLT1 and human SGLT2 were used in the sodium-dependent sugar uptake activity inhibition test. Cells were incubated in 1 mL of a pretreatment buffer solution (140 mM choline chloride, 2 mM KCl, 1 mM $CaCl_2$, 1 mM $MgCl_2$, 10 mM HEPES/5 mM Tris, pH 7.4) for 20 minutes. The pretreatment buffer solution was removed and 200 µL of an uptake buffer containing test compounds (methyl-α-D-glucopyranoside containing [$^{14}$C]methyl-α-D-glucopyranoside (0.1 mM for SGLT1 inhibition, 1 mM for SGLT2 inhibition), 140 mM NaCl, 2 mM KCl, 1 mM $CaCl_2$, 1 mM $MgCl_2$, 10 mM HEPES/5 mM Tris, pH 7.4) were added, and uptake reaction was performed at 37° C. for 30 minutes (SGLT1) or for one hour (SGLT2). After the reaction, cells were washed with 1 mL of a washing buffer (10 mM methyl-α-D-glucopyranoside, 140 mM choline chloride, 2 mM KCl, 1 mM $CaCl_2$, 1 mM $MgCl_2$, 10 mM HEPES/5 mM Tris, pH 7.4) twice and dissolved in 400 µL of 0.2 M NaOH solution. After Aquazole 2 (Perkin Elmer Corporation) was added and mixed well, radioactivity was measured with a liquid scintillation counter (Beckman Coulter Corporation). A buffer for uptake which contained no test compound was prepared as a control group. Another buffer solution for uptake containing choline chloride in place of NaCl was also prepared for basic uptake.

In order to determining an $IC_{50}$ value, the test compound was used at six suitable concentrations and the concentration of the compound at which glucose uptake was inhibited by 50% ($IC_{50}$ value) as compared with glucose uptake (100%) in the control group was calculated. The results of the test are shown in Table 3.

TABLE 3

| Compound No. | Human SGLT2 (µM) | Human SGLT1 (µM) | SGLT1/SGLT2 |
|---|---|---|---|
| Compound 74 | 1.190 | 15.3 | 12.8 |
| Compound 75 | 2.830 | 27.4 | 9.7 |
| Compound 76 | 0.080 | 1.2 | 14.6 |
| Compound 77 | 0.690 | 8.0 | 11.6 |
| Compound 78 | 1.040 | 120.0 | 115.4 |
| Compound 79 | 0.370 | 2.7 | 7.2 |
| Compound 80 | 0.190 | 2.9 | 15.2 |
| Compound 81 | 0.600 | 6.5 | 10.9 |
| Compound 82 | 3.780 | 15.0 | 4.0 |
| Compound 83 | 0.030 | 1.5 | 48.7 |
| Compound 84 | 0.170 | 2.1 | 12.5 |
| Compound 85 | 1.270 | 6.1 | 4.8 |
| Compound 86 | 0.060 | 1.1 | 18.3 |
| Compound 88 | 0.080 | 0.2 | 2.8 |
| Compound 89 | 0.065 | 6.3 | 97.5 |
| Compound 91 | 0.110 | 1.7 | 15.5 |
| Compound 92 | 0.030 | 0.2 | 7.7 |
| Compound 93 | 0.021 | 0.4 | 21.0 |
| Compound 94 | 0.250 | 0.3 | 1.3 |
| Compound 95 | 0.028 | 0.6 | 22.3 |
| Compound 96 | 0.062 | 7.3 | 116.3 |

TABLE 3-continued

| Compound No. | Human SGLT2 (µM) | Human SGLT1 (µM) | SGLT1/SGLT2 |
|---|---|---|---|
| Compound 98 | 0.015 | 0.1 | 6.5 |
| Compound 99 | 0.032 | 5.6 | 178.6 |
| Compound 100 | 1.520 | 4.4 | 2.9 |
| Compound 101 | 0.040 | 2.6 | 63.1 |
| Compound 102 | 0.040 | 3.5 | 86.6 |
| Compound 103 | 0.069 | 23.9 | 347.9 |
| Compound 104 | 0.034 | 1.0 | 29.8 |
| Compound 105 | 0.093 | 17.0 | 182.5 |
| Compound 127 | 1.120 | 0.7 | 0.6 |
| Compound 128 | 0.140 | 0.6 | 4.4 |
| Compound 129 | 3.000 | 12.8 | 4.3 |
| Compound 130 | 2.120 | >10 | — |
| Compound 131 | 0.890 | 4.1 | 4.7 |
| Compound 132 | 0.497 | 4.4 | 8.9 |
| Compound 134 | 2.910 | — | — |
| Compound 138 | 33.000 | — | — |
| Compound 139 | 114.000 | — | — |

INDUSTRIAL APPLICABILITY

According to the present invention, 1-thio-D-glucitol compounds which exhibit sodium-dependent glucose cotransporter (SGLT2) inhibitory activity and hypoglycemic effect by promoting urinary glucose excretion can be provided and thus a therapeutic drug for diabetes due to a novel skeleton which is not known conventionally can be provided. Besides, 1-thio-D-glucitol derivatives of the present invention has good crystallinity, and therefore, they do not require cocrystallization with amino acid, etc., and they are easy to be purified, stored and made into pharmaceutical preparations and are suitable for handling as a pharmaceutical product.

The invention claimed is:
1. A compound of the following formula XIII, or a salt thereof, or a hydrate of the compound or the salt:

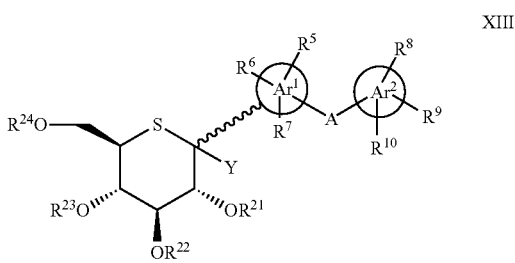

where Y represents a hydrogen atom or a hydroxyl group (provided that if Y is a hydrogen atom, the 1-position is of S-configuration), and $R^{21}$, $R^{22}$, $R^{23}$ and $R^{24}$ are the same or different, and each represent a hydrogen atom, a $C_{1-6}$ alkyl group, —Si$R^{a1}_3$, —$CH_2CH$=$CH_2$, —$CO_2R^{a2}$, —$COR^{b1}$, or a $C_{7-12}$ aralkyl group optionally substituted by one or more substituents selected from the group consisting of a halogen atom, —$NO_2$ and —OMe (where $R^{a1}$ and $R^{a2}$ each represent a $C_{1-6}$ alkyl group, and $R^{b1}$ represents a $C_{1-6}$ alkyl group, a $C_{7-10}$ aralkyl group, or a phenyl group), provided that if Y is a hydrogen atom, $R^{21}$, $R^{22}$, $R^{23}$ and $R^{24}$ are not hydrogen atoms at the same time;

A represents —$(CH_2)n$—, —$CONH(CH_2)n$-, —NHCO$(CH_2)n$-, —O—, —S—, —NH—, or —$(CH_2)nCH$=$CH$— (where n denotes an integer of 0 to 3), Ar¹ represents an arylene group, a heteroarylene group, or a heterocycloalkylene group, Ar² represents an aryl group, a heteroaryl group, or a heterocycloalkyl group, and $R^5$, $R^6$, $R^7$, $R^8$, $R^9$ and $R^{10}$ are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$(CH_2)m$-Q {where m denotes an integer of 0 to 4, and Q represents —CHO, —$NH_2$, —$NO_2$, —CN, —$CO_2H$, —$SO_3H$, —$OR^{c1}$, —$CO_2R^{a3}$, —$CONHR^{a4}$, —$CONR^{a5}R^{a5}$, —$COR^{d1}$, $OCOR^{d2}$, —$SR^{e1}$, —$SOR^{e2}$, —$SO_2R^{e3}$, —NHC(=O)H, —$NHCOR^{d3}$, —$NHCO_2R^{d4}$, —$NHCONH_2$, —$NHSO_2R^{e4}$, —$NHR^{a6}$, or —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)}, (vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or —$NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represent a $C_{1-6}$ alkyl group, a $C_{7-10}$ aralkyl group, a phenyl group, or a $C_{3-7}$ cycloalkyl group)}, (vii) —$OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); a $C_{7-10}$ aralkyl group optionally substituted by one or more substituents selected from the group consisting of a halogen atom, a hydroxyl group, a $C_{1-6}$ alkyl group, and —$OR^{a15}$ (where $R^{a15}$ represents a $C_{1-6}$ alkyl group); or a heterocycloalkyl group optionally substituted by one or more substituents selected from the group consisting of a halogen atom, a hydroxyl group, a $C_{1-6}$ alkyl group, and —$OR^{a16}$ (where $R^{a16}$ represents a $C_{1-6}$ alkyl group)}, (viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)}, (ix) a $C_{3-7}$ cycloalkyl group optionally substituted by one or more substituents selected from the group consisting of a halogen atom, a hydroxyl group, a $C_{1-6}$ alkyl group, and —$OR^{a18}$ (where $R^{a18}$ represents a $C_{1-6}$ alkyl group), (x) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), (xi) a $C_{7-10}$ aralkyl group optionally substituted by one or more substituents selected from the group consisting of a halogen atom, a hydroxyl group, a $C_{1-6}$ alkyl group, and —$OR^{a20}$ (where $R^{a20}$ represents a $C_{1-6}$ alkyl group), (xii) a heteroaryl group optionally substituted by one or more substituents selected from the group consisting of a halogen atom, a hydroxyl group, a $C_{1-6}$ alkyl group, and —$OR^{a21}$ (where $R^{a21}$ represents a $C_{1-6}$ alkyl group), (xiii) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group), (xiv) a $C_{2-6}$ alkenyl group, or (xv) a $C_{2-6}$ alkynyl group.

2. A compound of the following formula XIV, or a salt thereof, or a hydrate of the compound or the salt:

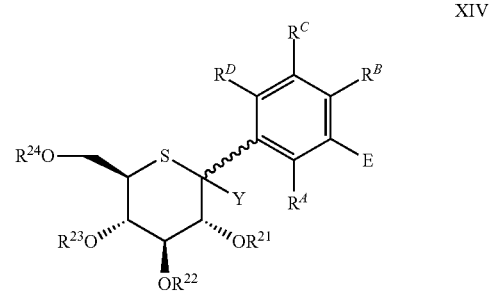

XIV where Y represents a hydrogen atom or a hydroxyl group (provided that if Y is a hydrogen atom, the 1-position is of S-configuration), E represents —CHO, —$CO_2H$, —$CO_2R^{a24}$ (where $R^{a24}$ represents a $C_{1-6}$ alkyl group), —$CH_2M^a$ (where $M^a$ represents a hydroxyl group or a halogen atom), a 1,3-dioxolan-2-yl group, or a 1,3-dioxan-2-yl group, $R^{21}$, $R^{22}$, $R^{23}$ and $R^{24}$ are the same or different, and each represent a hydrogen atom, a $C_{1-6}$ alkyl group, —$SiR^{a1}_3$, —$CH_2CH=CH_2$, —$CO_2R^{a2}$, —$COR^{b1}$, or a $C_{7-12}$ aralkyl group optionally substituted by one or more substituents selected from the group consisting of a halogen atom, —$NO_2$, and —OMe (where $R^{a1}$ and $R^{a2}$ each represent a $C_{1-6}$ alkyl group, and $R^{b1}$ represents a $C_{1-6}$ alkyl group, a $C_{7-10}$ aralkyl group, or a phenyl group), provided that if Y is a hydrogen atom, $R^{21}$, $R^{22}$, $R^{23}$ and $R^{24}$ are not hydrogen atoms at the same time, and at least one of $R^A$, $R^B$, $R^C$ and $R^D$ represents a hydrogen atom, and the other of $R^A$, $R^B$, $R^C$ and $R^D$ are the same or different, and each represent (i) a hydrogen atom, (ii) a halogen atom, (iii) a hydroxyl group, (iv) a $C_{1-8}$ alkyl group optionally substituted by one or more substituents selected from the group consisting of a halogen atom and a hydroxyl group, (v) —$(CH_2)m$-$Q^A$ {where m denotes an integer of 0 to 4, and $Q^A$ represents —$NH_2$, —$CO_2H$, —$OR^{c1}$, —$CO_2R^{a3}$, —$CONH_2$, —$CONHR^{a4}$, —$CONR^{a5}R^{a5}$, —$COR^{d1}$, —$OCOR^{d2}$, —$SR^{e1}$, —$SOR^{e2}$, —$SO_2R^{e3}$, —NHC(=O)H, —$NHCOR^{d3}$, —$NHCO_2R^{d4}$, —$NHCONH_2$, —$NHSO_2R^{e4}$, —$NHR^{a6}$, or —$NR^{a7}R^{a7}$ (where $R^{a3}$, $R^{a4}$, $R^{a5}$, $R^{a6}$, and $R^{a7}$ each represent a $C_{1-6}$ alkyl group, $R^{c1}$ represents a $C_{1-6}$ alkyl group optionally substituted by a halogen atom(s), $R^{d1}$, $R^{d2}$, $R^{d3}$ and $R^{d4}$ each represent a $C_{1-6}$ alkyl group, a $C_{7-10}$ aralkyl group, a phenyl group, or a $C_{3-7}$ cycloalkyl group, and $R^{e1}$, $R^{e2}$, $R^{e3}$ and $R^{e4}$ each represent a $C_{1-6}$ alkyl group, a phenyl group, or a tolyl group)}, (vi) —O—$(CH_2)m'$-Q' {where m' denotes an integer of 1 to 4, and Q' represents a hydroxyl group, —$CO_2H$, —$OR^{c2}$, —$CO_2R^{a8}$, —$CONH_2$, —$CONHR^{a9}$, —$CONR^{a10}R^{a10}$, —$NH_2$, —$NHR^{a11}$, —$NR^{a12}R^{a12}$, or —$NHCO_2R^{d5}$ (where $R^{a8}$, $R^{a9}$, $R^{a10}$, $R^{a11}$, and $R^{a12}$ each represent a $C_{1-6}$ alkyl group, $R^{c2}$ represents a $C_{1-6}$ alkyl group optionally substituted by a halogen atom(s), and $R^{d5}$ represent a $C_{1-6}$ alkyl group, a $C_{7-10}$ aralkyl group, a phenyl group, or a $C_{3-7}$ cycloalkyl group)}, (vii) —$OR^f$ {where $R^f$ represents a $C_{3-7}$ cycloalkyl group optionally substituted by one or more substituents selected from the group consisting of a halogen atom, a hydroxyl group, a $C_{1-6}$ alkyl group, and —$OR^{a13}$ (where $R^{a13}$ represents a $C_{1-6}$ alkyl group); an aryl group optionally substituted by one or more substituents selected from the group consisting of a halogen atom, a hydroxyl group, a $C_{1-6}$ alkyl group, and —$OR^{a14}$ (where $R^{a14}$ represents a $C_{1-6}$ alkyl group); or a $C_{7-10}$ aralkyl group optionally substituted by one or more substituents selected from the group consisting of a halogen atom, a hydroxyl group, a $C_{1-6}$ alkyl group, and —$OR^{a15}$(where $R^{a15}$ represents a $C_{1-6}$ alkyl group)}, (viii) —$NHR^g$ {where $R^g$ represents a $C_{7-10}$ aralkyl group optionally substituted by one or more substituents selected from the group consisting of a halogen atom, a hydroxyl group, a $C_{1-6}$ alkyl group, and —$OR^{a17}$ (where $R^{a17}$ represents a $C_{1-6}$ alkyl group)}, (ix) an aryl group optionally substituted by one or more substituents selected from the group consisting of a halogen atom, a hydroxyl group, a $C_{1-6}$ alkyl group, and —$OR^{a19}$ (where $R^{a19}$ represents a $C_{1-6}$ alkyl group), or (x) a heterocycloalkyl group optionally substituted by one or more substituents selected from the group consisting of a halogen atom, a hydroxyl group, a $C_{1-6}$ alkyl group, and —$OR^{a22}$ (where $R^{a22}$ represents a $C_{1-6}$ alkyl group).

\* \* \* \* \*